US010617300B2

(12) United States Patent
Rogers et al.

(10) Patent No.: US 10,617,300 B2
(45) Date of Patent: Apr. 14, 2020

(54) INJECTABLE AND IMPLANTABLE CELLULAR-SCALE ELECTRONIC DEVICES

(71) Applicants: THE BOARD OF TRUSTEES OF THE UNIVERSITY OF ILLINOIS, Urbana, IL (US); WASHINGTON UNIVERSITY IN ST. LOUIS, St. Louis, MO (US)

(72) Inventors: John A. Rogers, Champaign, IL (US); Michael Raymond Bruchas, St. Louis, MO (US); Robert Gereau, High Ridge, MO (US); Jordan Gary McCall, St. Louis, MO (US); Daniel Brenner, St. Louis, MO (US); Tae-il Kim, Gyeonggi-do (KR); Gunchul Shin, Urbana, IL (US); Jaewoong Jeong, Champaign, IL (US)

(73) Assignees: The Board of Trustees of the University of Illinois, Urbana, IL (US); Washington University, St. Louis, MO (US)

( * ) Notice: Subject to any disclaimer, the term of this patent is extended or adjusted under 35 U.S.C. 154(b) by 0 days.

(21) Appl. No.: 14/766,926

(22) PCT Filed: Feb. 11, 2014

(86) PCT No.: PCT/US2014/015825
§ 371 (c)(1),
(2) Date: Aug. 10, 2015

(87) PCT Pub. No.: WO2014/126927
PCT Pub. Date: Aug. 21, 2014

(65) Prior Publication Data
US 2016/0066789 A1 Mar. 10, 2016

Related U.S. Application Data

(60) Provisional application No. 61/764,410, filed on Feb. 13, 2013, provisional application No. 61/785,185,
(Continued)

(51) Int. Cl.
*A61B 5/00* (2006.01)
*A61N 1/05* (2006.01)
(Continued)

(52) U.S. Cl.
CPC ............ *A61B 5/0031* (2013.01); *A61B 5/685* (2013.01); *A61N 1/05* (2013.01); *A61N 5/062* (2013.01);
(Continued)

(58) Field of Classification Search
CPC ...... A61M 2037/0007; A61M 37/0015; A61M 2205/04; A61M 2205/05;
(Continued)

(56) References Cited

U.S. PATENT DOCUMENTS 5,487,739 A * 1/1996 Aebischer ............... A61F 2/022
424/424
6,018,673 A * 1/2000 Chin .................. A61B 5/14552
356/41
(Continued)

FOREIGN PATENT DOCUMENTS

WO WO 2012/054582 4/2012
WO WO 2012054582 A2 * 4/2012 ........... A61B 17/205

OTHER PUBLICATIONS

Bozkurt, Alper, and Banu Onaral. "Safety assessment of near infrared light emitting diodes for diffuse optical measurements." Biomedical engineering online 3.1 (2004): 9.*
(Continued)

Primary Examiner — Nilay J Shah
(74) Attorney, Agent, or Firm — Leydig, Voit & Mayer, Ltd.

(57) ABSTRACT

Provided are implantable or surface mounted biomedical devices and related methods for interfacing with a target tissue. The devices have a substrate and device component supported by the substrate. The components of the device are specially configured and packaged to be ultra-thin and mechanically compliant. In particular, device thicknesses are less than 1 mm and have lateral dimensions between about 1 m and 10 mm, depending on the application.
(Continued)

Delivery substrates may be incorporated to assist with device implantation and handling. The devices can be shaped to provide injection in a minimally invasive manner, thereby avoiding unnecessary tissue damage and providing a platform for long-term implantation for interfacing with biological tissue.

84 Claims, 80 Drawing Sheets

Related U.S. Application Data filed on Mar. 14, 2013, provisional application No. 61/883,524, filed on Sep. 27, 2013.

(51) Int. Cl.
*A61N 5/06* (2006.01)
*A61B 17/00* (2006.01)
*A61M 37/00* (2006.01)

(52) U.S. Cl.
CPC ..... *A61B 5/686* (2013.01); *A61B 2017/00004* (2013.01); *A61B 2562/0285* (2013.01); *A61B 2562/06* (2013.01); *A61B 2562/12* (2013.01); *A61M 2037/0007* (2013.01); *A61M 2037/0053* (2013.01); *A61M 2037/0061* (2013.01); *A61M 2205/04* (2013.01); *A61M 2205/05* (2013.01); *A61M 2205/054* (2013.01); *A61N 2005/0612* (2013.01)

(58) Field of Classification Search
CPC ............. A61M 2205/054; A61B 5/685; A61B 5/6848; A61B 5/6847; A61B 5/6846; A61B 5/686
See application file for complete search history.

(56) References Cited

U.S. PATENT DOCUMENTS

| | | | |
|---|---|---|---|
| 6,527,762 B1* | 3/2003 | Santini, Jr. | A61K 9/0009 216/2 |
| 7,195,733 B2 | 3/2007 | Rogers et al. | |
| 7,521,292 B2 | 4/2009 | Rogers et al. | |
| 7,557,367 B2 | 7/2009 | Rogers et al. | |
| 7,622,367 B1 | 11/2009 | Nuzzo et al. | |
| 7,704,684 B2 | 4/2010 | Rogers et al. | |
| 7,705,280 B2 | 4/2010 | Nuzzo et al. | |
| 7,799,699 B2 | 9/2010 | Nuzzo et al. | |
| 7,932,123 B2 | 4/2011 | Rogers et al. | |
| 7,943,491 B2 | 5/2011 | Nuzzo et al. | |
| 7,972,875 B2 | 7/2011 | Rogers et al. | |
| 7,982,296 B2 | 7/2011 | Nuzzo et al. | |
| 8,039,847 B2 | 10/2011 | Nuzzo et al. | |
| 8,198,621 B2 | 6/2012 | Rogers et al. | |
| 8,217,381 B2 | 7/2012 | Rogers et al. | |
| 8,367,035 B2 | 2/2013 | Rogers et al. | |
| 8,394,706 B2 | 3/2013 | Nuzzo et al. | |
| 8,440,546 B2 | 5/2013 | Nuzzo et al. | |
| 8,470,701 B2 | 6/2013 | Rogers et al. | |
| 8,552,299 B2 | 10/2013 | Rogers et al. | |
| 8,562,095 B2 | 10/2013 | Alleyene et al. | |
| 8,664,699 B2 | 3/2014 | Nuzzo et al. | |
| 8,666,471 B2 | 3/2014 | Rogers et al. | |
| 8,679,888 B2 | 3/2014 | Rogers et al. | |
| 8,722,458 B2 | 5/2014 | Rogers et al. | |
| 8,729,524 B2 | 5/2014 | Rogers et al. | |
| 8,754,396 B2 | 6/2014 | Rogers et al. | |
| 8,865,489 B2 | 10/2014 | Rogers et al. | |
| 8,895,406 B2 | 11/2014 | Rogers et al. | |
| 8,934,965 B2 | 1/2015 | Rogers et al. | |
| 8,946,683 B2 | 2/2015 | Rogers et al. | |
| 9,057,994 B2 | 6/2015 | Rogers et al. | |
| 9,061,494 B2 | 6/2015 | Rogers et al. | |
| 9,105,555 B2 | 8/2015 | Rogers et al. | |
| 9,105,782 B2 | 8/2015 | Rogers et al. | |
| 9,117,940 B2 | 8/2015 | Rogers et al. | |
| 2001/0047194 A1* | 11/2001 | Thompson | A61B 5/0031 607/59 |
| 2002/0087151 A1* | 7/2002 | Mody | A61B 18/1492 606/15 |
| 2003/0181788 A1* | 9/2003 | Yokoi | A61B 1/00087 600/160 |
| 2004/0243207 A1* | 12/2004 | Olson | A61N 1/05 607/116 |
| 2006/0049957 A1* | 3/2006 | Surgenor | A61B 5/0031 340/4.1 |
| 2008/0055581 A1 | 3/2008 | Rogers et al. | |
| 2008/0164275 A1* | 7/2008 | Poutiatine | A61J 7/0023 221/15 |
| 2010/0179438 A1* | 7/2010 | Heneghan | A61B 5/0205 600/484 |
| 2010/0190229 A1 | 7/2010 | Zhang et al. | |
| 2010/0317132 A1* | 12/2010 | Rogers | H01L 25/0753 438/27 |
| 2011/0040356 A1* | 2/2011 | Schiffer | A61N 5/0618 607/88 |
| 2011/0230747 A1* | 9/2011 | Rogers | A61B 5/05 600/377 |
| 2011/0316120 A1 | 12/2011 | Rogers et al. | |
| 2012/0034622 A1 | 2/2012 | Ignatius et al. | |
| 2012/0157804 A1 | 6/2012 | Rogers et al. | |
| 2012/0165759 A1 | 6/2012 | Rogers et al. | |
| 2012/0261551 A1 | 10/2012 | Rogers et al. | |
| 2012/0320581 A1 | 12/2012 | Rogers et al. | |
| 2013/0036928 A1 | 2/2013 | Rogers et al. | |
| 2013/0041235 A1 | 2/2013 | Rogers et al. | |
| 2013/0140649 A1 | 6/2013 | Rogers et al. | |
| 2013/0333094 A1 | 12/2013 | Rogers et al. | |
| 2014/0163390 A1 | 6/2014 | Rogers et al. | |
| 2014/0191236 A1 | 7/2014 | Nuzzo et al. | |
| 2014/0220422 A1 | 8/2014 | Rogers et al. | |
| 2014/0305900 A1 | 10/2014 | Rogers et al. | |
| 2014/0323968 A1 | 10/2014 | Rogers et al. | |
| 2014/0361409 A1 | 12/2014 | Rogers et al. | |
| 2014/0374872 A1 | 12/2014 | Rogers et al. | |
| 2015/0001462 A1 | 1/2015 | Rogers et al. | |
| 2015/0080695 A1 | 3/2015 | Rogers et al. | |
| 2015/0132873 A1 | 5/2015 | Rogers et al. | |
| 2015/0141767 A1 | 5/2015 | Rogers et al. | |
| 2015/0181700 A1 | 6/2015 | Rogers et al. | |
| 2015/0207012 A1 | 7/2015 | Rogers et al. | |
| 2015/0237711 A1 | 8/2015 | Rogers et al. | |
| 2015/0290938 A1 | 10/2015 | Rogers et al. | |
| 2015/0373831 A1 | 12/2015 | Rogers et al. | |
| 2015/0380355 A1 | 12/2015 | Rogers et al. | |
| 2016/0005700 A1 | 1/2016 | Rogers et al. | |
| 2016/0027737 A1 | 1/2016 | Rogers et al. | |

OTHER PUBLICATIONS

Adamantidis et al. (2007) "Neural substrates of awakening probed with optogenetic control of hypocretin neurons," Nature. 450:420-424.
Adamantidis et al. (2011) "Optogenetic interrogation of dopaminergic modulation of the multiple phases of reward-seeking behavior," J. Neurosci. 31:10829-10835.
Airan et al. (2009) "Temporally precise in vivo control of intracellular signalling," Nature. 458:1025-1029.
Al-Hardan et al. (2010) "The effect of oxygen ratio on the crystallography and optical emission properties of reactive RF sputtered ZnO films," Physica B. 405:1081-1085.
Al-Hasani et al. (Jun. 21, 2013) "Locus Coeruleus Kappa Opioid Receptors modulate Reinstatement of Cocaine Place Preference through a Noradrenergic Mechanism," Neuropsychopharmacology. 38(12):2484-2497.
Andosca et al. (May 2012) "Experimental and theoretical studies on MEMS piezoelectric vibrational energy harvesters with mass loading," Sensors and Actuators A. 178:76-87.

(56) References Cited

OTHER PUBLICATIONS

Angelopoulos et al. (Sep. 17-21, 2012) "Manufacturing aspects of an ultra-thin chip technology," In; The Proceedings of the European Solid-State Device Research Conference (ESSDERC) 2012. Bordeaux, France. Ed.: Yann Deval. pp. 141-144.
Anikeeva et al. (Dec. 4, 2011) "Optetrode: a multichannel readout for optogenetic control in freely moving mice," Nat. Neurosci. 15:163-170.
APC International, Ltd. (2011) Piezoelectric Ceramics: Principles and Applications. APC International. p. 16.
Aravanis et al. (2007) An optical neural interface: in vivo control of rodent motor cortex with integrated fiberoptic and optogenetic technology. J. Neural Eng. 4, S143-S156 (2007).
Baca et al. (2007) "Printable Single-Crystal Silicon Micro/Nanoscale Ribbons, Platelets and Bars Generated from Bulk Wafers," Adv. Funct. Mater. 17:3051-3062.
Barbottin et al. (1989) "Instabilities in Field Effect Transistors," Ch. 15. In; Instabilities in Silicon Devices. vol. 2. Elsevier. Amsterdam, The Netherlands. pp. 553-657.
Baskoutas et al. (2011) "Transition in the Optical Emission Polarization of ZnO Nanorods," J. Phys. Chem. C. 115:15862-15867.
Bernardini et al. (1997) "Spontaneous polarization and piezoelectric constants of III-V nitrides," Physical Review B. 56:R10024.
Bettinger et al. (2010) "Biomaterials-based organic electronic devices," Polym Int. 59:563-567.
Bettinger et al. (2010) "Organic thin-film transistors fabricated on resorbable biomaterial substrates," Adv. Mater. 22:651-655.
Blom et al. (1990) "Thin-film ZnO as micromechanical actuator at low frequencies," Sensors and Actuators 21:226-228.
Briscoe (Aug. 30, 2012) "Measured efficiency of a ZnO nanostructured diode piezoelectric energy harvesting device," App. Phys. Lett. 101:093902.
Bruchas et al. (2011) "Selective p38a MAPK Deletion in Serotonergic Neurons Produces Stress Resilience in Models of Depression and Addiction," Neuron. 71:498-511.
Burghartz et al. (2009) "A New Fabrication and Assembly Process for Ultrathin Chips," IEEE Trans. Electron Dev. 56:321-327.
Camacho et al. (2011) "Structural, optical and electrical properties of ZnO thin films grown by radio frequency (rf) sputtering in oxygen atmosphere," International Journal of the Physical Sciences. 6:6660-6663.
Cao et al. (2013) "An integrated µLED optrode for optogenetic stimulation and electrical recording," IEEE Trans. Biomed. Eng. 60:225-229.
Garcia et al. (2006) "High-performance ZnO thin-film transistors on gate dielectrics grown by atomic layer deposition," Appl. Phys. Lett. 88:123509.
Cardin et al. (2010) "Targeted optogenetic stimulation and recording of neurons in vivo using cell-type-specific expression of Channelrhodopsin-2," Nat. Protoc. 5:247-254.
Carson et al. (Aug. 31, 2012) "Transfer Printing Techniques for Materials Assembly and Micro/Nanodevice Fabrication," Adv. Mater. 24:5284-5318.
Carter et al. (2011) "Tuning arousal with optogenetic modulation of locus coeruleus neurons," Nat. Neuro. 13:1526-1533.
Cavanaugh et al. (Dec. 6, 2012) "Optogenetic inactivation modifies monkey visuomotor behavior," Neuron. 76:901-907.
Chang et al. (2010) "Direct-write piezoelectric polymeric nanogenerator with high energy conversion efficiency," Nano Lett. 10:726-731.
Chen et al. (2005) "Humidity Sensors: A Review of Materials and Mechanisms," Sensor Letters. 3:274-295.
Choi et al. (2003) "Investigation of Gate-Induced Drain Leakage (GIDL) Current in Thin Body Devices: Single-Gate Ultra-Thin Body, Symmetrical Double-Gate, and Asymmetrical Double-Gate MOSFETs," Jpn. J. Appl. Phys. 42:2073-2076.
Choi et al. (2009) "The effects of rapid thermal annealing on the performance of ZnO thin-film transistors," Journal of the Korean Physical Society. 55:1925-1930.

Choi-Yim et al. (1998) "The effect of silicon on the glass forming ability of the Cu47Ti34Zr11Ni8 bulk metallic glass forming alloy during processing of composites," J. Appl. Phys. 83:7993.
Chung et al. (2011) "Fabrication of Releasable Single-Crystal Silicon-Metal Oxide Field-Effect Devices and Their Deterministic Assembly on Foreign Substrates," Adv. Func. Mater. 21:3029-3036.
Clark et al. (2009) "Chronic microsensors for longitudinal, subsecond dopamine detection in behaving animals," Nat. Methods. 7:126-129.
Coque et al. (2011) "Specific role of VTA dopamine neuronal firing rates and morphology in the reversal of anxiety-related, but not depression-related behavior in the ClockΔ19 mouse model of mania," Neuropsychopharmacology. 36:1478-1488.
Csutak et al. (2002) "CMOS-compatible high-speed planar silicon photodiodes fabricated on SOI substrates," IEEE Journal of Quantum Electronics. 38:193-196.
Czekalla et al. (2008) "Spatial fluctuations of optical emission from single ZnO/MgZnO nanowire quantum wells," Nanotechnology. 19:115202.
Dagdeviren et al. (Apr. 19, 2013) "Transient, Biocompatible Electronics and Energy Harvesters Based on ZnO," Small. 9(20):3398-3404.
Danckwerts (1950) "Absorption by simultaneous diffusion and chemical reaction," Transactions of the Faraday Society. 46:300-304.
David et al. (Apr. 26, 2012) "Dissolution Kinetics and Solubility of ZnO Nanoparticles Followed by AGNES," J. Phys. Chem. C. 116:11758-11767.
Diester et al. (2011) "An optogenetic toolbox designed for primates," Nat. Neurosci. 14:387-397.
Dryden (Aug. 2013) "Shining Light on Cells," Washington University in St. Louis School of Medicine Magazine. Accessible on the Internet at URL: https://outlook.wustl.edu/2013/aug/light-research/.
Du Hoffmann et al. (2011) "An inexpensive drivable cannulated microelectrode array for simultaneous unit recording and drug infusion in the same brain nucleus of behaving rats," J. Neurophysiol. 106:1054-1064.
Ducéré et al. (2005) "A capacitive humidity sensor using crosslinked cellulose acetate butyrate," Sensors and Actuators B: Chemical. 106:331-334.
Elwassif et al. (2006) "Bio-heat transfer model of deep brain stimulation-induced temperature changes," J. Neural Eng. 3:306-315.
Esler et al. (2010) "Instrumentation for low frequency EIT studies of the human head and its validation in phantom experiments," Journal of Physics: Conference Series. 224:012007.
Federal Communications Comission (FCC) (1996) "Guidelines for Evaluating the Environmental Effects of Radiofrequency Radiation," FCC Publication Docket No. 93-62. Accessible on the Internet at URL: http://transition.fcc.gov/Bureaus/Engineering_Technology/Orders/1996/fcc96326.txt. [Last Accessed Dec. 9, 2015].
Fenno et al. (2011) "The Development and Application of Optogenetics," Annu. Rev. Neurosci. 34:389-412.
Fink et al. (2002) "Enhancement of device performance in vertical sub-100 nm MOS devices due to local channel doping," Solid State Electron. 46:387-391.
Fulati et al. (2009) "Miniaturized pH Sensors Based on Zinc Oxide Nanotubes/Nanorods," Sensors. 9:8911-8923.
Gerischer et al. (1992) "Chemical dissolution of zinc oxide crystals in aqueous electrolytes—An analysis of the kinetics," Electrochimica Acta. 37:827-835.
Gerits et al. (Apr. 26, 2013) "Optogenetics in primates: A shining future?" Trends Genet. 29(7):403-411.
Gradinaru et al. (2010) "Molecular and Cellular Approaches for Diversifying and Extending Optogenetics," Cell. 141:154-165.
Grosjean et al. (2006) "Hydrolysis of Mg-salt and MgH2-salt mixtures prepared by ball milling for hydrogen production," Journal of Alloys and Compounds. 416:296-302.
Gullapalli et al. (2010) "Flexible Piezoelectric ZnO-Paper Nanocomposite Strain Sensor," Small. 6:1641-1646.
Gupta et al. (2010) "Development of gas sensors using ZnO nanostructures," J. Chem. Sci. 122:57-62.

(56) References Cited

OTHER PUBLICATIONS

Han et al. (2009) "Millisecond-Timescale Optical Control of Neural Dynamics in the Nonhuman Primate Brain," Neuron 62:191-198.
Harrison et al. (2010) "A wireless neural/EMG telemetry system for freely moving insects," In; IEEE Int. Symp. Circuits Syst. ISCAS. Proc. 2010. pp. 2940-2943.
Hoffman et al. (2003) "ZnO-based transparent thin-film transistors," Appl. Phys. Lett. 82:733.
Huang et al. (2011) "A flexible pH sensor based on the iridium oxide sensing film," Sensors and Actuators A: Physical. 169:1-11.
Hudson et al. (2008) "The biocompatibility of mesoporous silicates," Biomaterials. 29:4045-4055.
Hwang et al. (2012) "A Physically Transient Form of Silicon Electronics," Science 337:1640-1644.
Ilican et al. (2008) "Preparation and characterization of ZnO thin films deposited by sol-gel spin coating method ," Journal of Optoelectronics and Advance Materials.10:2578-2583.
International Search Report with Written Opinion corresponding to International Patent Application No. PCT/US2014/015825, dated Apr. 29, 2014.
Irimia-Vladu et al. (2010) "Biocompatible and Biodegradable Materials for Organic Field-Effect Transistors," Adv. Funct. Mater. 20:4069-4076.
Ito et al. (2001) "Development and characteristics of a biological tissue-equivalent phantom for microwaves," Electronics and Communications in Japan (Part I: Communications). 84(4):67-77.
Iwai et al. (2011) "A simple head-mountable LED device for chronic stimulation of optogenetic molecules in freely moving mice," Neurosci. Res. 70:124-127.
Jennings et al. (Apr. 11, 2013) "Distinct extended amygdala circuits for divergent motivational states," Nature. 496:224-228.
Jeon et al. (2007) "Low-Voltage Zinc-Oxide Thin-Film Transistors on a Conventional SiO2 Gate Insulator Grown by Radio-Frequency Magnetron Sputtering at Room Temperature," Journal of the Korean Physical Society. 51:1999-2003.
Kim et al. (2008) "Stretchable and Foldable Silicon Integrated Circuits," Science. 320:507-511.
Kim et al. (2010) "Dissolvable films of silk fibroin for ultrathin, conformal bio-integrated electronics," Nat. Mater. 9:511-517.
Kim et al. (2010) "Waterproof AlInGaP optoelectronics on stretchable substrates with applications in biomedicine and robotics," Nat. Mater. 9:929-937.
Kim et al. (Apr. 10, 2012) "Optogenetic mimicry of the transient activation of dopamine neurons by natural reward is sufficient for operant reinforcement," Plos ONE. 7:e33612.
Kim et al. (Apr. 12, 2013) "Injectable, Cellular-Scale Optoelectronics with Applications for Wireless Optogenetics," Science. 340(6129):211-216.
Kim et al. (Apr. 2012) "Microscale Inorganic Light-Emitting Diodes on Flexible and Stretchable Substrates," IEEE Photonics J. 4:607-612.
Kim et al. (Aug. 12, 2011) "Epidermal electronics," Science 333:838-843.
Kim et al. (Jun. 8, 2012) "Material considerations for peripheral nerve interfacing," MRS Bull. 37:573-580.
Kim et al. (Mar. 20, 2013) "Diverging neural pathways assemble a behavioural state from separable features in anxiety," Nature. 496:219-223.
Kim et al. (Mar. 30, 2012) "High efficiency, microscale GaN LEDs and their thermal properties on unusually substrates," Small. 8:1643-1649.
Kim et al. (May 7, 2013) "Deterministic assembly of releasable single crystal silicon-metal oxide field-effect devices formed from bulk wafers," 102:182104.
Klapoetke et al. (Oct. 16, 2012) "Independent two-color optogenic excitation of neural populations in mouse cortical slices," In; The 42nd Annual Meeting of the Society for Neuroscience. New Orleans, Louisiana.—Presentation Abstract.

Knuesel et al. (2010) "Self-assembly of microscopic chiplets at a liquid-liquid-solid interface forming a flexible segmented monocrystalline solar cell," Proc. Natl. Acad. Sci. USA. 107:993-998.
Kozai et al. (2009) "Insertion shuttle with carboxyl terminated self-assembled monolayer coatings for implanting flexible polymer neural probes in the brain," J. Neuro. Met. 184:199-205.
Kravitz et al. (Nov. 21, 2012) "Optogenetic identification of striatal projection neuron subtypes during in vivo recordings," Brain Res. 1511:21-32.
Krejčiřík et al. (2007) "Non-Hermitian spectral effects in a PT-symmetric waveguide," Journal of Physics A: Mathematical and Theoretical. 41:244013.
Kumar et al. (2006) "Ultrasensitive DNA sequence detection using nanoscale ZnO sensor arrays," Nanotechnology. 17:2875-2881.
Kumar et al. (2011) "ZnO nanoparticle as catalyst for efficient green one-pot synthesis of coumarins through Knoevenagel condensation," J. Chem. Sci. 123:615-621.
Kuo (2004) "Deposition of Dielectric Thin Films for a-Si:H TFT," Ch. 6 In; Thin Film Transistors Materials and Processe. vol. 1. Klewer Academic. Norwell, Massachusetts.
Kurzweil (2009) "Metal Oxides and Ion-Exchanging Surfaces as pH Sensors in Liquids: State-of-the-Art and Outlook," Sensors (Basel). 9:4955-4985.
Lammel et al. (Oct. 14, 2012) "Input-specific control of reward and aversion in the ventral tegmental area," Nature. 491:212-217.
Lee et al. (2005) "Dielectrophoresis and Chemically Mediated Directed Self-Assembly of Micrometer-Scale Three-Terminal Metal Oxide Semiconductor Field-Effect Transistors," Adv. Mater. 17:2671-2677.
Legnani et al. (2008) "Bacterial cellulose membrane as flexible substrate for organic light emitting devices," Thin Solid Films. 517:1016-1020.
Li et al. (2008) "Cellular Level Biocompatibility and Biosafety of ZnO Nanowires," J. Phys. Chem. C. 112:20114-20117.
Li et al. (Jan. 21, 2013) "An Analytical Model of Reactive Diffusion for Transient Electronics," Advanced Functional Materials. 23:3106-3114.
Mack et al. (2006) "Mechanically Flexible Thin-Film Transistors that use Ultrathin Ribbons of Silicon Derived from Bulk Wafers," Appl. Phys. Lett. 88:213101.
Mannsfeld et al. (2010) "Highly sensitive flexible pressure sensors with micro-structured rubber as the dielectric layer," Nat. Mater. 9:859-864.
Martinez-Boubeta et al. (2010) "Self-assembled multifunctional Fe/MgO nanospheres for magnetic resonance imaging and hyperthermia," Nanomedicine: Nanotechnology, Biology, and Medicine. 6:362-370.
Masuda et al. (2003) "Transparent thin film transistors using ZnO as an active channel layer and their electrical properties," J. Appl. Phys. 93:1624.
Mattis et al. (2011) "Principles for applying optogenetic tools derived from direct comparative analysis of microbial opsins," Nat. Methods 18:159-172.
Mattsson et al. (2007) "Development of an infrared thermopile detector with a thin self-supporting SU-8 membrane," IEEE Sensors 2007 Conference. pp. 836-839.
McGranahan et al. (Jul. 27, 2011) "$\alpha 4\beta 2$ nicotinic acetylcholine receptors on dopaminergic neurons mediate nicotine reward and anxiety relief," J. Neurosci. 31:10891-10902.
Meitl et al. (2006) "Transfer printing by kinetic control of adhesion to an elastomeric stamp," Nat. Mater. 5:33-38.
Miyamoto et al. (2004) "High-electron-mobility ZnO epilayers grown by plasma-assisted molecular beam epitaxy," Journal of Crystal Growth. 265:34-40.
Modafe et al. (2005) "Embedded benzocyclobutene in silicon: An integrated fabrication process for electrical and thermal isolation in MEMS," Microelectron. Eng. 82:154-167.
Momose et al. (2002) "Ultrathin gate oxide CMOS on (111) surface-oriented Si substrate," IEEE Trans. Electron. Dev. 49:1597-1605.
Mondal et al. (2008) "Preparation of Al-Doped ZnO (AZO) Thin Film by SILAR," Journal of Physical Sciences. 12:221-229.

(56) References Cited

OTHER PUBLICATIONS

Moore et al. (1959) "II. Diffusion of zinc and oxygen in zinc oxide," Discussions of the Faraday Society. 28:86-93.
Moravej et al. (2011) "Biodegradable Metals for Cardiovascular Stent Application: Interests and New Opportunities," Int. J. Mol. Sci. 12:4250-4270.
Mudunkotuwa et al. (Nov. 28, 2011) "Dissolution of ZnO Nanoparticles at Circumneutral pH: A Study of Size Effects in the Presence and Absence of Citric Acid," Langmuir. 28:396-403.
Ondo-Ndong et al. (2003) "Electrical properties of zinc oxide sputtered thin films," Microelectronics Journal. 34:1087-1092.
Ordonez et al. (Jun. 8, 2012) "Thin films and microelectrode arrays for neuroprosthetics," MRS Bull. 37:590-598.
Osakada et al. (2011) "New Rabies Virus Variants for Monitoring and Manipulating Activity and Gene Expression in Defined Neural Circuits," Neuron. 71:617-631.
Osakada et al. (Jul. 25, 2013) "Design and generation of recombinant rabies virus vectors," Nat. Protoc. 8:1583-1601.
Pang et al. (Jul. 29, 2012) "A flexible and highly sensitive strain-gauge sensor using reversible interlocking of nanofibres," Nat. Mater. 11:795-801.
Panilaitis et al. (2003) "Macrophage responses to silk," Biomaterials. 24:3079-3085.
Park et al. (2008) "Theoretical and Experimental Studies of Bending of Inorganic Electronic Materials on Plastic Substrates," Adv. Funct. Mater. 18:2673-2684.
Park et al. (2009) "Printed Assemblies of Inorganic Light-Emitting Diodes for Deformable and Semitransparent Displays," Science. 325:977-981.
Pierret (1996) "Non Ideal MOS," Ch. 18 In; Semiconductor Device Fundamentals. Addison-Wesley. Natick, Massachusetts. pp. 645-690.
Qing et al. (2010) "Nanowire transistor arrays for mapping neural circuit in acute brain slides," Proc. Natl. Acad. Sci. USA. 107:1882-1887.
Reed et al. (Dec. 9, 2011) "Solubility of nano-zinc oxide in environmentally and biologically important matrices," Environ. Toxicol. Chem. 31:93-99.
Richter et al. (2008) "Review on Hydrogel-based pH Sensors and Microsensors," Sensors. 8:561-581.
Rogers et al. (2011) "Synthesis, assembly and applications of semiconductor nanomembranes," Nature. 477:45-53.
Ruiz et al. (Jun. 12, 2013) "Optogenetics through windows on the brain in the nonhuman primate," J. Neurophysiol. 110(6):1455-1467.
Saad et al. (2008) "Characterization of various zinc oxide catalysts and their activity in the dehydration-dehyrogenation of isobutanol," J. Serb. Chem. Soc. 73:997-1009.
Sato et al. (1999) "Anisotropic etching rates of single-crystal silicon for TMAH water solution as a function of crystallographic orientation," Sens. Actuators A. 73:131-137.
Sekitani et al. (2009) "Organic nonvolatile memory transistors for flexible sensor arrays," Science. 326:1516-1519.
Sekitani et al. (Mar. 2012) "Stretchable organic integrated circuits for large-area electronic skin surface," MRS Bull. 37:236-245.
Semprius.com (2014) "Semprius," Semprius, Inc. Accessible on the Internet at URL: http://www.semprius.com/. [Last Accessed Dec. 9, 2015].
Shahrjerdi et al. (Dec. 18, 2012) "Extremely Flexible Nanoscale Ultrathin Body Silicon Integrated Circuits on Plastic," Nano Lett. 13:315-320.
Shen et al. (2007) "Submicron particles of SBA-15 modified with MgO as carriers for controlled drug delivery," Chem. Pharm. Bull. 55:985-991.
Shimizu et al. (Jun. 2012) "Zinc Oxide Paste as Sunscreen in the Postoperative Period," Dermatologic Surgery. 38:965-966.
Solano et al. (2007) "Thermal and mechanical analysis of an SU8 polymeric actuator using infrared thermography," Proceedings of the Institution of Mechanical Engineers, Part C: Journal of Mechanical Engineering Science. 222(1):73-86.
Song et al. (2003) "Understanding Magnesium Corrosion—A Framework for Improved Alloy Performance," Advanced Engineering Materials. 5:837-858.
Song et al. (2009) "Mechanics of noncoplanar mesh design for stretchable electronic circuits," Journal of Applied Physics. 105:123516.
Sparta et al. (Dec. 8, 2011) "Construction of implantable optical fibers for long-term optogenetic manipulation of neural circuits," Nat. Met. 7:12-23.
Sparta et al. (May 16, 2013) Optogenetic strategies to investigate neural circuitry engaged by stress. Behav. Brain Res. 255:19-25.
Staiger et al. (2006) "Magnesium and its alloys as orthopedic biomaterials: a review," Biomaterials. 27:1728-1734.
Stamatakis et al. (Jun. 24, 2012) "Activation of lateral habenula inputs to the ventral midbrain promotes behavioral avoidance," Nat. Neuro. 12:1105-1107.
Stark et al. (Apr. 11, 2012) "Diode probes for spatiotemporal optical control of multiple neurons in freely moving animals," J. Neurophysiol. 108:349-363.
Stathis et al. (2006) "The negative bias temperature instability in MOS devices: A review," Microelec. Rel. 46:270-286.
Stauth et al. (2006) "Self-assembled single-crystal silicon circuits on plastic," Proc. Natl. Acad. Sci. USA. 19:13922-13927.
Stuber et al. (2011) "Excitatory transmission from the amygdala to nucleus accumbens facilitates reward seeking," Nature. 475:377-380.
Su et al. (Dec. 1, 2011) "Postbuckling analysis and its application to stretchable electronics," Journal of the Mechanics and Physics of Solids. 60:487-508.
Szarowski et al. (2003) "Brain responses to micro-machined silicon devices," Brain Res. 983:23-35.
Szuts et al. (2011) "A wireless multi-channel neural amplifier for freely moving animals," Nat. Neurosci. 14:263-269.
Takagi et al. (1994) "On the universality of inversion layer mobility in Si MOSFET's: Part II-effects of surface orientation," IEEE Trans. Electron Dev. 41:2363-2368.
Takei et al. (2010) "Nanowire active-matrix circuitry for low-voltage macroscale artificial skin," Nat. Mater. 9:821-826.
Takeuchi et al. (2004) "3D flexible multichannel neural probe array," J. Micromech. Microeng. 14:104-107.
Tan et al. (2012) "GABA neurons of the VTA drive conditioned place aversion," Neuron. 73:1173-1183.
Tao et al. (Jan. 20, 2012) "Silk-Based Conformal, Adhesive, Edible Food Sensors," Adv. Mater. 24:1067-1072.
Tian et al. (2010) "Three-diemensional, flexible, nanoscale field effect transistors as localized bioprobes," Science. 329:830-834.
Tian et al. (Aug. 26, 2012) "Macroprous nanowire nanoelectronic scaffolds for synthetic tissues," Nat. Mater. 11:986-994.
Trewyn et al. (2008) "Biocompatible mesoporous silica nanoparticles with different morphologies for animal cell membrane penetration," Chemical Engineering Journal. 137:23-29.
Tsai et al. (2009) "Phasic firing in dopaminergic neurons is sufficient for behavioral conditioning," Science. 324:1080-1084.
Tye et al. (2011) "Amygdala circuitry mediating reversible and bidirectional control of anxiety," Nature. 471:358-362.
Tye et al. (Mar. 20, 2012) "Optogenetic investigation of neural circuits underlying brain disease in animal models," Nat. Rev. Neurosci. 13:251-266.
Valtiner et al. (2008) "Stabilization and Acidic Dissolution Mechanism of Single-Crystalline ZnO(0001) Surfaces in Electrolytes Studied by In-Situ AFM Imaging and Ex-Situ LEED," Langmuir. 24:5350-5358.
Viventi et al. (2010) "A conformal, bio-Interfaced class of silicon electronics for mapping cardiac electrophysiology," Sci. Transl. Med. 2:24ra22.
Wales et al. (2003) "Stationary points and dynamics in high-dimensional systems," J. Chem. Phys. 119:12409-12416.
Wang et al. (1999) "Electromechanical coupling and output efficiency of piezoelectric bending actuators," IEEE Transactions on Ultrasonics, Ferroelectrics and Frequency Control. 46:638-646.
Wegner et al. (2006) "In situ formation and hydrolysis of Zn nanoparticles for H2 production by the 2-step ZnO/Zn water-splitting thermochemical cycle," International Journal of Hydrogen Energy. 31:55-61.

(56) References Cited

OTHER PUBLICATIONS

Wentz et al. (2011) "A wirelessly powered and controlled device for optical neural control of freely-behaving animals," J. Neural Eng. 8:046021.

Witten et al. (2011) "Recombinase-driver rat lines: tools, techniques, and optogenetic application to dopamine-mediated reinforcement," Neuron. 72:721-733.

Wong et al. (2000) "InxGa1-xN light emitting diodes on Si substrates fabricated by Pd-In metal bonding and laser lift-off," Appl. Phys. Lett. 77:2822-2824.

Yizhar et al. (2011) "Optogenetics in neural systems," Neuron. 71:9-34.

Zhai et al. (Oct. 23, 2012) "High-Performance Flexible Thin-Film Transistors Exfoliated from Bulk Wafer," Nano Lett. 12:5609-5615.

Zhang et al. (2010) "Optogenetic interrogation of neural circuits: technology for probing mammalian brain structures," Nat. Protoc. 5:439-456.

Zhang et al. (2010) "Fabrication and comparative study of top-gate and bottom-gate ZnO-TFTs with various insulator layers," J. Mater. Sci.: Mater. Electron. 21:671-675.

Zhang et al. (Oct. 19, 2012) "Serine 363 is required for NOPR desensitization, internalization, and arrestin signaling," J. Biol. Chem. 287(50):42019-42030.

Zhao et al. (2004) "Piezoelectric Characterization of Individual Zinc Oxide Nanobelt Probed by Piezoresponse Force Microscope," Nano Lett. 4:587-590.

Zhao et al. (2009) "Wireless Activation of Neurons in Brain Slices Using Nanostructured Semiconductor Photoelectrodes," Angew. Chem. Int. Ed. 48:2407-2410.

Zheng et al. (2009) "In Vitro and In Vivo Biocompatibility Studies of ZnO Nanoparticles," International Journal of Modern Physics B. 23:1566-1571.

Zhou et al. (2006) "Dissolving Behavior and Stability of ZnO Wires in Biofluids: A Study on Biodegradability and Biocompatibility of ZnO Nanostructures," Adv. Mater. 18:2432-2435.

Zhou et al. (Feb. 18, 2013) "Fast flexible electronics with strained silicon nanomembranes," Scientific Reports. 3:1291.

Zhu et al. (2010) "Flexible High-Output Nanogenerator Based on Lateral ZnO Nanowire Array," Nano Lett. 10:3151-3155.

Zorzos et al. (2010) "Multiwaveguide implantable probe for light delivery to sets of distributed brain targets," Opt. Lett. 35:4133-4135.

Zorzos et al. (Dec. 1, 2012) "Three-dimensional multiwaveguide probe array for light delivery to distributed brain circuits," Opt. Lett. 37:4841-4843.

* cited by examiner

The cable in subcutaneous tunnel deformed to accommodate mouse movements.

This bend in the cable as it passed through the subcutaneous tunnel formed spontaneously. It appears to have allowed excess length in the tunnel, permitting the mouse to flex and extend its back without disturbing the LED targeting.

There appeared to be no scar tissue in the tunnel immediately underneath healed scar, muscle architecture is intact. Implanted device is clearly visible diving beneath gluteus maximus

Flexible PCB

PCB Size = 13mm × 14mm

Battery

Battery capacity = 8mAh

System weight :

| Component | Weight (g) |
|---|---|
| Package Case | 0.705 |
| Battery (2) | 0.66 |
| PCB | 0.15 |
| Microfluidic Device | 0.34 |
| Total | 1.855 |

Previous
2 pin
connector

New
4-pin
connector

Previous
SU-8
needle

New
SUS
needle

INJECTABLE AND IMPLANTABLE CELLULAR-SCALE ELECTRONIC DEVICES

CROSS-REFERENCE TO RELATED APPLICATIONS

This application is a U.S. National Stage Application under 35 U.S.C. § 371 of International Application No. PCT/US2014/015825, filed Feb. 11, 2014, which claims the benefit of and priority to U.S. Provisional Patent App. Nos. 61/764,410 filed Feb. 13, 2013, 61/785,185 filed Mar. 14, 2013, and 61/883,524, filed Sep. 27, 2013, each of which is hereby incorporated by reference to the extent not inconsistent herewith.

STATEMENT REGARDING FEDERALLY SPONSORED RESEARCH OR DEVELOPMENT

This invention was made with government support under R01 NS081707, R00DA025182 and R01DA037152 awarded by the National Institutes of Health and DE-FG02-07ER46471 and DE-FG02-07ER46453 awarded by the Department of Energy. The government has certain rights in the invention.

BACKGROUND OF INVENTION

The field of the invention generally relates to implantation into biological tissues. The devices and methods utilize electronic devices arranged in ultrathin functional layers, along with stacking of those functional layers in a special geometric configuration, to achieve device implantation that is minimally invasive while providing the ability to interface with tissues on a cellular-scale resolution. Minimal disturbance of the tissue makes the devices particularly suitable for long-term implantation in biologically sensitive regions, including the brain.

Many conventional devices are designed for interfacing with a surface, such as biological tissue that is skin or an internal organ surface like the surface of the heart or the surface of the brain. An entirely different set of challenges arise wherein the application is for insertion into tissue. To accommodate a device within a tissue interior, surgery is generally required whether the tissue is physically opened to provide access to a device. Although improvements have been realized in the miniaturization of surgical instruments and devices, as well as arthroscopic techniques, there remains substantial tissue damage during the implantation procedure and, if necessary, device removal. Tissue damage associated with the relatively large size of conventional devices, including by cannula and fiber optics, results in inflammation and risk of adverse events associated with the immune response. Provided herein are ultra-thin and mechanically compliant devices for implanting into and interfacing with biological tissue.

SUMMARY OF THE INVENTION

Provided herein are electronic devices specially configured for implantation, injection or surface mount into or onto various soft tissues, such as biological soft tissues in living animals. Ultrathin and mechanically compliant electronic device components, for example, permit access to the interior of living tissues without unduly impacting biologic function. Because the physical devices provided herein are minimally invasive, they can be used even for long-term implantation to interface with tissue that is not normally physically accessible. For example, devices provided herein may be injected into a tissue with an attendant impact that is no more than that caused by a micro-needle. Furthermore, the electronic devices can be sized to a cellular and sub-cellular scale, thereby providing precise monitoring and control of biologic function on a cell-by-cell basis. This provides unique and technologically sophisticated applications that are not achieved with conventional systems that are confined to tissue surfaces or that are relatively short-term due to trauma associated with implantation and removal.

The device components and related functional electronic devices are specially packaged and integrated, thereby providing a number of important advantages. For example, although the sensors and actuators are arranged in an ultra-thin layout and may be as small as or smaller than biological cells, they remain highly-precise, robust, reliable and can be precisely positioned. While thin, lateral dimensions of the devices can have a wide range, such as from the cellular scale (e.g., micrometers) for individual cell monitoring, up to many millimeters (e.g., centimeter scale) for large-area interfacing. The ability to scale-up the system and package the electronics in a number of unique geometries, while maintaining an ultra-thin and mechanically compliant layout, ensures compatibility in a number of systems, including a number of biomedical applications. For example, large-area interfacing may still be on a cellular scale with an array of electronic devices each sized to a cellular scale to provide control or measurement with cell-size or better resolution.

The devices and systems provided herein are further advantageous in that they are readily applied to target tissue, such as by a process analogous to needle insertion for delivery of materials to a patient's tissue. One difference is that instead of a chemical injection, certain embodiments of the systems described herein provide device injection. Such device injection avoids disadvantages in the art associated with tissue trauma when devices are implanted. For example, tissue trauma is associated with a robust immune response along with heightened risk of adverse events ranging from device rejection requiring device removal, to thrombi, lesions and the like that can affect the tissue. This is avoided herein by providing implantation that is functionally equivalent to, and no more traumatic than, micro-needle insertion. In some embodiments, for example, the thickness of the implanted device may be no more than 100 µm thick, optionally 20 µm thick, thereby ensuring a minimum implantation footprint. Furthermore, the devices are amenable to providing multi-functionality, without unduly increasing device thickness or altering the device lateral dimension. Accordingly, any of the devices and methods provided herein is compatible with long-term implantation applications.

In an embodiment, the invention is an implantable, injectable or surface mounted biomedical device for interfacing with a target tissue. For example an implantable, injectable or surface mounted biomedical device may comprise a substrate and a device component comprising one or more inorganic semiconductor components; one or more metallic components; or one or more inorganic semiconductor components and one or more metallic components. The device component is supported by the substrate and the device component has a thickness that is less than or equal to 100 µm. The substrate and device component in combination have a lateral dimension and a thickness, such as a lateral dimension selected from a range that is greater than or equal to 1 µm and less than or equal to 10 mm; and a thickness selected from a range that is greater than or equal to 100 nm and less than or equal to 1 mm. As used herein, implantable refers to the functional capability of a device to be provided in a tissue, for example, in the bulk of a tissue at a selected depth. Certain implantable devices of the invention are also injectable, which refers to the functional capability of a device to be implanted and released in a tissue, for example, implanted and released into the bulk of a tissue at a selected depth. As used herein, surface mounted refers to the functional capability of a device to be provided on a surface of a tissue, such as an external surface of a tissue, and for some specific embodiments, provided in conformal contact with a surface of a tissue.

In an embodiment, the invention provides an implantable or surface mounted biomedical device having a device component comprising one or more electronic devices, optical devices, optoelectronic devices or arrays thereof. In an embodiment, for example, the invention provides an implantable or surface mounted biomedical device having a device component comprising an array of functional devices, such as one or more optical, mechanical, electrophysiological, acoustic, chemical, magnetic or thermal actuators; one or more optical, mechanical, electrophysiological, acoustic, chemical, magnetic or thermal sensor; or any combinations of these. In an embodiment, the invention provides an implantable or surface mounted biomedical device wherein the device component comprises one or more photodiode, a light emitting diode, a laser, an electrode, a piezoelectric element, an antenna, nanoelectromechanical (NEMS) device, microelectromechanical (MEMS) device, an acoustic source, a micro- or nano-heater, an integrated electronic circuit, energy source, chemical source, biological source or any combinations or arrays of these.

In preferred embodiments, the thickness of the device component and substrate in combination is less than about 100 µm, less than about 50 µm, less than about 20 µm, or about 10 µm. In these embodiments, the thickness of the device component is accordingly about less than 50 µm, less than 10 µm, or less than 1 µm. The substrate supporting the device component may be similarly thin, such as about less than 50 µm, less than 10 µm, or less than 1 µm. Use of such thin substrates and device components is useful for providing mechanically compliant, flexible and/or stretchable devices. In an embodiment, for example, the invention provides an implantable or surface mounted biomedical device wherein the device component has a thickness selected from the range of 500 nm to 50 µm. In an embodiment, for example, the invention provides an implantable or surface mounted biomedical device wherein the device component has a net bending stiffness of less than $1 \times 10^9$ GPa µm$^4$.

Devices of the invention include systems having active device components with lateral dimensions on the same order of magnitude (e.g., within a factor of 1 to 50) of the physical dimensions of cells and groups of cells of the target tissue. In an embodiment, for example, the device component or a portion thereof is individually addressed to a cell or group of cells of the target tissue. As used herein, individually addressed refers to a configuration wherein components of the implantable or surface mounted device, such as optical, electronic and optoelectronic devices or arrays thereof, are spatially aligned so as to be able to interact with a cell or group of cells of the target tissue. In an embodiment, for example, the invention provides an implantable or surface mounted biomedical device wherein the device component has an active area exposed to the target tissue less than or equal to $1 \times 10^6$ µm$^2$, or optionally for some embodiments, less than or equal to $1 \times 10^5$ µm$^2$. In an embodiment, for example, the invention comprises an implantable or surface mounted biomedical device wherein the device component has an active area exposed to the target tissue selected from the range of $1 \times 10^2$ µm$^2$ to $1 \times 10^6$ µm$^2$, and optionally selected from the range of $1 \times 10^3$ µm$^2$ to $1 \times 10^5$ µm$^2$. As used herein, active area refers to the portion of an optical, electronic, thermal, acoustic, chemical or biological device or device component that is functionally active. In some embodiments, for example, an active area of a device or device component generates or receives energy, one or more chemical agents and/or one or more biological agents. In an embodiment, for example, active area refers to the area of a device or device component for providing, receiving, reflecting or detecting light, or electrons, such as an emission area. In an embodiment, for example, active area refers to the area of a device or device component for establishing an electric potential, such as an electrode area. In an embodiment, for example, active area refers to the area of a device or device component for providing or receiving one or more chemical agents or biological agents. In an embodiment, for example, active area refers to the area of a device or device component for providing or receiving acoustic energy or heat.

In an embodiment, for example, the invention comprises an implantable or surface mounted biomedical device wherein the device component comprises one or more optical sources each independently having an emitting area selected less than or equal to $1 \times 10^5$ µm$^2$, and optionally for some applications less than or equal to $1 \times 10^5$ µm$^2$, and optionally for some applications less than or equal to $1 \times 10^4$ µm$^2$. In an embodiment, for example, the invention comprises an implantable or surface mounted biomedical device wherein the device component comprises one or more optical sources each independently having an emitting area selected from the range of $1 \times 10^3$ µm$^2$ to $1 \times 10^5$ µm$^2$, and optionally selected from the range of $1 \times 10^3$ µm$^2$ to $1 \times 10^4$ µm$^2$. In an embodiment, for example, the optical source provides a radiant output characterized by a plurality of different wavelength maxima, for example, for example characterized by at least two wavelength bands in the range of 300 nm to 1400 nm. In an embodiment, for example, the optical source provides a radiant output characterized by a surface power density of 0.1 mW mm$^2$ to 10 mW mm$^2$. In an embodiment, for example, the optical source provides a radiant output providing a change in the temperature of the target tissue equal to or less than 1° C.

In an embodiment, for example, the invention comprises an implantable or surface mounted biomedical device wherein the device component comprises one or more photodetectors each independently having an active light receiving area less than or equal to $1 \times 10^6$ µm$^2$, and optionally less than or equal to $1 \times 10^5$ µm$^2$. In an embodiment, for example, the invention comprises an implantable or surface mounted biomedical device wherein the device component comprises one or more photodetectors each independently having an active light receiving area selected from the range of $1 \times 10^3$ µm$^2$ to $1 \times 10^6$ µm$^2$, optionally selected from the range of $1 \times 10^3$ µm$^2$ to $1 \times 10^5$ µm$^2$. In an embodiment, for example, the invention comprises an implantable or surface mounted biomedical device wherein the device component comprises one or more electrodes each independently having an active electrode area selected from the range of $1 \times 10^2$ µm$^2$ to $1 \times 10^6$ µm$^2$, optionally selected from the range of $1 \times 10^3$ µm$^2$ to $1 \times 10^5$ µm$^2$. In an embodiment, for example, the invention comprises an implantable or surface mounted biomedical device wherein the device component comprises one or more electrodes each independently having an active electrode area less than or equal to $1\times10^6$ µm$^2$, or optionally less than or equal to $1\times10^5$ µm$^2$.

In an aspect, the device component and substrate form a functional layer comprising a functional electronic device that interfaces with the target tissue.

In an embodiment, any of the devices provided herein comprise a plurality of functional layers arranged in a stacked configuration, such as a number of layers selected from a range that is greater than or equal to 2 and less than or equal to 10. Use of a device component layout that is thin ensures that, in embodiments, even for multiple functional layers, the overall device remains thin. For example, the plurality of functional layers together may have a total thickness that is selected from a range that is greater than or equal to 500 nm and less than or equal to 100 µm, such as between about 10 µm and 50 µm, or about 20 µm. In addition, a stacked configuration does not alter the lateral dimension of the device, so that device footprint may remain small and target tissue interfacing area remains focused and coincident to each of the functional layers.

Multiple functional layers, wherein each functional layer is itself ultrathin, can be layered on top of each other in a stacked configuration. This allows the device to be multifunctional without changing lateral dimension and without sacrificing interfacing location, so that even for a small interface region multiple parameters may be controlled and/or measured. Multiple parameters can be measured and/or controlled, even on a cellular scale.

In an aspect, any of the devices provided herein are in a stacked configuration. An embodiment of this aspect is a stacked configuration having a shape that corresponds to a micro-needle. In this aspect, "micro-needle" refers to a small cross-sectional area, such as on the order of 10 mm$^2$, 1 mm$^2$, 10,000 µm$^2$, 1,000 µm$^2$ or less, or between about 1,000 µm$^2$ and 50,000 µm$^2$, with any desired length, such as long enough to ensure the stacked configuration device reaches the desired interior position, such as on the order of 5 mm to 10 cm, that is minimally invasive by minimizing or avoiding blunt-force trauma. The length will depend on the application of interest, with deeper target tissues having a correspondingly longer longitudinal length. In an aspect, the micro-needle shape further comprises one end that is shaped to penetrate tissue without causing undue tissue damage, such as by a sharpened leading edge of a substrate.

In an embodiment, one or more functional layers, device components or materials are positioned at, within, coincident with, and/or proximate to a neutral mechanical plane of the device or a layer of the device. For example, in embodiments, one or more inorganic semiconductor components and/or one or more metallic components are positioned coincident with or proximate to a neutral mechanical plane of the device or a layer of a device, such as a functional layer. Various device parameters are useful for adjusting or varying the position of the neutral mechanical plane within the device, such as a thickness of device components, substrates and encapsulation layers and or a Young's modulus of device components, substrates and encapsulation layers. In an aspect, providing one or more device components coincident with or proximate to a neutral mechanical plane provides the ability to protect sensitive device components from exposure to excessive strain, such as by providing strain-sensitive device components and/or strain sensitive layers at a location within a device such that the strain-sensitive components/layers are not exposed to strain levels that would fracture and/or otherwise damage the strain-sensitive components/layers.

Any of the devices and processes provided herein optionally include a plurality of functional layers that comprise at least two different functional layers. This results in a multifunctional implantable or surface mounted biomedical device, where each layer can provide a different function. For example, a multifunctional device may electrically, optically and thermally interface with the target tissue. In this manner, one device may monitor both temperature and electrical potential and, as necessary, also control electrical potential and temperature. That same device can also be used to image tissue, such as by optical detection, and provide electromagnetic radiation to the tissue. Such a system is extremely powerful and has a wide range of applications, from photo-dynamic therapy, heat therapy and/or electrical therapy.

The optical configurations and applications provided by devices herein are wide ranging and substantial. For example, light sources may be employed to deliver light at different angles allowing complete targeting of a plane or surface deep within the tissue. For example, referring to brain, dorsal-ventral targeting of deep brain structures is provided. Furthermore, multiple colors and sources of light can be independently controlled in a single device. Such a device can be further supplemented with additional functional layers providing independent sensing and actuation of any number of physical or biological parameters.

One example of a multifunctional device is for a plurality of functional layers in a stacked configuration that comprise the following layers: a microelectrode; an optical detector; an optical source; and a temperature sensor. The high quality electronic devices provided herein, allow for optical sources tailored for an application. For example, optical sources with appropriate emission spectra are tailored to specific therapeutic or imaging fluorophores that absorb at a specific wavelength. Similarly, optical detectors are tailored to match emission of corresponding therapeutic or imaging fluorophores to provide good imaging characteristics of deep tissue.

In an aspect, any of the multifunctional devices have a multifunctional interfacing that is substantially simultaneous or that is simultaneous.

The devices and processes provided herein are particularly useful in that they have well-defined interfacing regions that are described as highly localized or confined. This is advantageous as actuation or disturbances are confined to the region of interest, while also providing high sensitivity even on small size scales. In an aspect, the plurality of functional layers interface with an interfacing region that is confined to a localized region within a biological tissue, the interfacing region having an interfacing surface area selected from a range that is greater than or equal to 10 µm$^2$ and less than or equal to 100 mm$^2$. Generally, for larger surface areas, the devices are configured to have larger lateral dimensions. The interfacing surface area may have any desired shape, corresponding to the shape of the implanted device, such as substantially square or rectangular. Other shapes are readily obtained by laying out the functional electronic devices in a desired shape on their associated substrate. In this manner, each functional layer may have its own unique interfacing surface area and shape, while the overall substrate shape remains the same to provide the stacked configuration. This can be useful, for example, where one functional layer provides a biological stimulus or block, and other functional layers assess different cells that may be positioned at a distance from the stimulus or block (e.g., blocking synapses, measuring electric potential or fluorescent dyes in cells upstream and downstream from a synapse).

In an aspect, each functional layer has a corresponding interfacing region, and at least one functional layer interfacing region is distinct from another interfacing region.

Functional electronic device is used broadly to refer to a detector of, or an actuator of, a physical or biological property. The physical property may be one or more of an optical property, a thermal property, or an electrical property. Other physical properties may reflect biological response, such as oxygen levels or other biological or chemical concentrations that may be indicative of tissue or individual cell status.

The devices provided herein are optionally further described in terms of the properties of the device components. For example, the one or more inorganic semiconductor components or one or more metallic conductor components may: independently comprise one or more thin film structures; independently have a thickness selected from the range of 10 nm to 100 µm; or independently have a thickness less than or equal to 100 nm.

In an aspect, any of the devices comprise one or more inorganic semiconductor components, such as independently comprising: a nanomembrane structure; a polycrystalline semiconductor material, single crystalline semiconductor material or a doped polycrystalline or single crystalline semiconductor material.

To provide good flexibility or stretchability, at least one of the inorganic semiconductor components or one or more metallic conductor components is optionally a flexible or a stretchable structure. The flexible or stretchable structure may be an interconnect that connects island structures, such as island structures that tend to be relatively less stretchable or flexible. In this manner, the interconnects may accommodate stresses and strains associated with stretching or flexing.

In an aspect, at least one of the inorganic semiconductor components or one or more metallic conductor components is a nanoribbon, a nanomembrane, a nanowire, a transistor channel, a diode, a p-n junction, a photodiode, a light emitting diode, a laser or a combination of these.

In an aspect, at least one of the inorganic semiconductor components or one or more metallic conductor components has a Young's modulus selected from the range of 0.5 MPa to 10 GPa.

In an aspect, at least one of the inorganic semiconductor components or one or more metallic conductor components has a net bending stiffness less than or equal to $1 \times 10^8$ GPa µm$^4$.

In an embodiment, the substrate comprises a material selected from the group consisting of MgO, silk, collagen, gelatin, PLGA, polyvinylalcohol (PVA), PLA, $SiO_2$, polyanhydrides (polyesters), polyhydroxyalkanates (PHAs), polydimethylsiloxane (PDMS) and polyphosphates.

In an aspect, the substrate and device component in combination have a longitudinal length that corresponds to the penetration depth of the implanted device. For example, a longitudinal length selected from a range that is greater than or equal to 1 mm (corresponding to immediately below the surface) and less than or equal to 10 cm (deep tissue insertion).

In an aspect, the functional electronic device corresponds to the size of a biological component within the target tissue, such as the size of a cell within the target tissue, or a region or component thereof. In an aspect, the size of the biological component is an average diameter selected from a range that is greater than or equal to 1 µm and less than or equal to 100 µm. "Biological component" may refer to a component of a cell, such as a nucleus, membrane, mitochondria, or regions thereof, such as synapses in the case of nerve transduction.

Any of the devices provided herein may optionally have a functional layer comprising an array of functional electronic devices, such as an array of light sources, light detectors, electrodes and/or thermal sensors.

Any of the devices provided herein optionally further comprise an encapsulating material at least partially encapsulating one or more of the inorganic semiconductor components or one or more of the metallic conductor components. The encapsulating material may be a bioinert or biocompatible material, to further suppress or avoid unwanted immune response or reaction.

Any of the devices provided herein optionally further comprise a barrier layer that covers one or more of the inorganic semiconductor components or one or more of the metallic conductor components. The barrier layer may prevent unwanted leakage, such as current leakage, from the device to the surrounding tissue.

Any of the devices and processes provided herein optionally relate to shaping of substrates, such as a substrate first end that is tapered for insertion into the target tissue. The taper may be to a tip-point, similar to a needle, to facilitate transit through tissue and minimize or avoid blunt force trauma. Blunt force trauma refers to the force exerted against tissue when an object is inserted through or from the tissue. "Minimal blunt force trauma" refers to a force that is sufficiently small to avoid significant long-term tissue impact, such as associated by immune response, clotting, and/or scarring, where biological activity is measurably disturbed.

To further facilitate tissue transit, and to protect the device components during handling and transit, any of the devices optionally include a delivery substrate that supports the substrate. In an aspect, an adhesive layer is positioned between the delivery substrate and the substrate, such as an adhesive layer that dissolves or is bioresorbed and the delivery substrate removed after implantation. In an aspect, the adhesive layer comprises a silk material. Useful silk materials for adhesive layers include, for example, silkworm fibroin, modified silkworm fibroin, spider silk, insect silk, recombinant silk, and any combination of these. As used herein, modified silkworm fibroin refers to a polymer composition that is derived via chemical modification of silkworm fibroin.

In an aspect, the delivery substrate is further described using one or more mechanical properties, particularly a mechanical property that is substantially higher than a corresponding mechanical property of the device component and substrate. In an embodiment, the mechanical property is at least a factor of 10, at least a factor of 100, or between a factor of 10 and 1000 times higher in the delivery substrate. Such an elevated mechanical property optionally supports and protects the device component and substrate during handling and implantation. Alternatively, the delivery substrate may be geometrically configured to protect the device component and substrate, such as by wrapping or partially wrapping the device component and substrate. Examples of mechanical properties include Young's modulus, net bending stiffness or strength to failure.

Optionally, the delivery substrate has a shape that corresponds to the shape of the substrate that supports the device component, such having a first end that tapers, including that tapers to a tip. In an aspect, any of the devices provided herein are shaped into a micro-needle geometry and the device is injectable into target tissue.

The devices provided herein are specially configured and packaged to have a small cross-sectional area. This minimizes potential tissue trauma during insertion, minimizes the footprint of the implanted device, and provides extremely confined and localized interfacing. In an aspect, the cross-sectional surface area of the implanted device is selected from a range that is less than or equal to 1 mm$^2$, such as a cross-sectional surface area selected from a range that is greater than or equal 1000 µm$^2$ and less than or equal to 50,000 µm$^2$.

In an aspect, any the device components provided herein are partially or completely embedded within the substrate.

The devices and processes disclosed herein may be used in a target tissue that is soft tissue of a living animal. Alternatively, the devices and processes may be used with artificially engineered tissue, such as artificially engineered tissue for implantation into an animal. In this manner, any of the devices and processes may relate to ex vivo tissue or in vitro tissue.

In an aspect, the target tissue is selected from the group consisting of brain, heart, kidney, liver, lung, eye, blood vessel, and skin. In an aspect, the soft tissue is brain and the interfacing is at a penetration depth selected from a range that is greater than or equal to 1 mm and less than or equal to 10 cm from a soft tissue surface.

A particularly useful aspect of the devices and processes relates to wireless receiving and broadcasting, thereby avoiding the need for hard-wired connections between an implanted device and external systems or medical personnel. In an aspect, the device further comprises a wireless transmitter and a wireless receiver operably connected to the device for wirelessly receiving data and transmitting instructions to the device implanted in target tissue.

Optionally, any of the devices and processes disclosed herein comprise a microfluidic device or device component. For example, in embodiments the device comprises a microfluidic device or system providing one-way fluid communication with a target tissue. In embodiments, the devices include a microfluidic device providing two-way fluid communication with a target tissue. As used herein, "one-way fluid communication" refers to the ability of a device to either deliver a fluid to a tissue or withdraw or otherwise take up fluid from a tissue. As used herein, "two-way fluid communication" refers to the ability of a device to both deliver a fluid to a tissue as well as withdraw or otherwise take up fluid from a tissue. Devices incorporating a microfluidic component are useful for providing fluids to a tissue, such as a fluid comprising a pharmaceutical composition, a therapeutic composition, or a phototherapeutic composition. In an embodiment, a microfluidic device delivers a phototherapeutic to a tissue and an LED in the device subsequently exposes the phototherapeutic to electromagnetic radiation, thereby activating the phototherapeutic.

In an embodiment, a microfluidic device comprises a fluid reservoir positioned proximate to a heat or thermally expandable material, such as a fluid reservoir positioned to release its contents to a target tissue. To actuate the microfluidic device, in embodiments, the heat expandable material is positioned in thermal communication with a heat generating element, such as a resistive heater. Optionally, the fluid reservoir releases its contents due to a rupture in the fluid reservoir, such as a rupture generated by expansion of a thermally expandable material. Optionally, the microfluidic device comprises a two-way expandable material, such as an actuator comprising polypyrrole and/or platinum.

In exemplary embodiments, the microfluidic device or device component provides a fluid, such as to a tissue, at a temperature less than the temperature of the heat expandable material. For example, in embodiments, a temperature of 110° C. or greater is used to actuate the thermally expansive material, while the fluid in the device maintains a temperature less than 50° C. In various embodiments, a wireless control system provides a means for actuating the microfluidic device, thereby allowing the device to operate in a fully implanted condition.

Another useful aspect is devices that further comprise a probe connected to the substrate first end. The probe may be a detector that detects a signal from the target tissue to indicate when the tip is in a desired position. For example, the signal may be an optical signal, thermal signal, radiological tag, or other tag. In the case of tumor therapy, the tag may be specific to a cancer cell. Similarly, other adverse biological events may be tagged, or tags of a desired biological cell or component, so as to provide an appropriate position indication to the person injecting the device from the device itself without having to directly inspect the tissue. Accordingly, the probe may be a positioning probe to indicate device position within target tissue. In an aspect, the probe is confined to a probe confinement area on the substrate first end that is less than or equal to 1000 µm$^2$. In an aspect, the probe is confined to the distal most portion of the substrate. In an aspect, the probe is connected to the delivery substrate, so that after removal of the delivery substrate, the probe is also removed.

In another embodiment, any of the injectable and implantable or surface mounted biomedical devices for interfacing with a target tissue further comprise a delivery substrate having a first end that is tapered for insertion into the target tissue, wherein the delivery substrate supports the substrate and device component. In an aspect, a top surface of the delivery substrate supports a bottom surface of the substrate, with the device component supported by a top surface of the substrate. As discussed, the entire device remains relatively thin, including the device component and substrate which may be described as ultra-thin. "Ultra-thin" refers to device components that are less than 20 µm, less than 10 µm, or less than 1 µm thick, and corresponding substrates that are similarly thin. In an aspect, the delivery substrate may be somewhat thicker, thereby providing desirable mechanical stability and durability to the device during implantation and handling, such as a thickness selected from a range that is greater than or equal to 1 µm and less than or equal to 100 µm. In an aspect, the delivery substrate has a thickness that is at least 10 times thicker than the total thickness of all functional layers in the device.

Optionally, an adhesive layer adheres the base substrate to the substrate, wherein in response to a stimulus the adhesive layer dissolves or is bioresorbed and the delivery substrate is removed from the substrate. A wide range of adhesive layer/stimulus pairs are available, with the specific pair selected depending on the application of interest. In one embodiment, the adhesive layer comprises a silk material and the stimulus is a solvent that dissolves the silk material. The solvent may be within the tissue or may be external and applied to the device after implantation, such as via one or more solvent access openings.

The device may optionally be further characterized in terms of various cross-sectional areas, such as an insertion cross-sectional area of the device that is less than or equal to 4 mm$^2$ and/or an implanted cross sectional area is less than or equal to 1 mm$^2$. "Implanted cross sectional area" is the cross-sectional area of the device after the delivery substrate is removed. In an aspect, the ratio of cross-sectional insertion area to cross-sectional implantation area is selected from a range that less than or equal to 10 and greater than or equal to 2.

The invention further relates to various methods, such as a method of making or a method of using any of the devices provided herein. In an embodiment, the invention is a method of making an implantable or surface mounted biomedical device by providing a functional device layer comprising a functional electronic device. The functional device layer has a thickness that is less than or equal to 20 µm and a lateral dimension selected from a range that is greater than or equal to 1 µm and less than or equal to 10 mm, as well as one or more inorganic semiconductor components, one or more metallic components, or one or more inorganic semiconductor components and one or more metallic components. A delivery substrate is provided and the functional device layer and the delivery substrate are stacked relative to each other. The functional device layer is bonded to the delivery substrate.

The stacking is by shaping the surface area shape of the functional layer, the delivery substrate, or both to correspond to each other. In this manner, the shaping may be after the layer and substrate are bonded to each other, or the layer and substrate may be shaped before bonding with the shaped portions aligned and bonded. In an aspect, the surface area shape corresponds to a micro-needle, so that the device can be injected into tissue with minimal tissue damage.

In an aspect, at least one additional functional layer is provided to make a multifunctional implantable or surface mounted biomedical device, such as functional layers that number from a range that is greater than or equal to 2 and less than or equal to 6. Adjacent functional layers may be bonded to each other, with a bottom-most functional layer bonded to the delivery substrate.

In an aspect, the bonding step may be via a releasable adhesive layer between the delivery substrate and the functional layer, including an adhesive layer that is dissolved by an applied signal, such as heat, pH, pressure, light or chemical. In an aspect, the device itself is responsible for generating a signal to dissolve the adhesive layer (e.g., localized heat or light from a functional layer). Alternatively, a solvent may be applied, such a solvent that dissolves an adhesive layer that comprises a silk material.

Alternatively, other means known in the art may be used to remove the delivery substrate from the functional device layer, such as mechanical removal.

In an embodiment, the method further comprises the step of providing a physical access opening to the releasable adhesive layer for application of a signal to dissolve the releasable adhesive layer. In an aspect, the signal is a solvent that is provided in physical contact with the releasable adhesive layer, such as an exposed edge. In an aspect, the dissolution time of the adhesive layer is greater than or equal to 1 minute, and less than or equal to 30 minutes.

In another embodiment, the invention is a method of implanting any of the devices provided herein. For example, a method of implanting an injectable and implantable or surface mounted biomedical device by positioning the device adjacent to a soft tissue surface in which the target tissue is located, inserting the device into the soft tissue and adjacent to the target tissue, releasing the substrate and device component from the delivery substrate, and removing the delivery substrate from the soft tissue.

In an aspect, the inserting and removing steps are confined to a cross-sectional disturbance area in the soft tissue that is less than or equal to 5 mm$^2$, less than or equal to 2 mm$^2$, or less than or equal to 1 mm$^2$. Such a small disturbance area is further characterized as "minimally invasive."

In an aspect, the soft tissue is brain, and the interfacing is along a dorsal-ventral plane, such as by a multifunctional device where the interfacing comprises control or measurement of an optical property, an electrical property, or a thermal property. Any of the methods may further include interfacing the implanted substrate and device component with the target tissue, wherein the interfacing is wirelessly controlled and monitored.

In another aspect, the invention provides a method of treating a biological tissue comprising the steps of: (1) transforming one or more cells of the biological tissue with a nucleic acid encoding one or more light responsive proteins, thereby generating at least one transformed cell that is light responsive; (2) providing an implantable or surface mounted biomedical device in optical communication with the at least one transformed cell of the biological tissue; wherein the implantable or surface mounted biomedical device comprises: (i) a substrate; (ii) a device component comprising: one or more inorganic semiconductor components; one or more metallic components; or one or more inorganic semiconductor components and one or more metallic components; wherein the device component is supported by the substrate and the device component has a thickness that is less than or equal to 100 µm; wherein the substrate and device component in combination have a lateral dimension and a thickness; the lateral dimension selected from a range that is greater than or equal to 1 µm and less than or equal to 10 mm; and the thickness selected from a range that is greater than or equal to 100 nm and less than or equal to 1 mm; (3) exposing the at least one transformed cell to an optical stimulus from the implantable or surface mounted biomedical device; thereby treating the biological tissue. In an embodiment, for example, the exposing step is carried out in vivo. In an embodiment, for example, exposing the at least one transformed cell to the optical stimulus from the implantable or surface mounted biomedical device increases or decreases expression of the one or more light-responsive proteins. In an embodiment, for example, the implantable or surface mounted device or one or more components thereof individually addresses one or more transformed cells of the biological tissue.

In an embodiment, for example, the at least one transformed cell of the biological tissue expresses photoactivatable proteins, receptors or channels. In an embodiment, the invention provides methods further comprising the step of implanting the implantable or surface mounted biomedical device into the biological tissue, thereby providing the implantable or surface mounted biomedical device in optical communication with the at least one transformed cell of the biological tissue. In an embodiment, the invention provides methods comprising the step of providing the implantable or surface mounted biomedical device in conformal contact with the biological tissue, thereby providing the implantable or surface mounted biomedical device in optical communication with the at least one transformed cell of the biological tissue.

In an embodiment, the transformed cell is a mammalian neuron or glial cell, such as a dopaminergic neuron. In an embodiment of this aspect, for example, the exposing step provides controllable activation or inactivation of the neuron. In an embodiment of this aspect, for example, the exposing step provides controllable activation of the channelrhodopsin-2 ion channel of the neuron. In an embodiment of this aspect, for example, the exposing step provides control of intra cellular signaling via an optically sensitive G-protein coupled receptor. In an embodiment, the transformed cell is a smooth muscle cell, such as a vascular smooth muscle cell.

In an embodiment, the optical stimulus comprises exposure of the at least one transformed cell to one or more pulses of electromagnetic radiation. In an embodiment of this aspect, for example, each of the one or more pulses of electromagnetic radiation has an optical power density selected from the range of 0.1 mW mm$^{-2}$ to 100 mW mm$^{-2}$, optionally for some applications selected from the range of 0.1 mW mm$^{-2}$ to 10 mW mm$^{-2}$, and optionally for some applications selected from the range of 0.1 mW mm$^{-2}$ to 10 mW mm$^{-2}$. In an embodiment of this aspect, for example, each of the one or more pulses of electromagnetic radiation have wavelengths selected from the range of 400 nm to 1200 nm, optionally for some applications selected from the range of 400 nm to 800 nm. In an embodiment of this aspect, for example, the one or more pulses of electromagnetic radiation are provided at a frequency selected from the range of 0.1 to 50 Hz. In an embodiment of this aspect, for example, the one or more pulses of electromagnetic radiation include a first pulse corresponding to a first range of wavelengths and a second pulse corresponding to a second range of wavelengths that is different than the first range of wavelengths, and optionally wherein the first range of wavelengths does not overlap the second range of wavelengths. In an embodiment of this aspect, for example, the optical stimulus provides a change in temperature of the biological tissue of less than or equal to 0.5° C., and optionally for some applications less than or equal to 0.1° C. In an embodiment, the implantable or surface mounted biomedical device of the invention is powered wirelessly and, optionally, under conditions wherein the RF power that reaches a biological tissue is less than or equal to 3 mW/cm$^2$, and optionally for some applications less than or equal to 1 mW/cm$^2$, optionally for some applications less than or equal to 0.1 mW/cm$^2$.

In an embodiment, the device of the invention is implanted into, or provided on a surface (e.g., external surface) of, a biological tissue of a subject, for example, a subject undergoing a therapy. In an embodiment, for example, the device of the invention is implanted into a biological tissue of a subject at a depth selected from the range of 0.05 mm to 100 mm, optionally for some embodiments selected from the range of 0.1 mm to 10 mm.

In an embodiment, methods of the invention further comprise the step of sensing one or more optical, physical, physiological or thermal properties of the biological tissue using the implantable or surface mounted biomedical device. In an embodiment, for example, the one or more optical, physical, physiological or thermal properties are selected from the group consisting of temperature, extracellular potential, intensity of scattered light, pH, blood oxygen, glucose levels, and neurochemical detection.

In another aspect, the invention provides a method of treating a biological tissue comprising the steps of: (1) providing an implantable or surface mounted biomedical device comprising: (i) a substrate; (ii) a device component comprising: one or more inorganic semiconductor components; one or more metallic components; or one or more inorganic semiconductor components and one or more metallic components; wherein the device component is supported by the substrate and the device component has a thickness that is less than or equal to 100 µm; wherein the substrate and device component in combination have a lateral dimension and a thickness; the lateral dimension selected from a range that is greater than or equal to 1 µm and less than or equal to 10 mm; and the thickness selected from a range that is greater than or equal to 100 nm and less than or equal to 1 mm; (2) contacting the biological tissue with the implantable or surface mounted biomedical device; wherein the device provides one or more therapeutic agents to the biological tissue; and (3) optically activating the therapeutic agent in contact with the biological tissue; thereby treating the biological tissue. In an embodiment, for example, the one or more therapeutic agents comprise a phototherapeutic agent or a light-activated ion channel modulator. In an embodiment, for example, the one or more therapeutic agents are selected from the group consisting of sodium channel blockers, potassium channel openers, light-activated (uncaging) analgesic drugs, such as opiates and opioid-like ligands. In an embodiment, for example, the biological tissue is transformed with a nucleic acid encoding one or more light responsive proteins, thereby generating at least one transformed cell that is light-responsive.

In certain embodiments, the invention encompasses administering an implantable or surface mounted device to a patient or subject. A "patient" or "subject", used equivalently herein, refers to an animal. In particular, an animal refers to a mammal, preferably a human. The subject can either: (1) have a condition able to be monitored, diagnosed, prevented and/or treated by administration of an implantable or surface mounted device of the invention; or (2) is susceptible to a condition that is able to be monitored, diagnosed, prevented and/or treated by administering an implantable or surface mounted device of the invention. In an embodiment, a method of this aspect further comprises administering a device of the invention to a subject in need of treatment, for example, a subject having a disease, propensity for a disease or other pathological condition. The present devices and methods are particularly useful for treatment and management of a range of diseases or other pathological conditions including motor disorders including Parkinson's disease and Huntington's disease, traumatic brain injury, chronic and acute depression, stress disorders, addiction, epilepsy, coma or related chronic brain related trauma, Tourette's syndrome, regulation of cardiac function, chronic pain, terstitial cystitis, bladder pain syndrome (BPS), chronic pelvic pain syndrome, chronic prostatitis, overactive bladder, urinary incontinence, BS, or colonic inflammation.

Administering devices of the invention may be carried out in a variety of manners including surgically implanting the device on a surface of, or into, a target biological tissue of a subject, injecting the device into a target biological tissue of a subject, and providing the device in physical contact, and optionally in conformal contact, with a target biological tissue of the subject. In an embodiment, for example, the target biological tissue is a tissue type selected from the group consisting of brain tissue, peripheral nervous system tissue, nerve tissue, genito urinary tissue, vesicular tissue, bladder tissue, colon tissue, gastric tissue, smooth muscle tissue, cardiac tissue and vascular tissue. In an embodiment, for example, the target biological tissue is located in a region of the brain selected from the group consisting of subthalamic nucleus, hippocampus, cortex, globus pallidus, subgenual cingulate gyrus, nucleus accumbens, ventral capsule/ventral striatum, inferior thalamic peduncle, and the lateral habenula, and medial forebrain bundle; or is located in the lumen of the bladder or the peritoneum; or is subcutaneously on the abdomen for example over the bladder.

In an embodiment, the method of this aspect further comprises transforming cells and/or cell types of a target biological tissue of the subject, for example, via administration to a subject an appropriate vector including a nucleic acid providing for selective activation of modulation of the transformed cells. Therapeutic methods of some aspects of the invention include selective transformation of specific cells and/or cell types of a target biological tissue via administration to a subject an appropriate vector encoding one or more light responsive proteins, including light responsive receptors. In an embodiment, for example, the cell or cell type selected for transformation comprises neurons, including dopaminergic neurons, glial cells, urothelial cells, or muscle cells including smooth muscle cells.

In an embodiment, the method of this aspect further comprises delivering a therapeutically effective amount of electromagnetic radiation to the target biological tissue of the subject, for example, providing electromagnetic radiation to the target biological tissue having wavelengths, energy, fluence and/or power sufficient to achieve a desired therapeutic or diagnostic outcome. In an embodiment, the method of this aspect further comprises delivering a therapeutically effective amount of a therapeutic agent (e.g., a drug or drug precursor) to the target biological tissue of the subject, for example, providing the therapeutic agent at a concentration sufficient to achieve a desired therapeutic or diagnostic outcome.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

Figure 5:
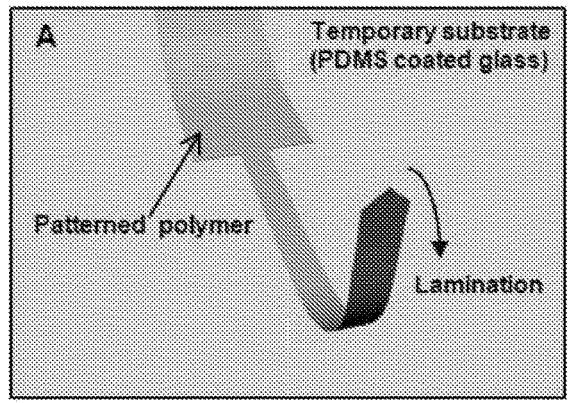
Figure 5:
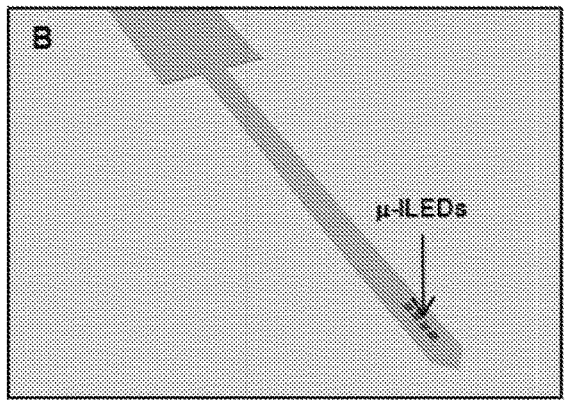
Figure 5:
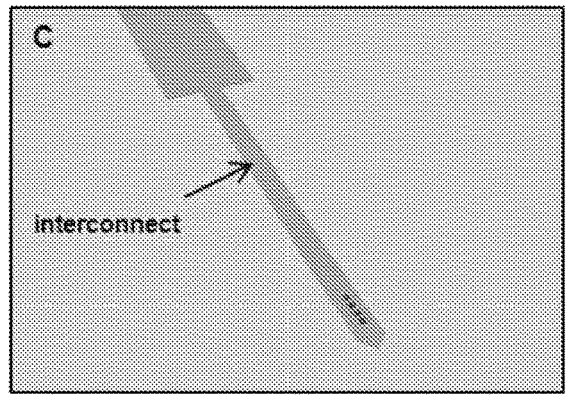
Figure 5:
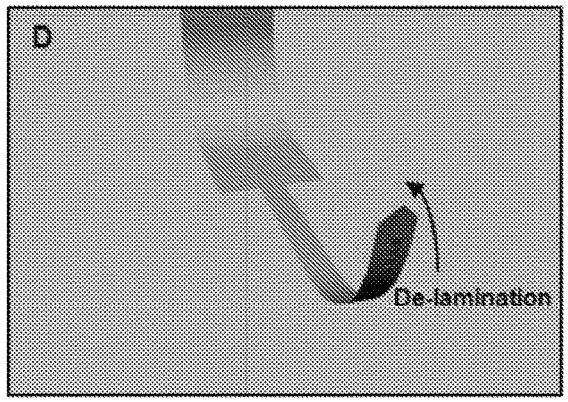

FIG. 5. Schematic illustration of steps for fabrication (A) thin (2.5 or 6.0 μm thick) microneedleshaped polymeric template laminated on a PDMS coated substrate, (B) μ-ILEDs integrated by transfer printing, (C) patterned passivation layers and interconnects, and (D) removal of the device from the PDMS coated substrate and transfer printing onto a releasable, injection microneedle substrate.

Figure 6:
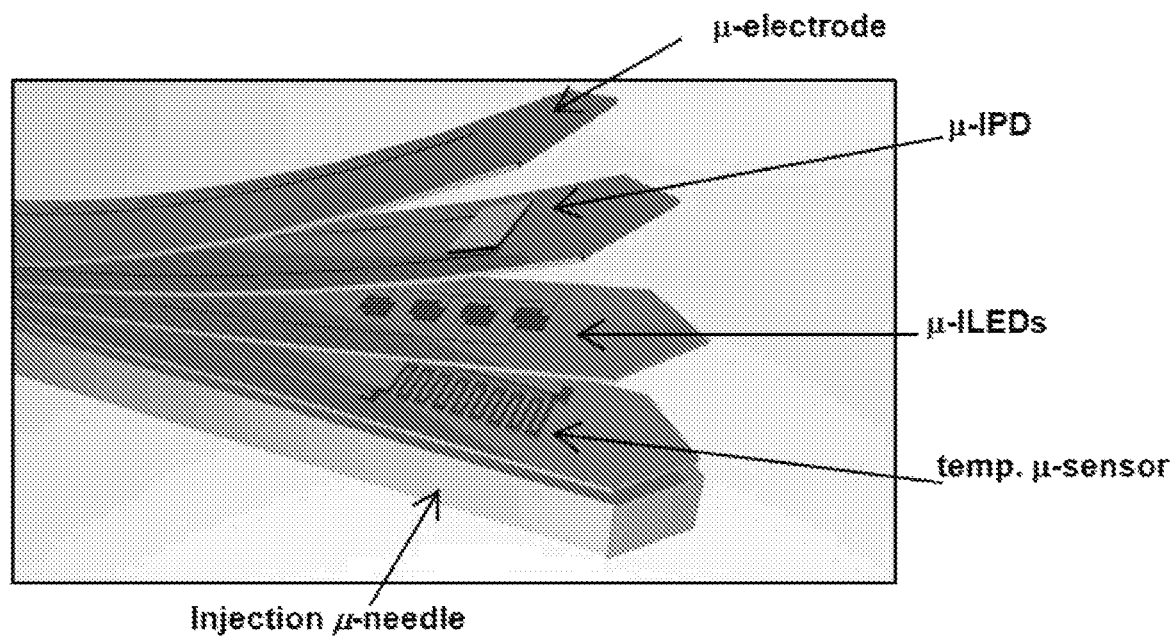

FIG. 6. Schematic illustration of a printed multifunctional μ-ILED system.

Figure 7:
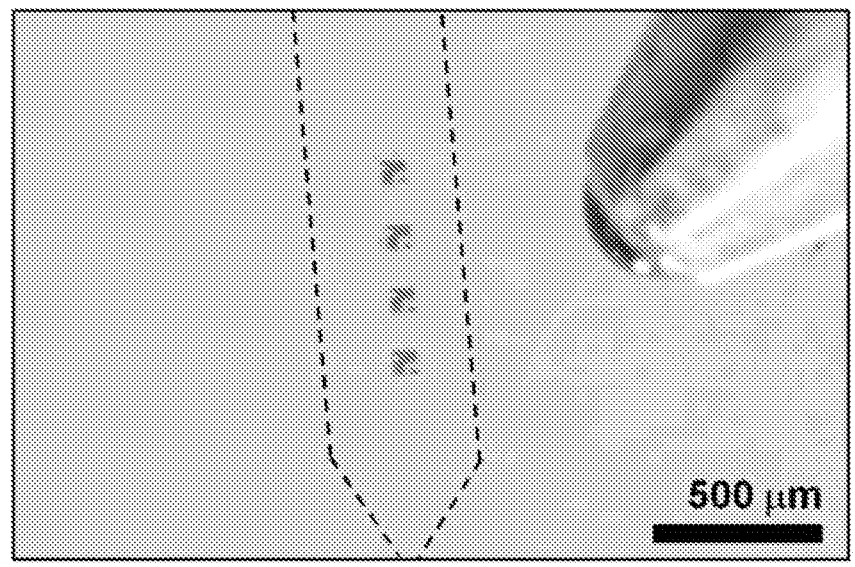

FIG. 7. Photograph of four printed μ-ILEDs next to the tip of a ballpoint pen (right), to set the scale. Each μ-ILED has lateral dimensions of 100×100 μm$^2$, with two 25×25 μm$^2$ metal pads for contacts and an L-shape current spreader.

Figure 8:
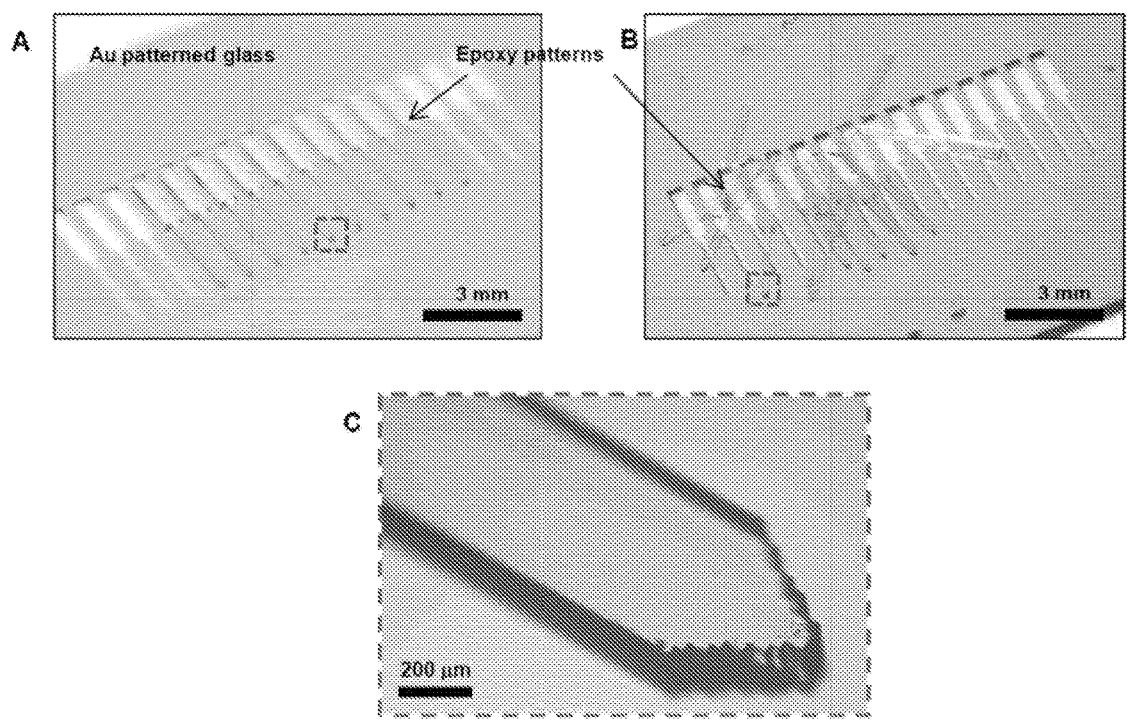

FIG. 8. Images of injection microneedles defined photolithographically using a UV-curable epoxy (250 μm thick, SU-8 100). (A) Photolithographic patterning of epoxy on a prepatterned glass substrate (B) microneedles delaminated by mechanical force from the glass substrate. (C) Tilted optical microscopic image of a single microneedle.

Figure 9:
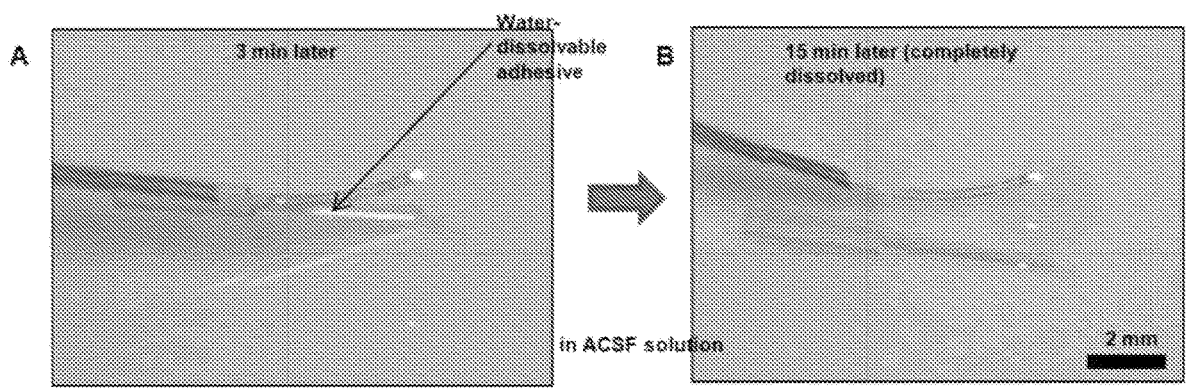

FIG. 9. Demonstration of silk as a water soluble, bioresorbable, releasable adhesive for injection microneedles. (A) Image of a device at the initial stages of silk dissolution, after 3 min and (B) after full dissolution and mechanical separation, after 15 min.

Figure 10:
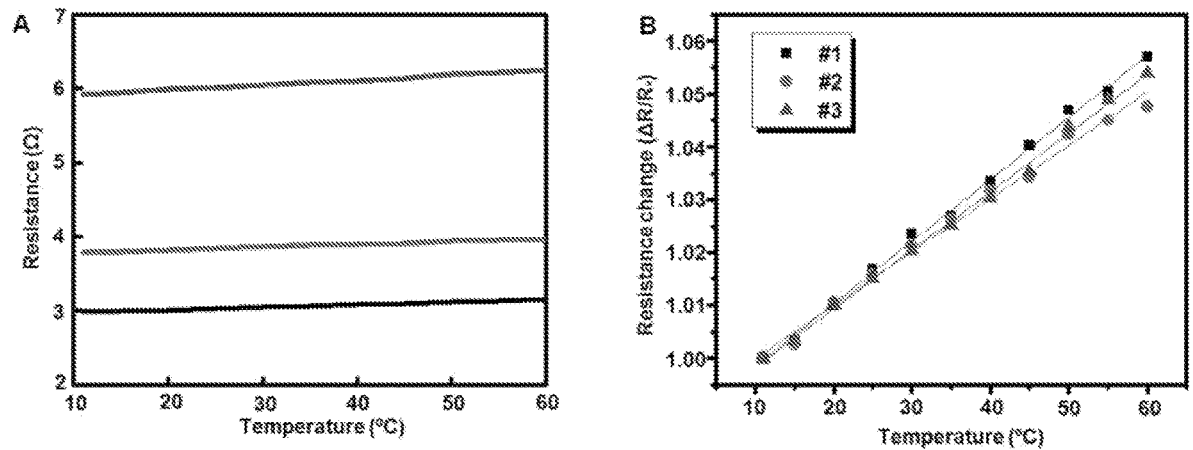

FIG. 10. Relationship between temperature and resistance of temperature sensors. (A) Change in resistance with temperature. (B) Fractional change in resistance as a function of temperature, for three different devices.

Figure 11:
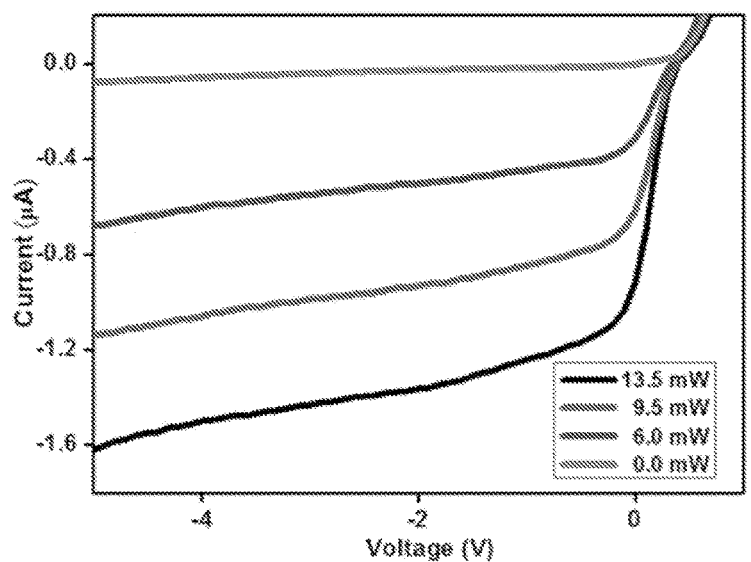

FIG. 11. Current-voltage (I-V) characteristics of a μ-IPD exposed to different light intensities generated by operation of four μ-ILEDs. Electrical DC input powers into the μ-ILEDs were 0, 6.0, 9.5, 13.5 mW.

Figure 12:
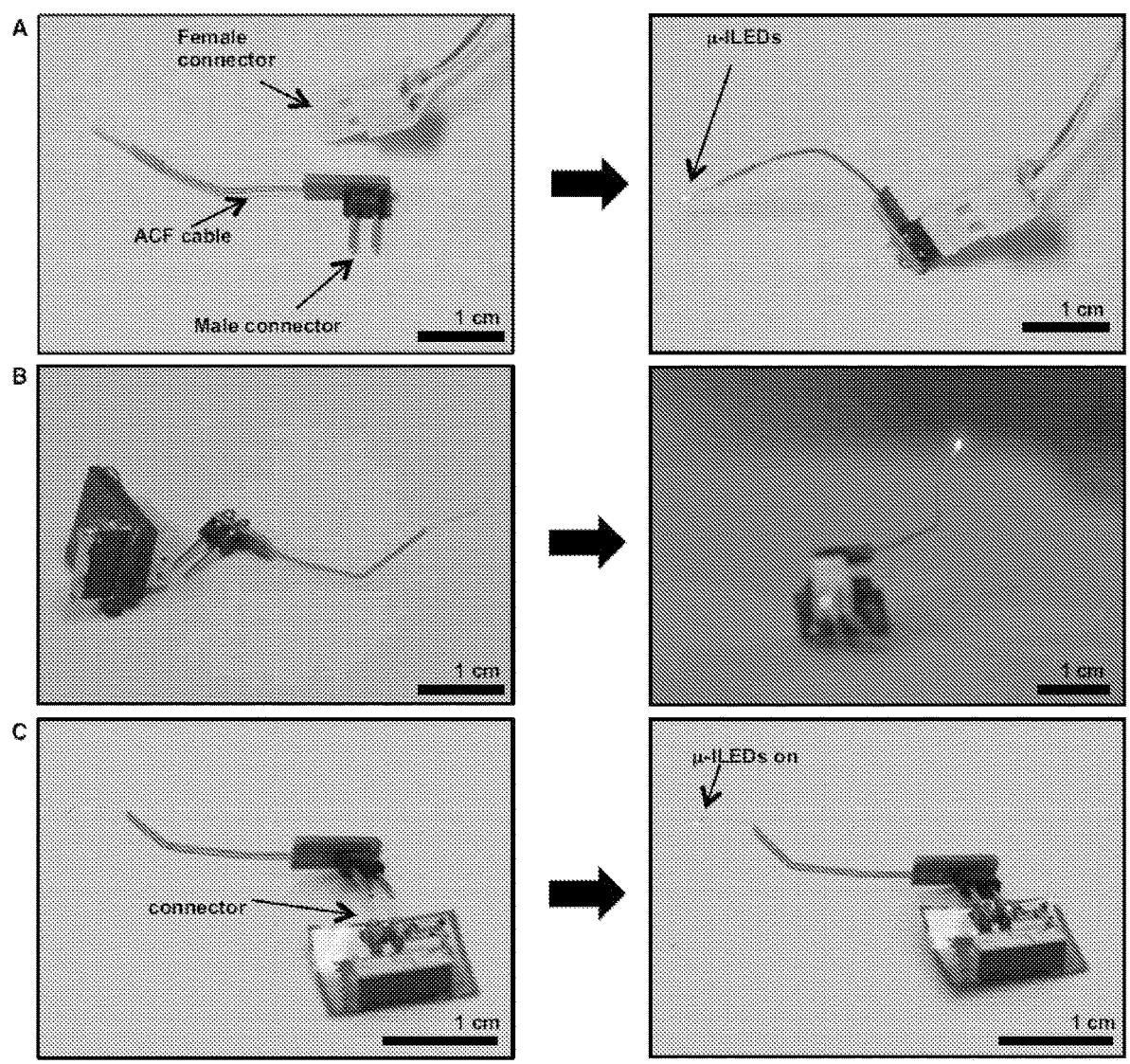

FIG. 12. Images of the plug-in geometry of the connection between power supplies and penetrating μ-ILED systems, for the case of a wired supply (A) and RF wireless units (B and C).

Figure 4:
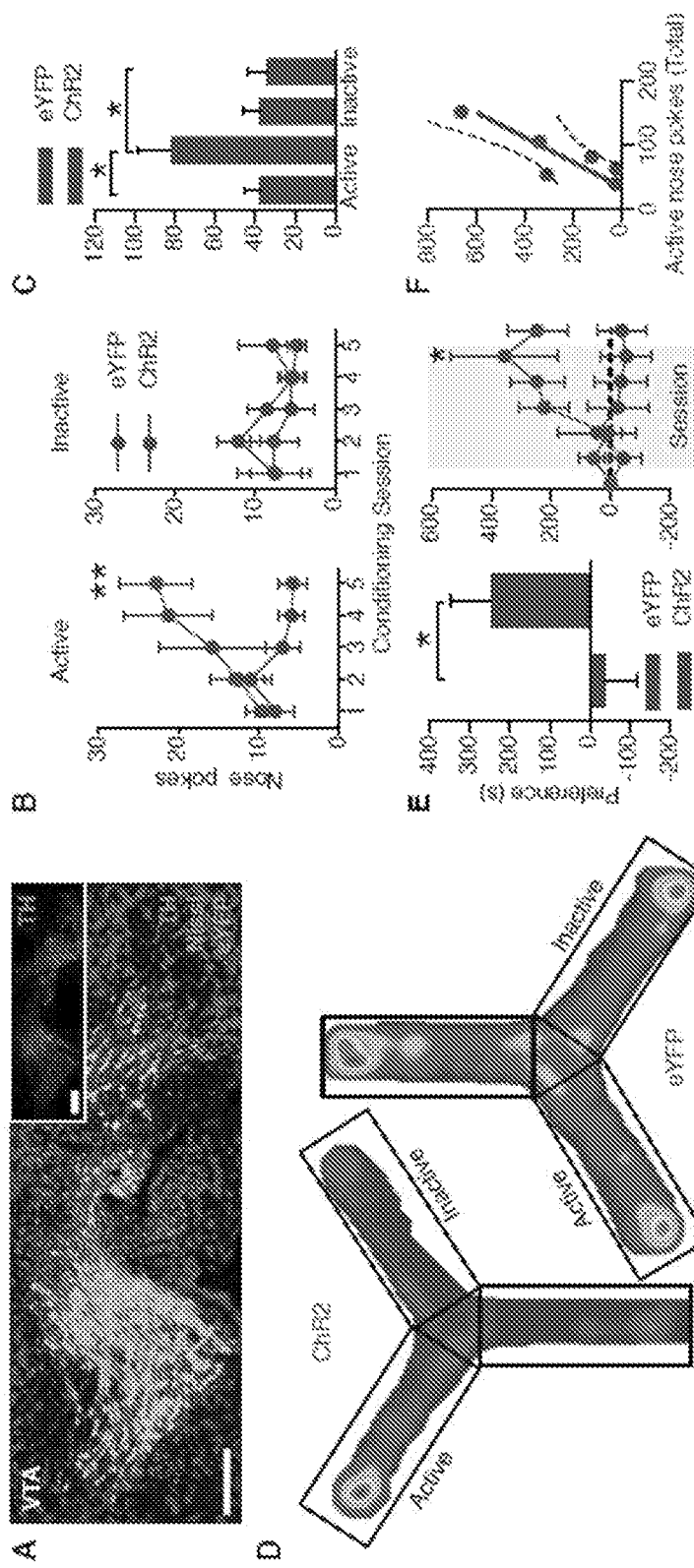
FIG. 4. Wirelessly powered µ-ILED devices operantly drive conditioned place preference. (A) Cell-type specific expression of ChR2(H134)-eYFP (green) in dopaminergic, TH (red) containing neurons of the VTA. For clarity, inset shows TH channel alone. All scale bars=100 µm. (B) Operant learning curve on the active (left) and inactive (right) nose poke devices over 5 days of 1-hour trials in the Y-maze. Active pokes drive 1 s of 20 Hz light (5 ms pulses) from the µ-ILED device on a fixed-ratio-1 schedule (n=6-8 mice/ group; Two-way ANOVA with Bonferroni post-hoc; **p<0.01). (C) Average numbers of nose pokes across all five conditioning sessions. (*p<0.05 t-test compared to controls) (D) Heat maps of activity during the post-test, hotter colors represent longer duration in a location in that part of the apparatus. (E) Left, place preference scores calculated as post-test minus pre-test in the active nose poke-paired context. Five days of self-stimulation significantly conditioned a place preference that developed over the course of the training sessions and remained during the post-test (right; *p<0.05 t-test compared to controls; *p<0.05 Two-way ANOVA with Bonferroni post-hoc). All error bars represent means±SEM (F) Scatter plot demonstrating positive correlation (r=0.8620, p=0.0272) between post-test preference and total number of active nose pokes during training in the ChR2(H134)-eYFP group.
Figure 13:
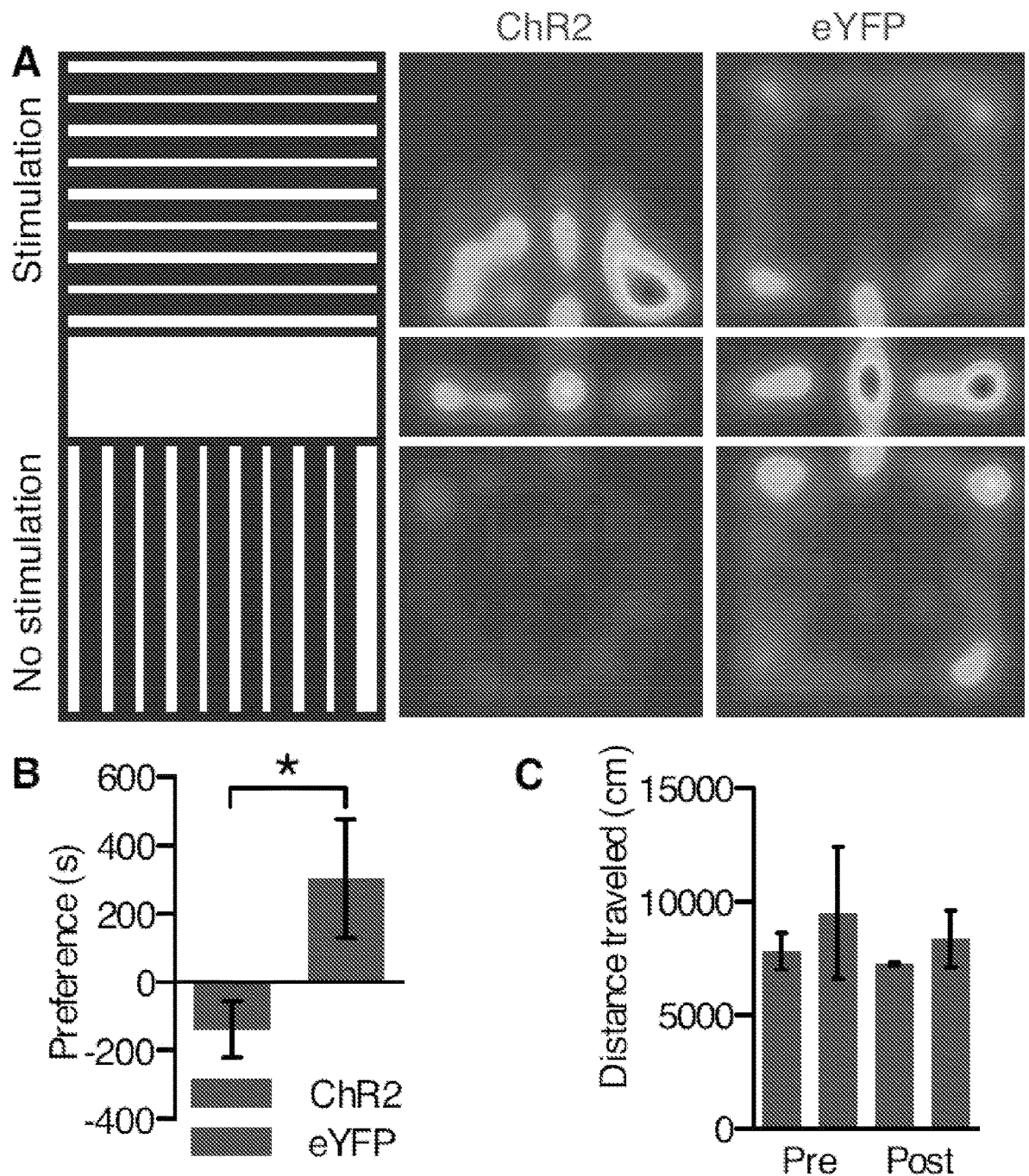

FIG. 13. μ-ILED devices drive a conditioned place preference using standard TTL signals. To demonstrate wired functionality, we selectively targeted ChR2(H134)-eYFP to VTA-DA neurons (FIG. 4A) and tested that phasic activation (20, 5 ms pulses every minute) of cells with a μ-ILED device is sufficient to drive robust place preference behavior without a change in locomotor activity. Animals were conditioned over three days for 30 minutes. μ-ILED devices were powered and controlled using standard function generator (Tektronix, AFG3022B or AMPI, Master-9). (A) Left, Diagram of three-chambered conditioned place preference apparatus. Right, representative heat maps of activity during the post-test, hotter colors represent longer duration at every location in the apparatus. (B) Place preference scores, calculated as post-test minus pre-test on the light stimulation-paired side (n=4-6/group; *p<0.05 t test compared to AAV5-DIO-eYFP controls). (C) Total activity during the pre- and post-tests shows no difference between the two groups. All bars represent means±SEM.

Figure 14:
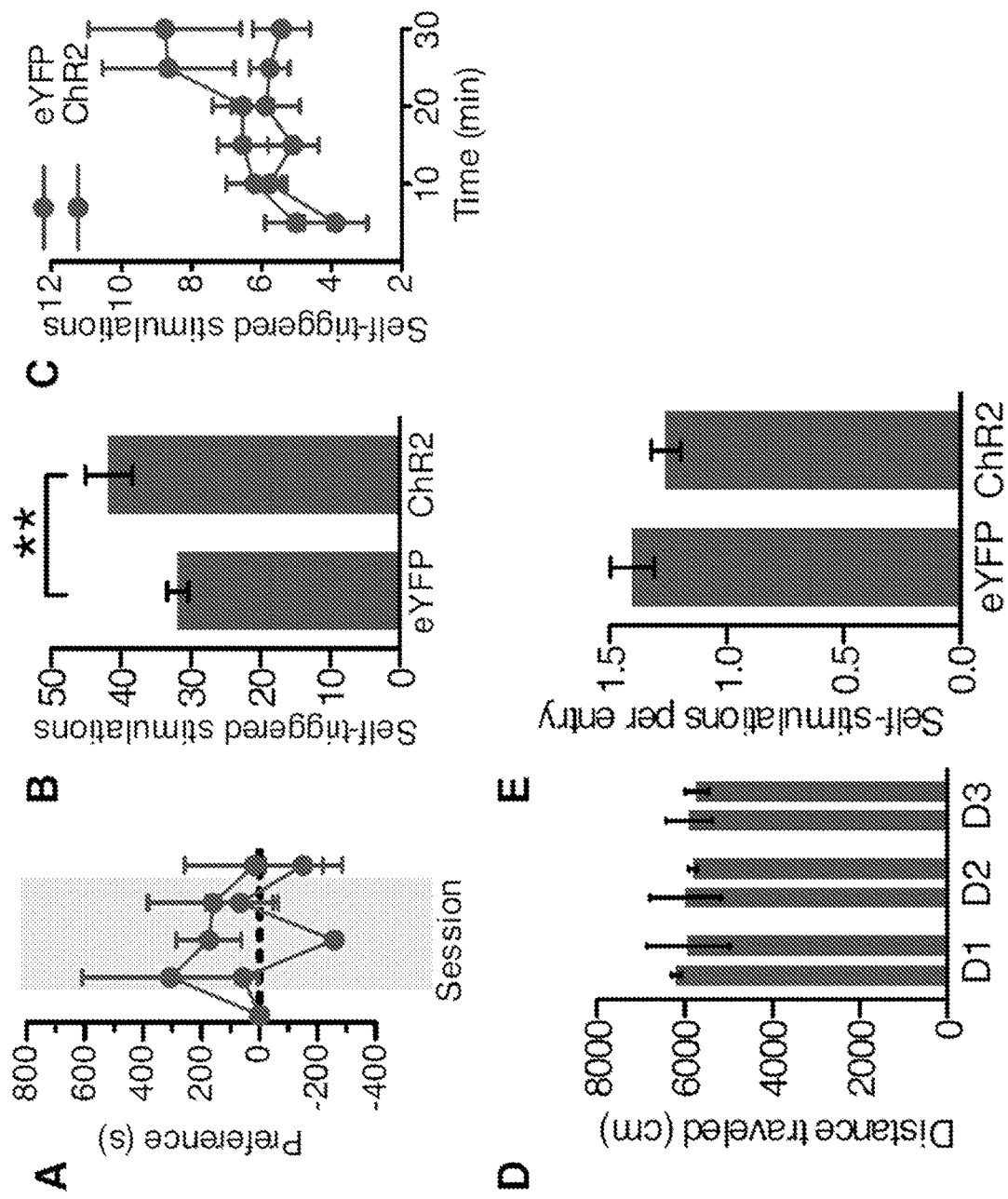

FIG. 14. Real-time assessment of reward seeking or aversion is possible by pairing an animal's behavioral response with self-triggered stimulation or inhibition (S17-S19). Real-time conditioning, animals allowed free access to the apparatus from FIG. 22A learn to selftrigger stimulations when 10, 5 ms pulses at 20 Hz light is delivered contingent on entry into the paired chamber. (A) Animals did not express either a real-time or conditioned place preference under this experimental design. (B) AAV5-DIO-ChR2 mice, however, did have increased numbers of passive, entry-triggered self-stimulations. (C) Passive self-stimulation is learned over the course of each trial. (D) Importantly, this difference is not due to a change in activity between the two groups (n=3/group, **p<0.01 t test compared to AAV5-DIO-eYFP controls). (E) Animals could receive subsequent stimulations if they remained in the stimulus-paired chamber for 60 seconds. ChR2 mice did not learn to remain in the chamber for these subsequent stimulations.

Figure 15:
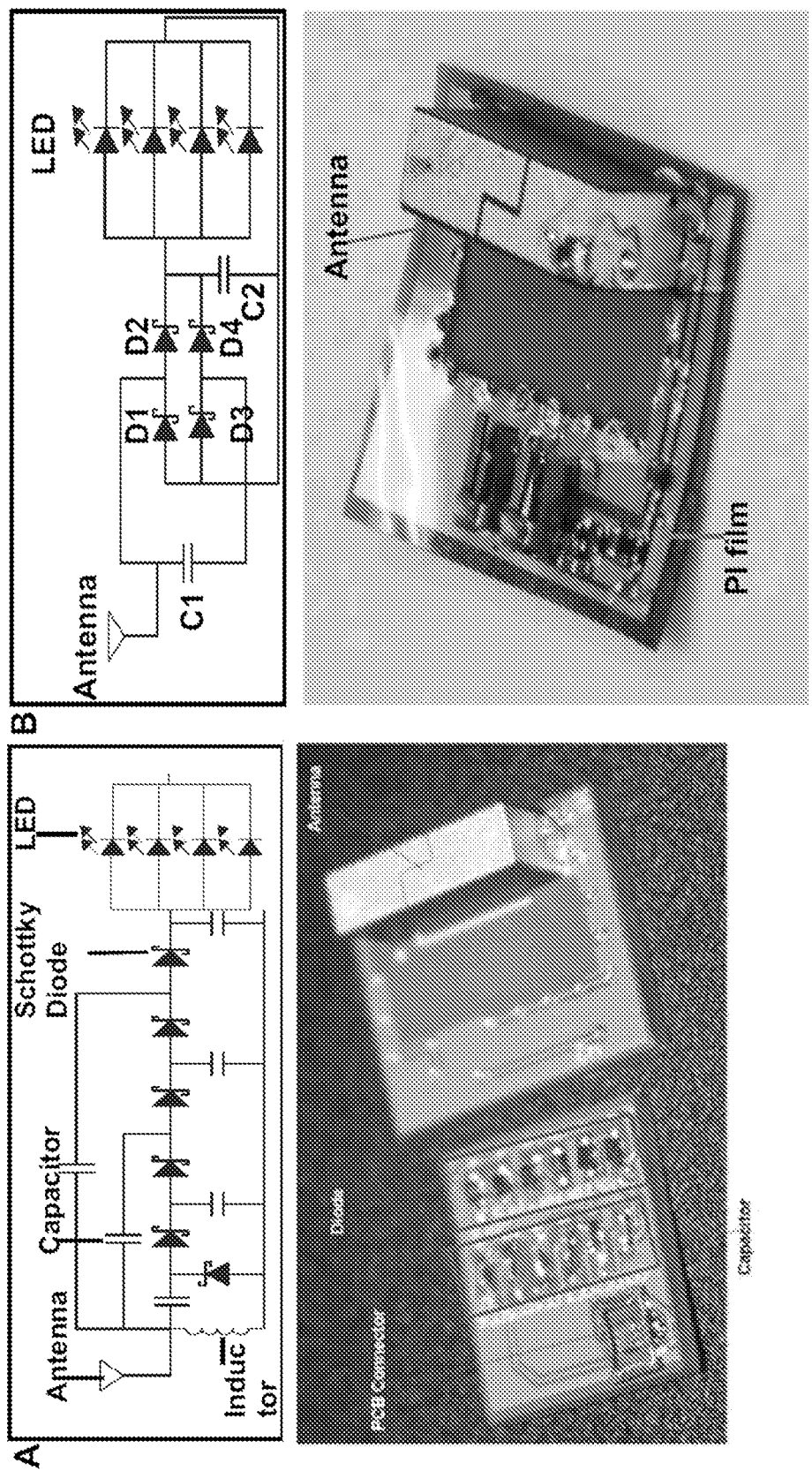

FIG. 15. Circuit diagrams for each RF powering scavenger and pictures of RF powering scavenger (left) and RF antenna (right), in a miniaturized PCB layout (A) and on polyimide film (B). The RF power scavenger contains a RF antenna that works at 910 MHz, an impedance matching inductor, a voltage multiplexer with cascaded combination of Schottky diodes and capacitors, and blue LEDs. The circuit of the RF power scavenger for (A) is on two stacked PCB boards that are connected with each other by a PCB connector. For RF power scavenger for (B), Au pre-patterned PI film supports all of components connected by silver epoxy.

Figure 16:
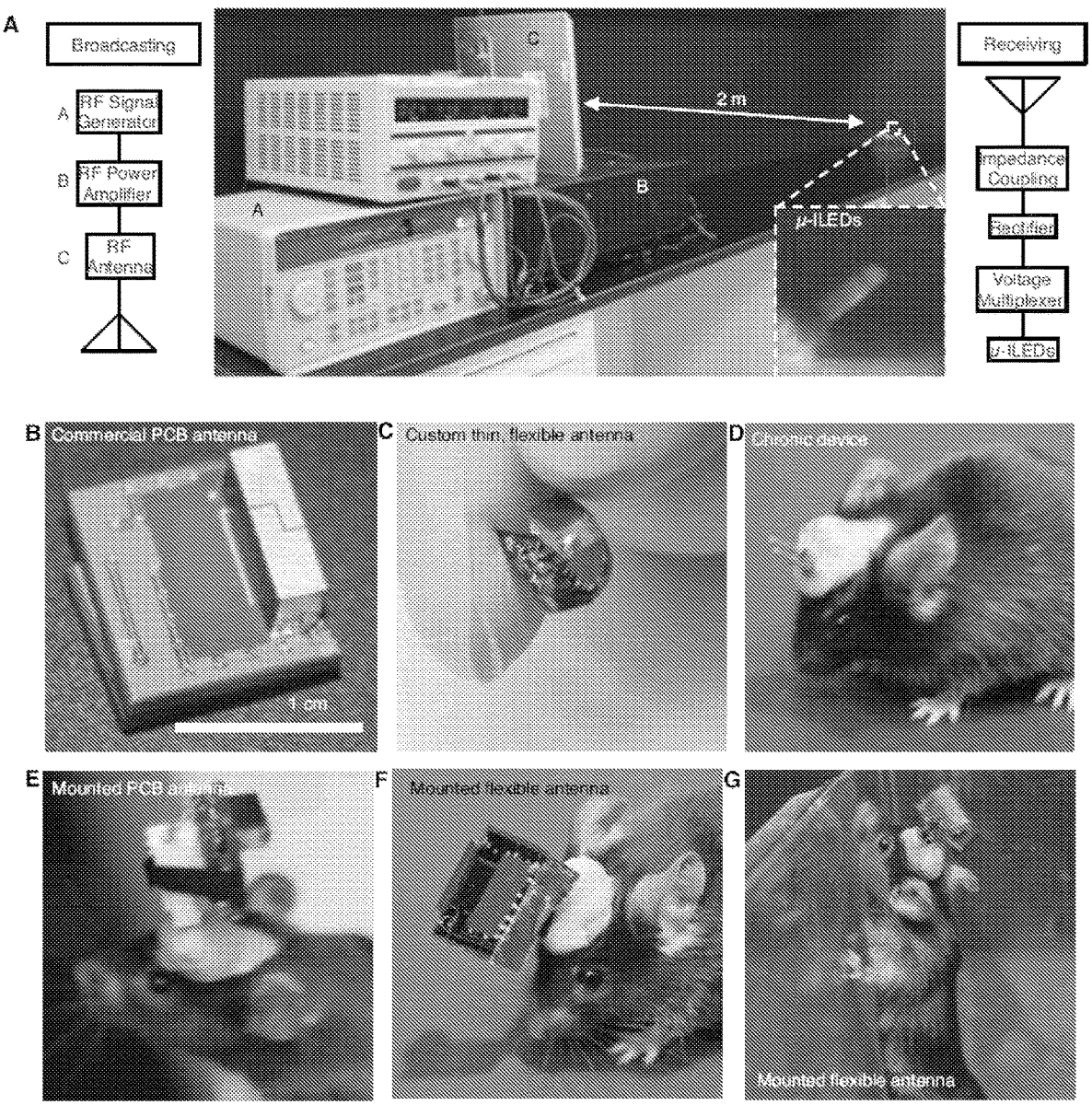

FIG. 16. Key components for wireless operation using RF power delivery. (A) Photo and diagram explaining the components of the system and demonstrating wireless power. Headstage antennas on PCB board (B) and on bent PI (C). (D) A mouse with a chronically implanted device. The nature of the interconnect allows for temporary coupling to either form of headstage antenna or a wired power source. (E,F,G) Mice with acutely mounted headstage antennas.

Figure 17:
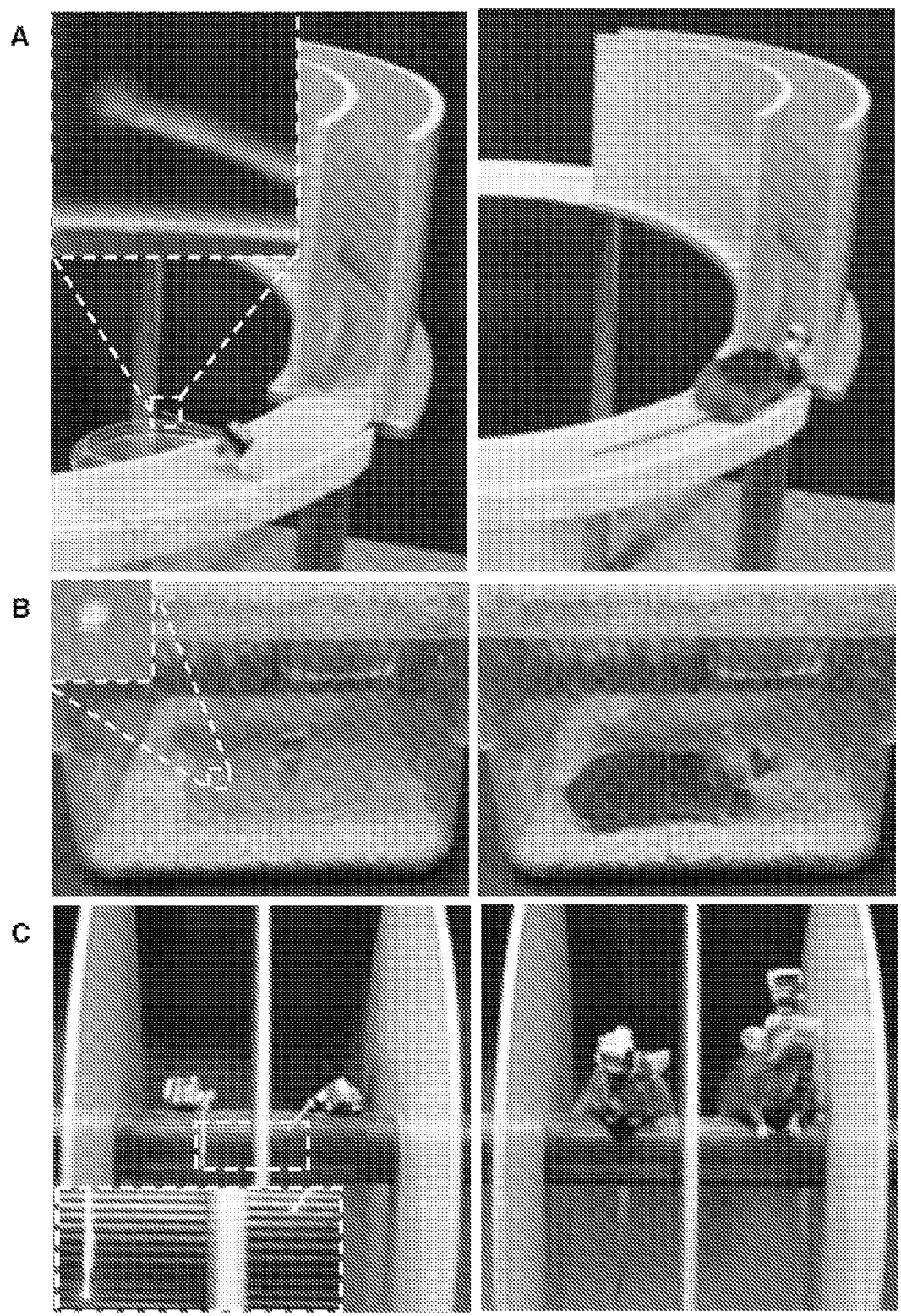

FIG. 17. Demonstration of wireless capabilities. For all panels the same environment is shown with wireless lit μ-ILEDs (left) and wirelessly stimulated mice (right). (A) Wireless mice can explore circular environments with no need for commutators or adaptations to the behavioral apparatus. (B) RF modulation can be used to power devices through covered arenas as seen here with a mouse in a traditional homecage environment. (C) Multiple wireless devices can be controlled using a single antenna. Here, two implanted mice receive identical optical stimulation simultaneously on a standard rotarod—a rotating wheel that provides numerous barriers for use with tethered animals.

Figure 18:
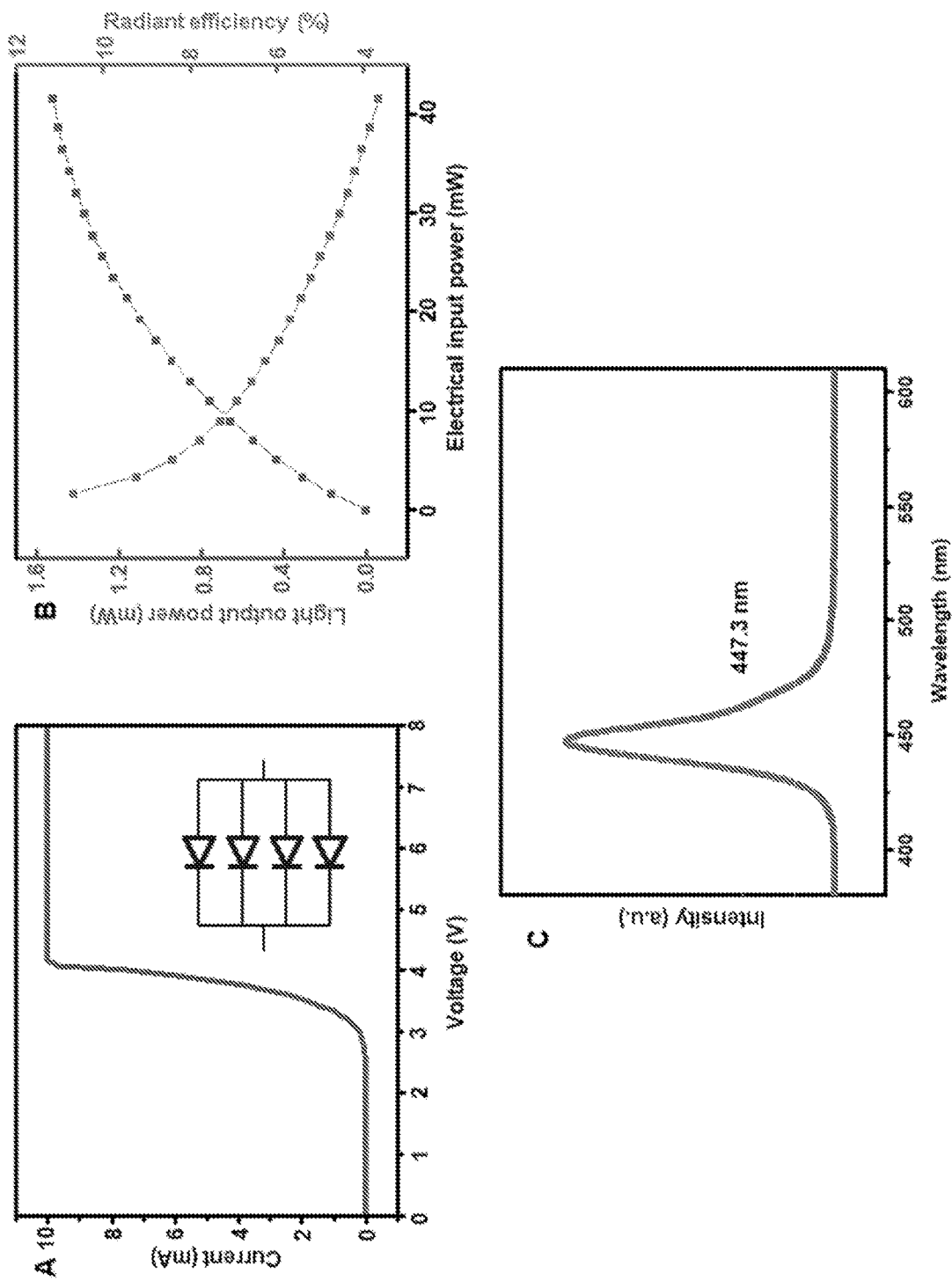

FIG. 18. Electrical and optical properties of an array of four μ-ILEDs connected in parallel. (A) Current-Voltage (I-V) characteristics, (B) light output power and radiant efficiency as a function of electrical input power, and (C) light emission intensity as a function of wavelength.

Figure 19:
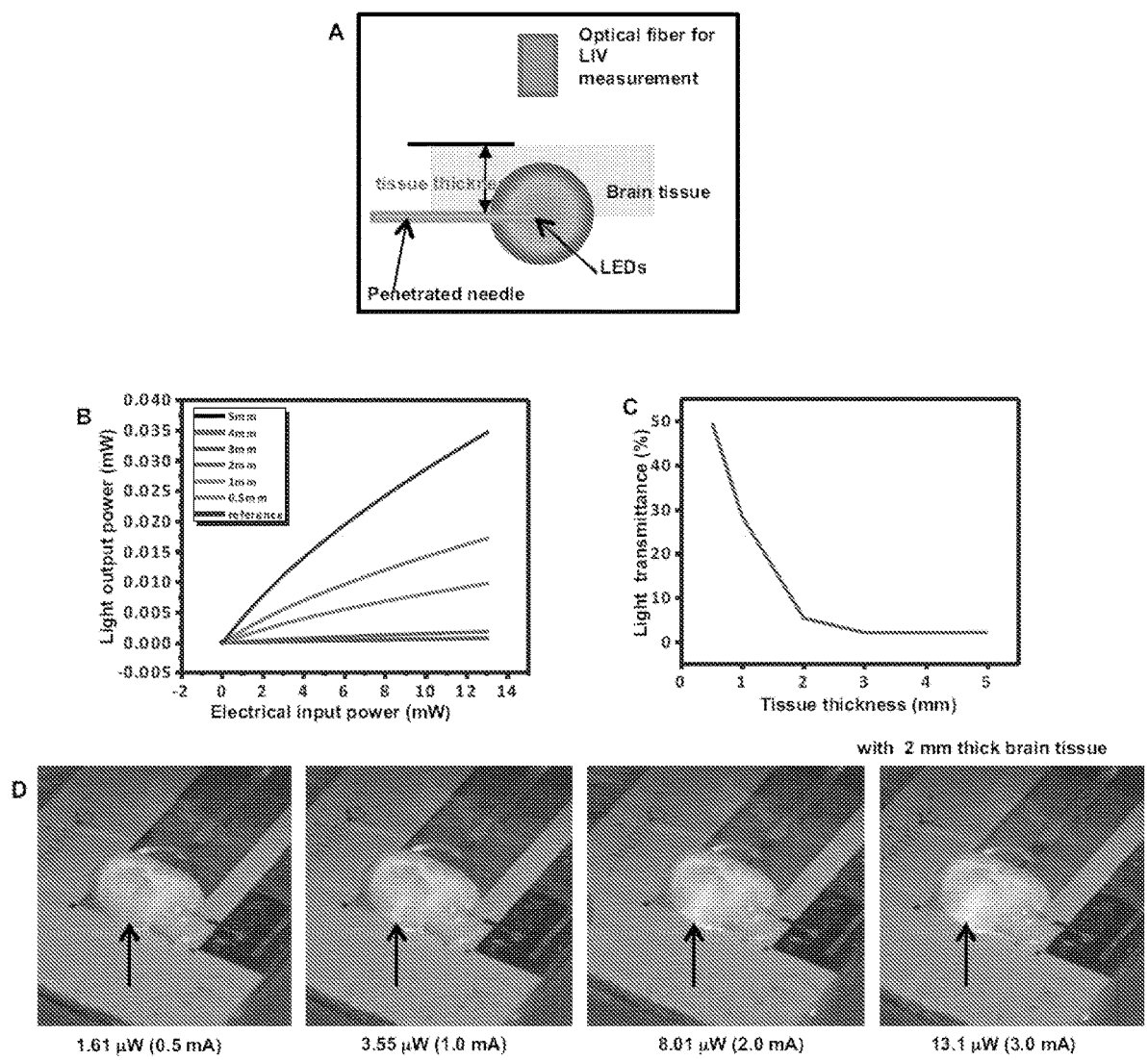

FIG. 19. Information related to tests of light penetration depth. (A) Schematic illustration of the experimental scheme, (B) light output-current and voltage (LIV) results collected using slabs of brain tissue with various thicknesses (0.5, 1, 2, 3, 4, 5 mm) and (C) their light transmission through the thickness of the tissue. (D) Light extraction through 2 mm thick slabs of brain tissue at various applied powers.

Figure 20:
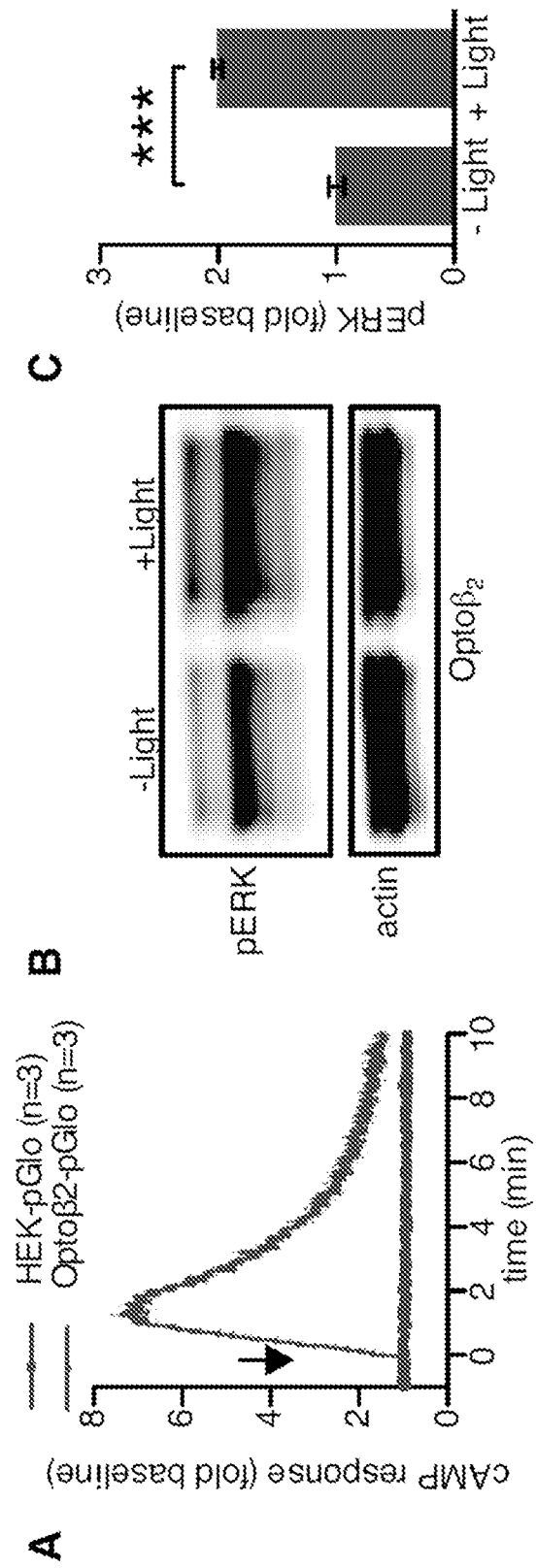

FIG. 20. μ-ILED-induced activation of cAMP and ERK phosphorylation in Optoβ$_2$ expressing cells. (A) Optoβ$_2$ cells co-expressing pGlo show a rapid and transient increase in cAMP following light (450 nm, 5 sec, 0.5 W/cm$^2$ pulse) stimulation (n=3). HEK293 cells expressing pGlo show no response to the same light stimulation (n=3). Data are expressed as mean±sem. (B). Representative pERK and actin Western Blots for Optoβ$_2$ and HEK293 cells following light (450 nm, 1 min, 0.5 W/cm$^2$ pulse) stimulation (n=3). (C). Quantitation of pERK normalized to actin in light stimulated Optoβ$_2$ and HEK293 cells. (*p<0.05, unpaired, two-tailed t-test).

Figure 21:
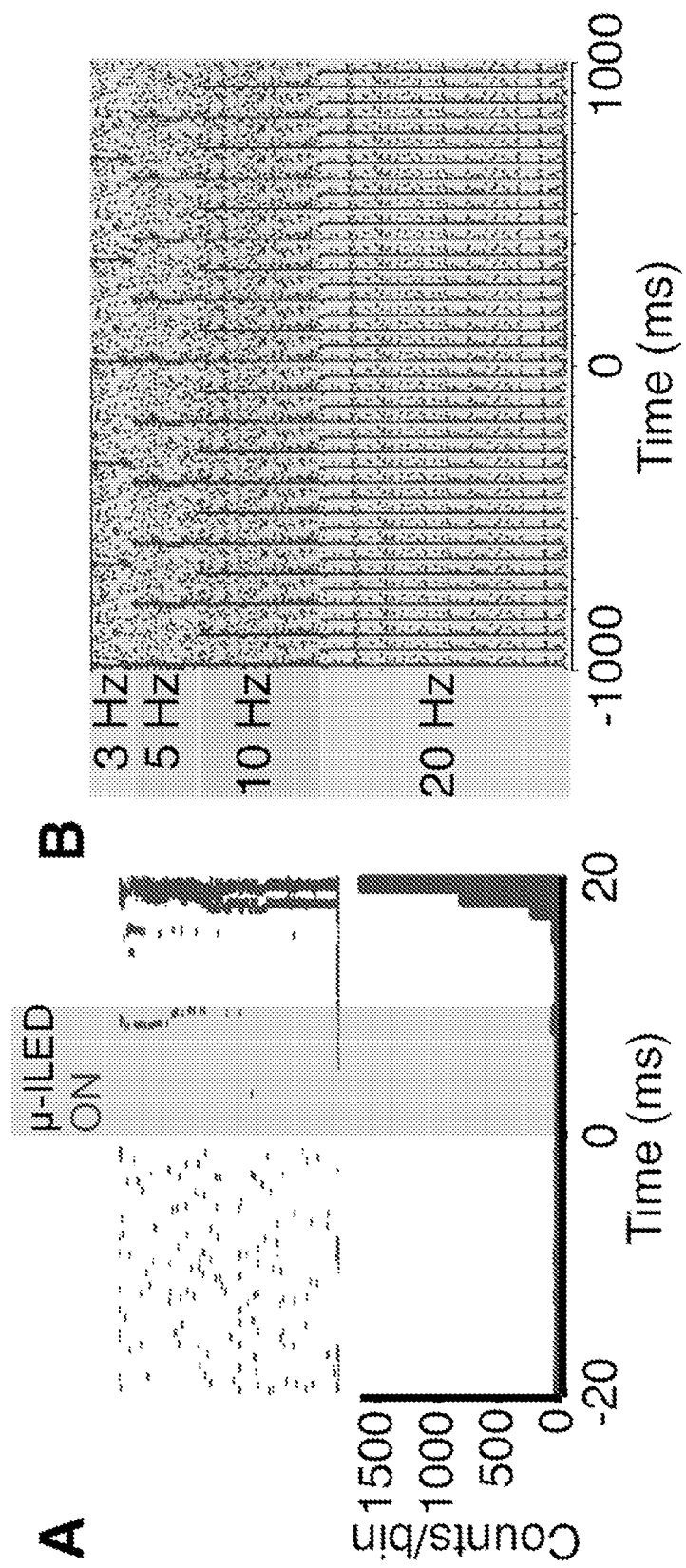

FIG. 21. μ-ILED-induced modulation of in vivo neuronal activity in the VTA via ChR2(H134)-eYFP expressing neurons. (A) Representative peri-light raster plot and histogram demonstrating increased cell firing within 20 ms of onset of a 450 nm, 0.5 W/cm$^2$ light pulse. (B) Raster plot showing activity from the same neuron (A) time locking with various frequencies of light delivery. Each light pulse is centered at 0 ms, the effects of prior and subsequent pulses are apparent in each line of the 2000 ms raster plot.

Figure 22:
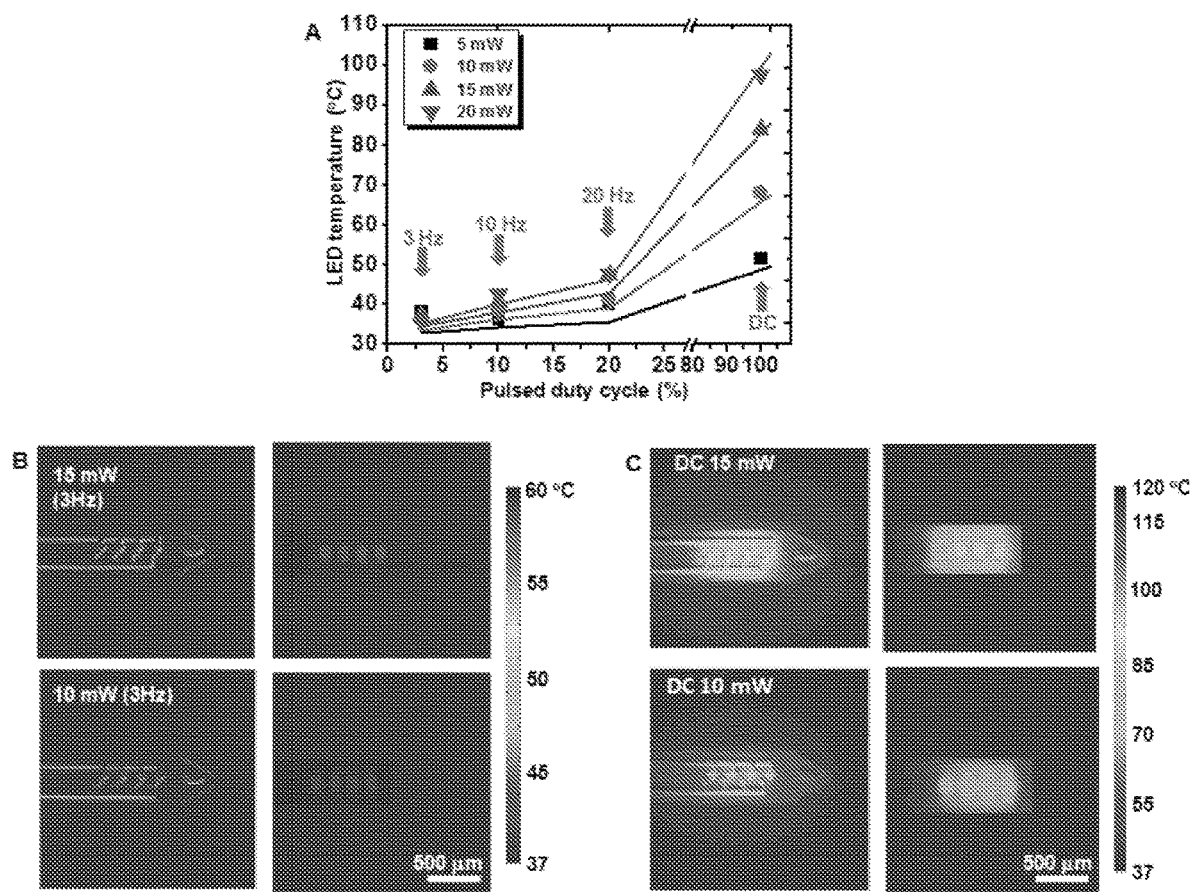

FIG. 22. Surface temperature of μ-LEDs on an injection microneedle, during operation at various power levels in open air. (A) Measured (dots) and calculated (lines) temperatures of μ-ILEDs at various pulse duty cycles and at DC power levels. All calculated temperatures (lines) are obtained by time-average results at 37° C. background temperature. The duration time (width) for all pulsed cases is 10 msec. (B) Measured (left) and calculated (right) temperatures at 15 and 10 mW applied power. The measured (calculated) temperatures are 37.44 (39.31) and 36.15 (38.54) ° C., respectively, with a 3 Hz pulse. (C) Measured (left) and calculated (right) temperature at 15 and 10 mW DC applied power. The measured temperatures (calculated) are 84.01 (86.95) and 86.31 (70.30) ° C., respectively, with a 3 Hz pulse.

Figure 23:
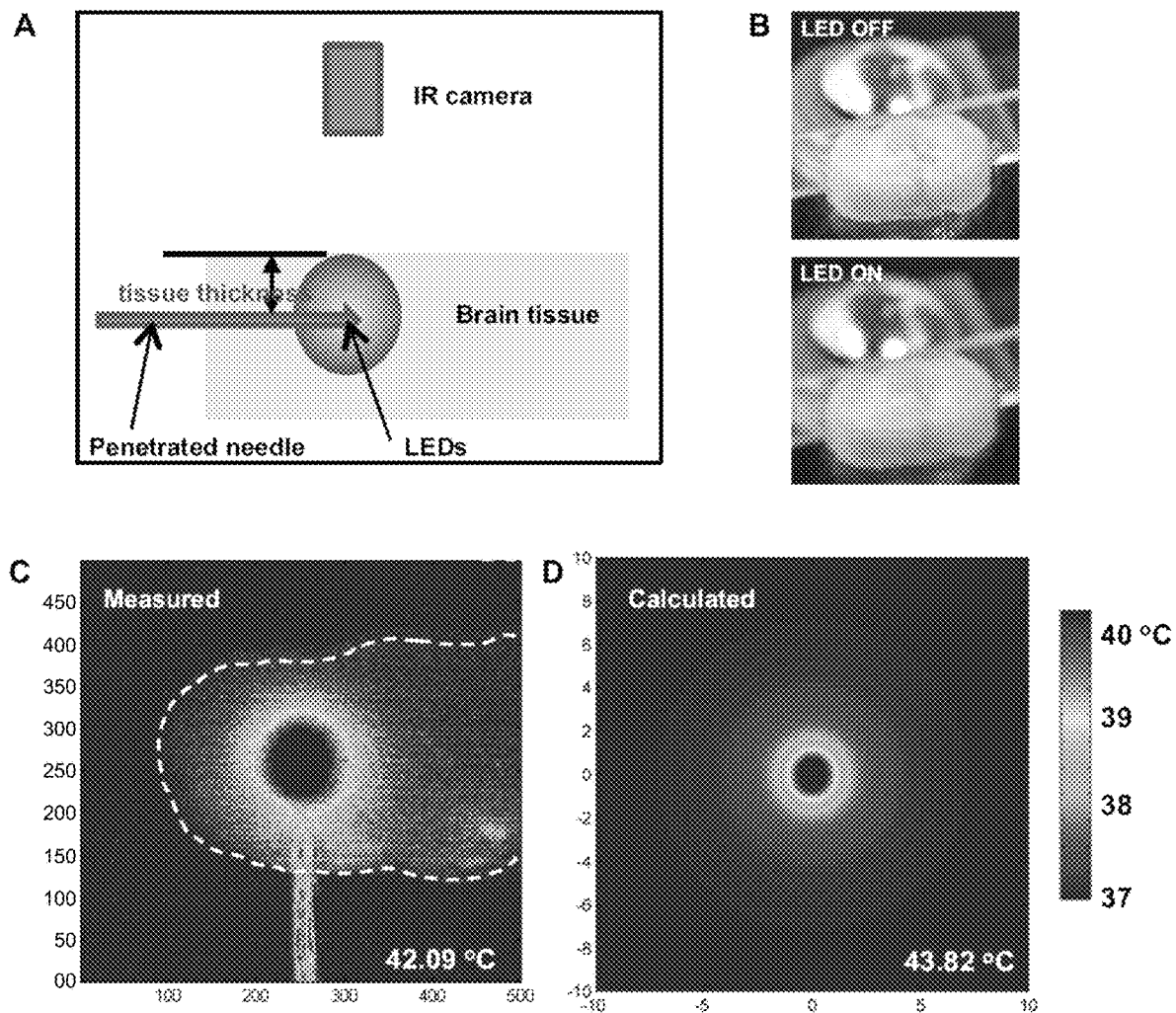

FIG. 23. Thermal imaging with a calibrated IR camera. (A) Schematic illustration and (B) pictures of the IR camera stage and μ-ILED devices injected in brain tissue. (C) Measured and (D) calculated tissue temperature with μ-ILEDs injected into a 0.3 mm thick slab of tissue, evaluated at the surface for the case of 10 mW DC input power. Measured and calculated temperatures are 42.09 and 43.82° C., respectively.

Figure 24:
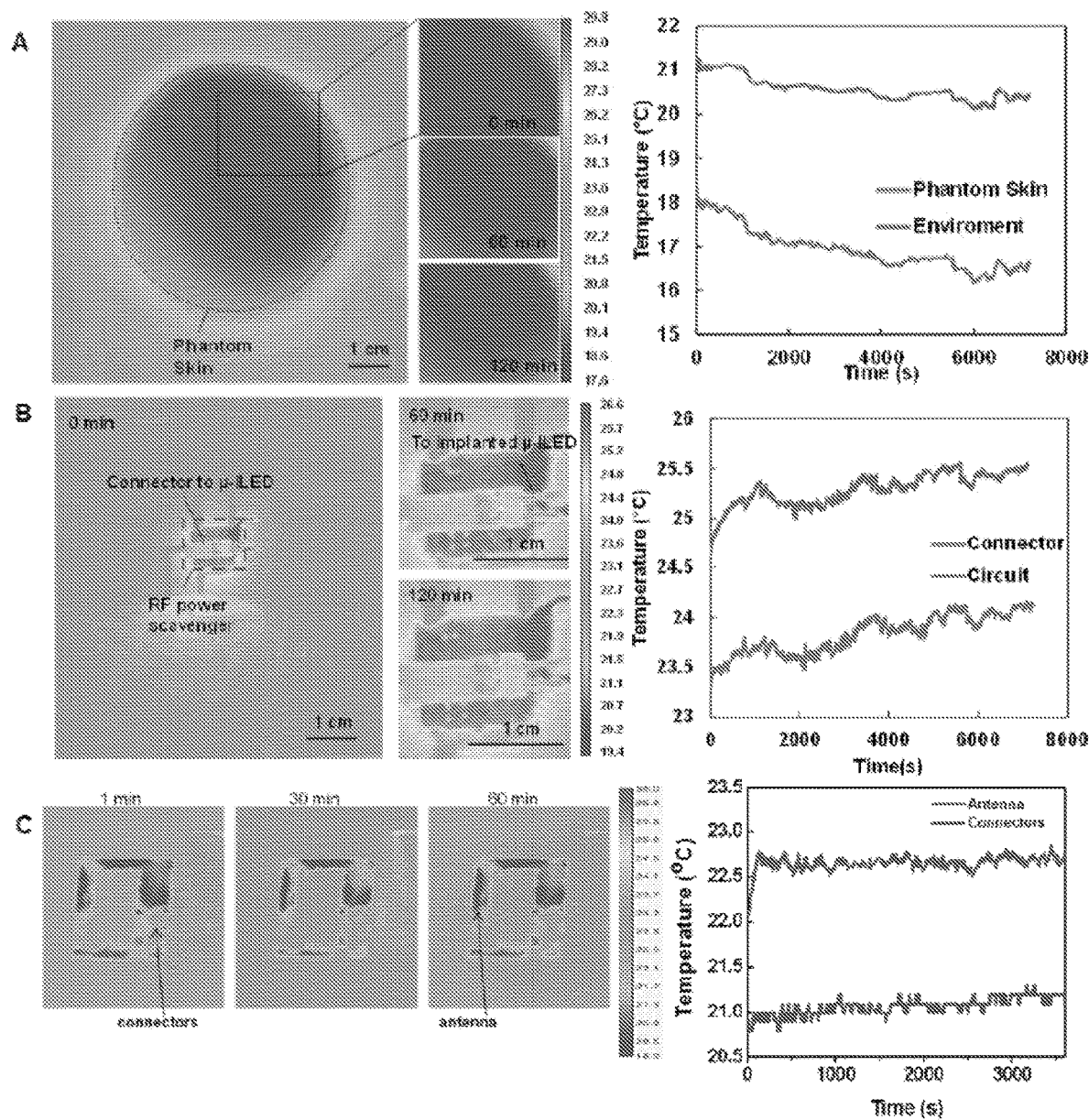

FIG. 24. IR images (left) and extracted average temperatures (right) of a phantom skin sample and the surrounding environment during prolonged exposure to RF radiation, starting at time=0 s. The results indicate no observable effects of heating due to RF. (A) The temperature variations in the phantom skin are small, and mostly due to variations in the environment, without any observable effect, even under constant RF power. (B) IR images (left) of a RF power scavenger circuit during exposure to constant RF radiation for various times. The images show changes in temperature when RF power is applied, and the μ-ILEDs are turned on, for 0 (left), 60 (right, top), and 120 (right, bottom) min. Spatially averaged changes in temperature (right) of the RF power scavenger circuit and connector during prolonged exposure to constant RF radiation, starting at time=0 s. The temperature change is less than 0.5° C. during this 2 hr period. (C) IR images (left) of a thin, lightweight flexible RF power scavenger circuit during exposure to pulsed (10 Hz) RF radiation for various times: 1 (left), 30 (middle), and 60 (right) min. There is no temperature change (right) in the thin, lightweight flexible RF power scavengers (near the antenna and the connectors) during prolonged exposure to pulsed RF radiation at 10 Hz.

Figure 25:
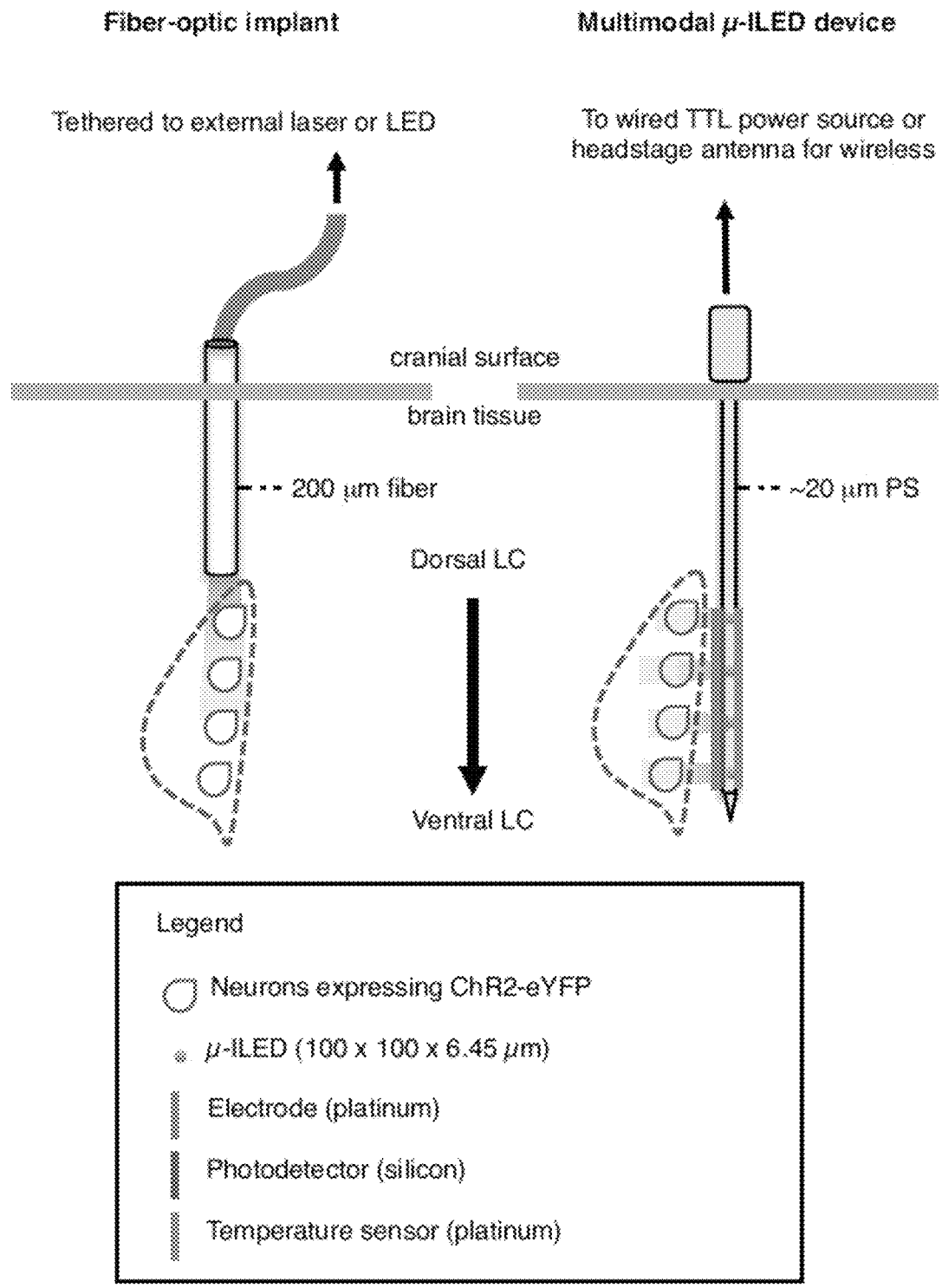

FIG. 25. Summary depicting the experimental strategy used in FIGS. 3B and 3C. μ-ILED devices allow for unique spatial targeting of brain structures (here the locus coeruleus) to provide consistent illumination along the entire dorsal-ventral plane of the structure.

Figure 26:

FIG. 26. The durability of the devices and the constituent component following chronic implantation. (A) Survival curve showing viability of μ-ILEDs, fully passivated sensors (temperature and μ-IPD), and animals following device injection. μ-ILEDs were considered viable if the all μ-ILEDs in each array were still emitting sufficient light to activated ChR2. Sensors were considered viable if performance was within 1% of original performance. Components performed reliably within the two-three week timespan of a normal behavioral experiment and often well beyond that range. Detailed information on each point of attrition or censorship is available in the Table below. (B) The μ-ILED devices are robust and capable of functioning properly months after implantation. Working devices one (top), three (center), and six (bottom) months after chronic implantation into freely moving mice.

Figure 27:
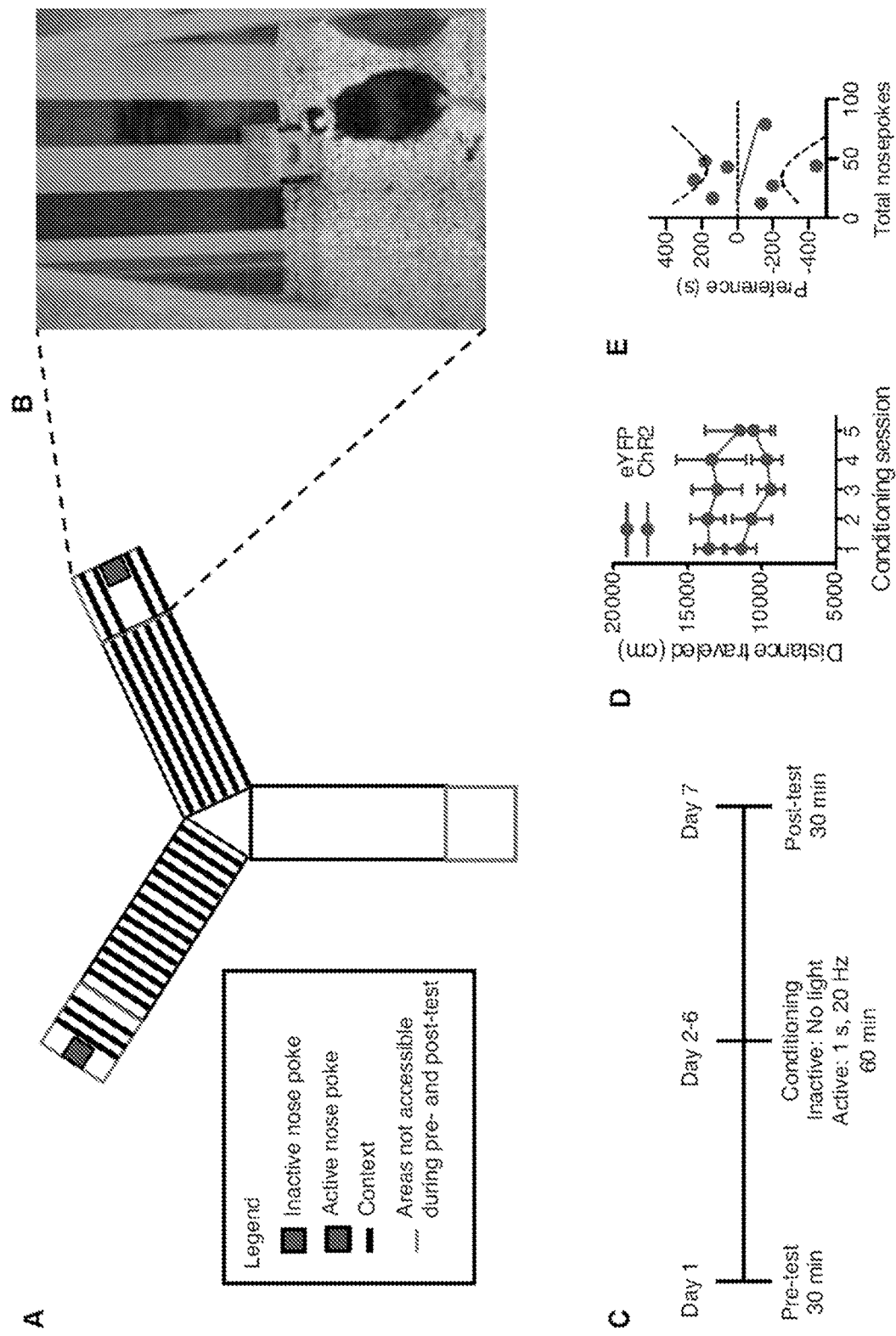

FIG. 27. Wireless μ-ILED devices drive an operantly conditioned place preference. (A) Schematic and (B) photo of Y-Maze with contexts and nose poke devices, red zones were not accessible during pre/post-tests. (C) Timeline of experimental approach. (D) Total activity during the conditioning shows increase in total ambulation of the ChR2 mice during the first four days of training. (E) Scatter plot demonstrating no correlation (r=−0.1707, p=0.6861) between post-test preference and total number of active nose pokes during training in the AAV-DIO-eYFP injected controls.

Figure 28:
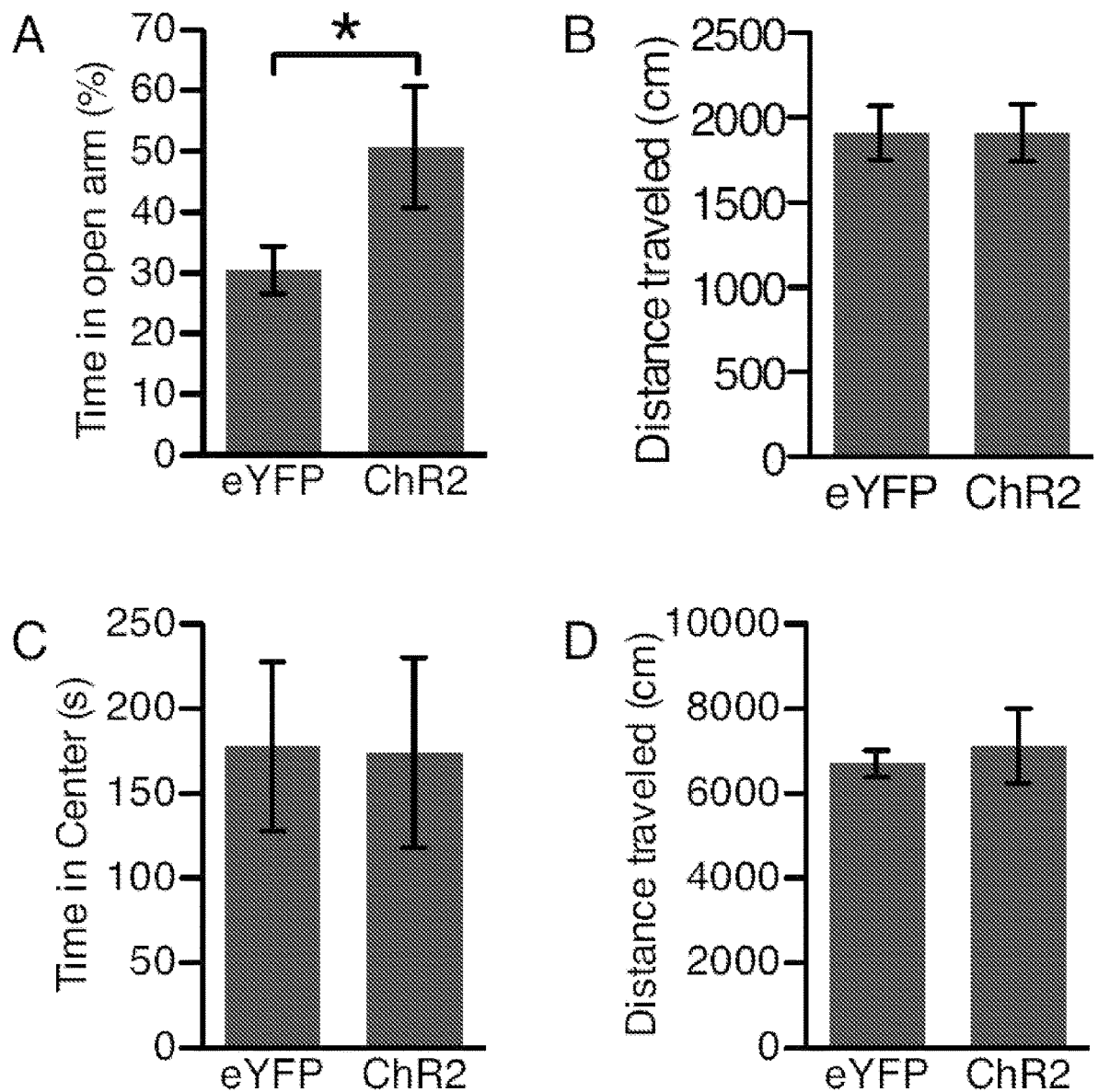

FIG. 28. Tonic, not phasic, activation of VTA-DA neurons induces anxiolytic-like behavior. (A) 5 Hz activation of VTA-DA neurons induces an anxiolytic-like behavioral response in an elevated zero maze independent of (B) locomotor effects (n=6-9; *p<0.05 t test compared to AAV5-DIO-eYFP controls). (C) Phasic (20, 5 ms pulses of 20 Hz light every minute) stimulation does not influence anxiety-like behavior or (D) locomotor activity in the open field test (n=6-8/group).

FIG. 29 is a schematic illustration of a functional layer having a plurality of functional electronic devices from device components supported on a substrate. A is a top view. B is a side view (not to scale) to illustrate thickness definitions.

FIG. 30 is a schematic illustration of an implantable biomedical device that can be injected into target tissue. A shows a stacked configuration of a plurality of functional layers on a delivery substrate. B shows a removable adhesive layer positioned between the delivery substrate and the functional layers which can be used to release the functional layers and remove the delivery substrate from the tissue.

Figure 31:
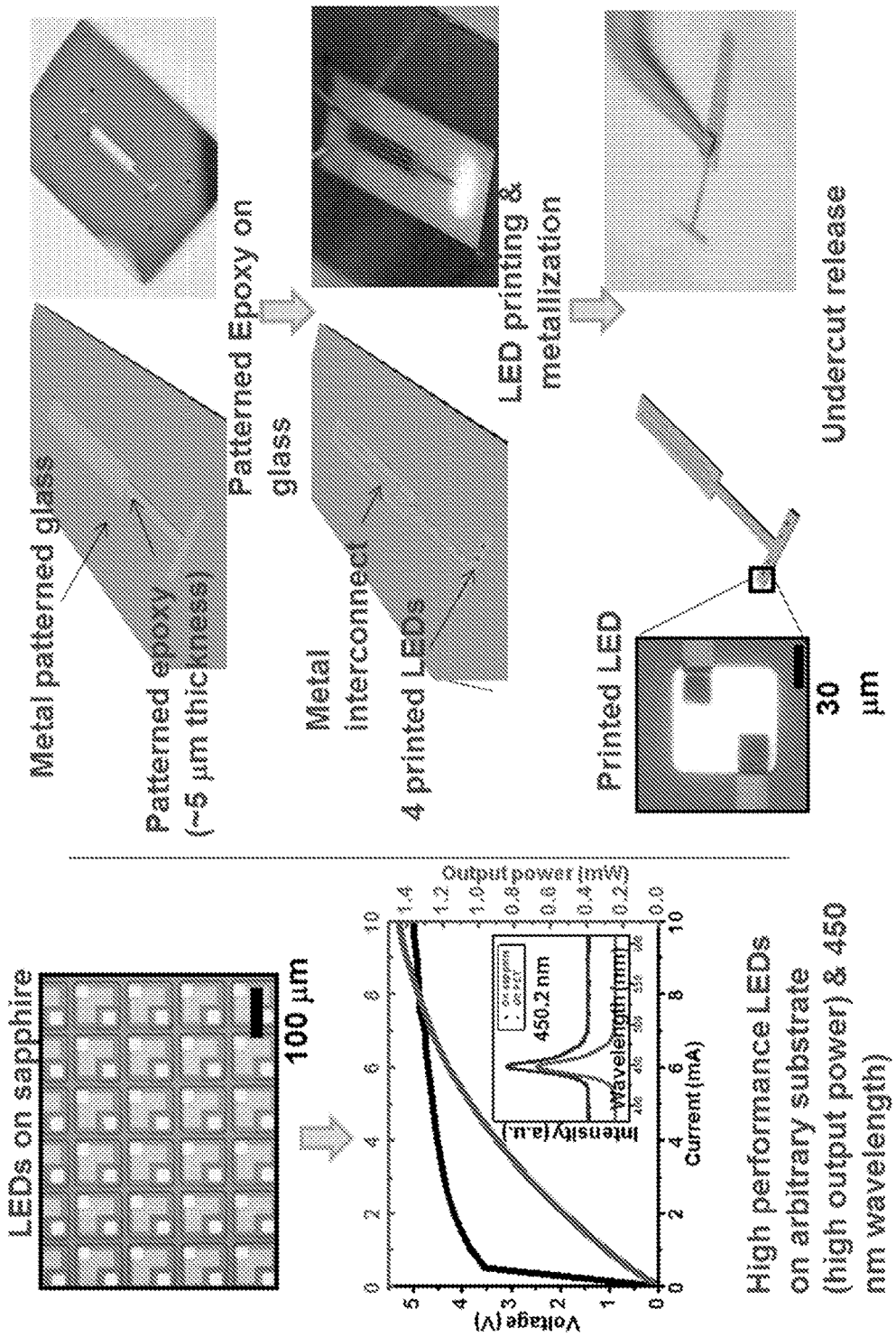

FIG. 31. Implantable device having printed LEDs useful for optogenetic applications.

Figure 32:
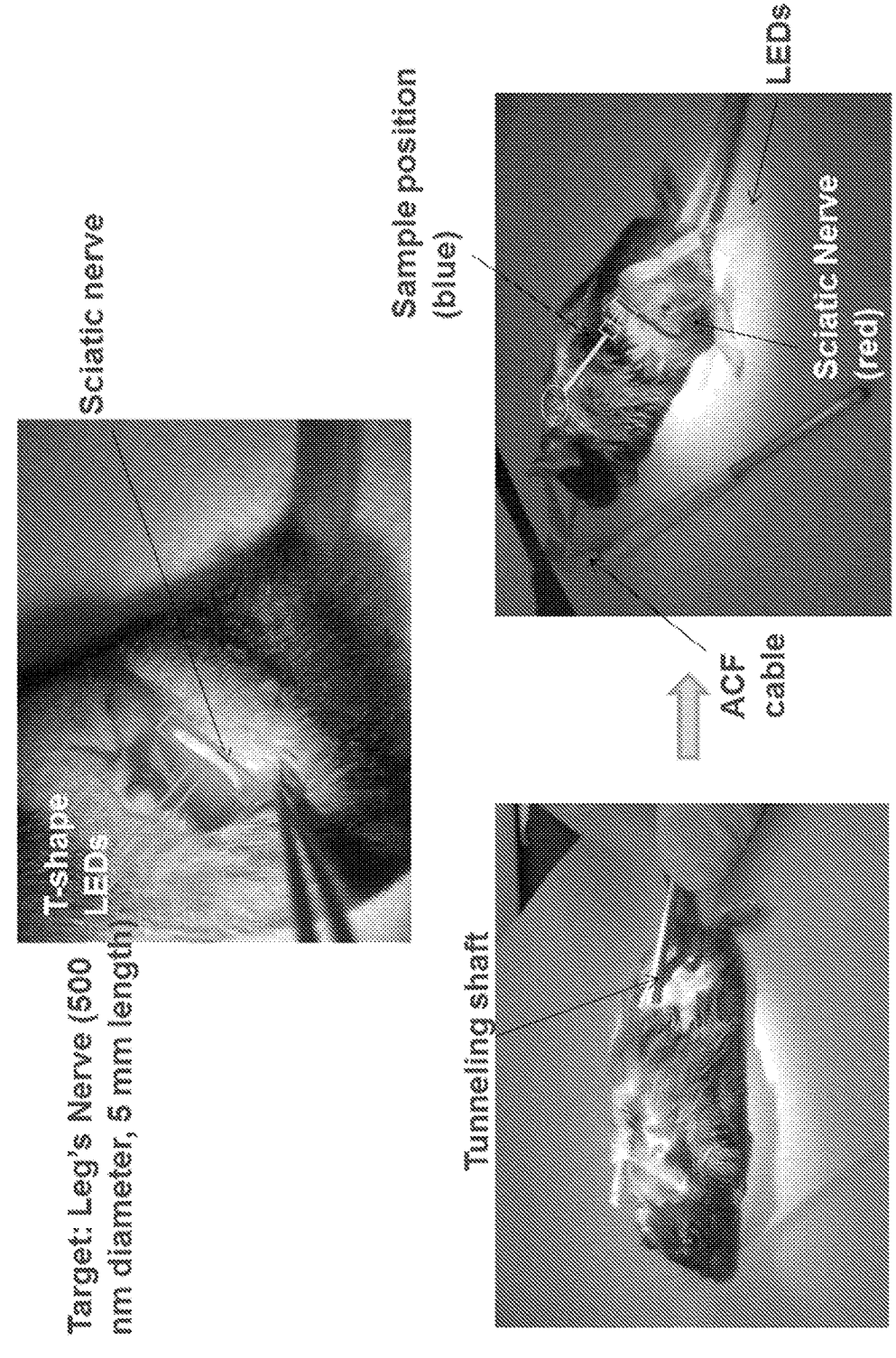

FIG. 32. Implantable biomedical device comprising LEDs implanted into a mouse leg and that interfaces with the sciatic nerve.

Figure 33:
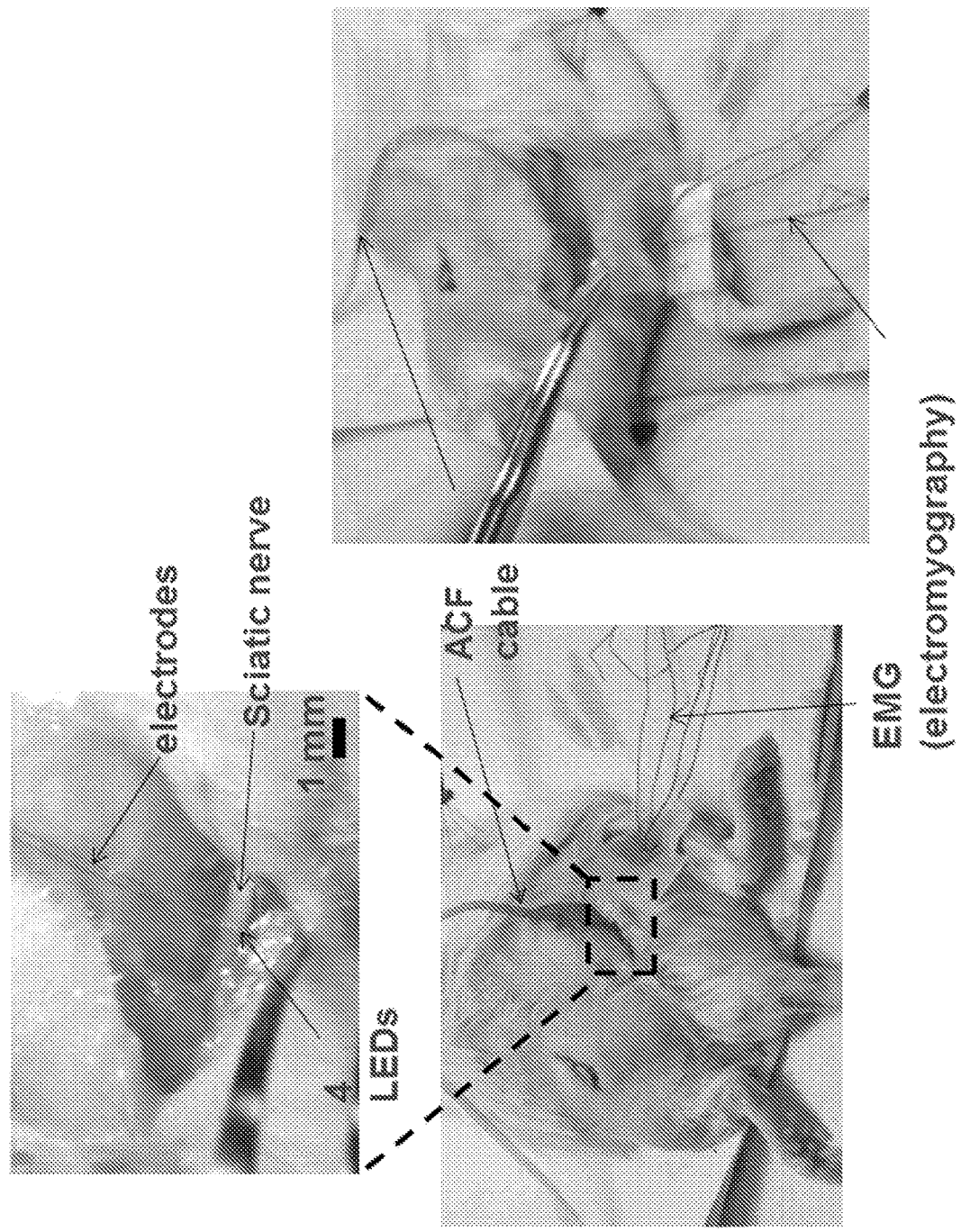

FIG. 33. Close-up view of the implanted biomedical device of FIG. 32, illustrating the electrodes that electrically connect to the LEDs that interface with the nerve. An ACF cable electrically connects the implanted portion of the biomedical device with controllers, transmitters, power sources and associated electronic devices that provide control and/or monitoring of the biomedical device. To facilitate operating characteristics of the biomedical device, an electromyograph monitors electrical activity of the nerve by electromyography (EMG).

Figure 34:
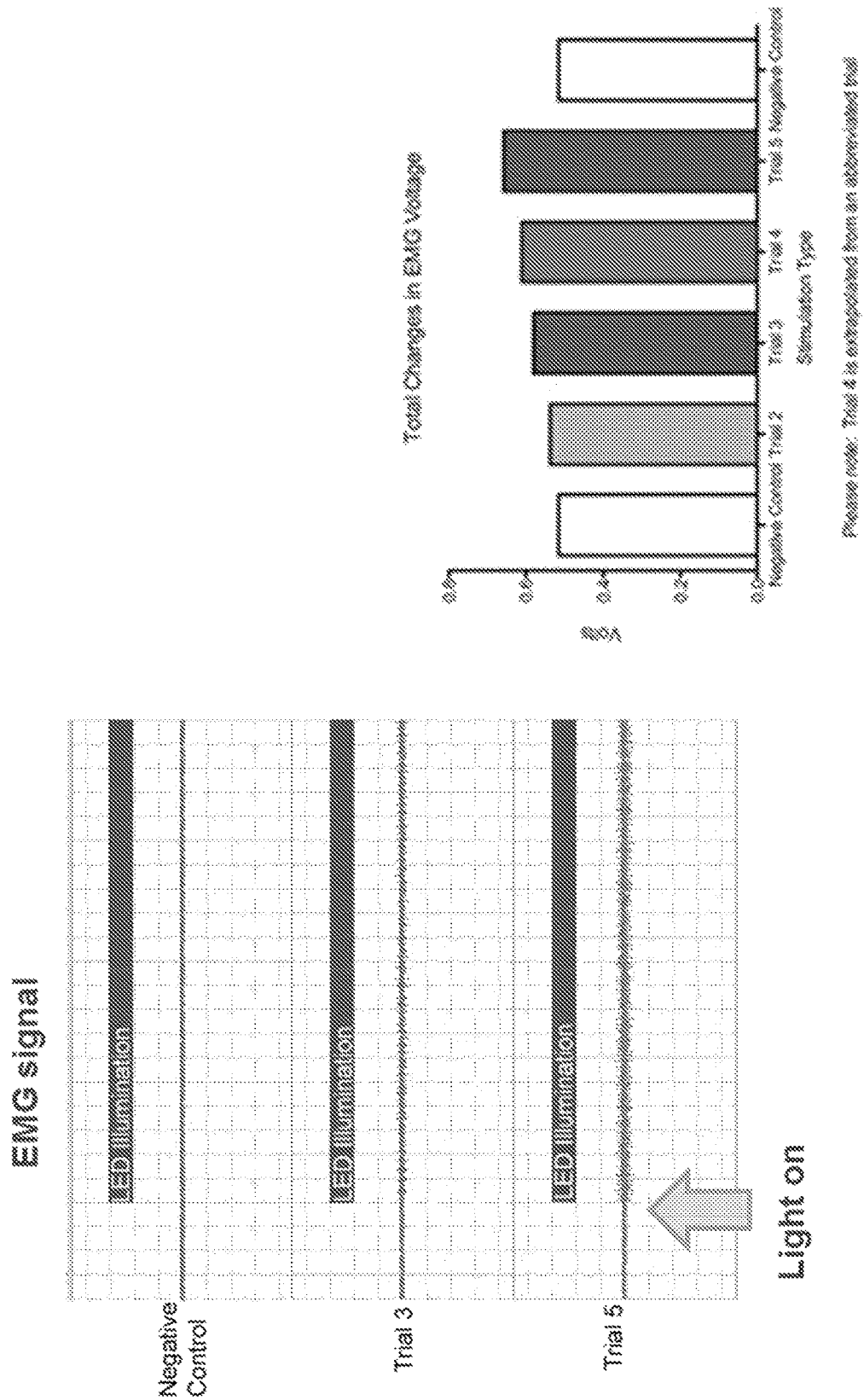

FIG. 34. Results of EMG signal from the system of FIG. 33. LED illumination of the sciatic nerve results in a change in the measured EMG voltage.

Figure 35:
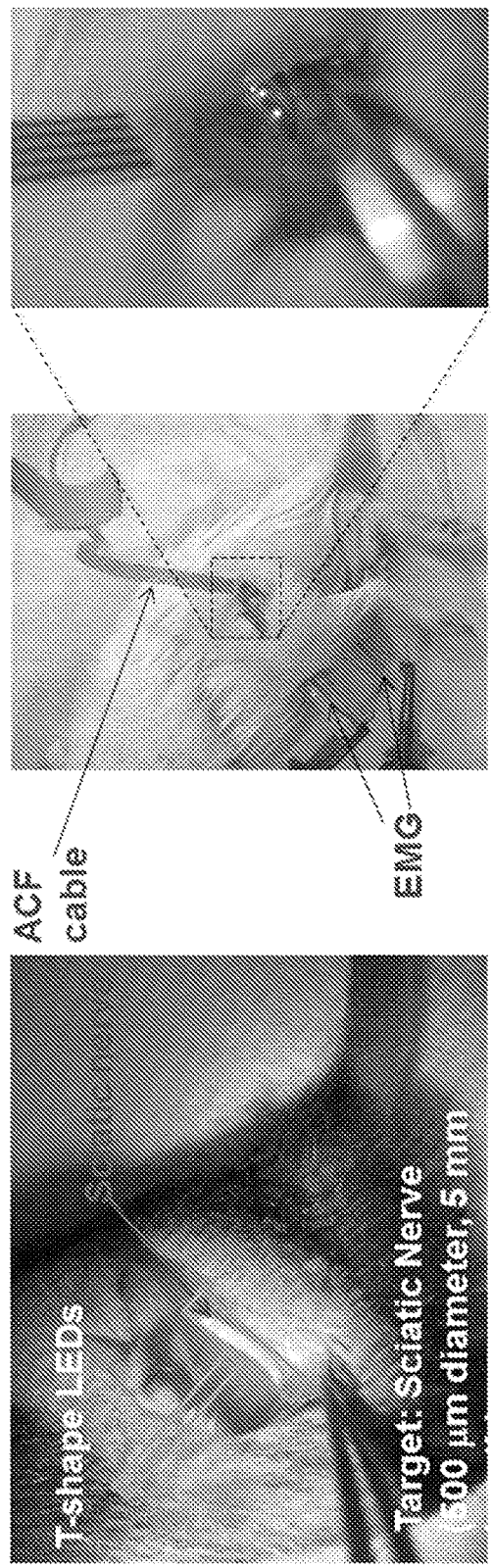
Figure 35:
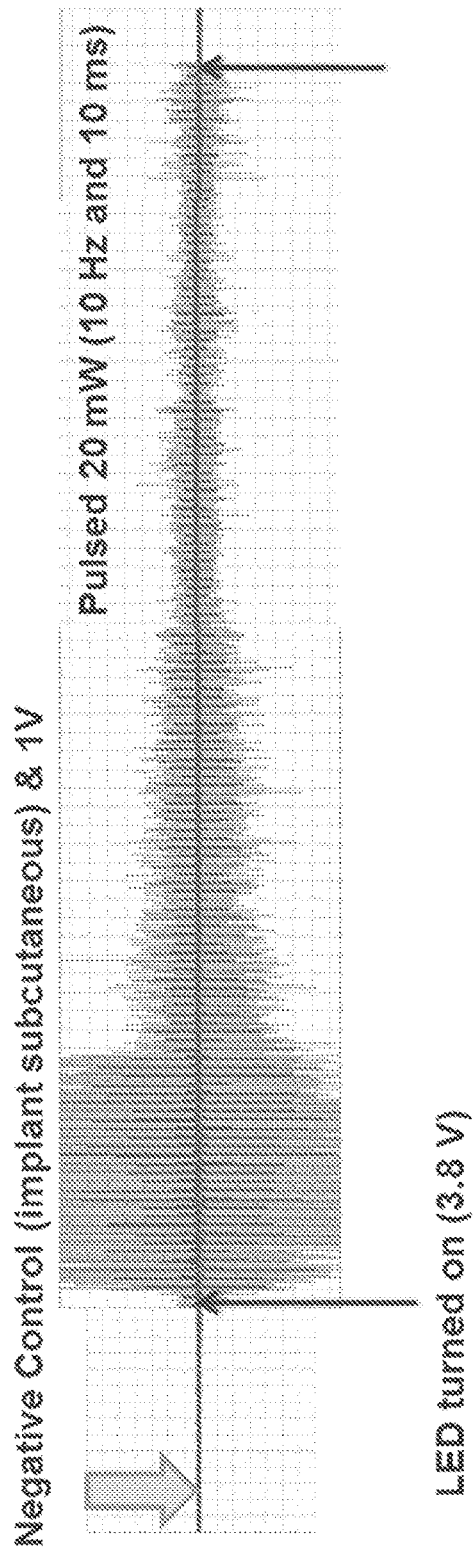

FIG. 35. Effect of pulsed light (10 Hz and 10 ms) from the implanted biomedical device on EMG signal in the mouse sciatic nerve.

Figure 36:
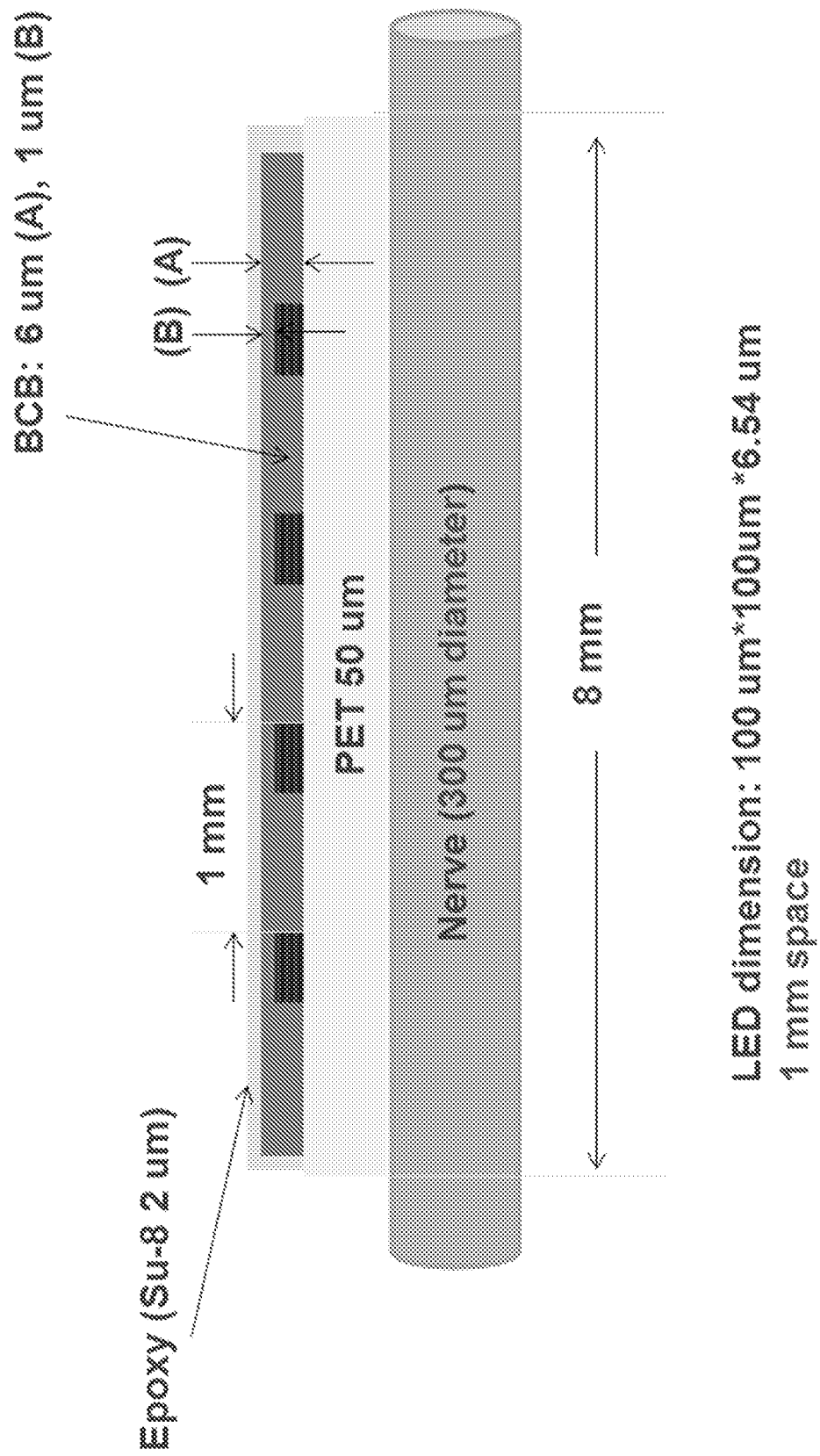

FIG. 36. Schematic illustration of an implanted biomedical device comprising four LEDs that interface with a nerve of diameter 300 μm.

Figure 37:
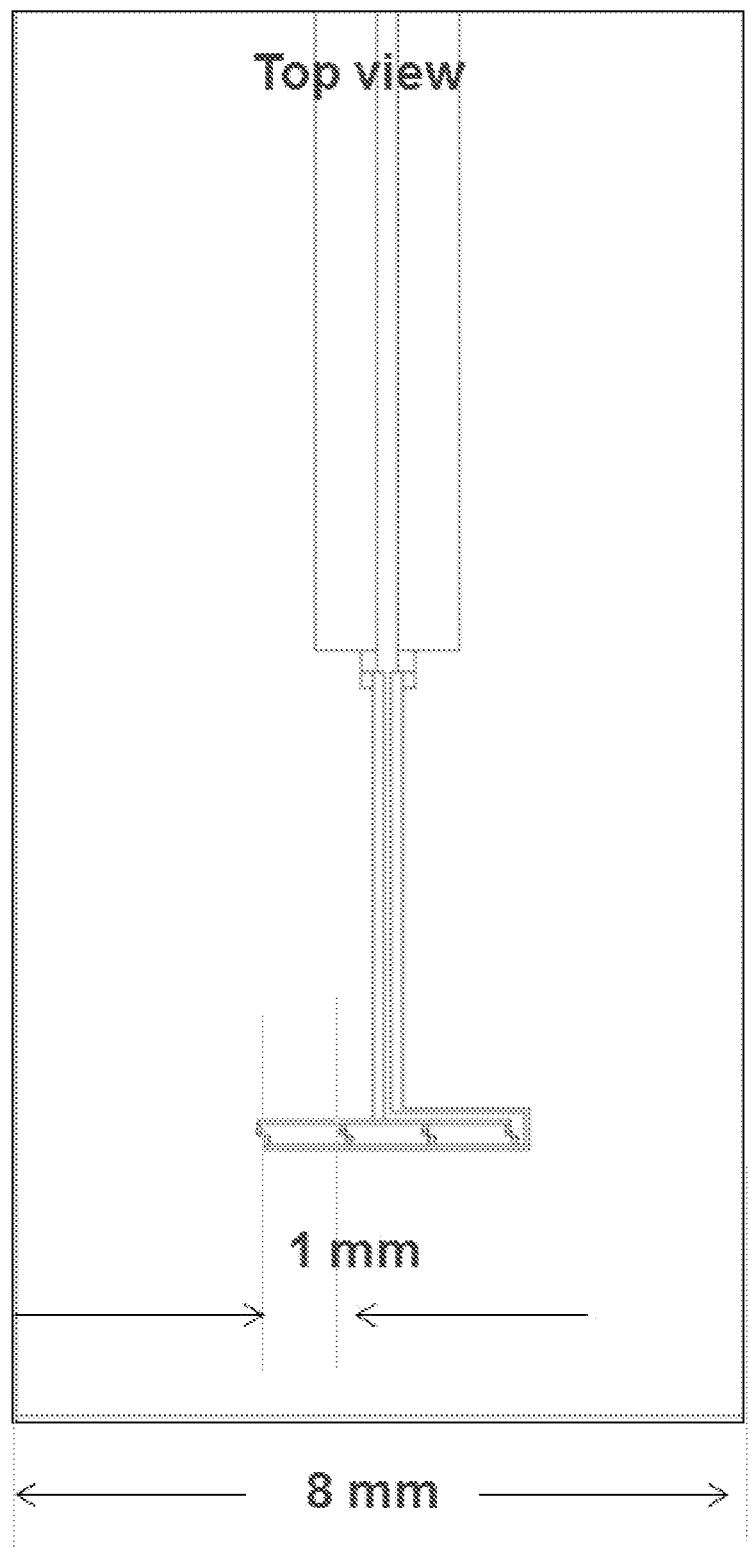

FIG. 37. Top view schematic of the biomedical device comprising a plurality of LEDs for optically interfacing with biological tissue.

Figure 38:
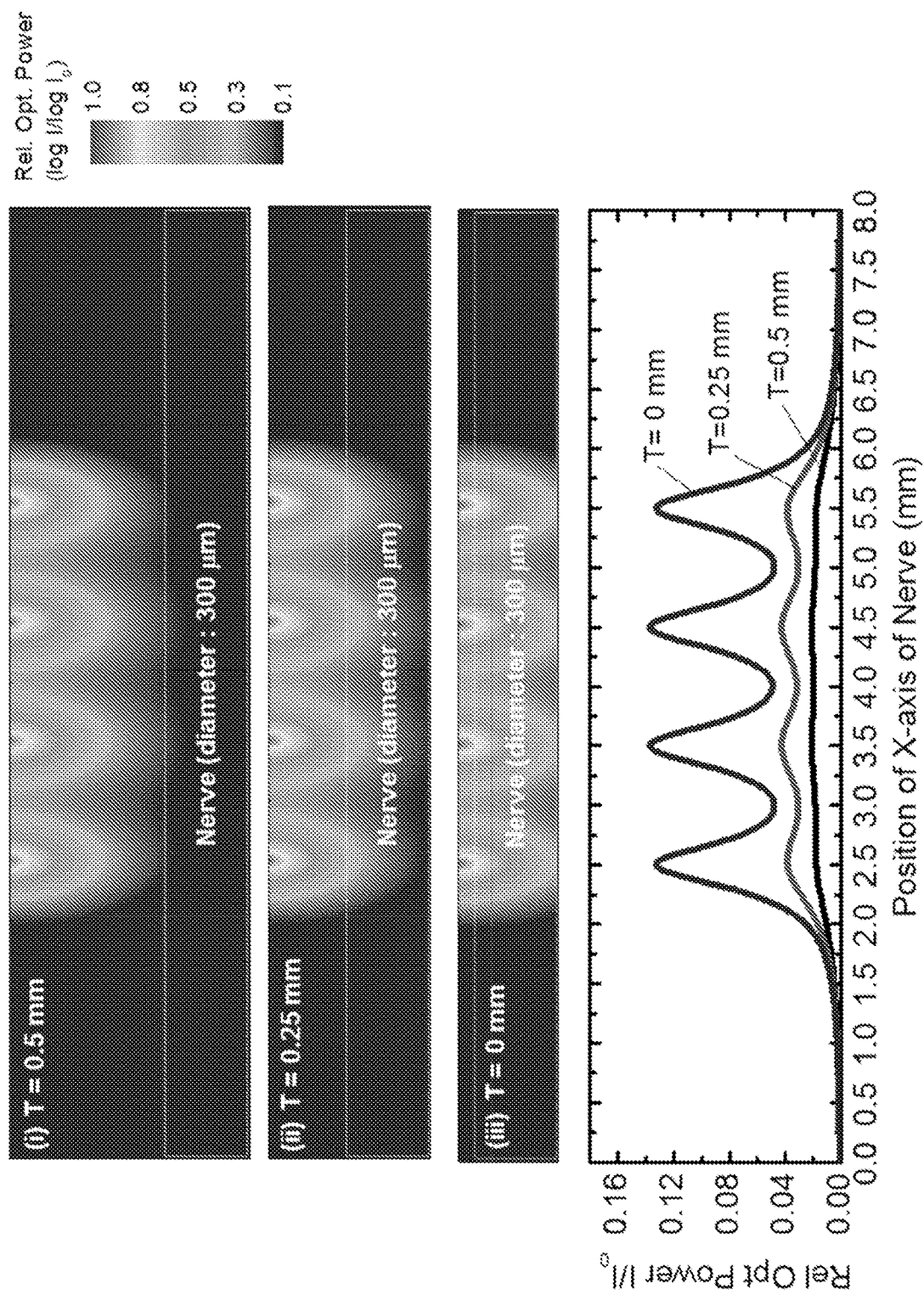

FIG. 38. Light distribution analysis for the four LEDs interfacing with the sciatic nerve at three different longitudinal positions.

Figure 39:
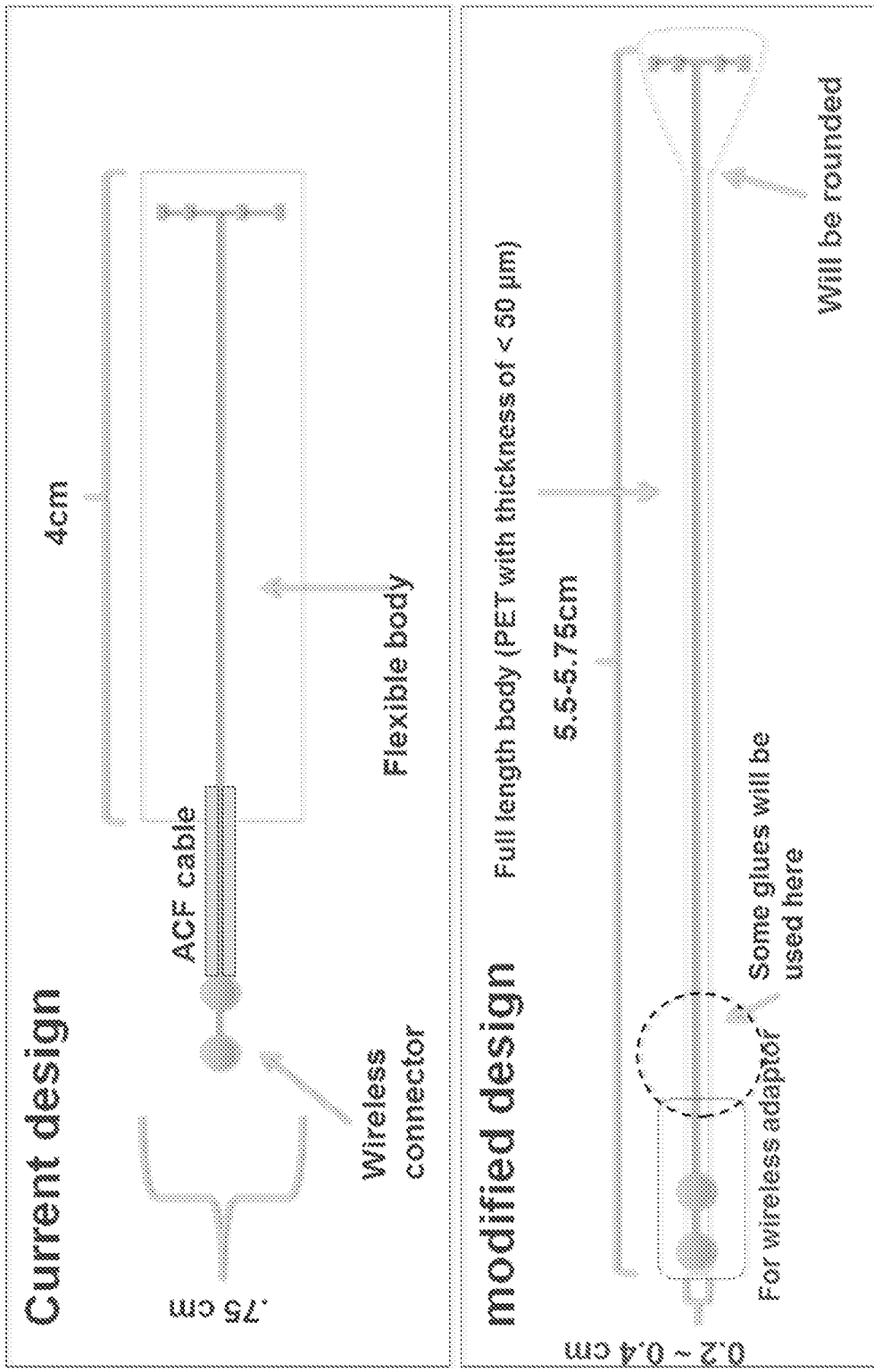

FIG. 39. Summary of device parameters that improve long-term electrical connectivity after implantation.

FIGS. 40-45 show an implanted device, including a wirelessly-controlled device, in a mouse.

Figure 46:
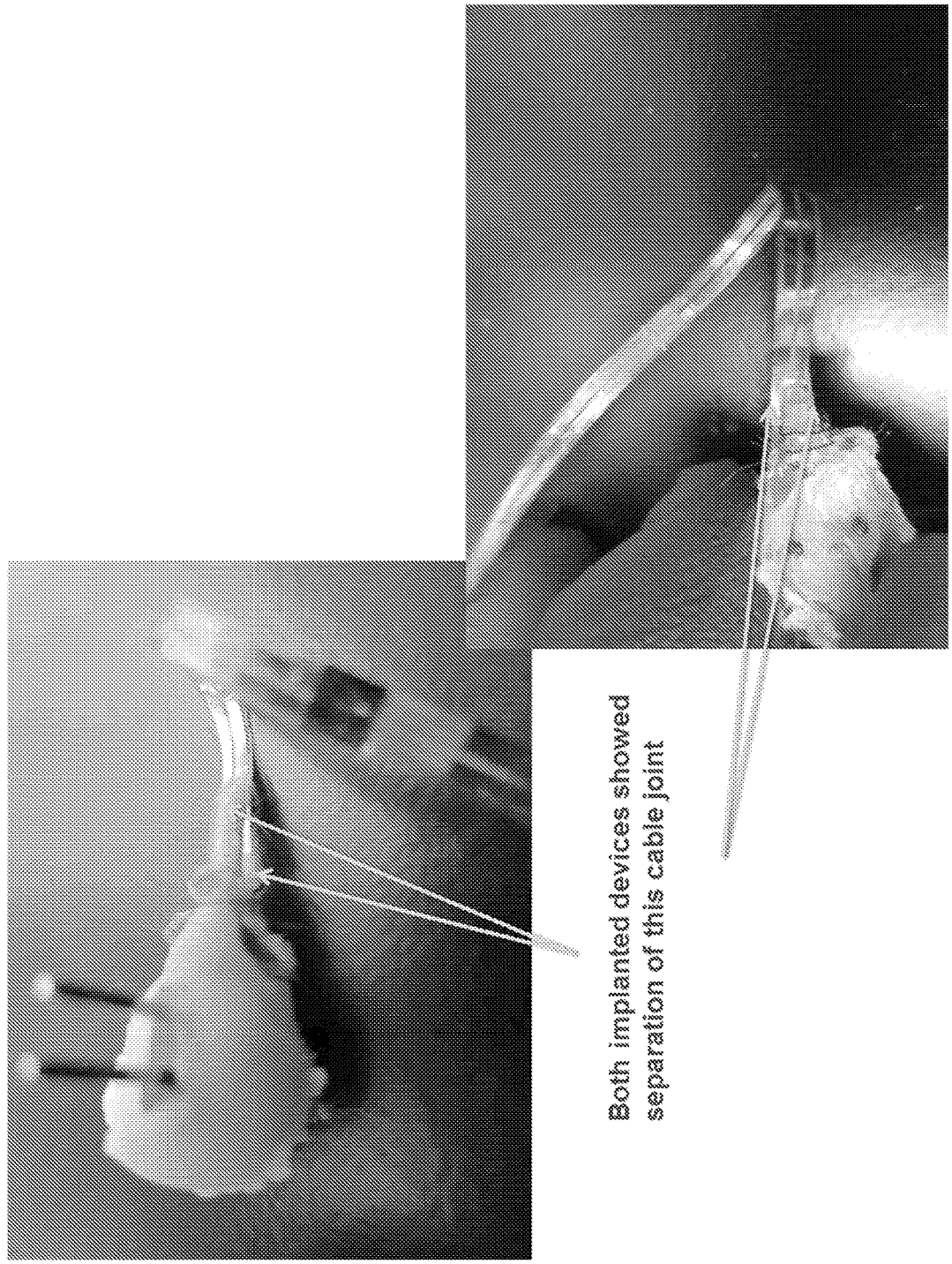
Figure 47:
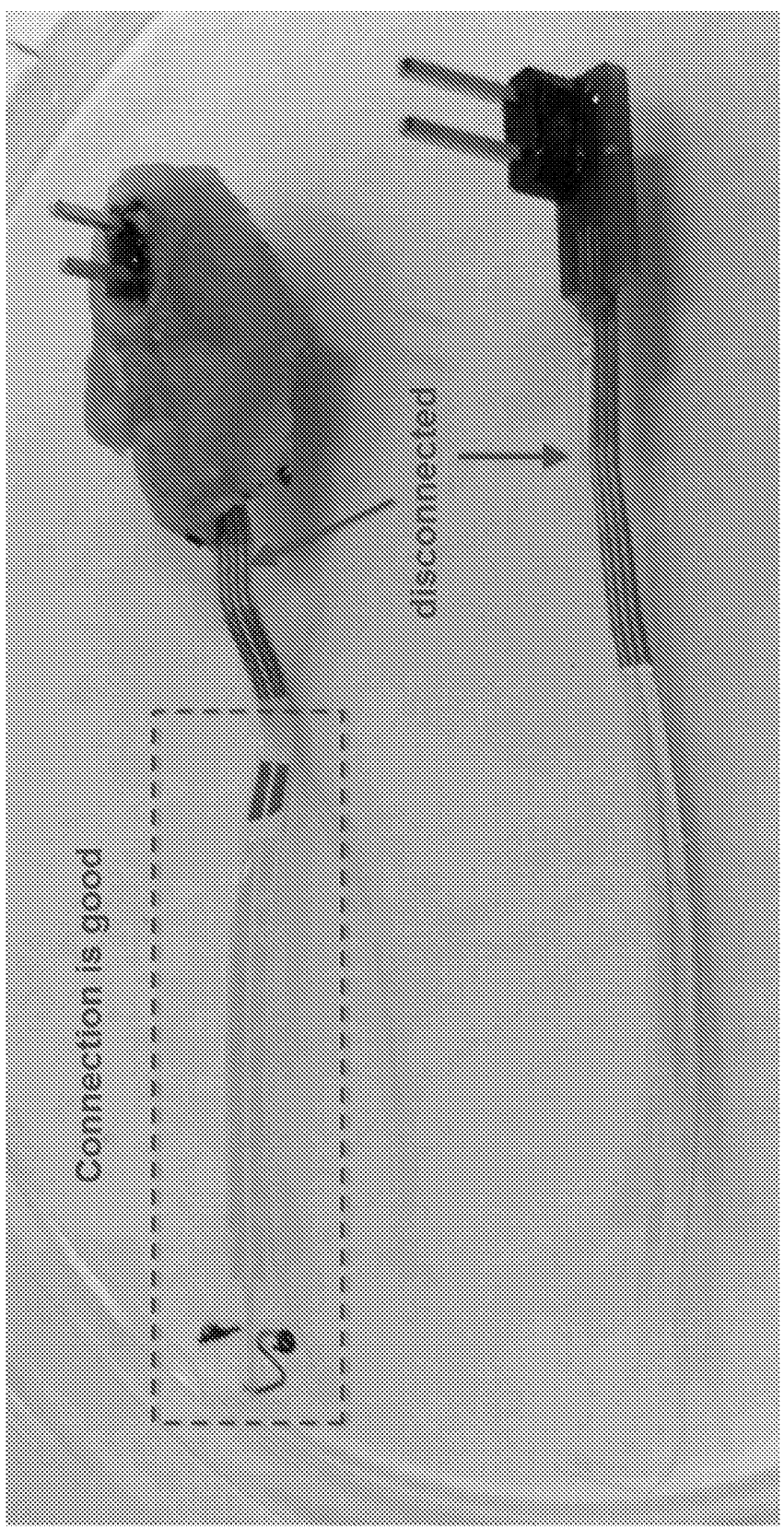

FIGS. 46-47. Illustrate that the point of electrical connection failure is at or near the cable joint.

Figure 48:
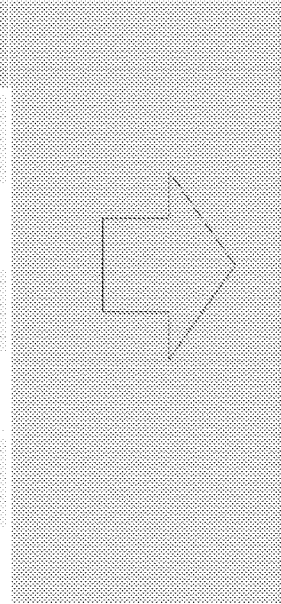
Figure 49:
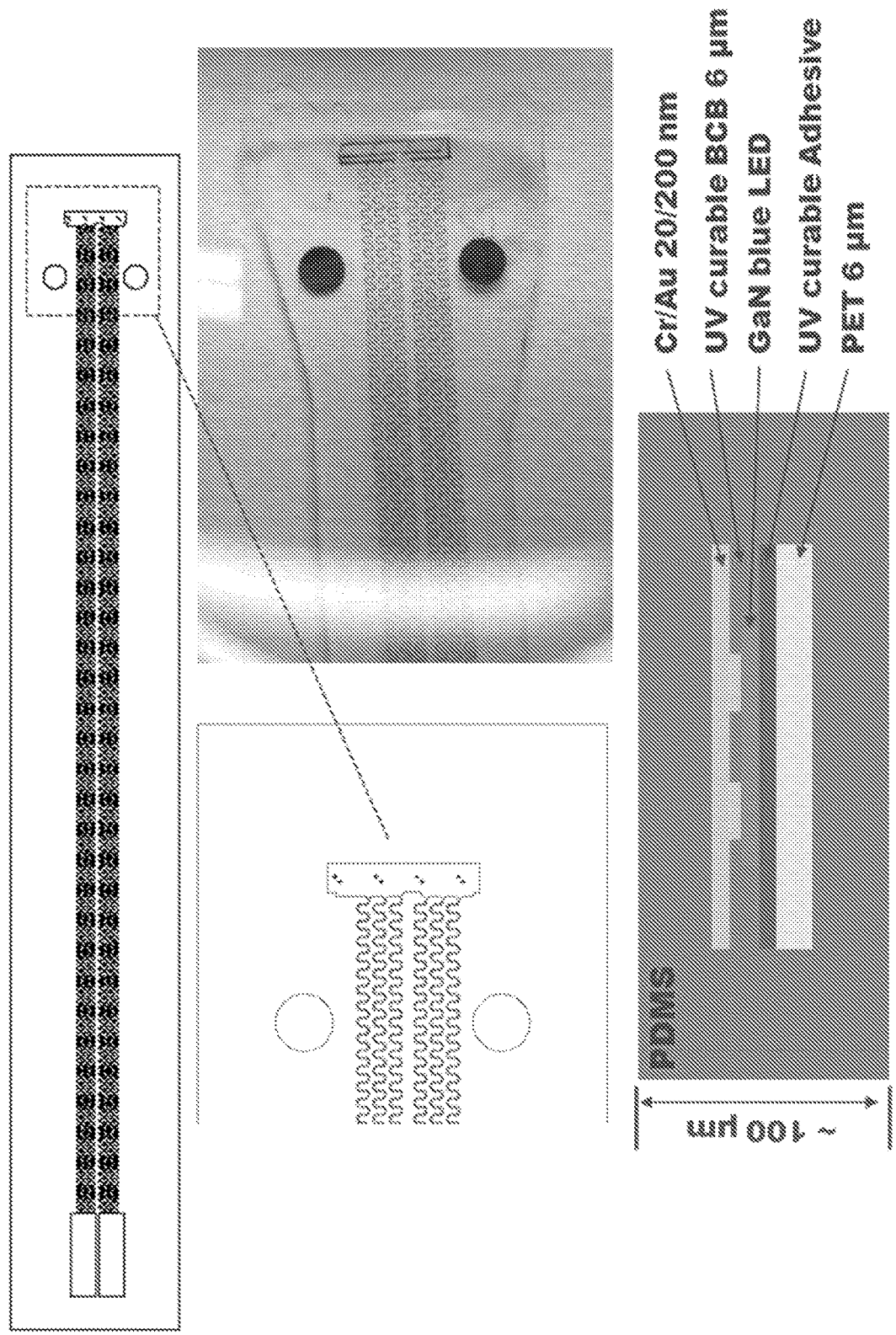
Figure 50:
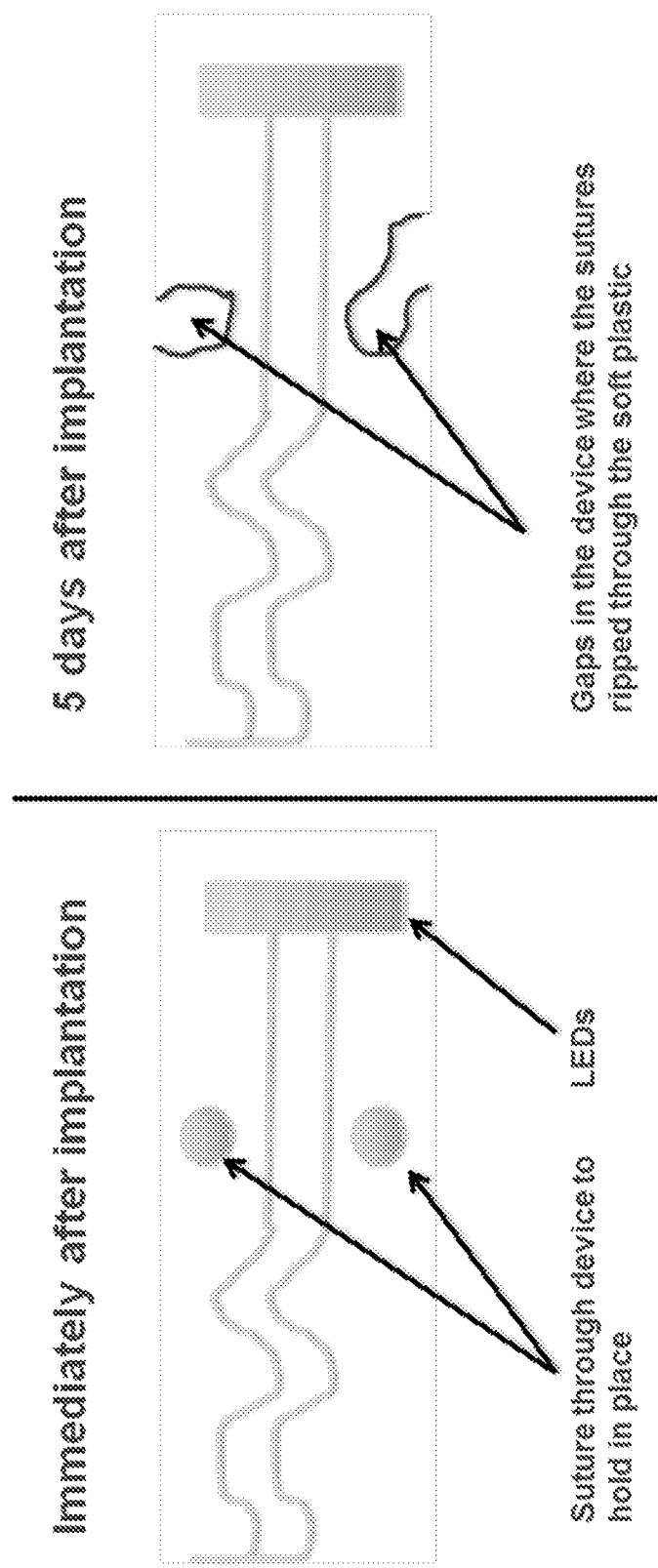

FIGS. 48-50 device modifications to improve robustness and resistance to tearing.

Figure 51A:
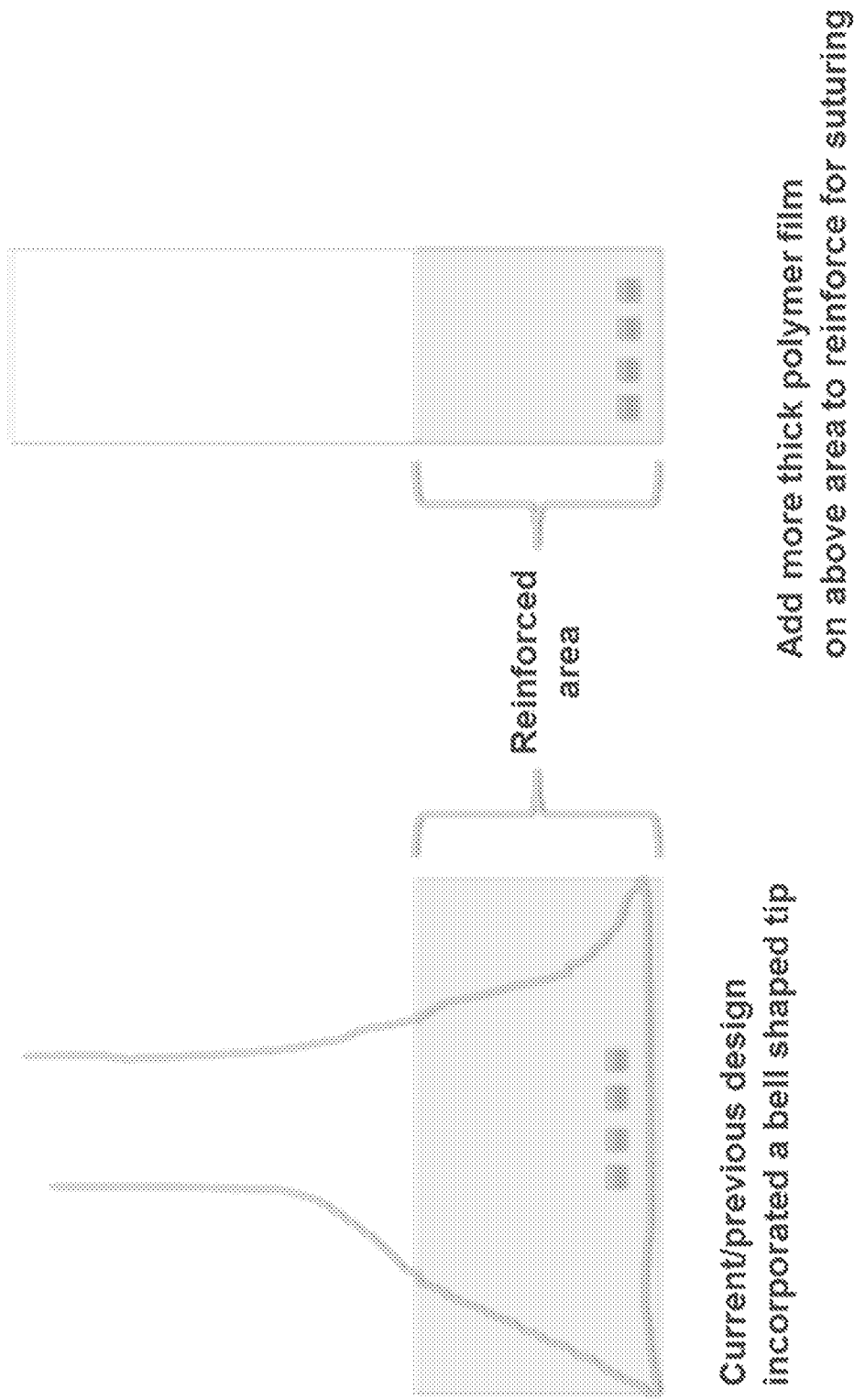
Figure 51B:
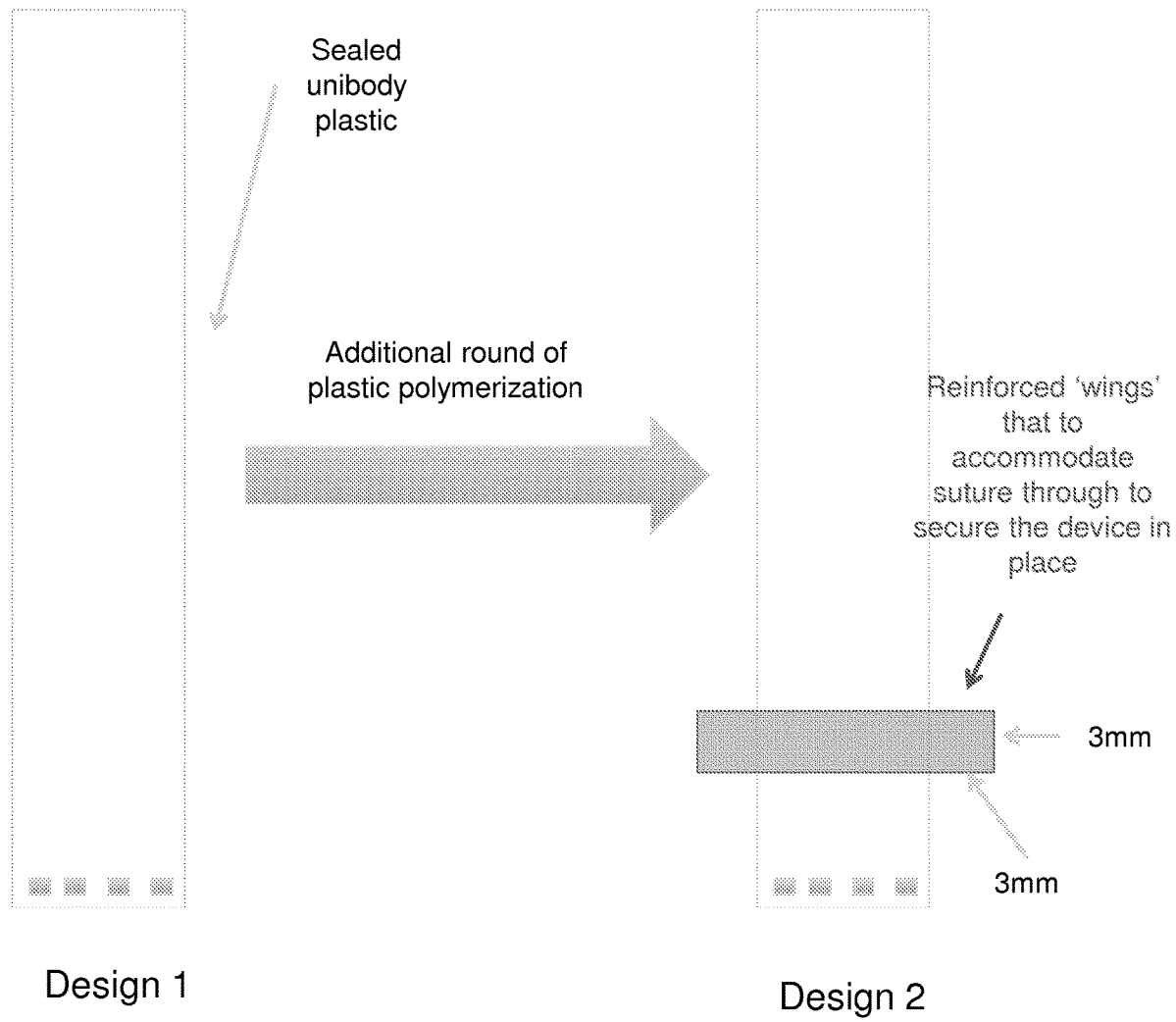

FIGS. 51A and 51B summarize device strategies for securing the implanted device to a specific location.

FIGS. 52-57 Photographs indicating the device and surgical procedure do not illicit adverse biological effects and device functionality is viable three-days post surgery.

Figure 58:
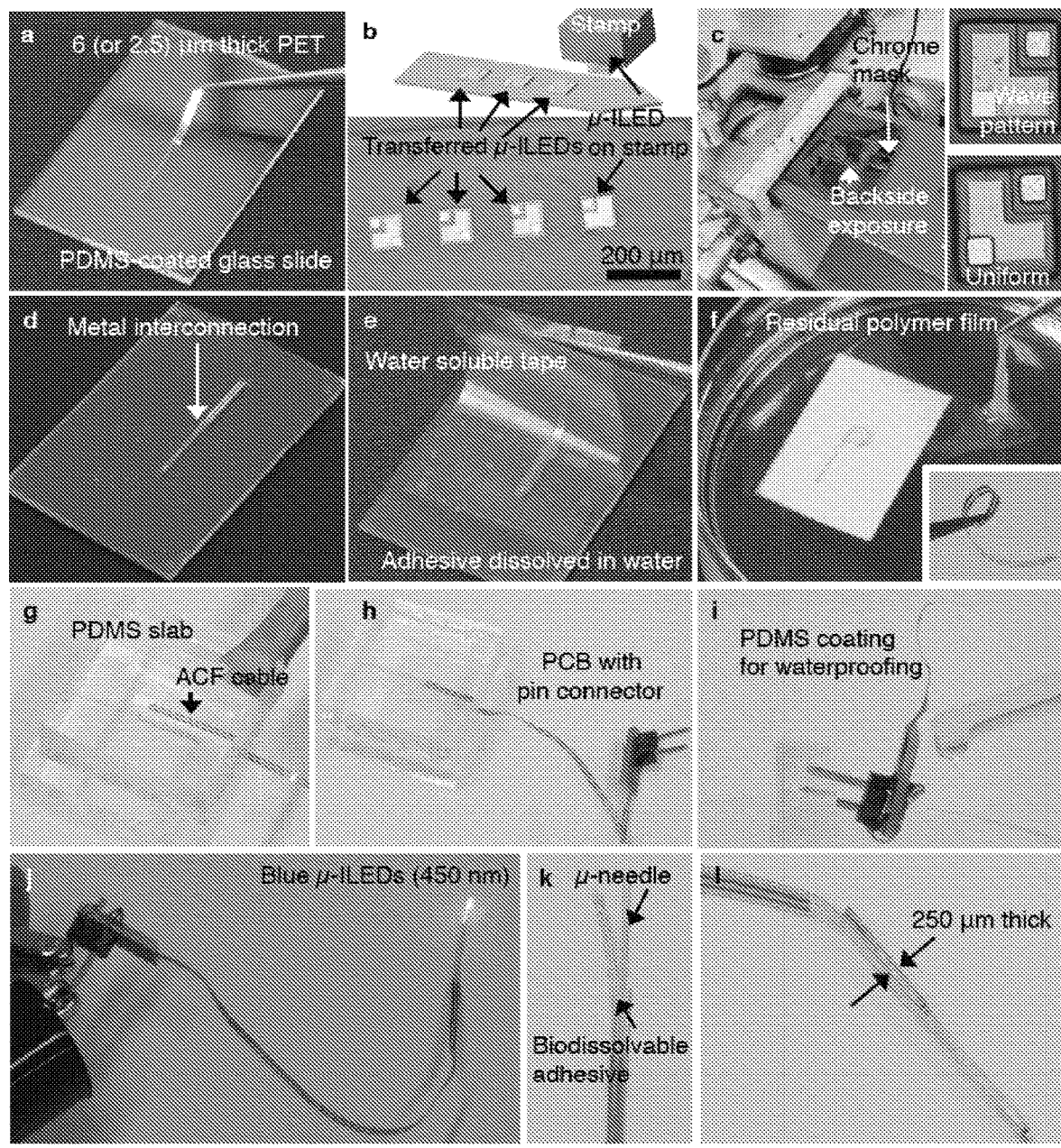

FIG. 58. Procedure for fabrication of injectable, multifunctional electronics. (a) Thin (~2.5 μm thick) needle-shaped polyethylene terephthalate (PET) is attached on temporary Polydimethylsiloxane (PDMS) coated glass substrate. (b) Schematic and photograph demonstrating the transfer printing of four μ-ILEDs onto the tip of the PET using a PDMS stamp. (c) Passivation approach with photocurable benzocyclobutene (BCB) polymer. The backside of BCB coated substrate is exposed to ultraviolet light. The wave pattern in the upper inset shows ununiformed coating of BCB. The lower inset shows successful uniformed coating. (d) The metal interconnection (Cr/Au) is generated by sputtering, photolithography and metal etching to electrically connect the four μ-ILEDs. (e) The connected device is picked up with water soluble tape. (f) The substrate is separated from the tape after the adhesive is dissolved in the water. The inset shows the μ-ILEDs on freestanding thin, flexible, needle-shaped PET. (g) The device is electrically connected to the ACF cable. The PDMS slabs on top and bottom are compressed using high temperature (~150° C.) to bond the ACF cable. (h) The other side of the ACF cable is connected to the PCB with pin connector for wireless or wired powering schemes. (i) The ACF cable and PCB is coated with PDMS for waterproofing. (j) Blue (450 nm) μ-ILEDs are powered. The μ-ILEDs and electrical connection should be checked prior to injection (k) The device is assembled with injection p-needle using biodissolvable silk adhesive. (l) Image of a completed device ready for injection into brain tissue.

Figure 59:
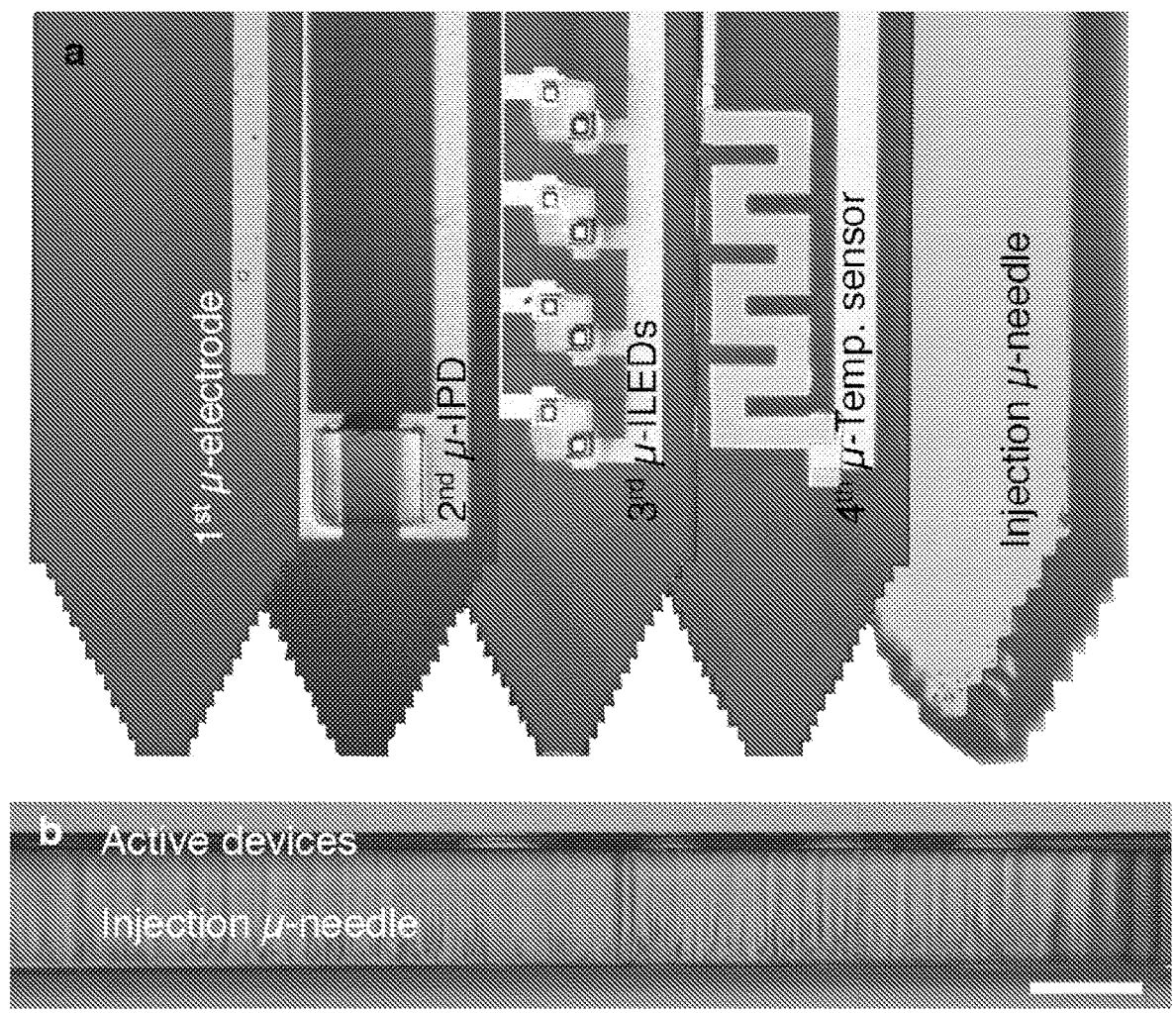

FIG. 59. Multifunctional sensors and optoelectronics. (a) Representative scheme for multifunctional, injectable electronics formed on injectable needle. The devices include electrophysiological sensor (μ-electrode); $1^{st}$ layer), silicon photodiode (μ-IPD; $2^{nd}$ layer), four microscale inorganic light-emitting diodes (μ-ILEDs; $3^{rd}$ layer), and temperature sensor (μ-temp. sensor; $4^{th}$ layer) based on platinum resistor are formed on injectable μ-needle fabricated from epoxy polymer. (b) Side view of such a device reveals the ultrathin nature of the active components of the device. Scale bar applies to both panels and =200 μm.

Figure 60:
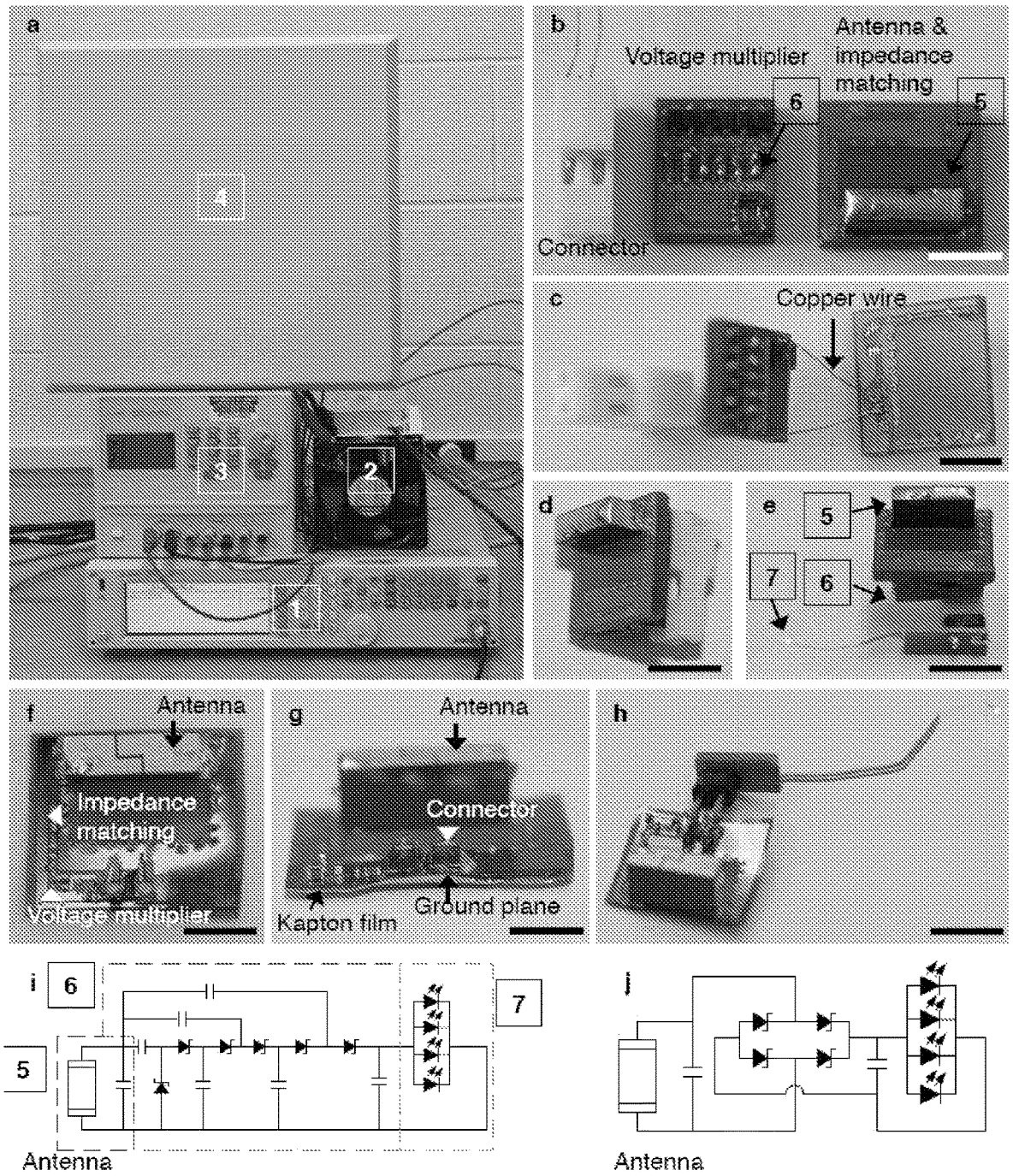

FIG. 60. Wireless operation and equipment. (a) An experimental setup for wireless power transmission. The setup contains a RF signal generator (1), a RF power amplifier (2), a DC power supply (3), and a panel antenna (4). Components for the wireless power harvester for μ-ILED powering with stacked PCB circuits (5: circuit contains a ceramic antenna and a capacitor is connected between the feed line of the antenna and the ground plane to match the impedance of the antenna with the next circuit. 6: a second circuit contains a voltage multiplier constructed with 6 pairs of capacitors and Schottky diodes in a cascaded connection). before (b) and after (c) connecting with copper wire. A completed wireless power harvester alone (d) and with (e) connection to μ-ILED device (7) for wireless operation. Top (f) and side views (g) of a flexible wireless power harvester on Kapton film with similar components as the wireless harvester on PCB circuits. (h) A completed flexible wireless power harvester with connection to μ-ILED device for wireless operation. All scale bars are 5 mm. (i) A schematic of the PCB-based power harvester. The numbered circuit components correspond to the same number shown in FIGS. 3b and 3e. (j) A schematic of the wireless power harvester.

Figure 61:
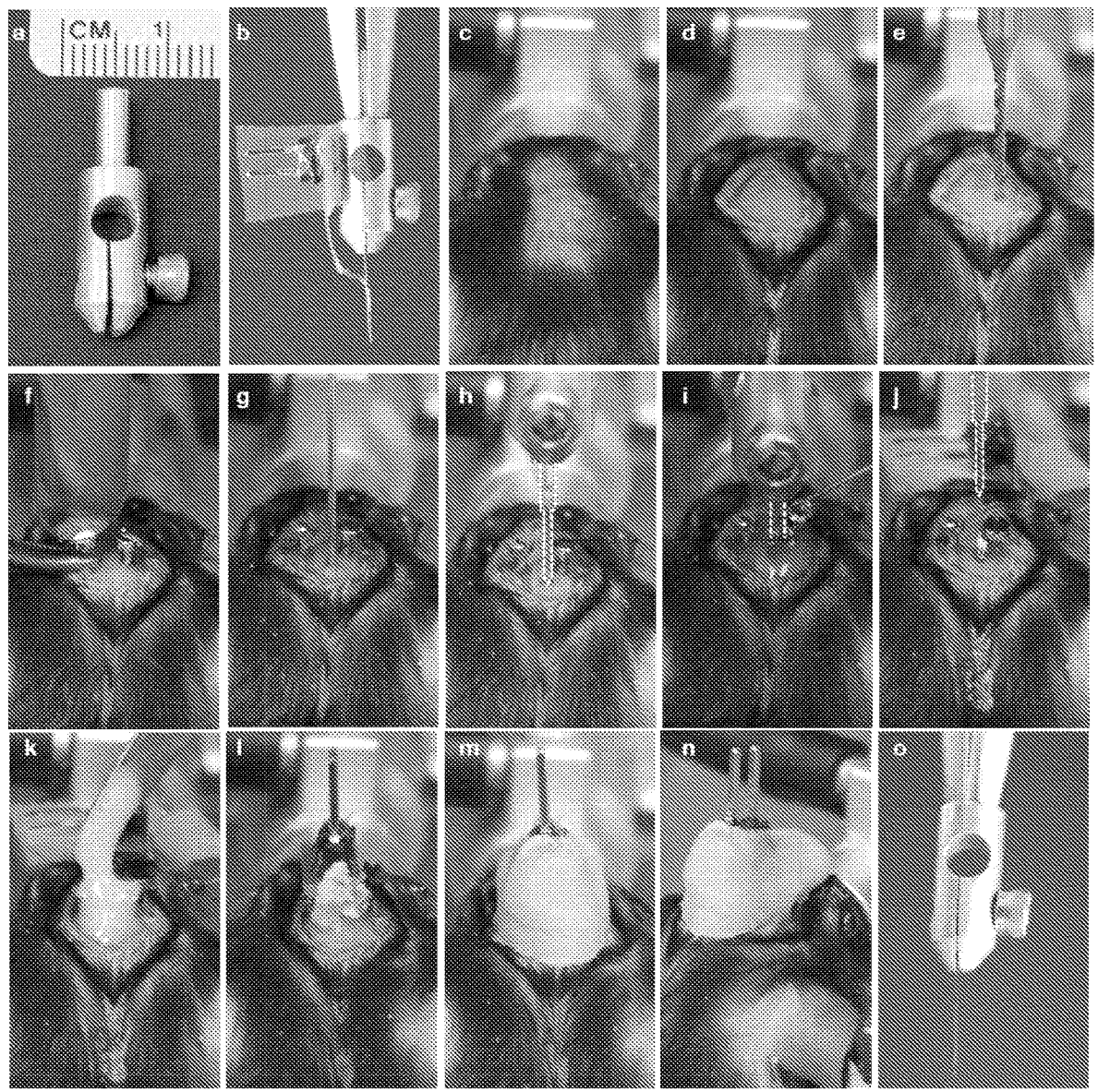

FIG. 61. Surgical procedure for injection of virus and μ-ILED devices into mouse brain. (a) Custom-built adapter for accurate stereotaxic placement of device (see EQUIPMENT SETUP). (b) Mounted μ-ILED device, ready for injection into the animal. The exposed p-needle is grasped with the adapter and a small piece of tape is used to secure the PCB during surgery. (c) A properly mounted mouse with head shaved and eyes-lubricated is ready for surgery. (d) Betadine and ethanol is used to prevent infection and the scalp is open to expose the skull. (e) After leveling the skull, the drill is used to create pilot holes for the bone screws. (f) Forceps and a spatula or jewelry screwdriver is used to drive the screws into the skull. (g) The syringe needle is lowered to the desired coordinates to deliver the virus containing the optogenetic construct. (h) A μ-ILED device prepared to be driven into the brain using the same craniotomy as the viral injection. Dashed lines outline the shape of the device for clarity. (i) The μ-ILED device is lowered into the tissue and ACSF is applied to the skull surface to dissolve any external silk adhesive. (j) After a 15 minute waiting period, the p-needle is carefully retracted from the skull. (k) Dental cement is applied directly to the craniotomy site to secure the μ-ILED device in its targeted position. (l) The PCB connector is secured above the bone screws using a second layer of dental cement. (m,n) The PCB connector is completely encapsulated in dental cement, taking care to ensure that no bonds are made directly to the soft tissue. (o) The adapter is shown following surgery, containing only the p-needle.

Figure 62:
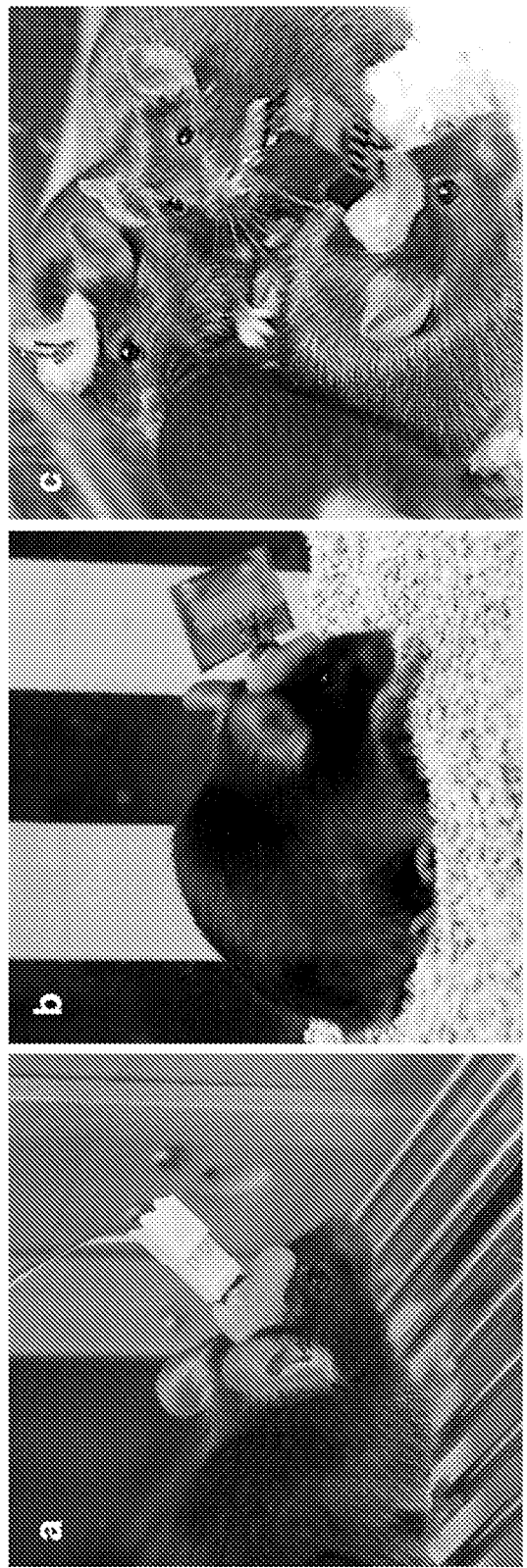

FIG. 62. Expected results following viral and device injection. Once a device is injected, the standard connection allows for temporary coupling multiple means of powering in a variety of behavioral assays: (a) A mouse connected for wired powering in a standard operant behavioral chamber, (b) the same mouse prepared for wireless powering using the lightweight, flexible power scavenger in a conditioned place preference environment, (c) Two mice with implanted devices amongst cage mates. The mouse in the foreground has a PCB-style RF scavenger for powering in a homecage environment.

Figure 63:
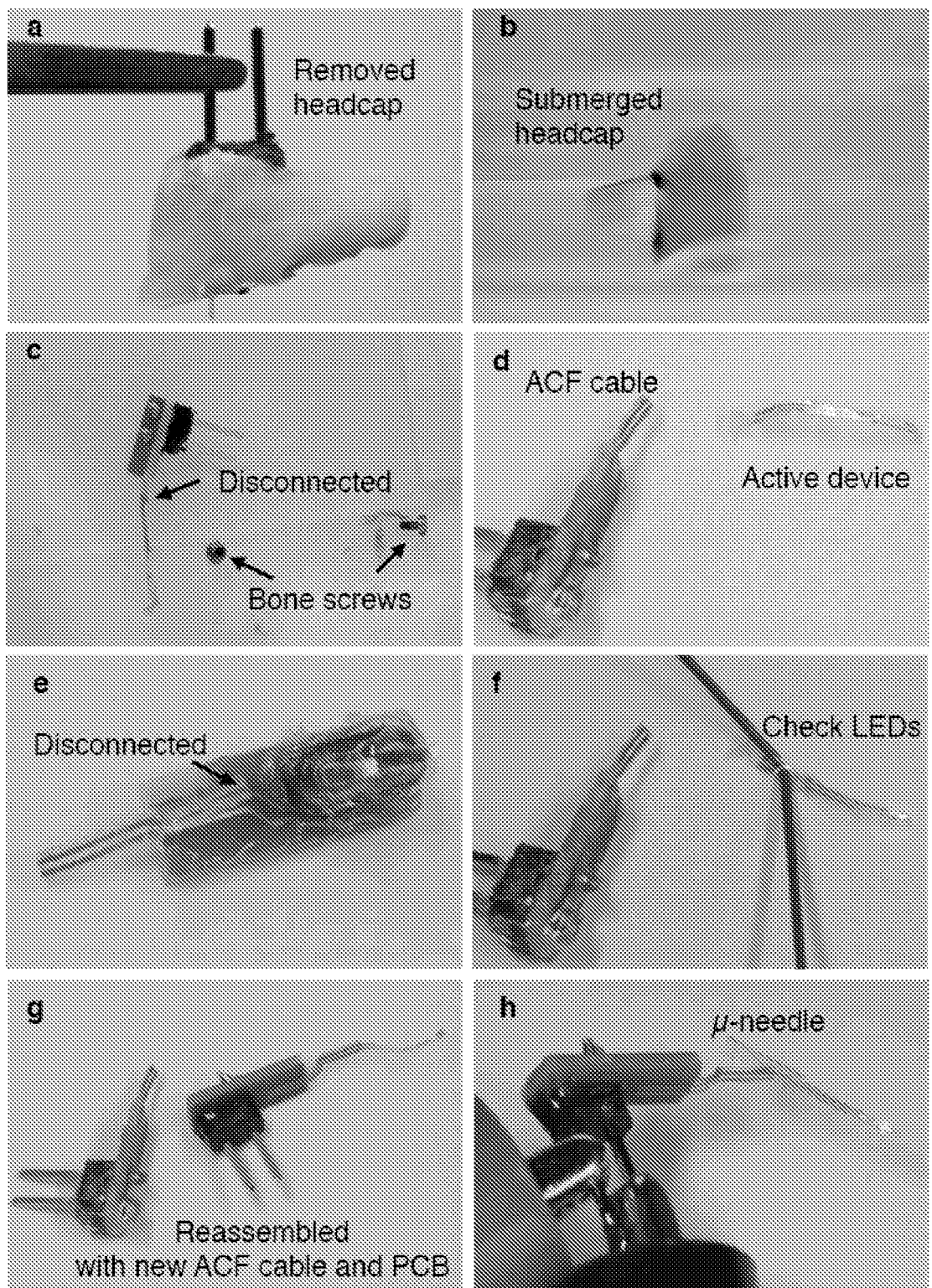

FIG. 63. μ-ILED device recycling and refabrication for subsequent use. (a) The same headcap from FIG. 4, removed from the animal post-mortem and cleaned of biological material. (b) The headcap should then be fully submerged in methyl methacrylate. (c) Following overnight incubation in the stabilized methyl methacrylate monomer, the PCB, connector, μ-ILED device, and bone screws will be freely available in the solution. (d,e) Both connections with the ACF cable will also dissolve, rendering the device nonfunctional. (f) The device should be checked for reusing. If non-functional, the device should be discarded and a new device should be fabricated. (g) The working device is reassembled with new ACF cable and PCB. (h) The electrical connection through the new ACF cable should be checked after the device is attached with injection p-needle again.

Figure 64:
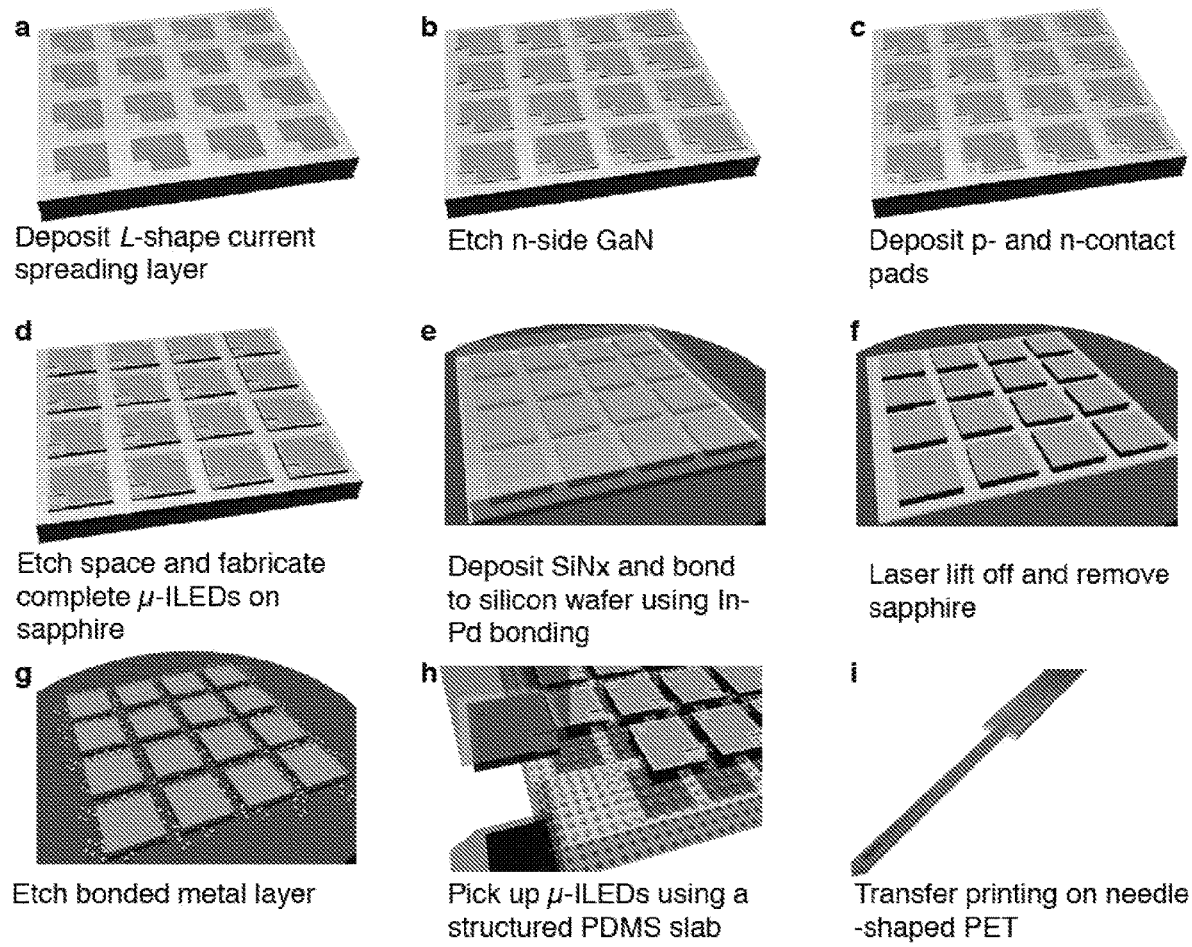

FIG. 64. Fabrication procedure for injectable μ-ILEDs. (a) L-shape current spreading layer (patterning of Ni/Au (15/15 nm) layers followed by 500° C. annealing) is formed on GaN blue lighting LED stacks grown on sapphire. (b) In order to expose n-type GaN semiconductors, etch rectangular shape of p-type one, multi quantum well (MQW), and spacer layers by reactive ion etching. (c) Generation of n- and p-contact pads (Cr/Au (15/300 nm) 25×25 mm$^2$ squares) on n- and p-type GaN sides. (d) Etch 20 mm width trench to define 100×100 mm$^2$ or smaller than 100×100 mm$^2$ lateral dimensions. (e) Bonding μ-ILEDs on sapphire with silicon wafer using In—Pd metallic alloy bond. (f) Expose laser on sapphire and mechanically remove sapphire from μ-ILEDs. (g) Wet etch the bonded metallic layer located on wafer. (h) Transfer of all μ-ILEDs onto structured PDMS slabs and selectively pick up single μ-ILEDs using a polydimethyl siloxane (PDMS) stamp. (i) Release 4 μ-ILEDs on needle-shaped polymer (polyester) followed by passivation, metal interconnect. [Part d, f, g and h reproduced with permission from ref. 12 © 2012 Wiley]

Figure 65:
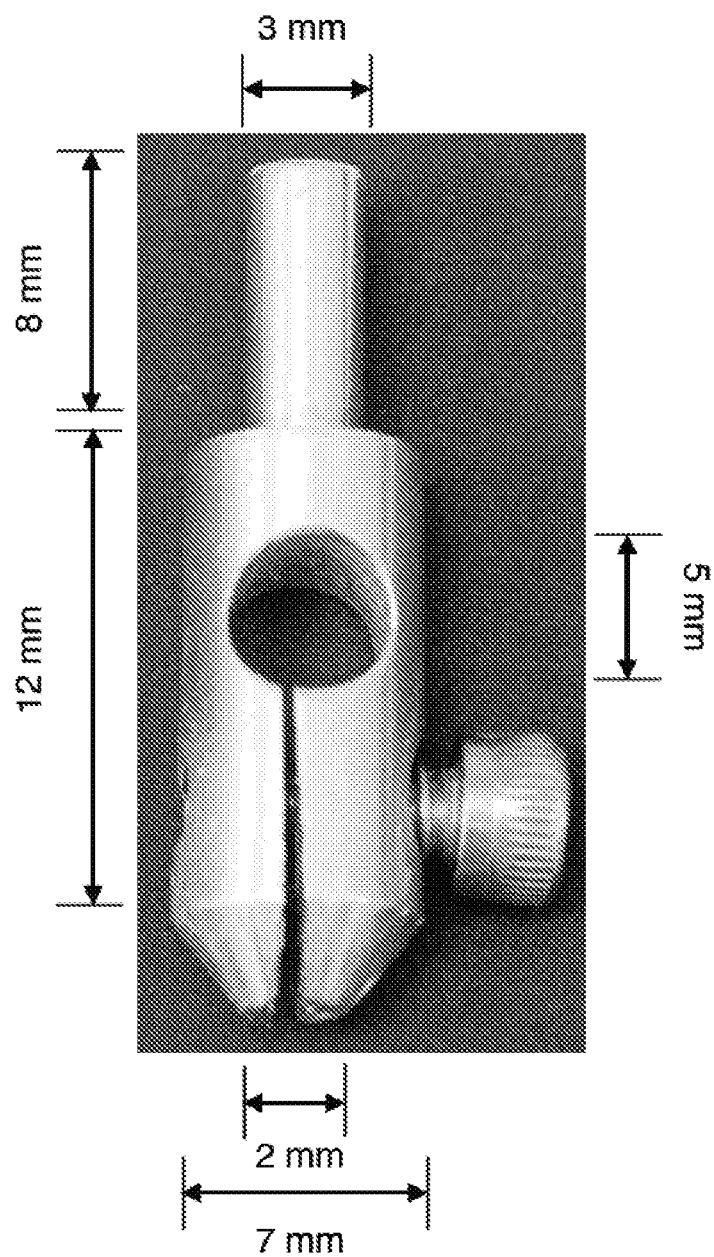

FIG. 65. Machining of the cannula holder adapter. This adapter is specifically designed for use with the KOPF Model 1966 Cannula Holder. The adapter is fashioned from aluminum with an 8 mm stalk (3 mm in diameter) that can be held by the Model 1966. The main body of the adapter is 14 mm in length with a 7 mm diameter. The are two orthogonal bore holes through the body. The first is a 5 mm hole from which the center slit is created through to the tip of the adapter. The second is a 2 mm screw-hole so that a screw can be tightened to reduce the size of the center slit to hold the p-needle. It is important that the center point of the adapter be in-line with the center point of the cannula holder itself to ensure accurate device injection. Note that this adapter is merely a suggestion, but we acknowledge there can be many other solutions to the problem of accurate injection of the devices. Most stereotaxic instrument manufacturers offer custom-built holders and it is likely that many standard electrode holders can be modified to suit the needs of the individual laboratory (e.g. KOPF Model 1768).

Figure 66:
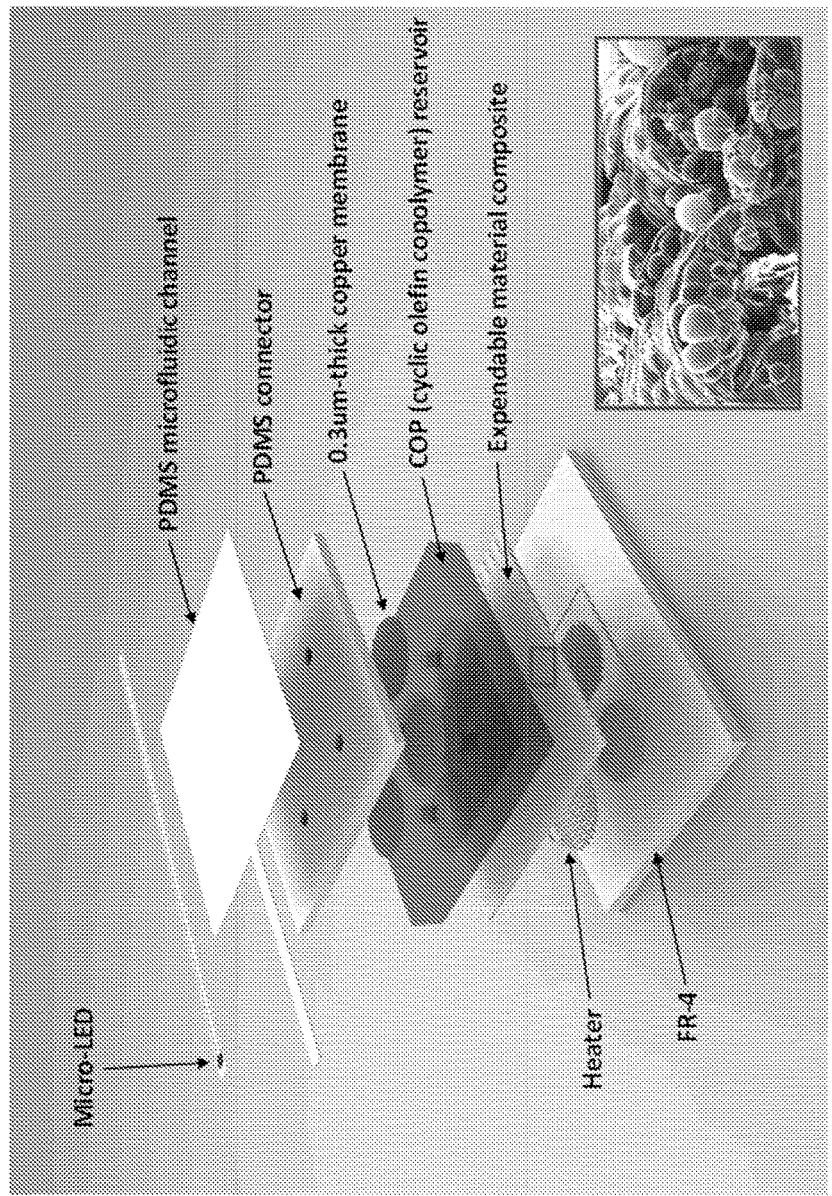

FIG. 66 provides an overview of the design of a microfluidic device embodiment showing different layers of the device.

Figure 67:
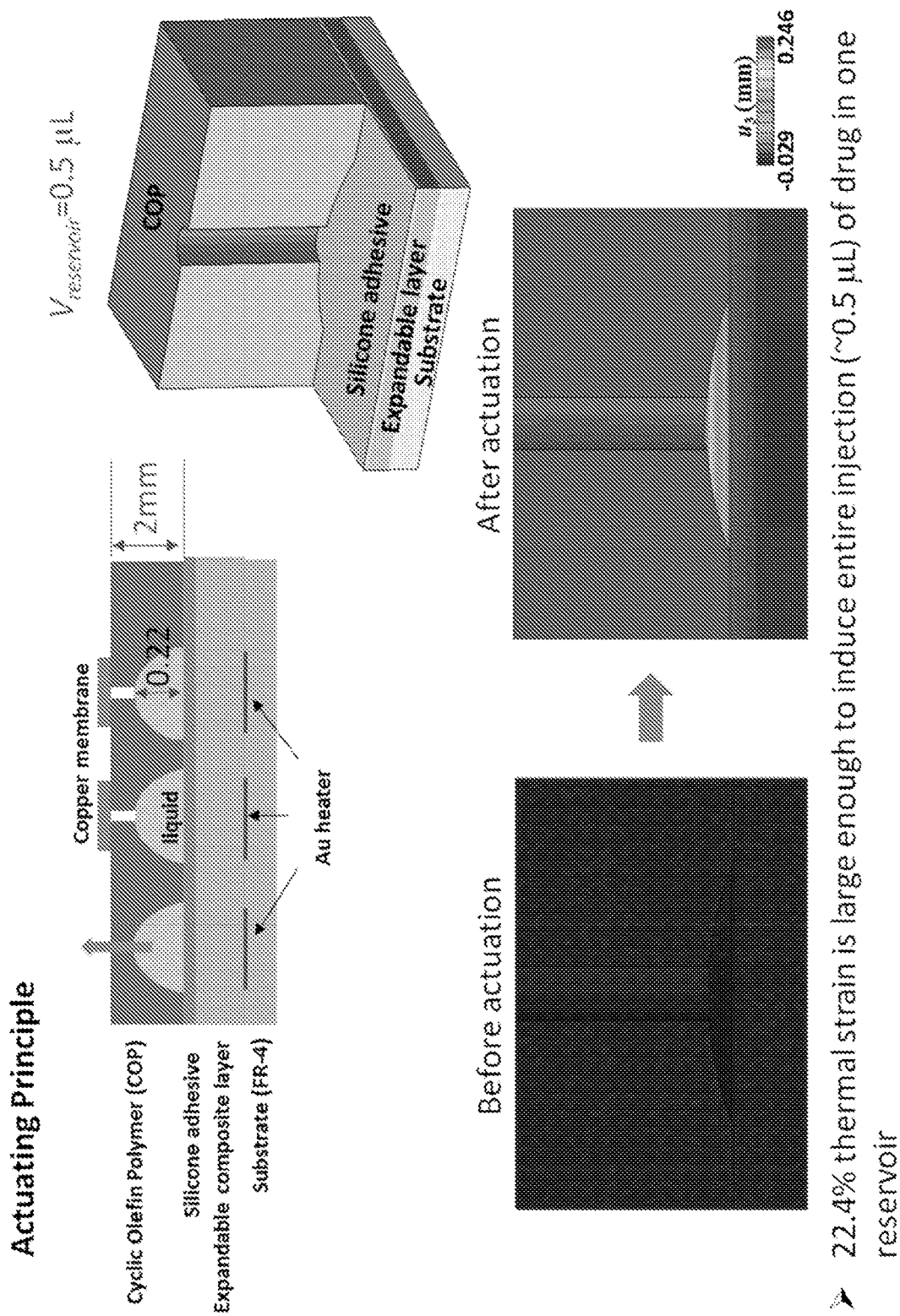

FIG. 67 provides an overview of the actuation principle of a microfluidic device embodiment.

Figure 68:
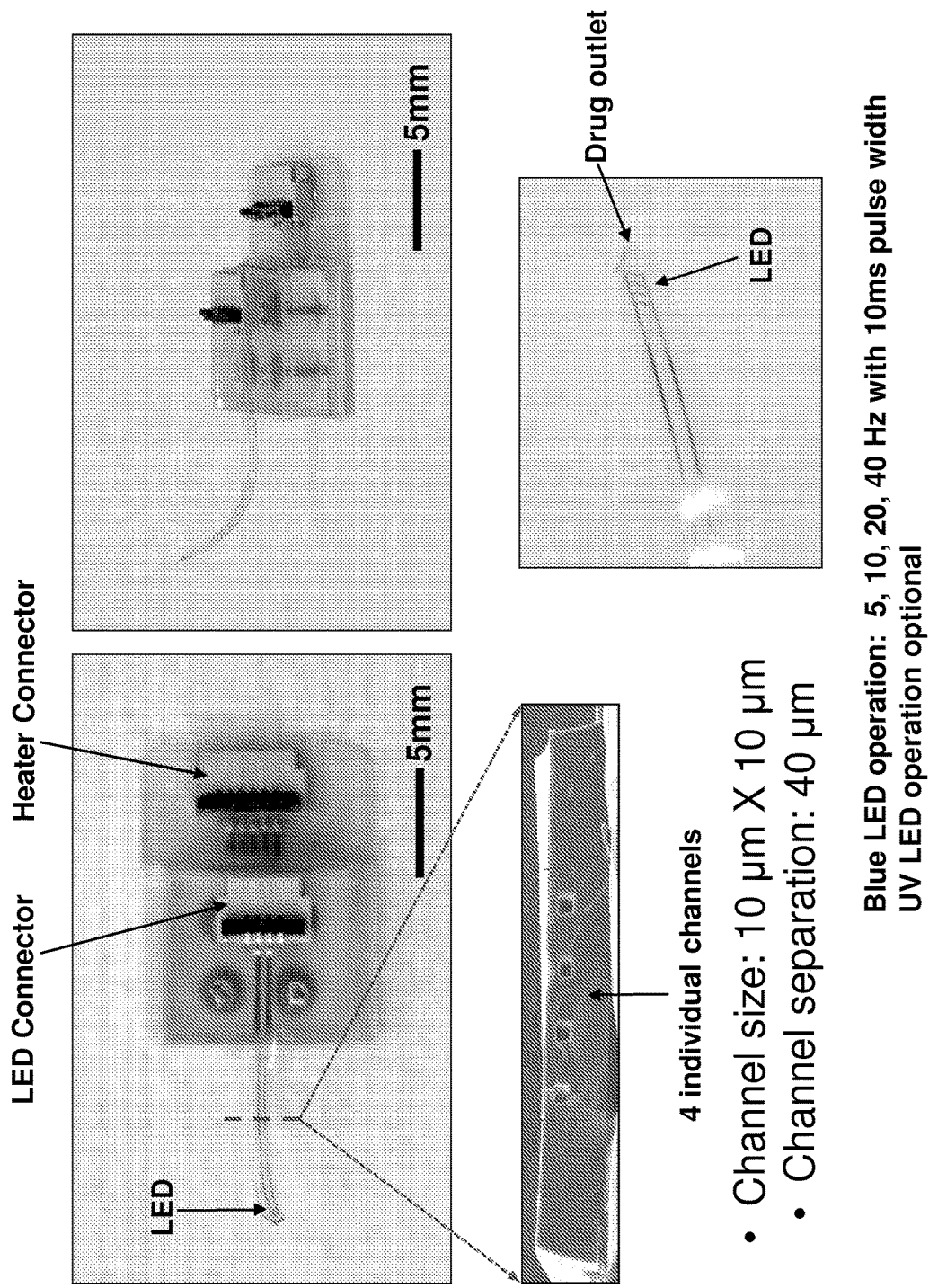

FIG. 68 provides images of a fabricated microfluidic device, providing additional details of the design of the device.

Figure 69:
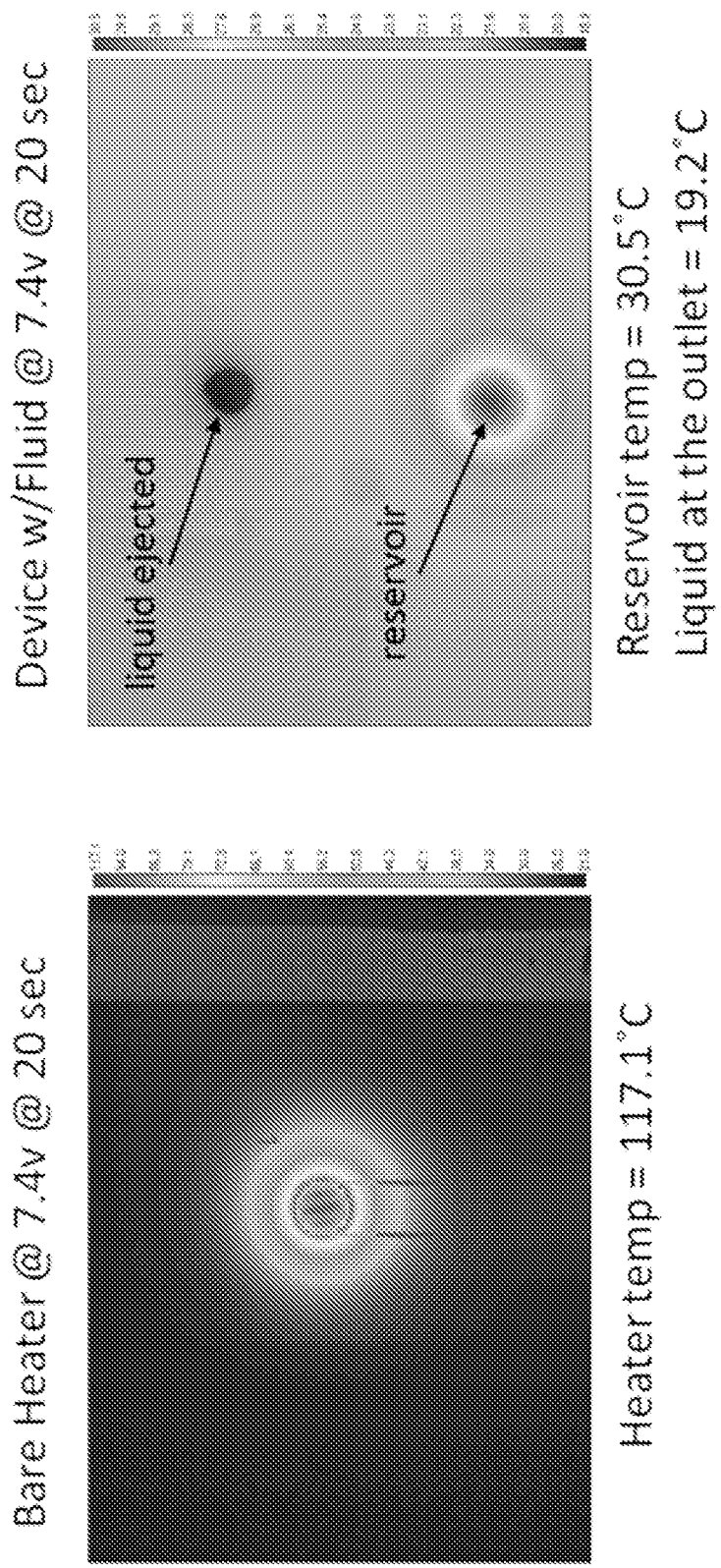

FIG. 69 provides an overview of thermal characteristics for a fabricated microfluidic device embodiment.

Figure 70:
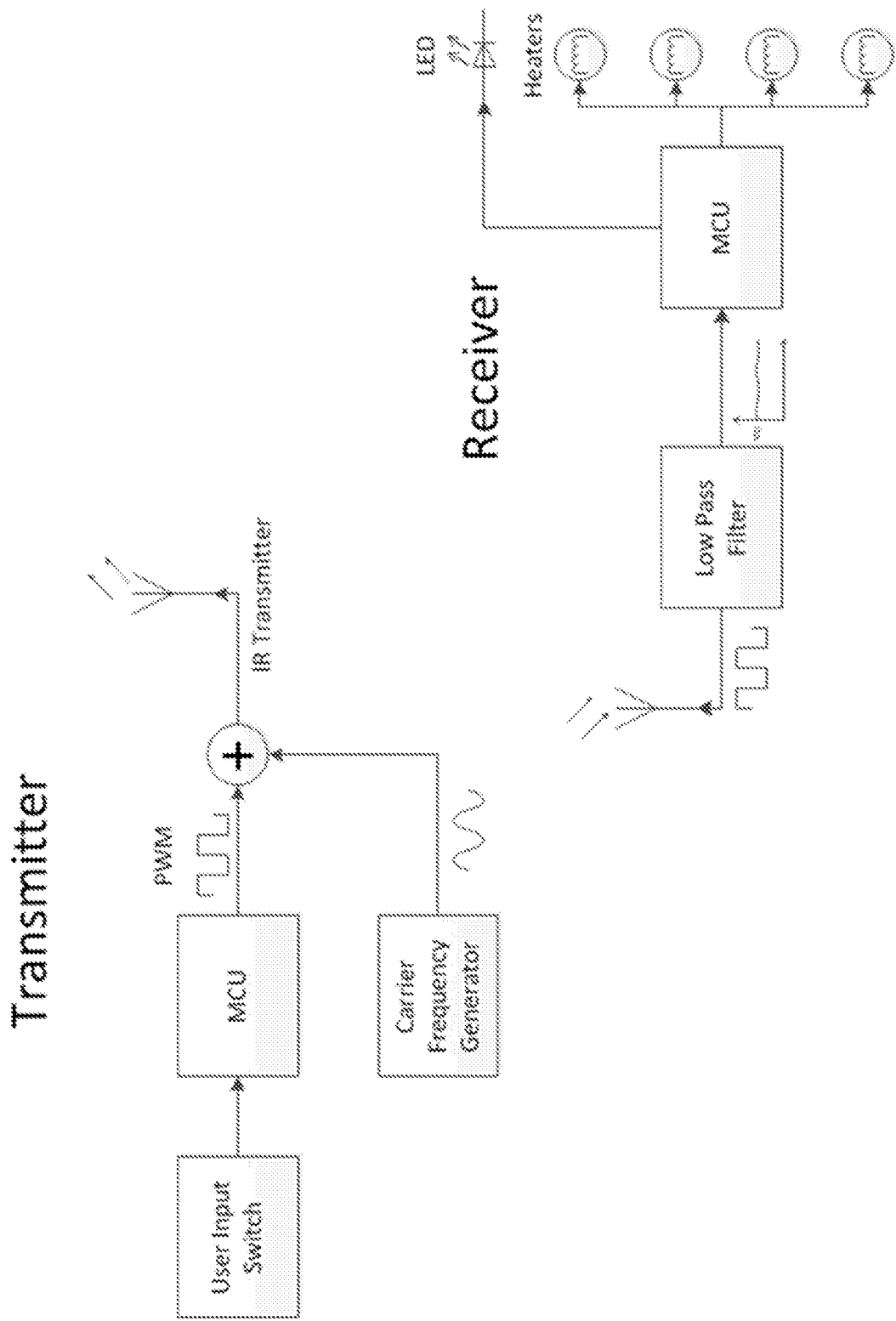

FIG. 70 provides a schematic illustration of a wireless control system embodiment for operation of a microfluidic device.

Figure 71:
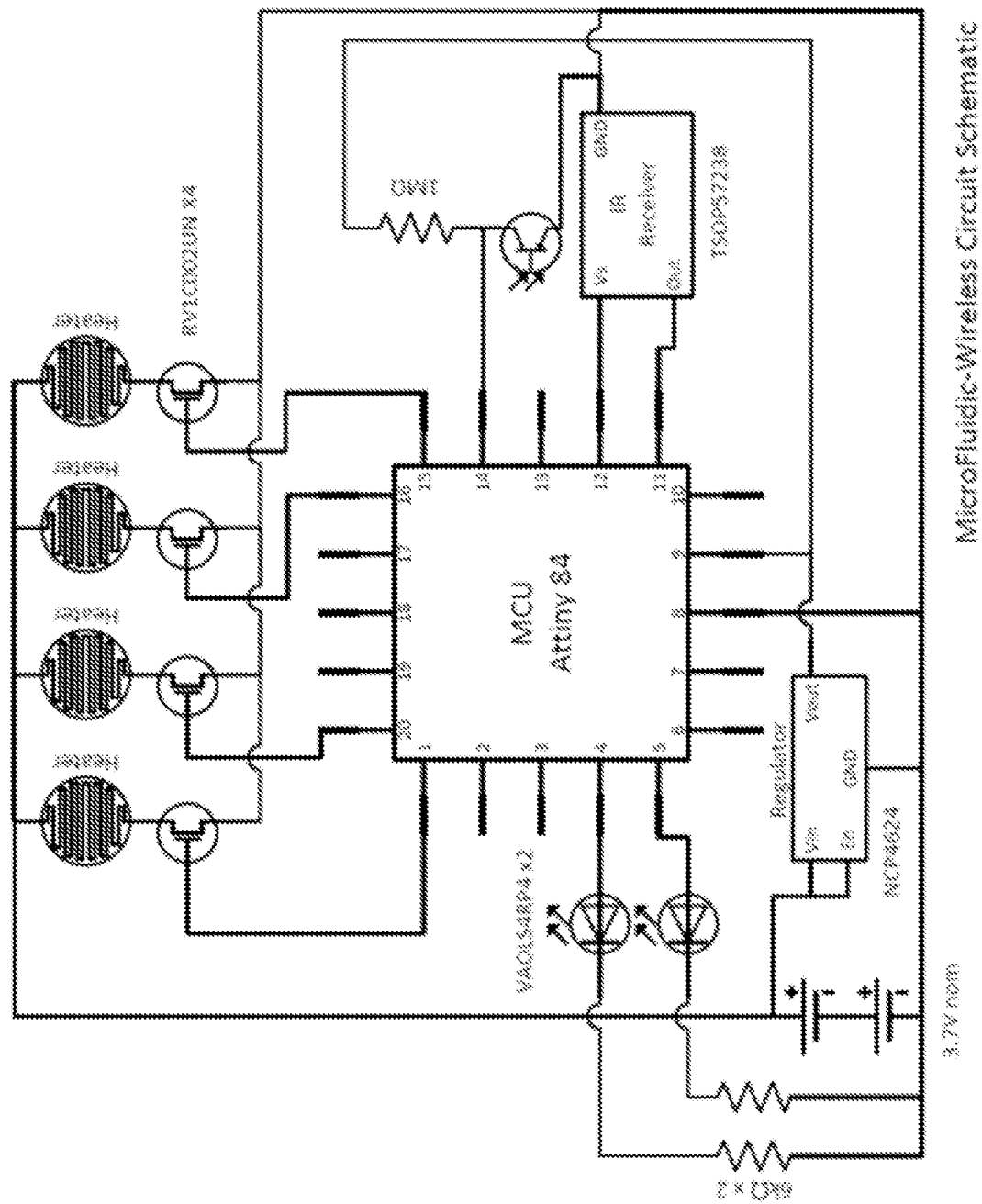

FIG. 71 provides a schematic diagram of a wireless receiver circuit embodiment.

Figure 72:
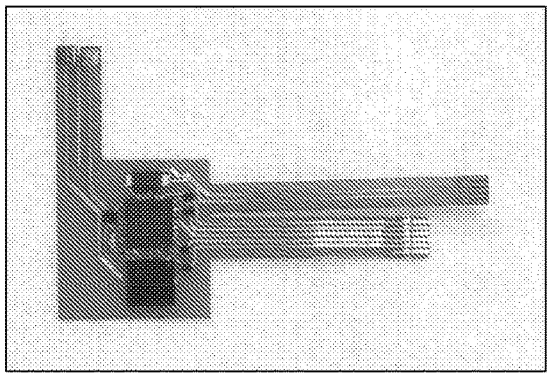
Figure 72:
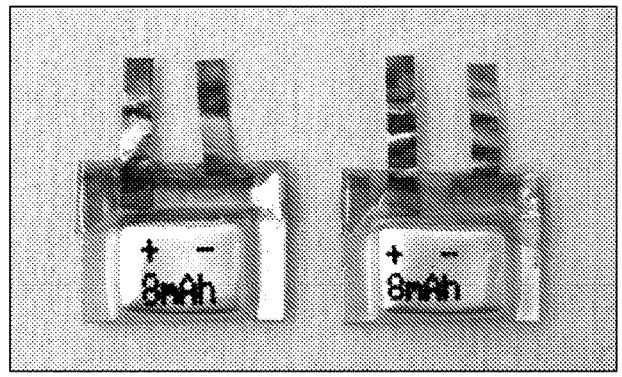

FIG. 72 provides images of a wireless receiver circuit on a flexible printed circuit board and batteries.

Figure 73:
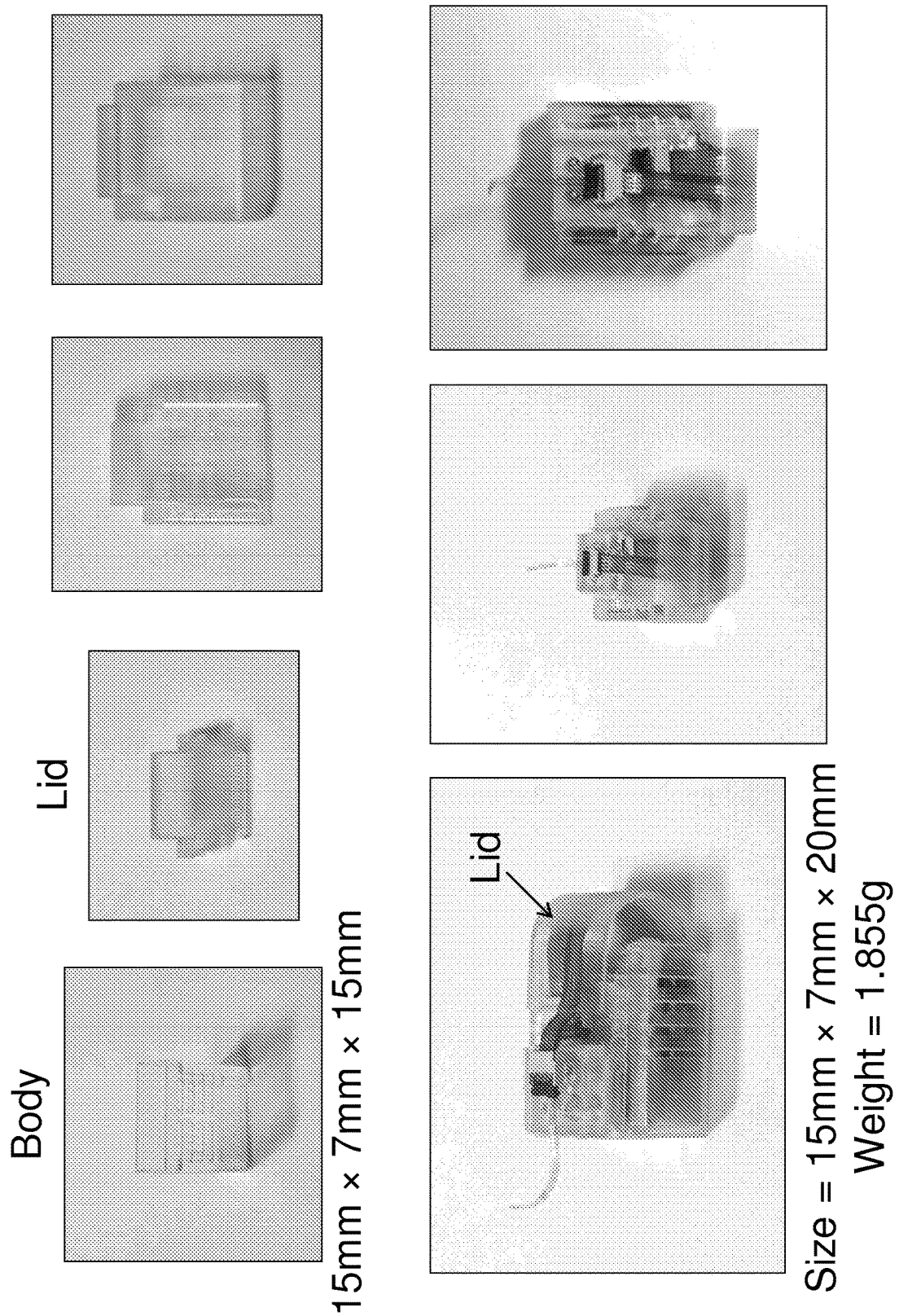

FIG. 73 provides images of a case and housing for a microfluidic device embodiment.

Figure 74:
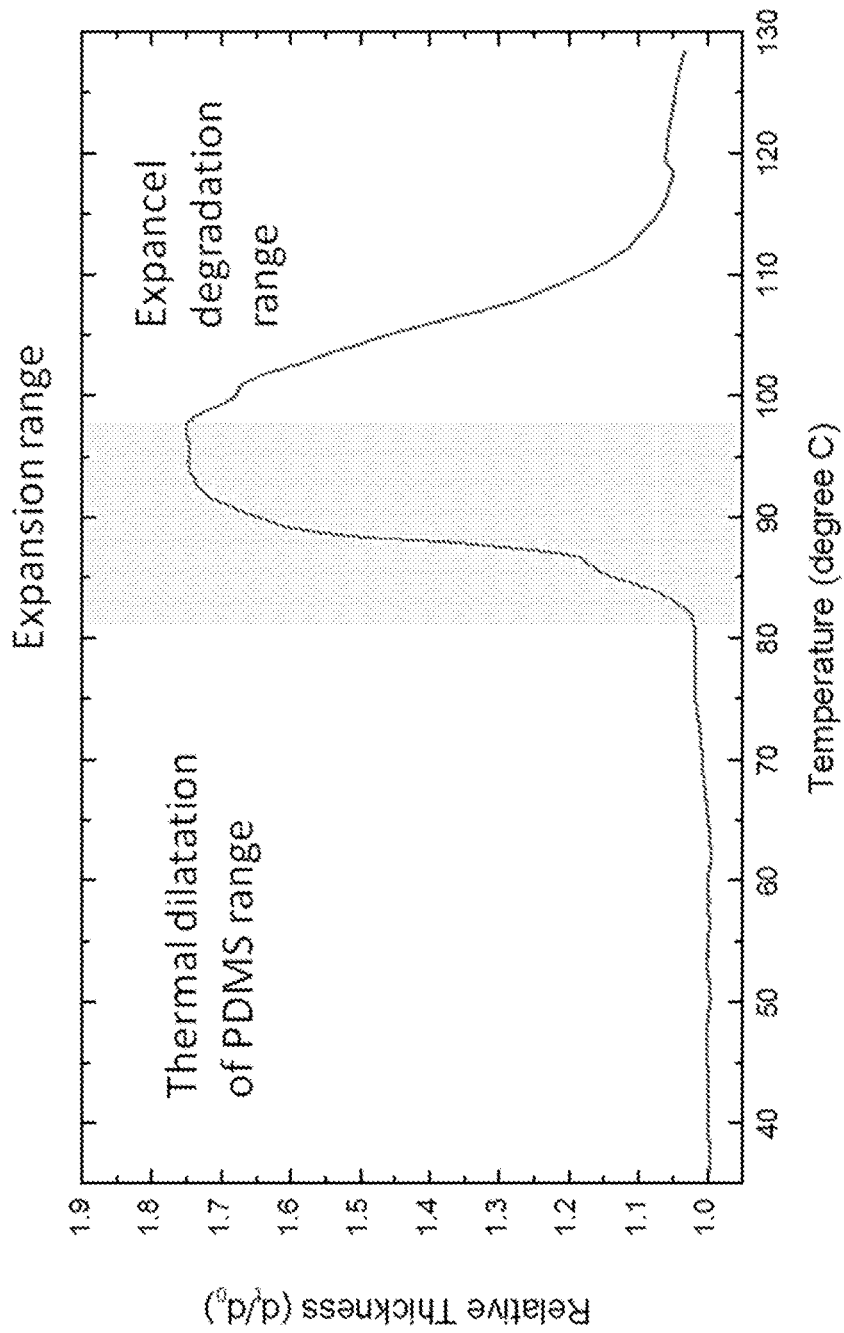

FIG. 74 provides data detailing the thermal expansion of an expandable layer in a microfluidic device.

Figure 75:
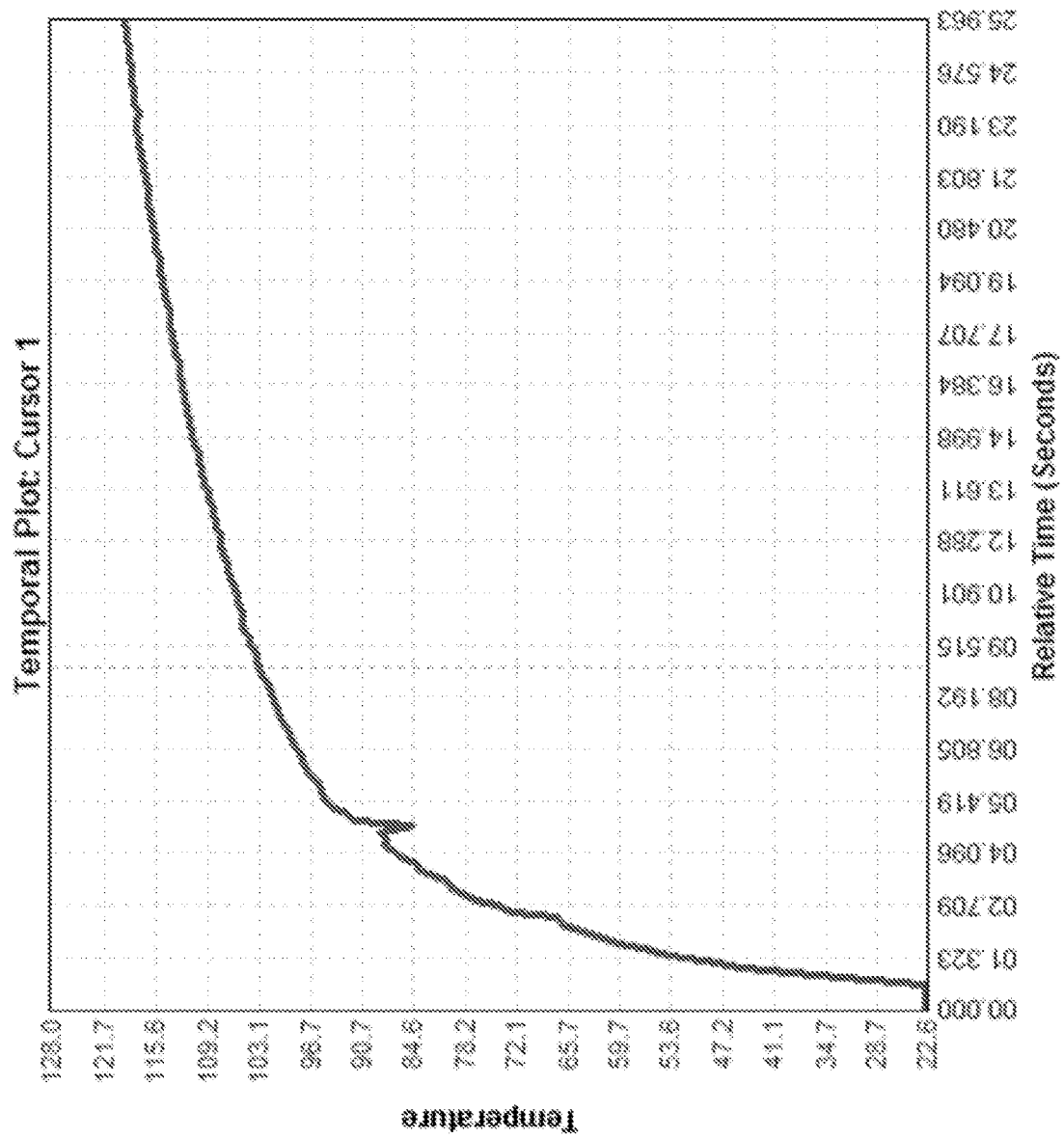

FIG. 75 provides data showing the temporal variation of the temperature of a heater with no polymer coating on it.

Figure 76:
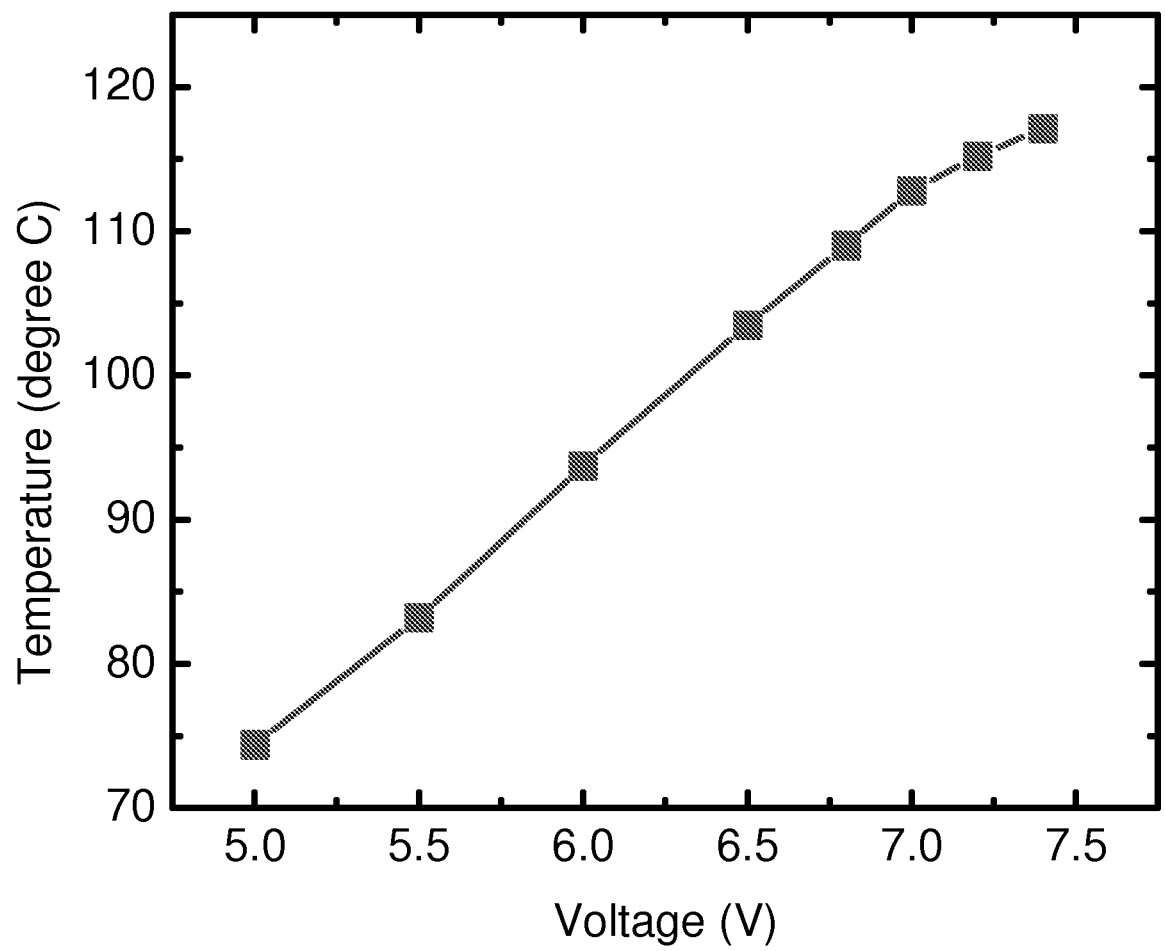

FIG. 76 provides data showing calibration of the heater temperature as a function of the actuation voltage after 20 seconds.

Figure 77:
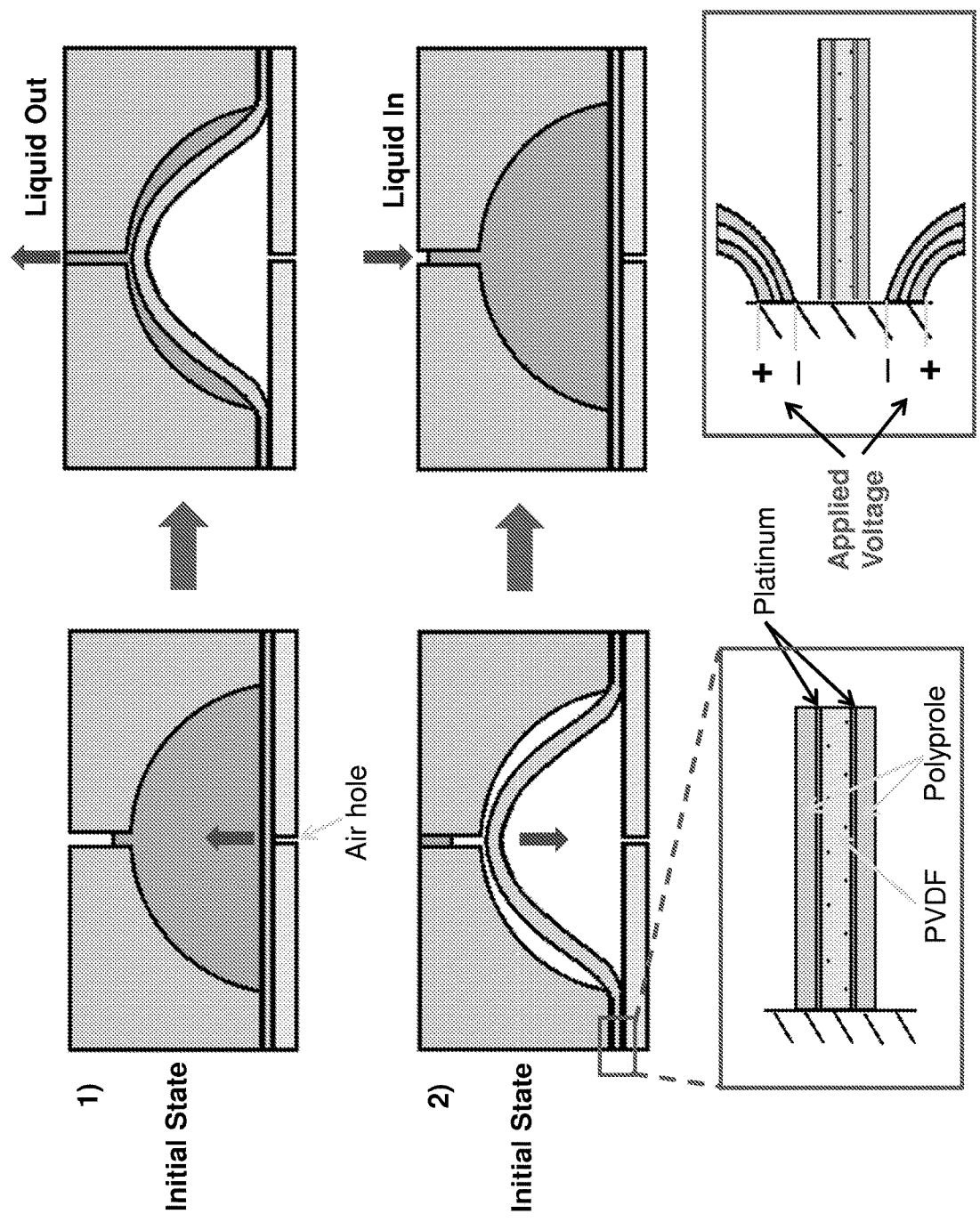

FIG. 77 provides an overview of a device embodiment providing two-way microfluidics.

Figure 78:
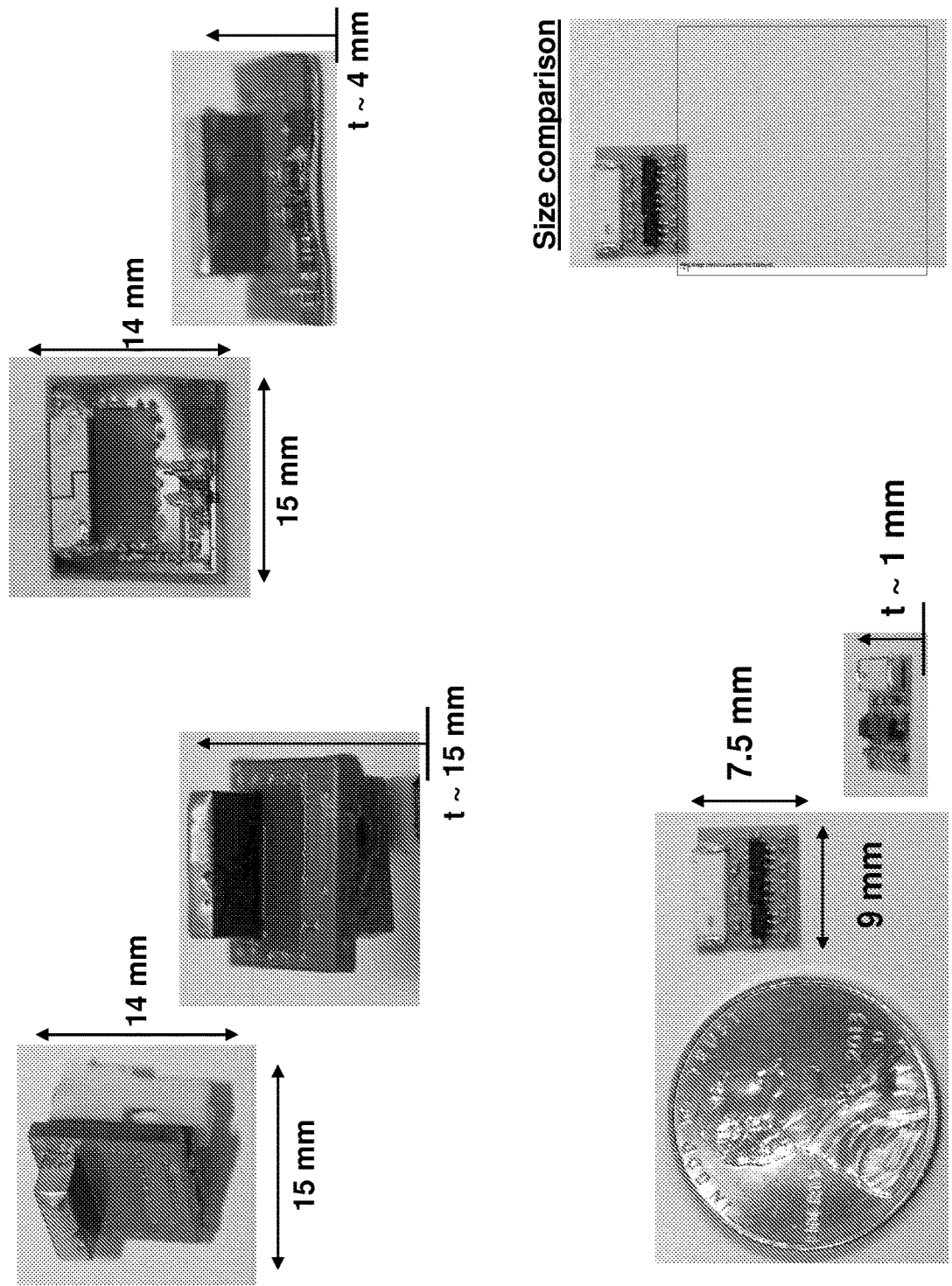

FIG. 78 provides images of implantable device embodiments.

Figure 79:
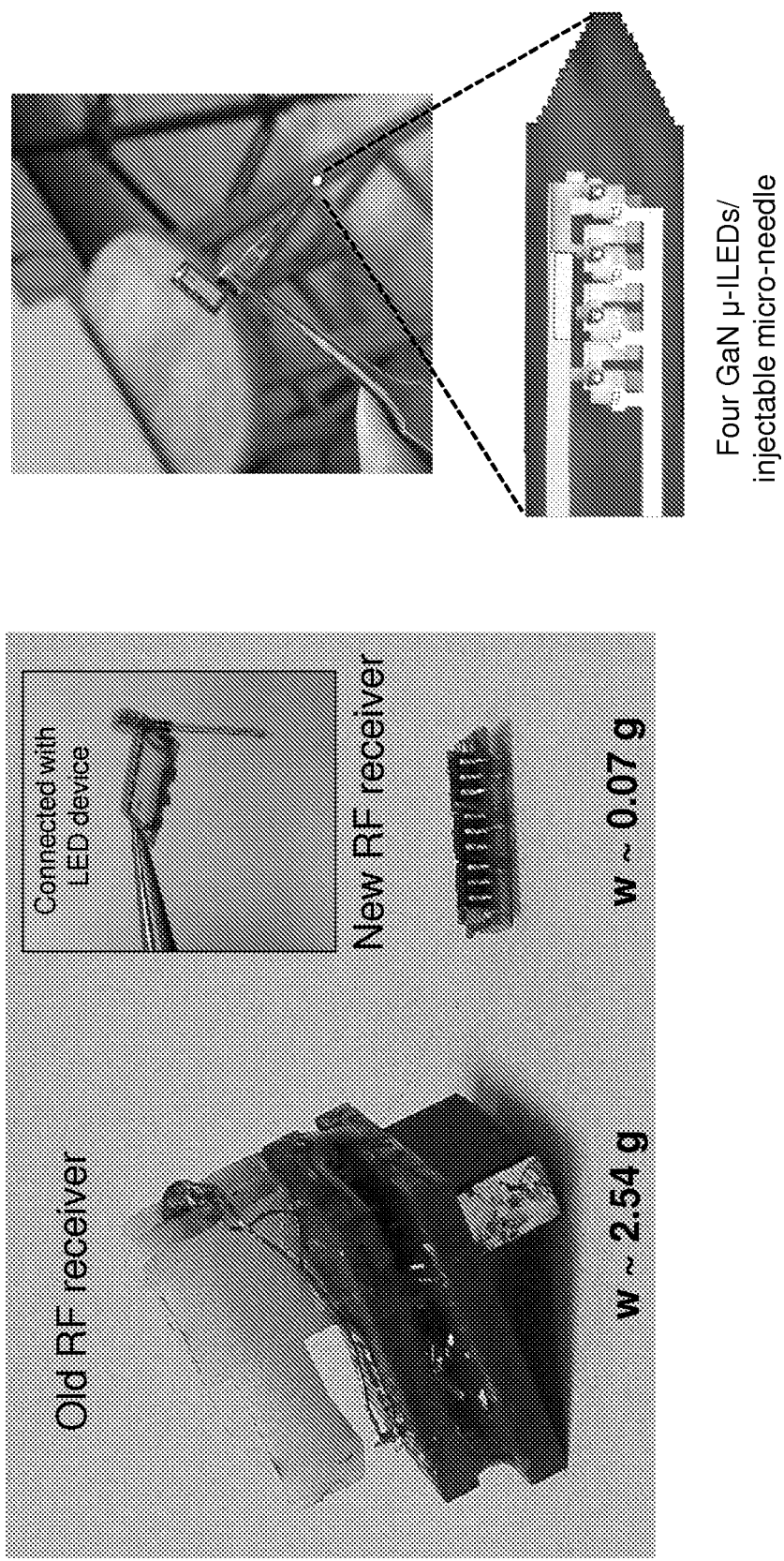

FIG. 79 provides images showing a comparison of device embodiment sizes and an injectable microneedle incorporating GaN LEDs.

Figure 80:
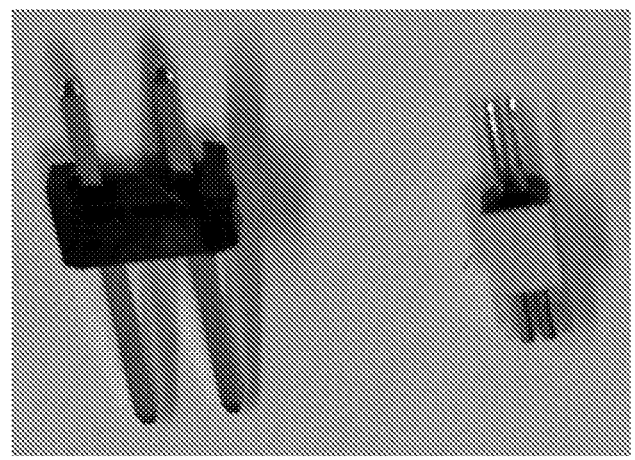
Figure 80:
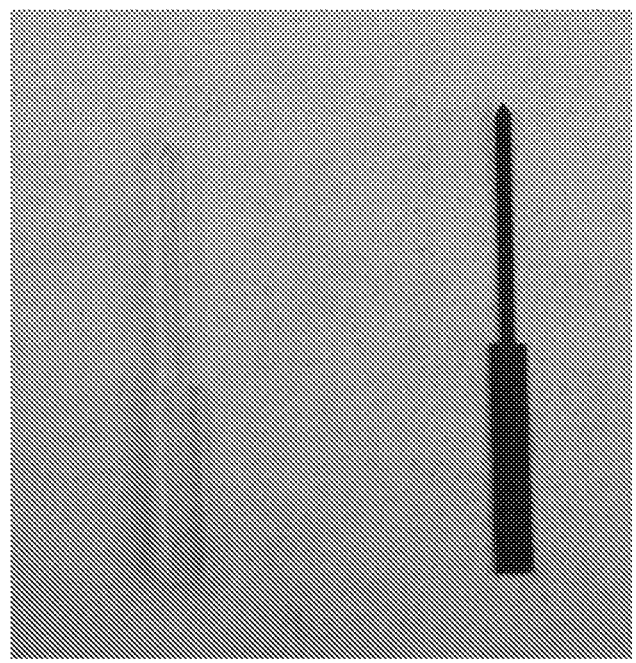

FIG. 80 provides images of device components, illustrating a reduction in size and increase in functionality achievable by the devices, methods and materials of the present invention.

Figure 81:
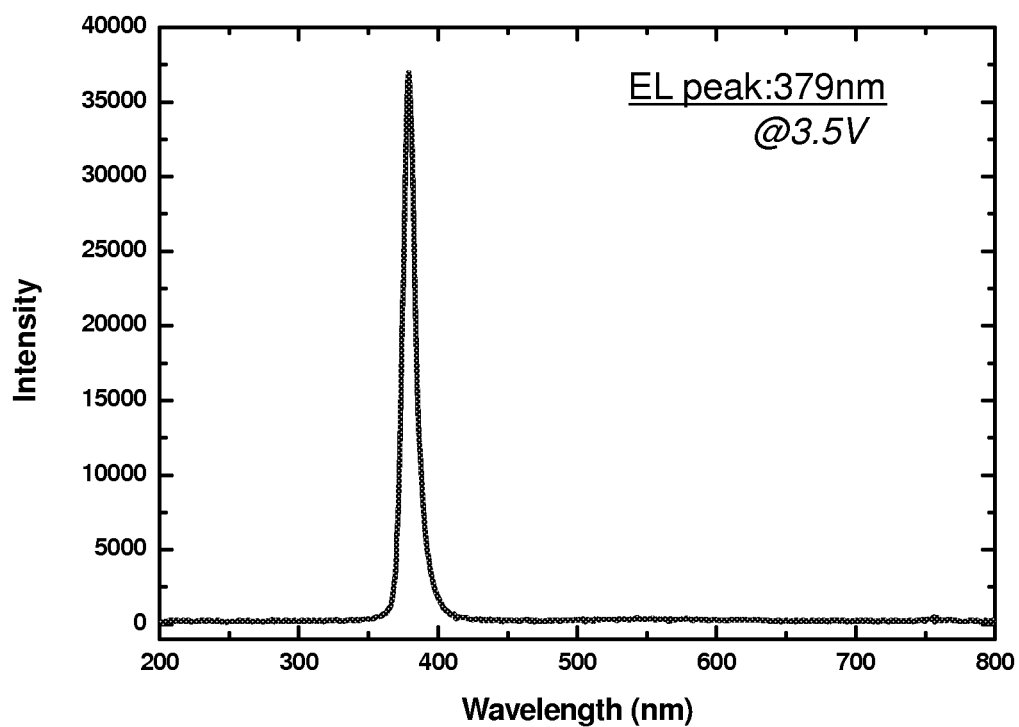
Figure 81:
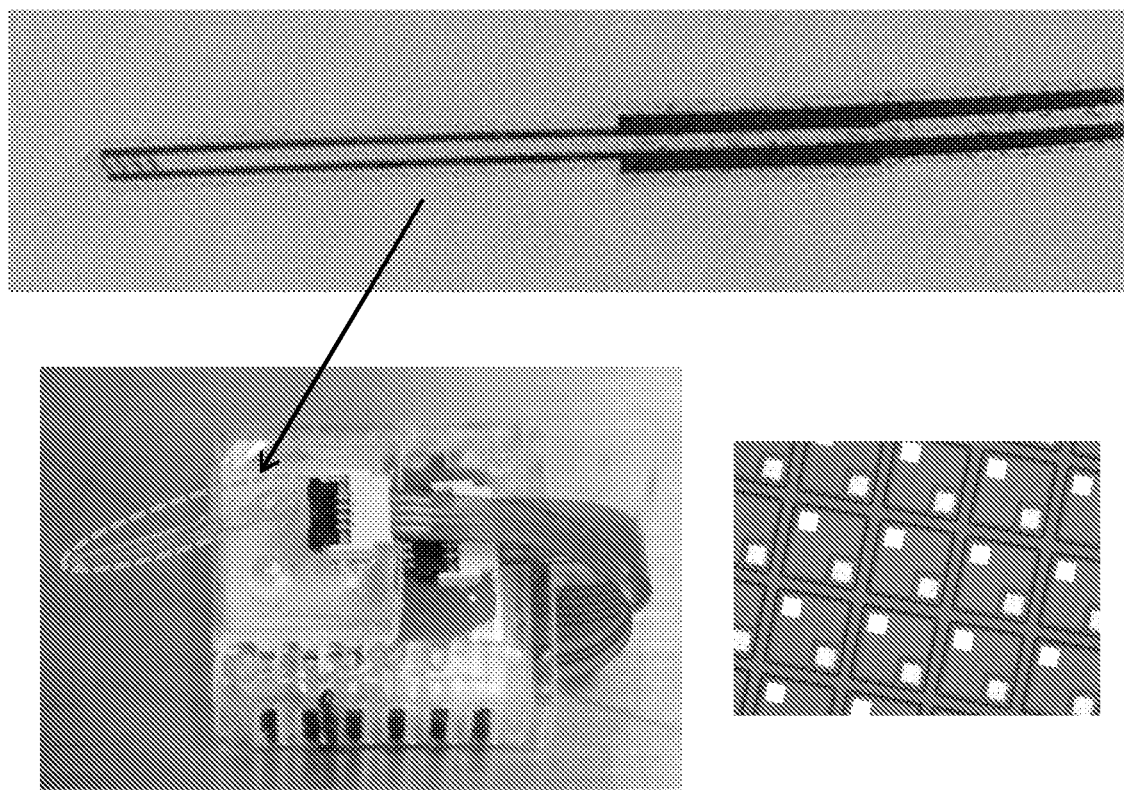

FIG. 81 provides data showing the emission spectrum of a UV μLED with images of the device.

Figure 82:
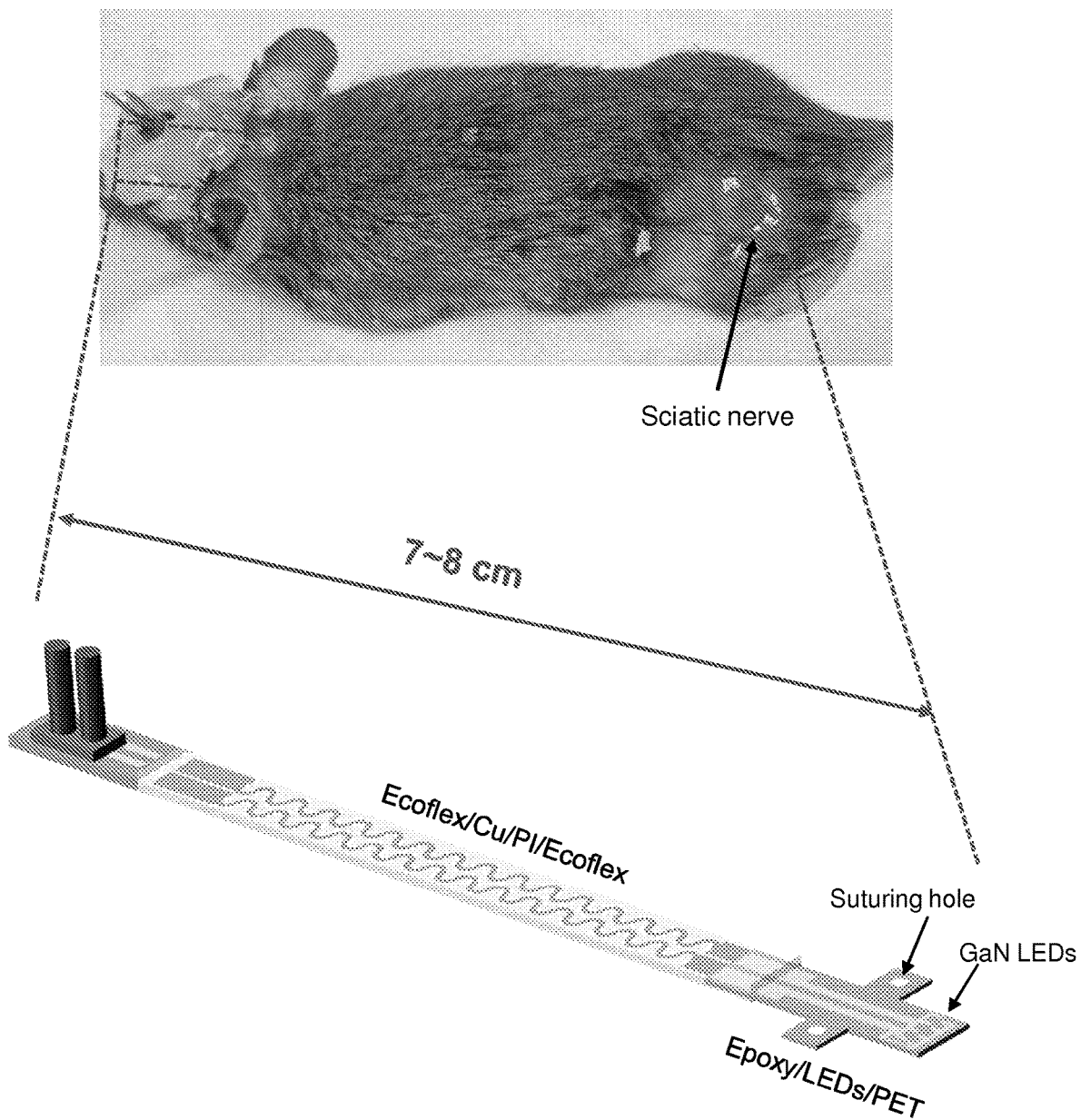

FIG. 82 provides an image of an animal with an implanted device, and a schematic diagram of the implanted device.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Implantable" refers to a device that is inserted into tissue, such as for interfacing with an interior portion of tissue that is not surface-accessible. "Interfacing" refers to measuring and/or controlling one or more parameters associated with the target tissue. For example, a physical parameter such as temperature or electrical potential may be measured and/or controlled. Similarly, a biological parameter, such as concentration of a biologic material, cell surface receptor blocking/activation, membrane porosity, may be measured and/or controlled. Accordingly, interfacing is used broadly to refer to passive measurement of a tissue or cell property, active control of a tissue or cell property, or both.

"Target tissue" refers to a tissue in which the device is implanted and, more specifically, a specific portion of tissue for which interfacing is desired. Target tissue is used broadly to refer to an interior region of tissue that is beneath a tissue surface and so is not visually or physically accessible without opening up of the tissue. Target tissue may refer to a plurality of cells defined over an interfacing surface area. Alternatively, target tissue may be a single cell, and even components thereof. The ability to package the functional layers in geometries provided herein allows access to individual cell interactions, and components thereof. For example, parameters associated with individual cells may be accessed by configuring the device components and functional devices to correspond to the size of individual cells and also for device positioning so that the functional electronic device is adjacent to an individual cell. Relevant components include cell portions, such as nucleus, mitochondria, cell surface receptors, and related biological pathways. Incorporating tags thereof facilitate interfacing with cellular components by any of the devices provided herein, particularly those having electronic devices that specifically interface with the cellular components.

Arrays of functional electronic devices, including by stacked functional layers or by arrays within an individual layer, facilitate multiple interfacing with different physical parameters, and/or along a plurality of positions within the target tissue, such as a plurality of cells. For example, individual or networks of neurons may be monitored at distinct locations, along with actuators for selectively turning on or blocking neurons at other locations.

"Substrate" refers to a material, layer or other structure having a surface, such as a receiving surface, that is capable of supporting one or more components or devices. A component that is "bonded" to the substrate refers to a component that is in physical contact with the substrate and unable to substantially move relative to the substrate surface to which it is bonded. Unbounded components or portions of a component, in contrast, are capable of substantial movement relative to the substrate. In an embodiment, the invention provides devices wherein one or more inorganic semiconductor components, one or more metallic conductor components and/or one or more dielectric components are directly or indirectly bonded to the substrate, for example, via a bonding layer or an adhesive layer. The direct bonding to the substrate may also include components that are embedded, either partially or completely, in the substrate.

"Functional layer" refers to a layer that imparts some functionality to the device. For example, the functional layer may contain semiconductor components, metallic components, dielectric components, optical components, piezoelectric components, etc. that form an electronic device. A "functional electronic device" refers to an electronic device, such as a sensor or actuator that interfaces with tissue in which the device is implanted. The functional layer may comprise multiple layers, such as multiple semiconductor layers, metallic layers or dielectric layers separated by support layers. The functional layer may comprise a plurality of patterned elements, such as interconnects running between electrodes or islands. The functional layer may be heterogeneous or may have one or more properties that are inhomogeneous. "Inhomogeneous property" refers to a physical parameter that can spatially vary, thereby effecting the position of a neutral mechanical plane within a multilayer device to thereby increase the bendability or deformability of the device.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices. Useful semiconductors include those comprising elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, $PbMnTe$, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

A "semiconductor component" broadly refers to any semiconductor material, composition or structure, and expressly includes high quality single crystalline and polycrystalline semiconductors, semiconductor materials fabricated via high temperature processing, doped semiconductor materials, inorganic semiconductors, and composite semiconductor materials.

A "component" is used broadly to refer to an individual part of a device. An "interconnect" is one example of a component, and refers to an electrically conducting structure capable of establishing an electrical connection with another component or between components. In particular, an interconnect may establish electrical contact between components that are separate. Depending on the desired device specifications, operation, and application, an interconnect is made from a suitable material. Suitable conductive materials include semiconductors and metallic conductors.

Other components include, but are not limited to, thin film transistors (TFTs), transistors, diodes, electrodes, integrated circuits, circuit elements, control elements, photovoltaic elements (e.g. solar cell), sensors, light emitting elements, actuators, piezoelectric elements, receivers, transmitters, microprocessors, transducers, islands, bridges and combinations thereof. Components may be connected to one or more contact pads as known in the art, such as by metal evaporation, wire bonding, and application of solids or conductive pastes, for example. Electronic devices of the invention may comprise one or more components, optionally provided in an interconnected configuration.

"Stacked configuration" refers to an arrangement of various layers and substrates having coincident surface areas, with adjacent layers or substrates positioned on top of each other. In this manner, multiple functionality can be achieved by stacking multiple functional layers on top of each other, without adversely affecting the device form factor or packaged shape. For example, use of ultra-thin functional layers ensures a stacked device remains extremely thin. This is advantageous for insertion as well as minimizing tissue disturbance area after insertion. Importantly, the ultra-thin layout ensures that the interfacing with the target tissue is precisely confined to an interfacing area that can be extremely small, such as corresponding to the cellular scale, even for multiple functional layers.

"Taper" refers to a shape of one end of a device, including layers thereof, that decreases from a maximum lateral dimension. In an aspect the taper is to a distal-most (relative to the tissue surface) end of a substrate having a minimal lateral dimension. In an aspect, the minimal lateral dimension at the distal-most end is a point tip. Such a taper is an advantageous feature to facilitate tissue insertion while minimizing damage during insertion and removal in a similar manner to application of a needle into a tissue for injection of drugs, vaccines or fluids into a patient. In an aspect, the taper is down to a minimum dimension that is less than 10 µm, less than 1 µm, less than 500 nm, or selected from a range that is greater than or equal to 10 nm and less than or equal to 1 µm. The distal end taper may span a longitudinal distance, such as less than 1 mm, less than 500 µm, less than 200 µm, or a range that is less than or equal to 1 mm and greater than or equal to 100 µm. The distal end taper may also be described in terms of a tissue-incident angle, such as an angle that is greater than or equal to 10° and less than or equal to 90°, or between about 30° and 70°. For aspects where the tip end has a visible end that is flat, the tissue-incident angle is measured from an imaginary vertex point where the lines formed by the substrate edges intersect. In general, the smaller the angle the lower the trauma to tissue during insertion, with a balance against the length of the distal end taper, with smaller angles requiring longer taper lengths.

"Neutral mechanical plane" (NMP) refers to an imaginary plane existing in the lateral, b, and longitudinal, l, directions of a device. The NMP is less susceptible to bending stress than other planes of the device that lie at more extreme positions along the vertical, h, axis of the device and/or within more bendable layers of the device. Thus, the position of the NMP is determined by both the thickness of the device and the materials forming the layer(s) of the device. In an embodiment, a device of the invention includes one or more inorganic semiconductor components, one or more metallic conductor components or one or more inorganic semiconductor components and one or more metallic conductor components provided coincident with, or proximate to, the neutral mechanical plane of the device.

"Coincident" refers to the relative position of two or more objects, planes or surfaces, for example a surface such as a neutral mechanical plane that is positioned within or is adjacent to a layer, such as a functional layer, substrate layer, or other layer. In an embodiment, a neutral mechanical plane is positioned to correspond to the most strain-sensitive layer or material within the layer.

"Proximate" refers to the relative position of two or more objects, planes or surfaces, for example a neutral mechanical plane that closely follows the position of a layer, such as a functional layer, substrate layer, or other layer while still providing desired conformability without an adverse impact on the strain-sensitive material physical properties. "Strain-sensitive" refers to a material that fractures or is otherwise impaired in response to a relatively low level of strain. In general, a layer having a high strain sensitivity, and consequently being prone to being the first layer to fracture, is located in the functional layer, such as a functional layer containing a relatively brittle semiconductor or other strain-sensitive device element. A neutral mechanical plane that is proximate to a layer need not be constrained within that layer, but may be positioned proximate or sufficiently near to provide a functional benefit of reducing the strain on the strain-sensitive device element when the device is conformed to a tissue surface. In some embodiments, proximate to refers to a position of a first element within 100 microns of a second element, or optionally within 10 microns for some embodiments, or optionally within 1 microns for some embodiments.

"Electronic device" generally refers to a device incorporating a plurality of components, and includes large area electronics, printed wire boards, integrated circuits, component arrays, biological and/or chemical sensors, physical sensors (e.g., temperature, strain, etc.), nanoelectromechanical systems, microelectromechanical systems, photovoltaic devices, communication systems, medical devices, optical devices and electro-optic devices. An electronic device may sense a property of the target tissue and/or may control a property of the target tissue.

"Sensing" and "sensor" refers to a functional electronic device or device component useful for detecting the presence, absence, amount, magnitude or intensity of a physical, biological state, and/or chemical property. Useful electronic device components for sensing include, but are not limited to electrode elements, chemical or biological sensor elements, pH sensors, temperature sensors, strain sensors, mechanical sensors, position sensors, optical sensors and capacitive sensors. Useful functional electronic devices include various device components operably arranged to provide electrodes for detecting adjacent electric potential, sensors for detecting a biological condition (e.g., disease state, cell type, cell condition) or a chemical, pH, temperature, pressure, position, electromagnetic radiation (including over desired wavelengths such as associated with a fluorescent dye injected into tissue), electric potential.

"Actuating" and "actuator" refers to a functional electronic device or device component useful for interacting with, stimulating, controlling, or otherwise affecting an external structure, material or fluid, for example a target tissue that is biological tissue. Useful actuating elements include, but are not limited to, electrode elements, electromagnetic radiation emitting elements, light emitting diodes, lasers and heating elements. Functional electronic devices include actuators that are electrodes for providing a voltage or current to a tissue, sources of electromagnetic radiation for providing electromagnetic radiation to a tissue, such LEDs. Actuators also include ablation sources for ablating tissue, thermal sources for heating tissue, displacement sources for displacing or otherwise moving a tissue, fluid reservoirs, such as reservoirs of biologics or chemicals for releasing biologics or chemicals to affect biological function, such as a biological response including cell death, cell proliferation, or cell therapy by application of biologics or chemicals.

"Removable adhesive layer" and "releasable adhesive layer" are used interchangeably to refer to a material that is physically and/or chemically removed under pre-selected or predetermined conditions such as conditions of time, pressure, temperature, chemical or biological composition, and/or electromagnetic radiation. In an embodiment, for example, a releasable adhesive layer is removed via a processes selected from the group consisting of decomposition, disintegration, dissolution, hydrolysis, resorption, bioresporption, photodecomposition, and depolymerization, optionally at a preselected time or at a preselected rate or in response to a preselected set of conditions or change in conditions. In an embodiment, for example, a selectively removable material is removed by undergoing a phase change, such as melting or sublimation, resulting in loss or relocation of the material, optionally at a preselected time or at a preselected rate or in response to a preselected set of conditions or change in conditions. The pre-selected condition(s) may occur naturally, for example, provided by conditions of a device environment (e.g., ambient temperature, pressure, chemical or biological environment, natural electromagnetic radiation, etc.) or may occur via artificial condition(s) provided to, or within, a transient electronic device, such as a user or device initiated temperature, pressure, chemical or biological environment, electromagnetic radiation, electronic conditions. When the releasable adhesive layer of a transient electronic device is exposed to the condition(s) that initiate removal of the material, the releasable adhesive layer may be substantially completely removed, completely removed or incompletely removed at a "pre-selected time" or at a "pre-selected rate". A selectively removable material that is "substantially completely" removed is 95% removed, or 98% removed, or 99% removed, or 99.9% removed, or 99.99% removed, but not completely (i.e., 100%) removed.

A "pre-selected time" refers to an elapsed time from an initial time, to. For example, a pre-selected time may refer to an elapsed time from a component/device fabrication or deployment, to a critical time, to, for example, when the thickness of a releasable adhesive layer exposed to a pre-selected condition(s) reaches zero, or substantially zero (10% or less of initial thickness, 5% or less of initial thickness, 1% or less of initial thickness). In an aspect, the time-scale for removal is on the order of minutes or less, and is appropriate for tissue implantation applications. In an aspect, the preselected time is calculated according to:

$$t_c = \frac{4\rho_m M(H_2O)}{kw_0 M(m)} \frac{\sqrt{\frac{kh_0^2}{D}}}{\tanh\sqrt{\frac{kh_0^2}{D}}};$$

where $t_c$ is the critical time, $\rho_m$ is the mass density of the material, $M(H_2O)$ is the molar mass of water, $M(m)$ is the molar mass of the material, $h_0$ is the initial thickness of the material, $D$ is the diffusivity of water, $k$ is the reaction constant for the dissolution reaction, and $w_0$ is the initial concentration of water.

"Degradable" refers to material that is susceptible to being chemically and/or physically broken down into smaller segments. Degradable materials may, for example, be decomposed, resorbed, dissolved, absorbed, corroded, de-polymerized and/or disintegrated. In some embodiments, the invention provides degradable devices or selected portions of the device that are degradable, such as adhesive layers, substrates, encapsulating layers, or barrier layers, in response to a stimulus.

"Bioresorbable" refers to a material that is susceptible to being chemically broken down into lower molecular weight chemical moieties by reagents that are naturally present in a biological environment. In an in-vivo application, the chemical moieties may be assimilated into human or animal tissue. A bioresorbable material that is "substantially completely" resorbed is highly resorbed (e.g., 95% resorbed, or 98% resorbed, or 99% resorbed, or 99.9% resorbed, or 99.99% resorbed), but not completely (i.e., 100%) resorbed. In some embodiments, the invention provides bioresorbable devices, devices or selected portions of the device that are bioresorbable, such as adhesive layers, substrates, encapsulating layers, or barrier layers.

"Biocompatible" refers to a material that does not elicit an immunological rejection or detrimental effect, referred herein as an adverse immune response, when it is disposed within an in-vivo biological environment. For example, in embodiments a biological marker indicative of an immune response changes less than 10%, or less than 20%, or less than 25%, or less than 40%, or less than 50% from a baseline value when a biocompatible material is implanted into a human or animal. Alternatively, immune response may be determined histologically, wherein localized immune response is assessed by visually assessing markers, including immune cells or markers that are involved in the immune response pathway, in and adjacent to the implanted device. In an aspect, a biocompatible device does not observably change immune response as determined histologically. In some embodiments, the invention provides biocompatible devices configured for long-term implantation, such as on the order of weeks to months, without invoking an adverse immune response. The implantation does contemplate some immune response as may occur for any minimally invasive procedures, such as needle insertion into tissue, so long as the immune response is locally confined, transient and does not lead to large-scale inflammation and attendant deleterious effects.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal. In some embodiments, the invention provides bioinert devices.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component). In this manner, a delivery substrate may be described as indirectly supporting a device component through intermediate components corresponding to an adhesive layer and a substrate.

"Island" refers to a relatively rigid component of an electronic device comprising a plurality of semiconductor components. "Bridge" refers to structures interconnecting two or more islands or one island to another component. Specific bridge structures include semiconductor and metallic interconnects. In an embodiment, a device of the invention comprises one or more semiconductor-containing island structures, such as transistors, electrical circuits or integrated circuits, electrically connected via one or more bridge structures comprising electrical interconnects. The bridge structures may be wavy (connected to wavy substrate), serpentine (in plane curvature) and/or in a pop-up (out of plane curvature) configuration, as described in various patent documents listed below in TABLE R1 (e.g., Atty refs. 134-06US; 213-07, 38-04D), which are specifically incorporated by reference herein.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50% or optionally 90%, of the external surfaces of the structure is surrounded by one or more structures. "Completely encapsulated" refers to the orientation of one structure such that it is completely surrounded by one or more other structures. The invention includes devices having partially or completely encapsulated inorganic semiconductor components, metallic conductor components and/or dielectric components, for example, via incorporation a polymer encapsulant, such as biopolymer, silk, a silk composite, or an elastomer encapsulant.

"Barrier layer" refers to a component spatially separating two or more other components or spatially separating a component from a structure, material, fluid or environment external to the device. In one embodiment, a barrier layer encapsulates one or more components. In some embodiments, a barrier layer separates one or more components from an aqueous solution, a biological tissue or both. The invention includes devices having one or more barrier layers, for example, one or more barrier layers positioned at the interface of the device with an external environment.

"Nanostructured material" and "microstructured material" refer to materials having one or more nanometer-sized and micrometer-sized, respectively, physical dimensions (e.g., thickness) or features such as recessed or relief features, such as one or more nanometer-sized and micrometer-sized channels, voids, pores, pillars, etc. The relief features or recessed features of a nanostructured material have at least one physical dimension selected from the range of 1-1000 nm, while the relief features or recessed features of a microstructured material have at least one physical dimension selected from the range of 1-1000 µm. Nanostructured and microstructured materials include, for example, thin films (e.g., microfilms and nanofilms), porous materials, patterns of recessed features, patterns of relief features, materials having abrasive or rough surfaces, and the like. A nanofilm structure is also an example of a nanostructured material and a microfilm structure is an example of a microstructured material. In an embodiment, the invention provides devices comprising one or more nanostructured or microstructured inorganic semiconductor components, one or more nanostructured or microstructured metallic conductor components, one or more nanostructured or microstructured dielectric components, one or more nanostructured or microstructured encapsulating layers and/or one or more nanostructured or microstructured substrate layers.

A "nanomembrane" is a structure having a thickness selected from the range of 1-1000 nm or alternatively for some applications a thickness selected from the range of 1-100 nm, for example provided in the form of a ribbon, cylinder or platelet. In some embodiments, a nanoribbon is a semiconductor, dielectric or metallic conductor structure of an electronic device. In some embodiments, a nanoribbon has a thickness less than 1000 nm and optionally less than 100 nm. In some embodiments, a nanoribbon has ratio of thickness to a lateral dimension (e.g., length or width) selected from the range of 0.1 to 0.0001.

"Dielectric" refers to a non-conducting or insulating material. In an embodiment, an inorganic dielectric comprises a dielectric material substantially free of carbon. Specific examples of inorganic dielectric materials include, but are not limited to, silicon nitride and silicon dioxide. Dielectric materials further include silk, silk composites, elastomers and polymers.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary conformal transfer devices useful in some methods of the invention include elastomeric transfer devices such as elastomeric stamps, molds and masks. The transfer device affects and/or facilitates material transfer from a donor material to a receiver material. In an embodiment, a method of the invention uses a conformal transfer device, such as an elastomeric transfer device (e.g. elastomeric stamp) in a microtransfer printing process, for example, to transfer one or more single crystalline inorganic semiconductor structures, one or more dielectric structures and/or one or more metallic conductor structures from a fabrication substrate to a device substrate.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of a tissue in a biological environment.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In an embodiment, a method of the invention comprises establishing conformal contact between a conformal transfer device and one or more single crystalline inorganic semiconductor structures, one or more dielectric structures and/or one or more metallic conductor structures, for example, in a microtransfer printing process, such as dry transfer contact printing.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components, such as substrate, encapsulating layer, inorganic semiconductor structures, dielectric structures and/or metallic conductor structures, having a low Young's modulus. In an embodiment, a device of the invention has an overall low Young's modulus.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire material.

"Low modulus" refers to materials having a Young's modulus less than or equal to 10 MPa, less than or equal to 5 MPa or less than or equal to 1 MPa. In an aspect, the functional layer has a low modulus and the delivery substrate has a higher Young's modulus, such as 10 times, 100 times, or 1000 times larger than the functional layer Young's modulus.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Described herein are implantable biomedical devices for sensing a parameter associated with a target tissue and/or actuating a target tissue in a biological environment, as well as methods for making and using the implantable biomedical devices. These devices are capable of intimate integration on the soft, curvilinear surfaces of biological tissues as well as for insertion into an interior portion of the biological tissue that is not otherwise accessible. The devices are useful for monitoring and/or treating medical conditions in real time and with high spatial precision. The devices are also useful for controlling the biological state of the tissue surrounding the implanted device. The disclosed devices and methods also include those especially suited for monitoring and/or actuating tissues in-vivo. The approaches rely on specially configured and packaged electronic devices in an ultra-thin layout to minimally disturb tissue during insertion.

Figure 29A:
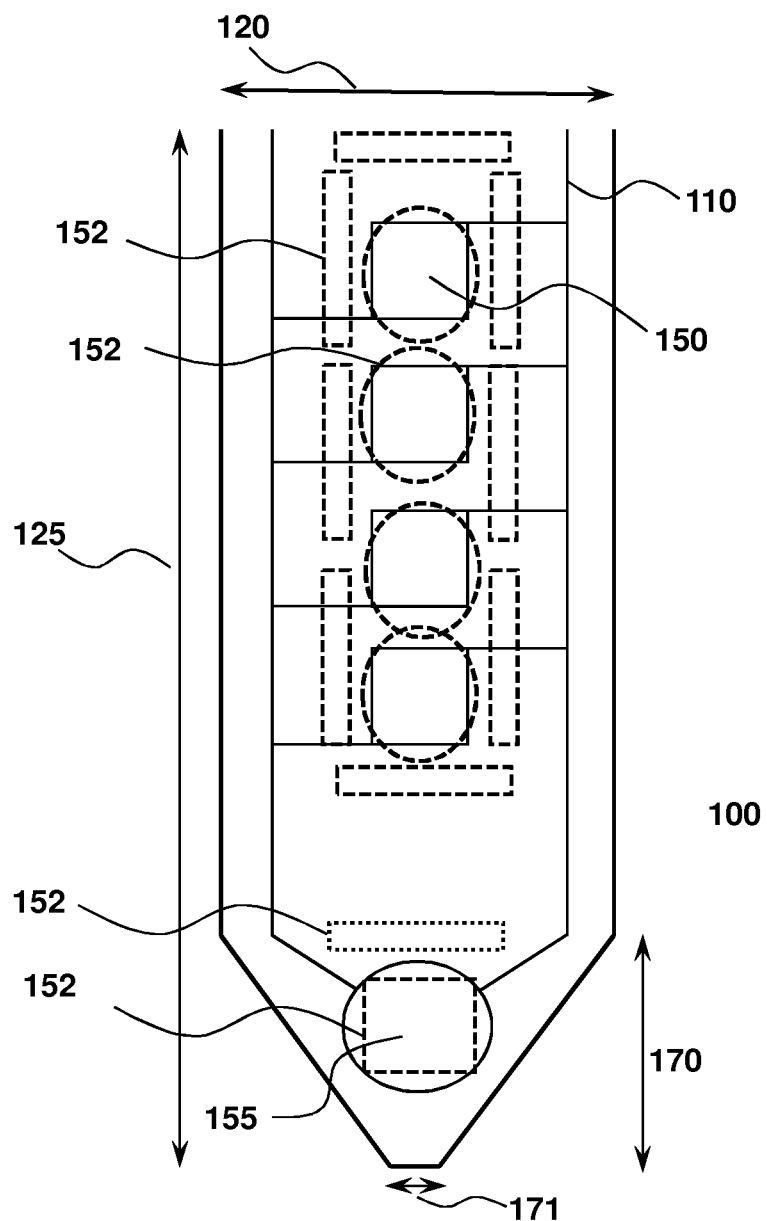
Figure 29B:
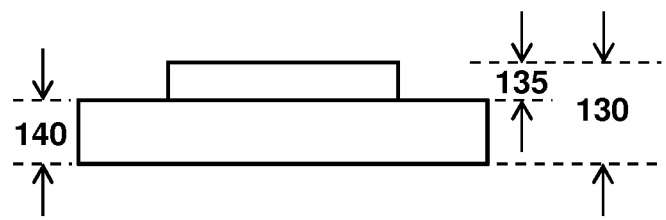

FIGS. 29-30 are highly schematized illustrations of a biomedical device that can be implanted into tissue. Referring to FIG. 29A, a top view of the device showing substrate 100 supporting various device components, including 110 to provide a functional electronic device component that is a µ-ILED 150. In this example, the functional layer comprises a plurality of functional electronic devices that are arranged in a linear array. As desired, the functional electronic devices may have any spacing or patterning, such as distributed to interface with individual cells in a tissue in an optionally independent manner. The lateral dimension is indicated by 120 and the longitudinal length by 125. The substrate has a first end (or "distal end") 170 that is tapered toward a minimum lateral dimension 171, to facilitate insertion into and removal from, soft tissue. In an aspect, minimum lateral dimension corresponds to a distal end observable as a point. In addition, the distal end provides the ability to position any of the devices herein in a precise position relative to a biological component, such as next to a particular cell or cell type, tissue type, cluster of cells, or other position that is not normally accessible without substantial trauma. Optionally, a positioning sensor 155 is provided toward substrate first end 170 for positioning the device in a desired location that is not visually accessible to the person positioning the device. The positioning sensor may be an optical sensor (for detecting light of a desired wavelength), a temperature sensor, a pressure sensor, an electrical sensor, or a combination thereof. As desired, other functional electronic devices of the device may be employed as desired to assist with positioning. For example, a µ-ILED 150 may emit light at a suitable excitation wavelength to excite a fluorescent dye that is contained in the target tissue. FIG. 29B illustrates various thickness, including device component thickness 135, substrate thickness 140 and device component and substrate thickness in combination 130. Of course, due to the ultra-thin layouts of the instant invention, the schematics are not drawn to scale.

Optionally, an implantable or surface mounted biomedical device of the invention may further comprise one or more optical structures schematically depicted as elements 152 (shown in dashed lines) in FIG. 29A. Optical structures 152 of the present devices include structures supported by substrate 100 for selectively modulating or otherwise manipulating the intensity, wavelengths, spatial dimensions, etc. outgoing light, for example light originating from the device for interaction with a target tissue, and/or incoming light, such as light directed upon the device, for example light detected by the device. Optical structures 152 of this aspect include fully or partially optically transmissive structures, optically reflective structures and/or optically opaque structures. Optical structures 152 of this aspect include structures for focusing, collimating, spatially filtering, beam shaping, frequency filtering, reflecting and any combination of these. Optical structures 152 of this aspect may comprise one or more thin film structures including thin film multilayer structures or one or more nanostructured and/or microstructured structures and combinations of these. Optical structures 152 of this aspect may comprise a range of materials including conductors, semiconductors, dielectrics, ceramics and combinations of these. Optical structures 152 of this aspect include one or more light baffles, lenses, Fresnel lenses, mirrors, coatings, baffles, cavities, Fabry Perot structures, filters and combinations of these. In an embodiment, for example, a device of the invention includes one or more optical structures 152 having a thickness selected from the range of 50 nm to 50 µm, and optionally for some applications selected from the range of 100 nm to 1 µm, and lateral dimensions lateral dimension selected from a range of 100 nm to 10 mm and optionally for some applications selected from the range of 500 nm to 10 µm. In an embodiment, for example, optical structures 152 of this aspect are positioned on top of, adjacent to, or below a device component of the implantable or surface mounted biomedical device, such as positioned on top of, adjacent to, or below a light source, such as a LED or laser, or a light detector, such as a photodetector.

Figure 30A:
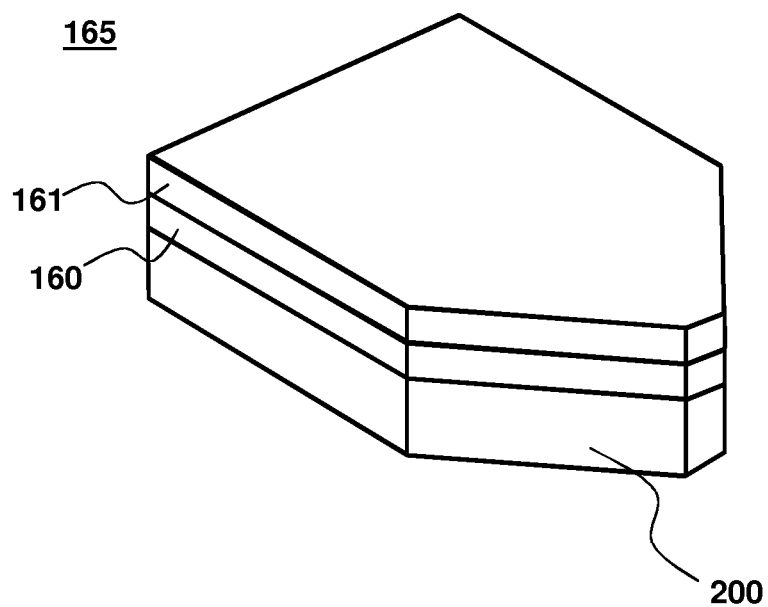
Figure 30B:
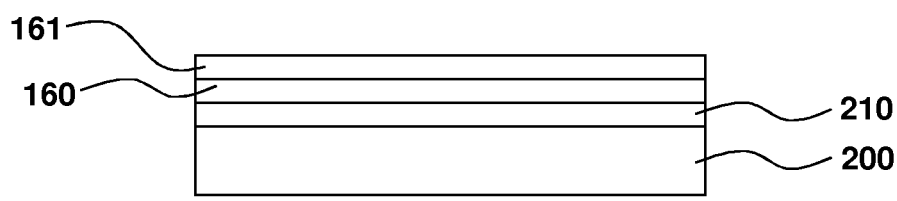

FIG. 30A focuses on the first end of the device that is in a stacked configuration 165. A plurality of functional layers 160 161 are stacked on top of each other. For clarity, the device components and functional electronic devices are not shown. The functional layers are stacked on a delivery substrate 200. As discussed in FIG. 29A, as desired, a positioning probe 150 may instead be supported by the delivery substrate, either on a bottom surface or a top surface as the purpose of the positioning probe is satisfied once the device is implanted and so can be removed along with the delivery substrate 200. Any means known in the art may be used to remove the delivery substrate 200 from an adjacent functional layer 160, such as mechanical means. One example or removing means is provided in FIG. 30B, which illustrates an adhesive layer 210 positioned between delivery substrate 200 and functional layer 160. Upon insertion, a stimulus applied to the adhesive layer 210 results in dissolution of the adhesive layer 210. For example, a solvent may be applied to the adhesive layer 210, such as a naturally-occurring solvent that is biological material or an solvent applied externally after the device is implanted. Examples of other suitable signals include temperature (as the body temperature is generally higher than room temperature), light (which may be applied by a functional layer), pressure, or electric potential. Any of the signals may be inherent in the tissue or externally applied.

Example 1: Injectable, Cellular-Scale Optoelectronics with Applications for Wireless Optogenetics Successful integration of advanced semiconductor devices with biological systems will accelerate basic scientific discoveries and their translation into clinical technologies. In neuroscience generally, and in optogenetics in particular, an ability to insert light sources, detectors, sensors and other components into precise locations of the deep brain could yield versatile and important capabilities. Here, we introduce an injectable class of cellular-scale optoelectronics that offers such features, with examples of unmatched operational modes in optogenetics, including completely wireless and programmed complex behavioral control over freely moving animals. The ability of these ultrathin, mechanically compliant, biocompatible devices to afford minimally invasive operation in the soft tissues of the mammalian brain foreshadow applications in other organ systems, with potential for broad utility in biomedical science and engineering. This example provides cellular-scale optoelectronic devices injected into the brain, which facilitates wireless control over biological function such as behavior. This technology can be generalized for use in other areas of biomedicine.

Electronic systems that integrate with the body provide powerful diagnostic and therapeutic capabilities for basic research and clinical medicine. Recent research establishes materials and mechanical constructs for electronic circuits, light emitting diodes (LEDs), sensors and other components that can wrap the soft, external surfaces of the brain, skin and heart, for diverse function in analytical measurement, stimulation and intervention (1-10). A significant constraint in operating those devices, however, follows from their surface-mounted configurations and inability to provide direct interaction into the volumetric depths of the tissues. Passive penetrating electrodes or optical fibers with interconnections to externally located electronic control/acquisition systems or light sources can be valuable in many contexts, particularly in neuroscience, engineering and surgery (7, 10-14). Direct biological integration is limited by challenges from tissue lesions during insertion, persistent irritation, and engineering difficulties in thermal management, encapsulation, scalable interconnection, power delivery and external control. Many of these issues constrain attempts to insert conventional, bulk LEDs into brain tissue (15), and to use semiconductor nanowire devices as cellular probes or active, in vitro tissue scaffolds (3,16). In optogenetics, engineering limitations of conventional, tethered fiber optic devices restrict opportunities for in vivo use and widespread biological application. As a solution, we developed mechanically compliant, ultrathin multifunctional optoelectronic systems that mount on releasable injection needles for insertion into the depth of soft tissue. These wireless devices incorporate cellular-scale components ranging from independently-addressable multi-colored microscale, inorganic light emitting diodes (μ-ILEDs) to co-located, precision optical, thermal and electrophysiological sensors and actuators.

Figure 1:
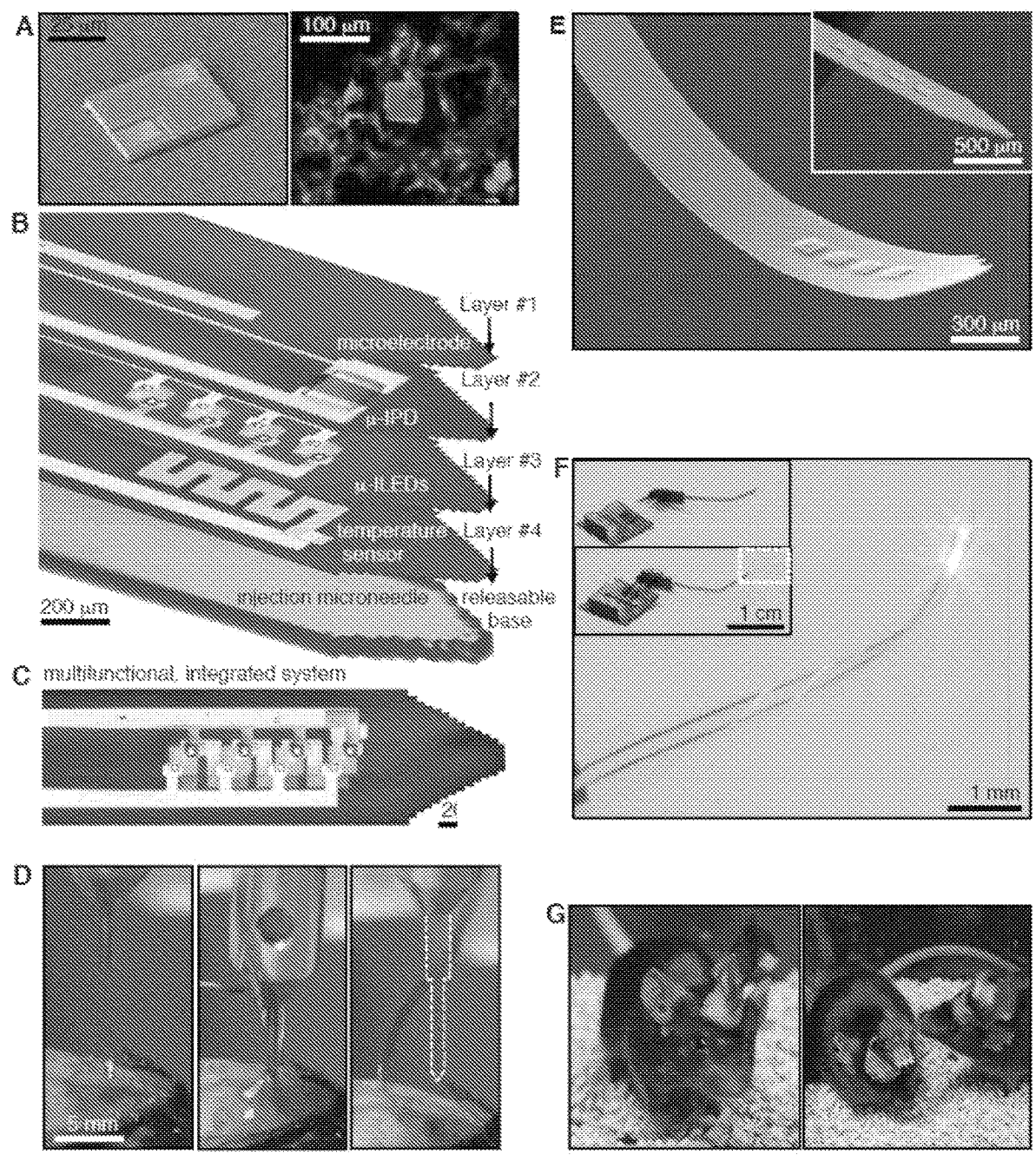
FIG. 1. Injectable, cellular-scale semiconductor devices, with multifunctional operation in stimulation, sensing and actuation. (A) Left, SEM (left) of a GaN µ-ILED (~6.45 µm thick, and 50×50 µm$^2$; contacts—gold; spreading layer—red). Right, fluorescent image of a µ-ILED (blue) with cultured HEK293 cells that express an eYFP tagged transmembrane protein (green). (B) A multifunctional, implantable optoelectronic device, in a tilted exploded view layout illustrating a plurality of functional layers and various components. The system includes layers for electrophysiological measurement (#1; Pt contact pad, microelectrode), optical measurement (#2; silicon p-IPD), optical stimulation (#3; µ-ILED array), and temperature sensing (#4; serpentine Pt resistor), in a stacked configuration and bonded to a releasable structural support (delivery substrate) for injection (microneedle). (C) Top view of the integrated device shown in (B). (D) Process of injection and release of the microneedle. After insertion, aCSF (center) dissolves the external silk-based adhesive. The microneedle is removed (right) leaving only the active device components in the brain. (E) SEM of an injectable array of µ-ILEDs. The total thickness is 8.5 µm. Inset shows rigid device before coating with a passivation layer. (F) Integrated system wirelessly powered with RF scavenging. Insets show a connectorized device unplugged (top) and plugged into (bottom) the wireless power system. (G) Healthy, freely-moving mice with lightweight, flexible (left) and rigid (right) wireless systems powering GaN p-LED arrays in the VTA.

FIG. 1A presents a scanning electron micrograph (SEM) of an isolated GaN μ-ILED, as a constituent component of these systems, and an epifluorescent image of a device among cultured HEK293 cells to illustrate the similar sizes. Each such 'cellular-scale' μ-ILED (6.45 μm thick, 50×50 μm$^2$) uses high-quality epitaxial material grown on sapphire, processed to establish contacts (15×15 μm$^2$ square pads in the corners, and an L-shaped current spreading layer for the p-contact) and then released, to allow transfer printing onto narrow, thin plastic strips. The μ-ILEDs are more than a thousand times smaller than conventional LEDs (typically 100 μm thick, with lateral dimensions of 1 mm$^2$) and fiber optic probes, as discussed subsequently (17). The small sizes of μ-ILEDs allow for spatially precise, cellular-scale delivery of photons, highly effective thermal management, reduced tissue damage, and minimized inflammation for prolonged use in vivo.

Figure 2:
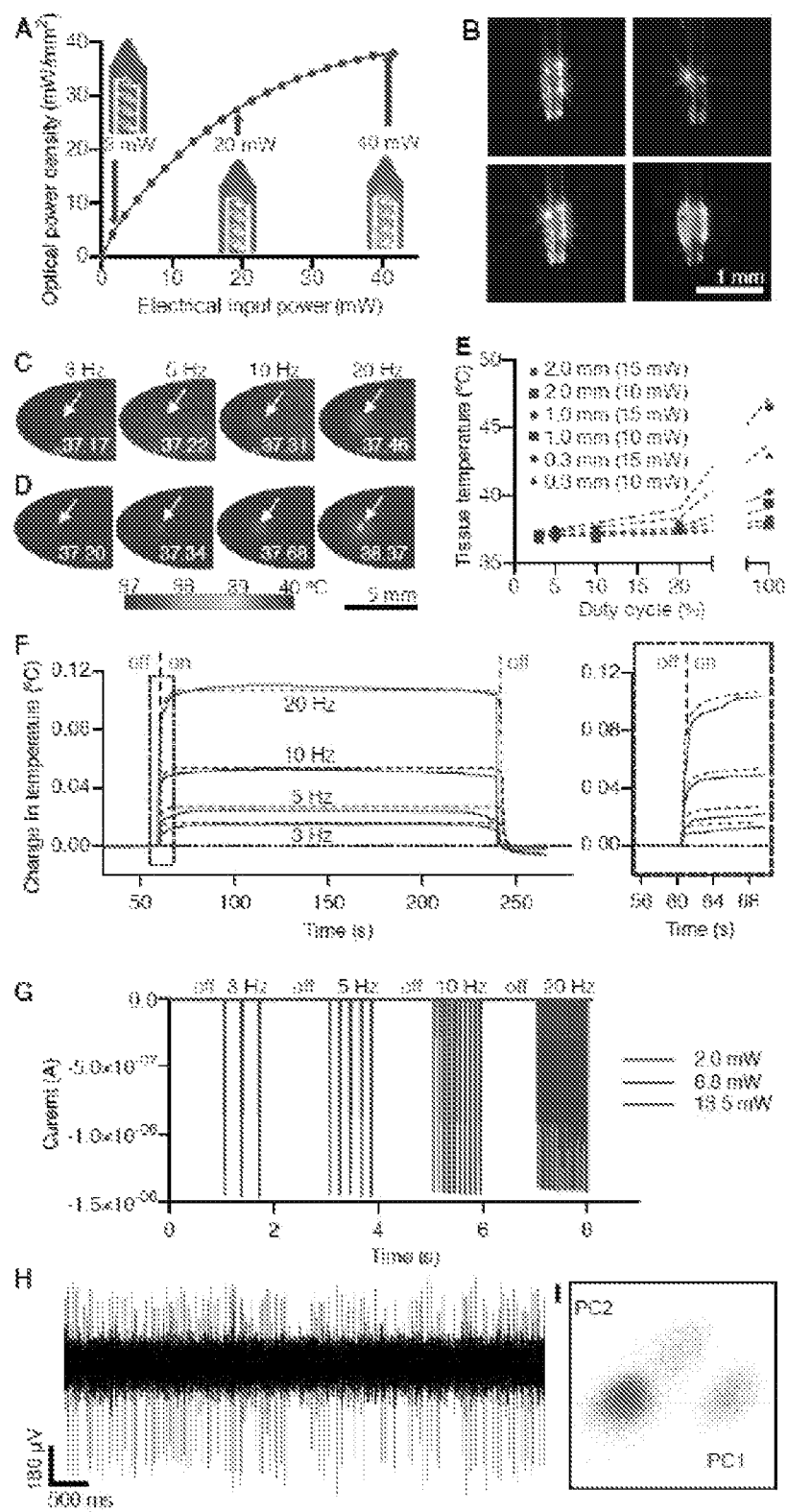
FIG. 2. Optical, thermal, and electrophysiological studies with corresponding theoretical analyses. (A) Total optical power density as a function of electrical input power applied to an array of four GaN µ-ILEDs; optical images show operation at 3, 20 and 40 mW. (B) A single device has one 675 nm GaAs µ-ILED and four 450 nm GaN µ-ILEDs that can be activated independently (upper left and upper right) or concurrently (lower left). The same device is coated in a fluorescein sodium salt phosphor for 530 nm light (lower right). (C) Measured and (D) calculated temperatures in explanted brain tissue near implanted µ-ILEDs at a depth of 0.3 mm and operated at 10 mW of electrical input power. (E) Temperatures in a system similar to that of (C, D), as a function of duty cycle in the operation of the µ-ILEDs and at three different depths of implantation (0.3, 1.0, 2.0 mm) and two different electrical input powers (10, 15 mW). (F) Change in brain temperature as a function of time, measured using an integrated temperature sensor co-located with an array of four µ-ILEDs in a lightly anesthetized mouse. Results evaluated at a peak input electrical power of 8.65 mW, in 3, 5, 10, and 20 Hz pulses (10 ms duration). The vertical dashed lines indicate onset (at 60 s) and offset (at 240 s) of the µ-ILEDs. Colored dashes lines correspond to theoretical models for the temperature. The right frame shows the time dynamics as the device is powered. (G) Change in photocurrent as a function of time, measured using an integrated µ-IPD, for three different electrical input powers to an array of µ-ILEDs: 2.0 mW (blue trace), 8.8 mW (red trace), and 13.5 mW (black trace) at different pulse frequencies (10 ms pulses at 3, 5, 10, and 20 Hz). (H) 5 s extracellular voltage trace of spontaneous neuronal activity gathered using the integrated Pt microelectrode. (I) The same data is filtered and sorted using principal components analysis to identify single units.

Combining μ-ILEDs with electronic sensors and actuators yields multifunctional integrated systems that can be configured in single or multilayer (e.g. stacked) formats. FIGS. 1B and C illustrate the latter option, in which the sensors/actuators include a Pt microelectrode for electrophysiological recording or electrical stimulation (Layer #1; a 20×20 μm$^2$ exposure defines the active area), a microscale inorganic photodetector (μ-IPD) based on an ultrathin silicon photodiode (Layer #2; 1.25 μm thick, 200×200 μm$^2$), a collection of four μ-ILEDs connected in parallel (Layer #3) and a precision temperature microsensor or microheater (Layer #4; Pt serpentine resistor) (more details in FIGS. 5-7)(18). Each layer is processed on separate substrates shaped to match a releasable, photolithographically-defined epoxy microneedle (FIG. 8). A thin layer (~500 nm) of epoxy joins each of the layers in a precisely aligned, stacked configuration. The microneedle bonds to the bottom layer with a thin, bio-resorbable adhesive based on a film of purified silk fibroin, for removal of the microneedle after implantation (FIGS. 1D and 9). The microelectrodes measure extracellular voltage signals in the direct vicinity of illumination, and can also be used for stimulation (FIG. 2H). The temperature sensors determine the degree of local heating, with a precision approaching ~1 mK, and can also be used as microheaters. The μ-IPD can measure the intensity of light from the μ-ILEDs while implanted deep in brain tissue and/or enable basic spectroscopic evaluations of absorption, fluorescence, diffuse scattering, etc. For detailed information see FIGS. 10 and 11 (18).

Injection of such flexible devices into the brain follows steps shown in FIG. 1D. The injected multifunctional optoelectronic systems, have a total thickness of ~20 μm. This exceptionally thin geometry, low bending rigidity, and high degree of mechanical flexibility (FIGS. 1E and F) allows for minimally invasive operation. Wired control schemes use standard transistor-transistor logic (TTL) and are therefore compatible with any readily available electrical commutator. Details on wired powering strategies and demonstration of wired optogenetic functionality in rodent behavioral assays are presented in FIGS. 12, 13, and 14. (18). FIG. 1F shows implementation of a wireless power module based on radiofrequency (RF) scavenging. A custom flexible polyimide film-based lightweight (~0.7 g) power scavenger or a rigid printed circuit board-based scavenger (~2.0 g; FIGS. 1G and 15) can be acutely and temporarily mounted on freely moving animals without constraint in natural animal behavior (FIG. 1G). The entire system comprises a wireless power transmitter and RF signal generator, an RF source (910 MHz; power output between 0.02 and 0.1 mW), a power supply, an RF power amplifier (gain of 49 dB at 910 MHz; power output between 1.6 and 7.9 W), and a panel antenna (gain of 13 dBi), as in FIGS. 15 and 16. The low-frequency signal generator provides user-controlled amplitude modulation for programmed operation. The RF power that reaches the animals, under normal operating conditions at a distance of ~1 m, is between 0.15 and 0.77 mW/cm$^2$, which is substantially smaller than the maximum permissible exposure (MPE) limits (3.03 mW/cm$^2$) for humans in controlled environments (19). Wireless control allows access to complex and ethologically relevant models in diverse environmental settings, including social-interactions, homecage behaviors, wheel running, complex maze navigation tasks, and many other behavioral outputs (FIGS. 1G and 17).

Figure 3:
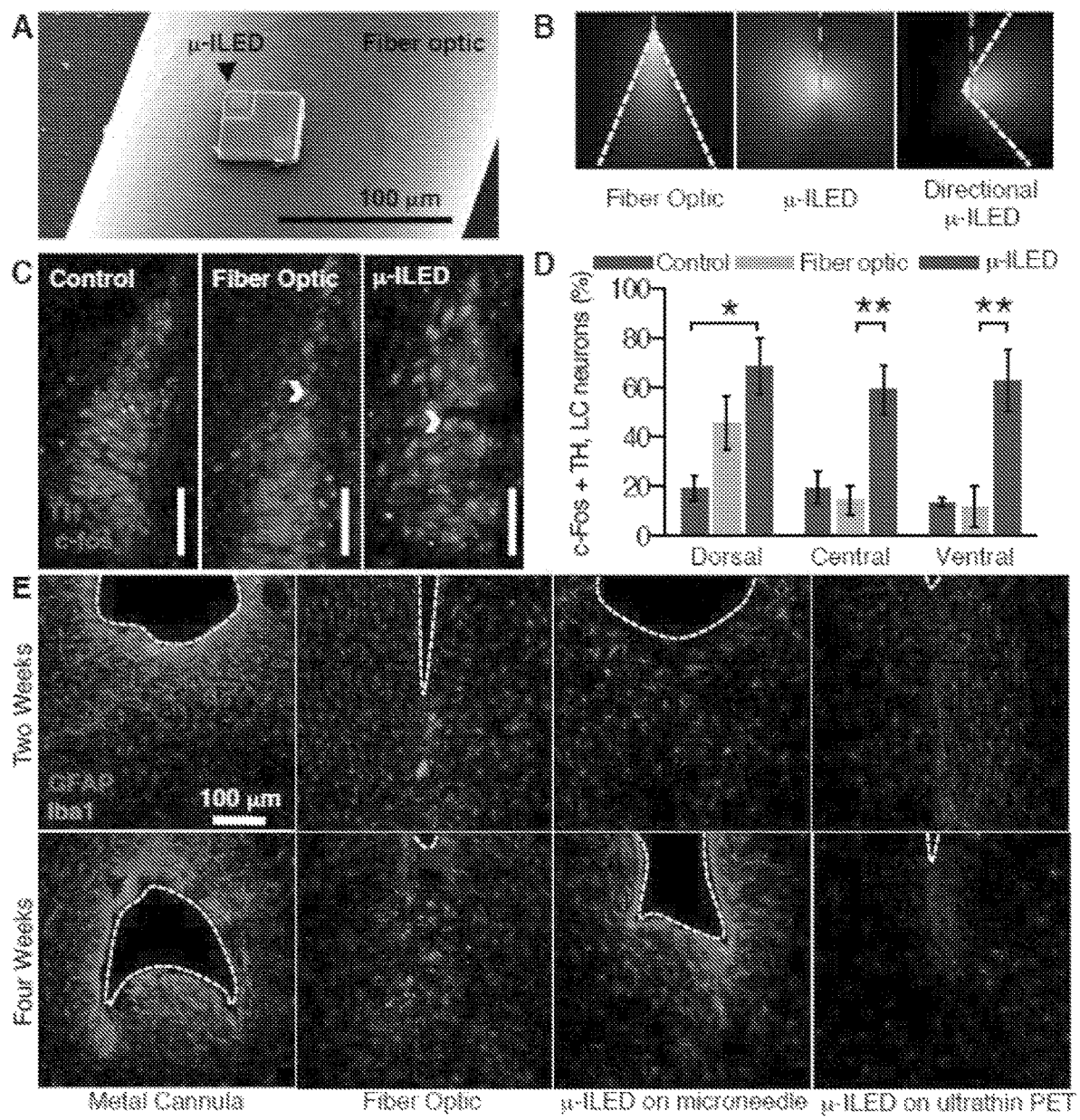
FIG. 3. µ-ILED devices improve spatial targeting and reduce gliosis. (A) Colorized SEM (left) of a µ-ILED mounted on a standard 200 µm fiber optic implant. (B) Left, a dorsal-ventral oriented light cone (outlined in white) from a 200 µm bare fiber implant (blue dash) emitting 465 nm light in 30 µM fluorescein water. Center, near omnidirectional light escape from a µ-ILED device (blue dash) with four 450 nm µ-ILEDs. Right, lateral light escape (outlined in white) from a modified p-ILED device (blue dash) to allow unique spatial targeting including flanking positions along the dorsal-ventral axis of brain loci. (C) Confocal fluorescence images of 30 µm brainstem slices containing the LC show staining for tyrosine hydroxylase (TH) and c-fos in control (left), fiber optic implanted (center), and µ-ILED device implanted (right) animals following 1 hour 3 Hz photostimulation (15 ms pulses, 5 mW output power). Scale bar=100 µm. (D) Fiber optic and µ-ILED treatments specifically increase co-immunoreactivity. Ventral portions of the LC the µ-ILED devices express a higher proportion of tyrosine hydroxylase (TH, blue) and c-fos (red) co-immunoreactive neurons than fiber optic or control groups (n=3 slices per brain from 3 brains for each group; Two-way ANOVA with Bonferroni post-hoc; All error bars represent means±SEM; *p<0.05, **p<0.01). (E) Confocal fluorescence images of 30 µm striatal slices show staining for astrocytes (GFAP, red) and activated microglia (Iba1, green) at the ventral tip of each implanted device (dashed outline). Gliosis is smallest with the µ-ILED device at both two- and four-week time points.

The electrical, optical and thermal characteristics of the devices when operated in biological environments are important for optogenetics and other biomedical applications. FIG. 2A shows the total optical power density of the four μ-ILEDs in this device as a function of electrical input power (more details in FIGS. 18 and 19)(18). This performance is comparable to similarly designed, state-of-the-art conventional GaN LEDs (17). Many optogenetic constructs can be activated with ~1 mW/mm$^2$, at wavelengths near 450 nm (13). These conditions are well matched to the output of the GaN μ-ILEDs. Input power of ~1.0-1.5 mW (FIG. 2A) is sufficient for both activation of the channelrhodopsin-2 (ChR2(H134)) ion channel and precise control of intracellular signaling (cAMP and ERK 1/2) via an optically sensitive G-protein coupled receptor (OPTO-β2) (20) (FIGS. 3C and D, 20 and 21). Wirelessly, at a distance of one meter, the RF scavenger outputs 4.08 mW of electrical power resulting in an optical power density 7 mW/mm$^2$. Other wavelengths are possible using different types of μ-ILEDs, either in multicolored or uniform arrays. FIG. 2B shows an example of the latter, with blue and red (GaAs) μ-ILEDs, and the former, with green devices (produced using fluorescein sodium salt phosphor on a blue GaN μ-ILED).

FIGS. 2C and D show μ-ILED-induced changes in temperature determined by infrared imaging and by analytical calculation, respectively. The μ-ILEDs were implanted 0.3 mm into an explanted piece of brain tissue held at 37° C. The time-averaged temperatures measured at light-pulse (10 ms) frequencies of 3, 5, 10, and 20 Hz with peak electrical powers of 10 mW are 37.17, 37.22, 37.31, and 37.46° C., respectively. These results are similar to calculated time-averaged temperatures of 37.20, 37.34, 37.68, and 38.37° C., respectively. Importantly, the input power used in these tests is ten times greater than what is necessary to activate many optogenetic constructs (13). The cellular-scale dimensions of the μ-ILEDs enable high rates of passive thermal spreading and the brain tissue itself operates as an efficient heat sink. The latter is apparent in studies of the dependence of operating temperature on tissue thickness, operating power and duty cycle (FIG. 2E). As in FIG. 2D, the experiment and theory agree remarkably well in spite of the indirect correlation between infrared imaging results and temperature at the location of the devices (Details appear in FIGS. 22 and 23)(18). Perfusion in living tissue further increases the efficacy of these biological heat sinks. FIG. 2F shows changes in temperature measured in vivo using an integrated temperature sensor (FIG. 10) compared to calculated results. Collectively, these results indicate that changes in temperature associated with operation of μ-ILEDs can be less than 0.10° C. for pulse frequencies less than 20 Hz, typical of many neuronal firing rates. These values are much lower than those that occur in human deep brain stimulation (DBS) regulation, ~2° C. (21). Furthermore, in wireless operation, there is no appreciable change in temperature associated with operation at the headstage antenna or the skull (FIG. 24).

Other components of this multifunctional platform exhibit similarly good characteristics. To demonstrate functionality of the silicon μ-IPD, FIG. 2G shows photocurrents generated by different intensities of light from μ-ILEDs at different pulse frequencies. Finally, the Pt microelectrode has a 400 μm$^2$ exposure site with ~1.0 MΩ impedance at 1 kHz capable of measuring extracellular potentials on the pV scale necessary to distinguish individual action potentials (FIG. 2H) as demonstrated with clear clustering in the principal component analysis of spike data (FIG. 2I).

For use in optogenetics, such devices eliminate the need for lasers, bulk LEDs, fiber coupling systems, tethers, and optomechanical hardware used in conventional approaches (FIG. 12). Furthermore, the fundamental optics of μ-ILEDs is much different than typical fiber optic implants. Absorbing/reflecting structures around the emissive areas of the μ-ILEDs enable precise delivery of light to cellular subregions. FIGS. 3A and B compare relative size and the different patterns of light emission from μ-ILEDs to fiber optic probes. Fiber optics typically approach brain structures dorsally. This approach preferentially illuminates cells in the dorsal portion of the targeted region with greater light intensity near the point of light escape (22) (FIG. 3B left, & FIG. 25). Targeting ventral cell bodies or terminals requires lesion of dorsal regions or the use of substantially greater, and potentially phototoxic (23), amounts of light to the site of interest. Neither option protects the intact architecture of a complete brain locus. Though recent advances have spatially restricted light from implanted fiber optics (24, 25), those approaches require the use of invasive metal cannulae (FIG. 3E) or rely on sophisticated and sensitive optomechanical engineering that may limit use in awake, behaving animals. The architecture of the μ-ILEDs enables light delivery medial or lateral to the intended target brain region. Native light escape from μ-ILEDs is nearly omni-directional (FIG. 3B, center), but can be restricted to a wide range of angles with absorbing or reflective structures on the device (FIG. 3B, right).

We acutely implanted both μ-ILEDs and fiber optics into animals expressing ChR2(H134)-eYFP in the LC (FIG. 25). One hour of output-matched photostimulation induced c-fos expression (26), a biochemical marker of neuronal activation, in both groups of ChR2(H134)-eYFP expressing mice that was not seen in GFP expressing controls (FIGS. 3C and 3D). The spatial distribution of c-fos expression, however, differed markedly between the fiber optic and μ-ILED groups. μ-ILED devices produced significantly greater activation in the ventral LC (FIG. 3D).

The physical sizes and mechanical properties of the μ-ILED systems reduce lesioning, neuronal loss, gliosis, and immunoreactivity. Glial responses are biphasic with an early phase featuring widespread activation of astrocytes and microglia and a late, prolonged phase hallmarked by restriction of the gliosis to the area closest to the implanted substrate (27). The μ-ILED devices produced substantially less glial activation and caused smaller lesions as compared to metal cannulae and fiber optics, at both early (two weeks) and late (four weeks) phases (FIG. 3E). Furthermore, the brain tolerates the thin, flexible devices better than rigid structures (FIG. 3E), consistent with reports on passive electrode devices (28). Finally, we examined the chronic functionality of the devices and demonstrated that they are well tolerated in freely moving animals with encapsulated sensors and μ-ILEDs maintaining function over several months (FIG. 26).

We next implemented a fully wireless system for dissecting complex neurobiology and behavior. Phasic neuronal firing of VTA-dopaminergic (VTA-DA) neurons encodes salient stimuli and is sufficient for behavioral conditioning (29-32). We selectively targeted ChR2(H134)-eYFP to VTA-DA neurons (FIG. 4A) and tested whether mice would engage in wireless, optical self-stimulation (20, 5 ms pulses every nose poke) of their dopamine reward pathway. To increase the contextual salience of the stimulation and demonstrate wireless function of the μ-ILED devices, the mice were free to explore a complex environment (FIG. 27, A-C). In the absence of physical reward, the same stimulation of VTA-DA neurons that drives a traditional conditioned place preference (FIG. 13) (29,30) is actively sought with a cued nose poke when paired within a discrete environmental context. ChR2(H134)-eYFP mice learned to self-stimulate their dopamine neurons (FIGS. 4B and C) and, furthermore, developed a robust place preference (FIGS. 4D and E) for the environmental context containing the active nose poke for VTA-DA stimulation. ChR2(H134)-eYFP animals showed strong correlation (r=0.8620, p=0.0272) between the number of active nose pokes and the magnitude of conditioned place preference that was absent in eYFP controls (FIG. 4F and FIG. 27E). In addition, we examined the effects of wireless tonic stimulation of VTA-DA neurons on anxiety-like behavior. 5 Hz tonic stimulation reduced anxiety-like behavior (FIGS. 28A and B). Consistent with previous findings, phasic activation of VTA-DA neurons did not have an effect on anxiety-like behavior (FIGS. 28C and D). These findings are consistent with the anxiolytic actions of nicotine on VTA-DA neurons as well as the behavioral phenotypes seen in the ClockΔ 19 mice that have increased tonic firing of VTA-DA neurons (33, 34) and further establish the utility of wireless optogenetic control in multiple environmental contexts.

These experiments demonstrate that these devices can be readily used in optogenetic experiments. Additional uses are in closed-loop operation, where actuators (heat, light, electrical, etc.) operate in tandem with sensors (temperature, light, potential, etc) for altering light stimulation in response to physiological parameters such as single unit activity, pH, blood oxygen or glucose levels, or neurochemical changes associated with neurotransmitter release. Many of the device attributes that make them useful in optogenetics are applicable for broader use throughout biology and medicine. The demonstrated compatibility of silicon technology in these injectable, cellular-scale platforms foreshadows sophisticated capabilities in electronic processing and biological interfaces. Biocompatible deep tissue injection of semiconductor devices and integrated systems such as those reported here will accelerate progress in both basic science and translational technologies.

Example 2: Methods of Making and Using Injectable Cellular-Scale Optoelectronics Preparation of μ-ILEDs:

Fabrication begins with epitaxially grown GaN on a sapphire wafer (500 μm thick double polished sapphire with 2" diameter, Cermet Inc.). The GaN stack layers consisted of undoped GaN (3.8 μm), n-type GaN (2 μm), spacer (0.4 μm), MQW (0.14 μm), and p-type GaN (0.2 μm). Residual metal ions and GaN oxide on the surface were removed by rinsing with diluted HCl (33%). L-shaped current spreading layers of Ni (15 nm) and Au (15 nm) were formed by sputter deposition (AJA ATC 2000), followed by annealing at 500° C. for 5 min in an oxygen and nitrogen atmosphere to form an ohmic contact. After exposing n-type regions defined using photolithography (40×40 μm$^2$ recessive square with thick AZ 2035, Microchem Inc) and etched using chorine based inductively coupled plasma reactive ion etching (ICP RIE, Plasmatherm, SLR-770), both n- and p-contact pads, each 25×25 μm$^2$ in dimension, of 15 nm of Cr and 300 nm of Au were deposited by electron beam evaporation (Temescal, FC-1800). To define the lateral dimensions of the devices (100×100 μm$^2$), chorine based ICP RIE was used to remove GaN down to the sapphire substrate, with negative tone photoresist as an etching mask (AZ 2070, Micorchem Inc).

After deposition of a passivation layer of SiNx (200 nm) by plasma enhanced chemical vapor deposition (PECVD; STS, Mesc Multiple) the processed substrate was bonded to a silicon wafer using a layer of palladium (Pd)-indium (In) chemical alloy, followed by laser lift off (KrF, intensity, ~0.9 J/cm$^2$) to remove the sapphire from the μ-ILEDs. Here, the laser light triggered thermal decomposition at the GaN-sapphire interface, allowing easy mechanical removal of sapphire substrate upon heating to 70° C. on a hotplate. Wet etching with 5 wt % diluted HCl selectively removed the underlying unalloyed In layer, leaving residual porous structures of In—Pd alloy that served as anchors to tether the μ-ILEDs to the silicon wafer. In this configuration, the devices were easily lifted onto the surfaces of microstructured (3 μm in diameter, 1.2 μm in height, and 5 μm in space) slabs of poly(dimethylsiloxane) (PDMS; Sylgard 184, Dow Corning) via the action of van der Waals forces. Etching the exposed unalloyed Pd and passivation layer (SiNx) removed all of residual metal on the μ-ILEDs. The result was an array of μ-ILEDs on microstructured PDMS, suitable for manipulation by transfer printing, for integration onto microneedles.

Fabrication of Releasable, Injection Microneedles:

To fabricate penetrating polymeric microneedles, suitable shapes are first defined in layers of Cr (15 nm) and Au (300 nm) deposited on a glass slide (5×3.5 cm$^2$) by photolithography and wet etching. Photo-curable epoxy (SU-8 100, Microchem Inc) was then spin cast (1100 rpm for 250 μm and 1800 rpm for 150 μm thickness) on the slide, and ultraviolet light was passed (380 mJ/cm$^2$) through the backside to define a pattern of exposure in the epoxy, with the geometry of the microneedle. Developing away the unexposed regions followed by thermal annealing (150° C. for 10 min) defined and fully cured the epoxy to complete the fabrication of microneedles, typically in array geometries. Poor adhesion between the glass and the epoxy allowed easy mechanical removal of the microneedles, with tweezers, stamps or other implements. The left image of FIG. 9 shows an array of epoxy microneedles on glass. The left and right three microneedles are removed before this image was collected.

To fabricate 6 μm thick (or 2.5 μm thick for μ-ILED) polyester device substrates (Mylar® film, Chemplex® industries) with similar microneedle layouts, the films are first laminated on a PDMS coated substrate. Patterns of Cr (100 nm thickness) in microneedle geometries are used as etching masks for oxygen plasma RIE (March polymer RIE) of the exposed regions of the films. Wet etching of the Cr completes the fabrication.

Fabrication of Sensors:

For microelectrodes and temperature sensors, 6 μm thick, patterned polyester films on PDMS coated glass, formed according to procedures described above, are used. To fabricate the electrophysiological sensor, 100 μm wide and 100 nm thick lines of Pt are formed on the needle by photolithography and lift-off using negative tone resist (AZ 2070, Microchem Inc). To measure electrophysiological signals from a single nerve, an epoxy passivation layer (SU-8 2, Microchem Inc.) defined 20×20 μm$^2$ openings to the underlying Pt, as the sensing locations. For temperature sensors, 20 nm thick and 20 μm wide Pt serpentine structures served as resistors, connected by Au electrodes at both ends. For the photodetectors, the top silicon layer of an silicon on insulator (SOI) wafer (1.25 μm thick silicon on a 400 nm thick layer of silicon dioxide on a silicon substrate, Soitec) was p- and n-doped sequentially through masking layers of silicon dioxide (900-nm thick) deposited by plasma-enhanced chemical vapor deposition and patterned by photolithography and etching. For p-doping, the sample was exposed to a boron source for 30 min at 1000° C. in an N$_2$ environment. The n-doping used a phosphorous source under the same conditions for 10 min. A single cell had a size of 200 μm×200 μm including p- and n-doped parts with 200 μm×40 μm (active area: 200 μm×120 μm), isolated by reactive ion etching through the silicon layer in a geometry patterned by photolithography. The buried oxide layer of the SOI wafer was partially etched to slightly undercut silicon layer. Next, photolithography defined photoresist structures at the four corners of each square cell to hold the silicon layers to the underlying silicon wafer during complete removal of the silicon dioxide layer with HF.

Measurements on μ-IPD:

The current responses of μ-IPDs at different current injection levels (0 to 9 mA) into four blue μ-ILEDs, in an array, are measured at biases of −5V to 5V. For time dependent light response measurements, AC current with four different frequencies (i.e., 3, 5, 10, and 20 Hz) are applied to the p-ILEDs using a pulse generator (Global Specialities®). The current response of the p-IPDs at a bias of −3V is measured for 8 s with a sampling rate of 160 Hz.

Impedance Measurements on Microelectrode:

Impedance is measured using a potentiostat (Gamry instruments, reference 600) with phosphate buffered saline (PBS, Sigma-Aldrich). The PBS solution is diluted in 1 liter deionized water for 0.01 M, pH 7.4 at 25° C. To measure impedance, we applied frequency ranging from 11.0 KHz to 1 KHz.

Fabrication of μ-ILED Arrays and Interconnects on Microneedles:

A PDMS stamp with posts (100×100 μm and heights of 100 μm) is positioned above μ-ILEDs on a structured PDMS slab and then used to remove an μ-ILED, one at a time, for integration onto a thin UV curable adhesive coated on a 2.5 μm thick microneedle shaped substrate (patterned polyester film on PDMS coated glass, fabricated using steps similar to those described above for the sensors). The printing is performed using a modified mask aligner (Karl Suss, MJB). To form interconnected arrays of μ-ILEDs, the SiNx passivation layer is first removed by reactive ion etching (RIE; Plasmatherm 790). Coating with an adhesion promoter (Dow, AP3000) and then a layer of photosensitive benzocyclobutene (6 μm thick; BCB) prepared the devices for backside exposure to ultraviolet light, through the transparent substrate. This light exposed the BCB in all regions except those above the opaque n-, and p-contact pads. Developing away the unexposed BCB (Advanced Developer, DS2100) and blowing with a stream of $N_2$ removes the residual developer, to complete the patterning process for via holes. After fully curing the BCB in an Ar atmosphere in a glove box at 210° C. for 3 hr, remaining BCB residues on the contacts are removed by oxygen RIE. To form metallization lines to the contacts, 15 nm of Or and 300 nm of Au are sputter deposited, and then wet etched through a photopatterned layer of photoresist. Finally, an epoxy layer (2 μm thick, SU-8 2 Microchem) is spin cast and cured to form insulating coatings on the electrodes.

Forming Multi-Functional μ-ILED Systems on Releasable Injection Microneedles:

Separately fabricated thermal and electrophysiological sensors and printed μ-ILEDs, each on polyester thin film substrates, are stacked in an aligned configuration on a penetrating epoxy microneedle substrate using a modified mask aligner (Karl Suss, MJB). A thin layer of UV curable epoxy (SU-8 2) serves as an adhesive for bonding the sensors and the μ-ILEDs. For bonding the entire stack to the penetrating microneedle, a thin layer of purified silk (7 wt %) is used, to allow release of after implantation. After curing or drying, the adhesives in all cases have thicknesses of a few hundred nanometers.

Characterization of Optical and Thermal Properties:

Optical measurements of the emission spectra and light output are obtained with a spectrometer (HR4000 and FOIS-1 fiber optics integrating sphere, Ocean Optics). Thermal measurements are performed using a MWIR-based InDb thermal imager (InfraScope, GFI) with a base temperature of 37° C.

Wired Powering:

μ-ILED devices are connected to a function generator (AMPI, Master-9 or Tektronix, AFG3022B) and TTL modulation (low 0V, high 4V) is used to power the μ-ILEDs at the stated frequencies and pulse widths.

Wireless Powering and RF Powering Scavenger:

The wireless power transmitter includes a low-frequency signal generator, an RF signal generator, a power supply, a RF power amplifier, and a panel antenna. The low frequency signal generator outputs an amplitude modulation signal to modulate the RF power generator. The RF power amplifier that is powered by the power supply enlarges the modulated RF signal from the RF signal generator. The RF power is then transmitted from the panel antenna on 75 μm thick polyimide layer or commercialized PCB board. The RF signal generator has a power output from −10 to −17 dBm at 910 MHz, which corresponds to a power ranging from 0.1 mW to 0.02 mW. The power amplifier has a gain of 49 dB, thus the power output from the power amplifier is from 1.6 to 7.9 W. Under an antenna gain of 13 dBi and at a distance that is approximately 1 meter away from the antenna, the RF power that reaches the mice is approximately 4 mW, given an exposure area of the mice of ~32 cm². Mice with chronically implanted μ-ILED devices are acutely connected to the headstage antenna immediately prior to any wireless photostimulation.

Numerical Modeling of Temperature in the μ-ILEDs:

A three dimensional (3D) model is established to study the temperature distributions in the system in the pulsed mode and DC mode. Eight-node, hexahedral brick elements in the finite element software ABAQUS were used to discretize the geometry. The μ-ILEDs are modeled as heat sources. The bottom surface of device is set as a constant temperature, while the other surfaces are free heat convection boundary with the convection heat transfer coefficient 25 W/(m²·K). The initial temperature of the device is set as the environmental temperature $T_\infty$. The dimensions and layout of the device can be found in the main text. The microelectrodes and the sensors are neglected in the finite element simulations due to their small thickness (~300 nm) compared to that of other layer (~6 μm). The thermal conductivity, density and thermal capacity are 317 W/(m·K), 19300 kg/m³ and 130 J/(kg·K) (Si) for Au, 0.2 W/(m·K), 1190 kg/m³ and 1200 J/(kg·K) for epoxy (S2), 0.15 W/(m·K), 1050 kg/m³ and 1270 J/(kg·K) for polyester (S3, S4), 230 W/(m·K), 2330 kg/m³ and 700 J/(kg·K) for μ-ILEDs (S6), and 0.29 W/(m·K), 1050 kg/m³ and 2180 J/(kg·K) for BCB (S7).

FIG. 20A shows the time-average temperature of μ-ILEDs operated in pulsed modes (3, 10, and 20 Hz) and DC mode at 5, 10, 15 and 20 mW input power when the background temperature is $T_\infty=37°$ C. The finite element results (line) agree well with the experimental measurements (dot). FIGS. 20B and C show the surface temperature distribution from experiments and finite element simulations. They agree reasonably well with each other and the discrepancy is due to the assumption of heat source only for μ-ILEDs since other parts (e.g., Au interconnect) may also serve as heat sources.

Analytical modeling of temperature in the tissue: An analytical model is established to obtain the steady temperature in the tissue when the device is inserted into the mouse brain tissue. The μ-ILED is modeled as a disk heat source with a radius $r_0=L/\sqrt{\pi}$ corresponding to the same area of μ-ILED (L×L) and a heat generation of Q(t). Since the thickness of tissue (~4 mm) is much larger than that of device (~100 μm), we ignore the device structure in the analytical modeling. Once we have the temperature due to a single μ-ILED, the temperature due to four μ-ILEDs can be obtained by the superposition theorem.

The heat transfer equation in cylindrical coordinate with the origin as the center of μ-ILED is $$\frac{\partial^2 T}{\partial r^2} + \frac{1}{r}\frac{\partial T}{\partial r} + \frac{\partial^2 T}{\partial z^2} - \frac{c\rho}{k}\frac{\partial T}{\partial t} = 0 \qquad (1)$$

where k is thermal conductivity of tissue, ρ is density of tissue, c is specific heat capacity of tissue. The thermal diffusivity of tissue is α=k/(cρ). By setting θ=T−$T_\infty$, where $T_\infty$ is the remote temperature, the above equation becomes $$\frac{\partial^2 \theta}{\partial r^2} + \frac{1}{r}\frac{\partial \theta}{\partial r} + \frac{\partial^2 \theta}{\partial z^2} = \alpha\frac{\partial \theta}{\partial t} \qquad (2)$$

Boundary conditions involve the adiabatic condition on the top surface (z=−$h_0$) and a constant temperature $T_\infty$=37° C. on the bottom surface (z=$h_1$). At the μ-ILED interface (z=0), discontinuous heat flow Q(t) is assumed as a means to introduce the input pulsed power. Let's consider a unit pulsed power P(t) for time between 0 an $t_0$ with a period T, which can be expanded into Fourier Series $$P(t) = \begin{cases} 1 & 0 < t \leq t_0 \\ 0 & t_0 < t \leq T \end{cases} = a_0 + \sum_{n=1}^{\infty} a_n \cos n\omega t + \sum_{n=1}^{\infty} b_n \sin n\omega t \quad (3)$$

where $\omega=2\pi/T$, $a_0=t_0/T$, $a_n=2\sin(n\omega t_0)/(n\omega T)$, $b_n=2[1-\cos(n\omega t_0)]/(n\omega T)$. For each cos(nwt) [or sin(nwt)] in the power expression of Eq. (3), we can assume the solution of Eq. (2) to be $\theta(r, z, t) = \psi(r,z)\exp(n\omega t i)$. Equation (2) then becomes $$\frac{\partial^2 \psi}{\partial r^2} + \frac{1}{r}\frac{\partial \psi}{\partial r} + \frac{\partial^2 \psi}{\partial z^2} - q^2\psi = 0 \quad (4)$$

where $$q^2 = \frac{n\omega i}{\alpha}.$$

Equation (4) can be solved by applying the Hankel transformation.

For $-h_0 \leq z \leq 0$, we obtain the solution as $$\psi(r, z; n\omega) = \int_0^{+\infty} A_0 \left[\exp(z\sqrt{s^2 + q^2}) + \exp(-z\sqrt{s^2 + q^2} - 2h_0\sqrt{s^2 + q^2})\right] J_0(sr)s\,ds, \quad (5)$$

where $A_0 = \frac{r_0 J_1(sr_0)}{2k_s\sqrt{s^2+q^2}} \cdot \frac{1-\exp(-2h_1\sqrt{s^2+q^2})}{1+\exp(-2h_0\sqrt{s^2+q^2} - 2h_1\sqrt{s^2+q^2})}$.

The temperature increase due to the power of cos(nwt) [or sin(nwt)] is then equal to $|\omega(r,z;n\omega)|\cos(n\omega t+\beta_n)$ [or $|\omega(r,z;n\omega)|\sin(n\omega t+\beta_n)$] where $\tan(\beta_n)=\text{Im}(\psi)/\text{Re}(\psi)$. The temperature due to the power P(t) in Eq. (3) is given by $$\psi(r, z, t) = a_0\psi(r, z; 0) + \sum_{n=1}^{\infty} a_n|\psi(r, z; n\omega)|\cos(n\omega t + \beta_n) + \sum_{n=1}^{\infty} b_n|\psi(r, z; n\omega)|\sin(n\omega t + \beta_n) \quad (6)$$

The temperature due to the four μ-ILEDs with total power $Q(t)=Q_0*P(t)/4$ can then be given by $$\psi_{tot}(r, z, t) = \frac{Q_0}{4}\sum_{i=1}^{4}\psi_i(r, z, t) \quad (7)$$

In vitro experiments, the thermal conductivity k of the issue is 0.6 W/(m·K), the density ρ is 1040 Kg/m³, the specific heat c is 3650 J/(kg·K)(S8). The predicted surface temperature ($z=-h_0$) agrees well with experimental measurement as shown in FIG. 21, and FIGS. 2D and E. In vivo experiments, there is a heat loss due to blood flow and we fit an effective power to be 0.62 mW at 3 Hz. Then the predicted the time-averaged temperature at the location of temperature sensor (z=−6 μm) agrees very well with that in experiments at other frequencies with ~5% error. To further verify the analytical solution in Eq. (7), a full 3D finite element model for the device/tissue system is also established. The time history of average temperature in FIG. 2F shows a good agreement between finite element simulation and experimental measurement.

Preparation of Phantom Skin and IR Measurement of RF Scavenger:

The potential localized heating effect of RF power is characterized using a phantom skin sample that is placed in the RF field. The phantom skin (S9, S10) is a gelatin-based material that is made of the combination of water, agar, polyethylene, sodium chloride, sodium azide (Sigma-Aldrich Co.), and TX 151 (Oil Center Research), and has similar electrical properties as animal skin at the RF range. The thermal imaging is taken using an infrared camera (A655sc, FLIR Systems, Inc.), which has high resolution and a measurement accuracy at ±2% of the reading value.

Experimental Subjects:

Adult (25-35 g) male C57BL/6J and TH::IRES-Cre backcrossed to C57BL/6J mice are group-housed, given access to food pellets and water ad libitum (except where noted) and maintained on a 12 h:12 h light:dark cycle (lights on at 7:00 AM). All animals are held in a facility in the lab 1 week prior to surgery, post-surgery and throughout the duration of the behavioral assays to minimize stress from transportation and disruption from foot traffic. All procedures are approved by the Animal Care and Use Committee of Washington University and conformed to US National Institutes of Health guidelines.

Viral Preparation:

Plasmids coding pAAV-EF1a-DIO-EFYP, pAAV-EF1a-double floxed-hChR2(H134R)-EYFP-WPRE-HGHpA, and pLenti-EF1a-hChR2(H134R)-EYFP-WPRE were obtained from Addgene (Addgene.org) originally from the Deisseroth Laboratory at Stanford University. The DNA was amplified with a Maxiprep kit (Promega) and packaged into AAV5 serotyped viruses by the WUSTL Hope Center Viral Core. LV-PGK-GFP was provided by the WUSTL viral core facility. The final viral concentration was $2-5\times10^{12}$ genome vg/mL for the adeno-associated viruses and $1.1-1.3\times10^8$ IU/ml for all the lentivirus used.

| Plasmid | Source | Packaged by | Serotype | Titer |
|---|---|---|---|---|
| pAAV-EF1a-DIO-EFYP | Deisseroth Laboratory (Stanford) | WUSTL Hope Center Viral Core | AAV5 | 5 × 10^12 vg/ml |
| pAAV-EF1a-double floxed-hChR2(H134R)-EYFP-WPRE-HGHpA | Deisseroth Laboratory (Stanford) | WUSTL Hope Center Viral Core | AAV5 | 2 × 10^13 vg/ml |
| pLenti-EF1a-hChR2(H134R)-EYFP-WPRE | Deisseroth Laboratory (Stanford) | WUSTL Hope Center Viral Core | N/A | 1.1 × 10^8 IU/ml |
| pRRLsinPGK-GFPppt | Sands Laboratory (WUSTL) | WUSTL Hope Center Viral Core | N/A | 1.3 × 10^8 IU/ml |

Stereotaxic Surgery:

After the animals are acclimatized to the holding facility for seven to nine days, they are anaesthetized in an induction chamber (4% Isolflurane) and placed in a stereotaxic frame (Kopf Instruments, Model 1900) where they are maintained at 1-2% isoflurane. A craniotomy is performed and mice are injected with 1 ul of AAV5-DIO-ChR2 or AAV5-DIO-eYFP, LV-Ef1α-ChR2-eYFP, or LV-Ef1α-GFP unilaterally into the VTA (stereotaxic coordinates from bregma: −3.20 anterior-posterior (AP), +/−0.50 medial-lateral (ML), −4.90 mm dorsal-ventral (DV)), LC (−5.45 AP, +/−1.25 ML, −4.00 DV), or the ventral striatum (1.3 AP, +/−1.0 ML, −4.00 DV). Mice are then implanted with metal cannula (PlasticsOne; coordinates adjusted from viral injection 0.00 AP, +/−0.25 ML, +1.00 DV), fiber optic implants (coordinates adjusted from viral injection 0.00 AP, +/−0.25 ML, +1.00 DV)(S11), or a μ-ILED device (same coordinates as viral injection). Custom adapters (WUSTL Instrument Machine Shop) for the Kopf cannula holder (Model 1966) are used to implant the fiber optics and the μ-ILED devices. For biodissolvable samples, the device is implanted at the desired target, ACSF is applied to the portion of the device that remained outside of the skull to facilitate dissolution of the adhesive, and then the epoxy needle is removed after a delay of 15 minutes. The implants are secured using two bone screws (CMA, 743102) and affixed with TitanBond (Horizon Dental Products) and dental cement (Lang Dental). Mice are allowed to recover for 3-5 weeks prior to behavioral testing; this interval also permits optimal AAV expression and Cre recombinase activity.

Immunohistochemistry:

Immunohistochemistry is performed as described (S12) Briefly, mice are anesthetized with pentobarbital and intracardially perfused with ice-cold 4% paraformaldehyde in phosphate buffer (PB). Brains are dissected, post-fixed for 24 hr at 4° C. and cryoprotected with solution of 30% sucrose in 0.1 M PB at 4° C. for at least 24 hr, cut into 30 μm sections and processed for immunostaining. 30 μm brain sections are washed three times in PBS and blocked in PBS containing 0.5% Triton X-100 and 5% normal goat serum. Sections are then incubated for ~16 hr at room temperature in rabbit anti c-fos antibody (1:20000, Millipore), guinea pig anti-GFAP (1:500, Synaptic Systems), rabbit anti-Iba1 (1:300, Wako Chemicals) and/or chicken anti-TH (1:2000, Aves Labs). Following incubation, sections are washed three times in PBS and then incubated for 2 hr at room temperature in Alexa Fluor 488 goat anti-mouse IgG (1:500, Invitrogen), Alexa Fluor 594 goat anti-rabbit IgG (1:500, Invitrogen-), goat anti-chicken Alexa Fluor 633(1:500, Invitrogen) and/or goat anti-guinea pig Alexa Fluor 546(1:500, Invitrogen) are then washed three times in PBS and followed by three 10-min rinses in PB and mounted on glass slides with Vectashield (Vector Labs) and sealed with nail polish for microscopy. All sections are imaged on both epifluorescent (Olympus BX61) and confocal (Olympus Fluoview 500) microscopes. Gain and exposure time were constant throughout, and all image groups were processed in parallel using Adobe Photoshop CS5 (Adobe Systems).

| Antibody | Species | Dilution | Source |
| --- | --- | --- | --- |
| GFAP | Guinea Pig | 1:500 | Synaptic Systems |
| Iba1 | Rabbit | 1:300 | Wako Chemicals |
| TH | Chicken | 1:2000 | Aves Labs |
| c-fos | Rabbit | 1:20,000 | Millipore |
| Alexa Fluor 488 anti-mouse IgG | Goat | 1:500 | Invitrogen |
| Alexa Fluor 594 anti-rabbit IgG | Goat | 1:500 | Invitrogen |
| Alexa Fluor 633 anti-chicken IgG | Goat | 1:500 | Invitrogen |
| Alexa Fluor 546 anti-guinea pig IgG | Goat | 1:500 | Invitrogen |
| Alexa Fluor 594 anti-chicken IgG | Goat | 1:500 | Invitrogen |

Cell Culture and Transfection of NOPR-YFP Expressing, HEK293 Cells:

A single 50×50×6.45 μm μ-ILED is printed onto a standard glass coverslip (Fisherbrand, 12-545-80). The glass is coated with Poly-L-lysine (Sigma-Aldrich, P4707) to facilitate cell adhesion. Stable HEK293 cells expressing pcDNA3 containing nociceptin opioid peptide receptor-YFP (NOPR-YFP) are generated as previously described (S13). The NOPR-YFP expressing cells are grown on the coverslip in a 24-well plate and placed in a 37° C. 5% $CO_2$ incubator. Cells are washed three times with PBS and then fixed in 4% paraformaldehyde for 20 min, washed in PBS, washed in 0.1 M PB, and mounted using VECTASHIELD (Vector Laboratories) and sealed with clear nail polish. Images are captured using Metamorph 7.6 (Molecular Devices) and processed with ImageJ 1.440 (NIH).

cAMP Assay:

HEK293 cells are co-transfected with Optoβ$_2$ (S14 and pGloSensor-22F cAMP plasmid (Promega E2301) in 96-well format. Using a SynergyMx microplate reader (BioTek; VT, USA), baseline luminescence recordings are taken. In the presence of 9-cis retinal (1 μM), cells are exposed to μ-ILED light (450 nm, 5 sec, 0.5 W/cm$^2$ pulse) and relative luminescent units taken every 2 sec using GloSensor cAMP Assay (Promega). Relative luminescent units are normalized to an initial 1 min recording of baseline. Data are expressed as ±S.E.M.

Immunoblotting:

Western blots for phospho-MAPKs were performed as described previously (S13). Briefly, Optoβ$_2$ expressing HEK293 cells are serum-starved 4-6 h prior to treatment. Cells are light treated (450 nm, 1 min, 0.5 W/cm$^2$ pulse), lysed in 70 μl of lysis buffer (50 mM Tris-HCl, 300 mM NaCl, 1 mM EDTA, 1 mM Na3VO4, 1 mM NaF, 10% glycerol, 1% Nonidet P-40, 1:100 of phosphatase inhibitor mixture set 1 (Calbiochem), and 1:100 of protease inhibitor mixture set 1 (Calbiochem)), sonicated for 20 s, centrifuged for 15 min (14000×g, 4° C.). 50 pg of total protein is loaded onto non-denaturing 10% bisacrylamide precast gels (Invitrogen) and run at 150 V for 1.5 h. Blots are transferred to nitrocellulose (Whatman, Middlesex, UK) for 1.5 h at 30 mV, blocked in TBS/5% bovine serum albumin for 1 hr, incubated overnight at 4° C. with a 1:1000 dilution of goat-anti-rabbit phospho-ERK 1/2 (Thr-202/Tyr-204) antibody (Cell Signaling) and mouse actin (1:20,000, AbCam). Following overnight incubation, membranes are washed 4×15 min in TBST (Tris-buffered saline, 1% Tween 20) and then incubated with IRDye 800- and 700 conjugated affinity-purified anti-rabbit or anti-mouse IgG at a dilution of 1:5000 (pERK) or 1:20,000 (actin) in a 1:1 mixture of 5% milk/TBS and Li-Cor blocking buffer (Li-Cor Biosciences, Lincoln, Nebr.) for 1 h at room temperature, washed 3×10 min in TBST, 1×10 min in TBS and analyzed using the Odyssey infrared imaging system (Li-Cor Biosciences). Band intensity is measured using Odyssey software following background subtraction and integrated band density in high-resolution pixels calculated. All subtypes of ERK (1 and 2) are quantified together. All pERK bands are normalized to actin, as an equal protein loading control and plotted using GraphPad (GraphPad Prism 5.0) software. Statistical significance is taken as *$p<0.05$ as determined by unpaired two-tailed t-test.

In Vivo Electrophysiology:

To demonstrate the ability of the incorporated electrode, spontaneous cellular activity is monitored in the deep midbrain (FIG. 2H). For light modulated responses, an array of 16 (35-μm tungsten wires, 150-μm spacing between wires, 150-μm spacing between rows, Innovative Physiology) is epoxied to a rigid μ-ILED device and lowered into the VTA of a lightly (~1% isoflurane) anesthetized, TH-Cre mouse expressing ChR2(H134)-eYFP in the VTA (FIG. 19). Two skull screws are arbitrarily placed anterior to bregma on either side of the midline and used to ground the electrode array. In either approach, voltage readings from each electrode are bandpass-filtered with activity between 250 and 8,000 Hz analyzed as spikes. The signal is amplified and digitally converted using commercially available hardware and software (Omniplex and PlexControl, Plexon). Spikes are sorted using principal component analysis and/or evaluation of t-distribution with expectation maximization (Offline sorter, Plexon).

Light Path Visualization:

A 200 µm, 0.48 NA diameter fiber optic coupled to a 465 nm blue LED (Plexon) or devices with four, 100×100×6.45 µm 450 nm blue µ-ILEDs are adjusted to have the same (~280 µW) light output. The light sources are submerged in 30 µM fluorescein sodium salt (Sigma-Aldrich, F6377) (S15) in deionized water and the photos are taken in a dark room with an exposure of 1/1000 s and an f-number of 5.6 from ~50 cm away for all images. Each photo was cropped using Photoshop (Adobe Systems), but no other processing is used.

c-Fos Expression:

C57BL/6J mice are injected with LV-Ef1α-ChR2-eYFP or LV-PGK-GFP into the LC as described above. Three weeks later, animals are anesthetized, mounted on the stereotaxic instrument, and fiber optics or µ-ILED devices are acutely implanted to target the LC. 5 mW, 3 Hz blue light stimulation is delivered for 1 hour (S16), animals are perfused immediately following, and immunohistochemistry is performed as above. Slices from the LC originated from approximately −5.45 mm caudal to bregma are mounted and imaged. For quantification, the LC is divided into three (dorsal, central, and ventral) 100×100 µm compartments. TH and c-fos labeled channels are separated, the compartment mask is applied, an exclusive threshold was set and positive staining for each channel is counted in a blind-to-treatment fashion using Metamorph. The counts from each channel are then overlaid and percent TH+ cells expressing c-fos are reported.

Immuno-Glial Response in Implanted Tissues:

C57BL/6J mice (n=16) are implanted with devices into the ventral striatum and allowed to recover for either 2 or 4 weeks before perfusion. Immunohistochemistry is performed as described.

Conditioned Place Preference:

VTA injected (AAV5-DIO-eYFP or AAV5-DIO-ChR2-eYFP; n=4-6/group) mice are trained in an unbiased, balanced three-compartment conditioning apparatus as described (S12). Briefly, mice are pre-tested by placing individual animals in the small central compartment and allowing them to explore the entire apparatus for 30 min. Time spent in each compartment is recorded with a video camera (ZR90; Canon) and analyzed using Ethovision 8.5 (Noldus). Mice are randomly assigned to light and no-light compartments and received no light in the morning and light (20, 5 ms pulses every minute) in the afternoon at least 4 h after the morning training on three consecutive days. CPP is assessed on day 5 by allowing the mice to roam freely in all three compartments and recording the time spent in each. Scores are calculated by subtracting the time spent in the light stimulus-paired compartment post-test minus the pre-test.

Real-Time Place Preference:

VTA injected (AAV5-DIO-eYFP or AAV5-DIO-ChR2-eYFP; n=3/group) TH-Cre mice are trained in an unbiased, balanced three-compartment conditioning apparatus as described (S12) Mice are trained in the same conditioning apparatus as described above, and the pretesting phase (day 1) is identical. However, on days 2-4, mice are still allowed to freely roam all three compartments. On these conditioning days, entry into one compartment is paired with 20, 5 ms pulses of light that would repeat every minute the animal remained in the light-paired chamber. On day 5, the post-testing is identical as the above. Scores are calculated by subtracting the time spent in the light stimulus-paired compartment each day minus the pre-test.

Operantly Conditioned Place Preference:

VTA injected (AAV5-DIO-eYFP or AAV5-DIO-ChR2-eYFP; n=6-8/group) TH-Cre mice are prepared for nose poke training by mildly restricting daily food to four grams to stabilize body weight and facilitate behavioral responding. Mice are trained in an unbiased, balanced three-compartment Y-Maze. Each arm of the Y-Maze was 50 cm by 10 cm, a 50 $cm^2$ equilateral triangle connected all three arms (for a total area of 1550 $cm^2$), and each arm is outfitted with a unique context (white, horizontal black stripes, or vertical black stripes). At the distal end of each of the striped arms a nose poke device (Med Associates, ENV-313M). On day 1, the headstage antenna is attached and mice are pre-tested by placing individual animals in the intersection of the three arms and allowing them to explore the entire apparatus for 30 min. During the pre-test and post-test sessions, a wall is placed to prohibit access to the nose poke apparatus and the final 15 cm of each arm. On days 2-6, the headstage antenna is attached and mice are allowed access to the entire Y-Maze for 1 hour. During these conditioning sessions a cue light was on to indicate a stimulation could be achieved nose poke and turned off for 500 ms following a poke on either device. A nose poke on the active device triggered an optical stimulation (20 pulses, 20 Hz, 5 ms pulse duration) on a fixed ratio-1 schedule, while a poke on the inactive device resulted in the cue light turning off for 500 ms. Nose pokes are recorded using a Med Associates TTL-I/O Interface connected to the Noldus Ethovision I/O Box. On day 7, the post-testing is conducted in an identical manner as the pre-test. All activity and position data is recorded using Ethovision and analyzed using Microsoft Excel and Graph-Pad Prism 5.0. Place preference scores are calculated by subtracting the time spent in the active nose poke-paired compartment each day minus the pre-test.

Open Field Test:

OFT testing is performed in a sound attenuated room maintained at 23° C. Lighting is measured and stabilized at 200 lux, and performed in the afternoon between 13:00-1600 hrs. The open field is a 55×55 cm square enclosure and is cleaned with 70% ethanol between testing trials. For testing, VTA injected (AAV5-DIO-eYFP or AAV5-DIO-ChR2-eYFP; n=6-8/group) TH-Cre mice are connected to cables coupled to a function generator and placed in the center of the open field and allowed to roam freely for 15 min. During the entire trial, animals receive 20, 5 ms pulses of photostimulation. Movements are video-recorded and analyzed using Ethovision. The center is defined as a square comprised of 50% the total area of the OFT. Time in the center expressed as percentages total time is the primary measure of anxiety-like behaviors.

Elevated Zero Maze: EZM testing is performed in a sound attenuated room maintained at 23° C. Lighting was 200 lux, and performed in the afternoon between 13:00-1600 hrs. The EZM (Harvard Apparatus) is made of grey plastic (Dimensions: 200 cm in circumference comprised of four 50 cm sections: two opened, two closed. The maze is elevated 50 cm above the floor and had a path width of 4 cm with a 0.5 cm lip on each open section) and is cleaned with 70% ethanol between trials. For testing, VTA injected (AAV5-DIO-eYFP or AAV5-DIO-ChR2-eYFP; n=6-9/group) TH-Cre mice are connected to the headstage antenna and placed at the threshold of a closed section facing the open section and allowed to roam freely for 9 min. For the first and the final 3 minutes of each trial there is no photostimulation. For minutes 4-6, animals receive 5 Hz, 5 ms width stimulation. Movements are video-recorded and analyzed using Ethovision (Noldus). Open section times expressed as percentages total time the primary measures of anxiety-like behaviors.

Data Analysis/Statistics: Data are expressed as means±SEM. Data are normally distributed, and differences between groups are determined using independent t-tests or one-way ANOVA, or two-way ANOVAs followed by post hoc Bonferroni comparisons if the main effect is significant at $p<0.05$. Statistical analyses are conducted using Prism 5.0 (GraphPad).

Genotyping of mouse lines: DNA is isolated from tail tissue obtained from weanling mice (21-28 days of age), and PCR screening is performed using the following primers: Cre recombinase (forward: 5'-GCA TTA CCG GTC GAT GCA ACG AGT GAT GAG-3' (SEQ ID NO:1) and reverse: 5'-GAG TGA ACG AAC CTG GTC GAA ATC AGT GCG-3' (SEQ ID NO:2)) yielding a 400-bp PCR product in Cre positive animals. Fatty acid-binding protein intestinal primers (forward: 5'-TGG ACA GGA CTG GAC CTC TGC TTT CCT AGA-3' (SEQ ID NO:3) and reverse: 5'-TAG AGC TTT GCC ACA TCA CAG GTC ATT CAG-3' (SEQ ID NO:4)) are used as positive controls and yield a 200-bp PCR product.

TABLE OF REFERENCES FOR EXAMPLES 1 AND 2:

1. D.-H. Kim et al., Dissolvable films of silk fibroin for ultrathin, conformal bio-integrated electronics. *Nat. Mater.* 9, 511 (2010).
2. J. Viventi et al., A conformal, bio-Interfaced class of silicon electronics for mapping cardiac electrophysiology. *Sci. Transl. Med.* 2, 22 (2010).
3. B. Tian et al., Three-diemensional, flexible, nanoscale field effect transistors as localized bioprobes. *Science* 329, 830 (2010).
4. D.-H. Kim et al., Epidermal electronics. *Science* 333, 838 (2011).
5. Q. Qing et al., Nanowire transistor arrays for mapping neural circuit in acute brain slides. *Proc. Natl. Acad. Sci. USA.* 107, 1882 (2010).
6. T. Sekitani, T. Someya, Stretchable organic integrated circuits for large-area electronic skin surface. *MRS Bull.* 37, 236 (2012).
7. J. Ordonez, M. Schuettler, C. Boehler, T. Boretius, T. Stieglitz. Thin films and microelectrode arrays for neuroprosthetics. *MRS Bull.* 37, 590 (2012).
8. S. C. B. Mannsfeld et al., Highly sensitive flexible pressure sensors with micro-structured rubber as the dielectric layer. *Nat. Mater.* 9, 859 (2010).
9. T. Sekitani et al., Organic nonvolatile memory transistors for flexible sensor arrays. *Science* 326, 1516 (2009).
10. S. Takeuchi, T. Suzuki, K. Mabuchi, H. Fujita, 3D flexible multichannel neural probe array. *J. Micromech. Microeng.* 14, 104-107 (2004).
11. E. Stark, T. Koos, G. Buzsáki. Diode probes for spatiotemporal optical control of multiple neurons in freely moving animals. *J. Neurophysiol.* 108, 349-363 (2012).
12. Y.-T. Kim and M. I. Romero-Ortega, Material considerations for peripheral nerve interfacing. *MRS Bull.* 37, 573 (2012).
13. J. Mattis et al., Principles for applying optogenetic tools derived from direct comparative analysis of microbial opsins. *Nat. Methods* 18, 159 (2011).
14. P. Anikeeva et al., Optetrode: a multichannel readout for optogenetic control in freely moving mice. *Nat. Neurosci.* 15, 163 (2012).
15. H. Cao, L. Gu, S. K. Mohanty, J.-C. Chiao, An integrated μLED optrode for optogenetic stimulation and electrical recording. *IEEE Trans. Biomed. Eng.* in press (DOI: 10.1109/TBME.2012.2217395).
16. B. Tian et al., Macroprous nanowire nanoelectronic scaffolds for synthetic tissues. *Nat. Mater.* 11, 986-994 (2012).
17. T.-I. Kim et al., High efficiency, microscale GaN LEDs and their thermal properties on unusually substrates. *Small* 8, 1643-1649 (2012)
18. Materials and methods are available as supporting material on *Science* Online.
19. Federal Communications Comission (FCC), *Guidelines for Evaluating the Environmental Effects of Radiofrequency Radiation* (FCC Publication Docket No. 93-62, 1996; website transition.fcc.gov/Bureaus/Engineering_Technology/Orders/1996/fcc96326.txt)
20. R. D. Airan, K. R. Thompson, L. E. Fenno, H. Bernstein, K. Deisseroth, Temporally precise in vivo control of intracellular signalling. *Nature* 458, 1025-1029 (2009).
21. M. M. Elwassif, Q. Kong, M. Vazquez, M. Bikson, Bio-heat transfer model of deep brain stimulation-induced temperature changes. *J. Neural Eng.* 3, 306 (2006).
22. A. M. Aravanis et al., An optical neural interface: in vivo control of rodent motor cortex with integrated fiberoptic and optogenetic technology. *J. Neural Eng.* 4, S143-S156 (2007).
23. O. Yizhar, L. E. Fenno, T. J. Davidson, M. Mogri, K. Deisseroth, Optogenetics in neural systems. *Neuron* 71, 9-34 (2011). 24. K. M. Tye et al., Amygdala circuitry mediating reversible and bidirectional control of anxiety. *Nature* 471, 358-362 (2011).
25. A. N. Zorzos, J. Scholvin, E. S. Boyden, and C. G. Fonstad, Three-dimensional multiwaveguide probe for light delivery to distributed brain circuits. *Opt. Lett.* 37, 4841-3 (2012).
26. M. E. Carter et al., Tuning arousal with optogenetic modulation of locus coeruleus neurons. *Nat. Neuro.* 13, 1526-1533 (2011).
27. D. H. Szarowski et al., Brain responses to micro-machined silicon devices. *Brain Res.* 983, 23-35 (2003).

-continued

TABLE OF REFERENCES FOR EXAMPLES 1 AND 2:

28. T. D. Yoshida Kozai1, D. R. Kipke. Insertion shuttle with carboxyl terminated self-assembled monolayer coatings for implanting flexible polymer neural probes in the brain. *J. Neuro. Met.* 184, 199-205 (2009).
29. H. Tsai et al., Phasic firing in dopaminergic neurons is sufficient for behavioral conditioning. *Science* 324, 1080-1084 (2009).
30. A. R. Adamantidis et al., Optogenetic interrogation of dopaminergic modulation of the multiple phases of reward-seeking behavior. *J. Neurosci.* 31, 10829-10835 (2011).
31. I. B. Witten et al., Recombinase-driver rat lines: tools, techniques, and optogenetic application to dopamine-mediated reinforcement. *Neuron* 72, 721-733 (2011).
32. K. M. Kim et al., Optogenetic mimicry of the transient activation of dopamine neurons by natural reward is sufficient for operant reinforcement. *Plos ONE* 7, e33612 (2012).
33. T. M. McGranahan, N. E. Patzlaff, S. R. Grady, S. F. Heinemann, T. K. Booker, $\alpha 4\beta 2$ nicotinic acetylcholine receptors on dopaminergic neurons mediate nicotine reward and anxiety relief. *J. Neurosci.* 31, 10891-902 (2011).
34. L. Coque et al., Specific role of VTA dopamine neuronal firing rates and morphology in the reversal of anxiety-related, but not depression-related behavior in the Clock$\Delta$19 mouse model of mania. *Neuropsychopharmacology* 36, 1478-1488 (2011).
S1. F. P. Incropera, D. P. Dewitt, T. L. Bergman, A. S. Lavine. Fundamentals of heat and mass transfer (Eds: J. Hayton), John Wiley & Sons, New York 2006.
S2. B. Solano, S. Rolt and D. Wood, Thermal and mechanical analysis of an SU8 polymeric actuator using infrared thermography. *Proc. IMechE 222 Part C: J. Mech Eng Sci*, 222, 73-86 (2007).
S3. C. G. Mattsson et al., Development of an infrared thermopile detector with a thin self-supporting SU-8 membrane, *IEEE SENSORS 2007 Conference*, 836-839 (2007).
S4. A. K. van der Vegt en L. E. Govaert. Polymeren, ISBN 2005.
S5. S. A. Campbell, The Science and Engineering of Microelectronic Fabrication. Oxford University Press, New York (2001).
S6. T.-I. Kim et al., High efficiency, microscale GaN LEDs and their thermal properties on unusually substrates. Small 8, 1643-1649 (2012)
S7. A. Modafe et al., Embedded benzocyclobutene in silicon: An integrated fabrication process for electrical and thermal isolation in MEMS. *Microelectron. Eng.* 82, 154-167 (2005).
S8. M. M. Elwassif, Q. Kong, M. Vazquez, M. Bikson, Bio-heat transfer model of deep brain stimulation-induced temperature changes. J. Neural Eng. 3, 306 (2006).
S9. B. Esler, T. Lyons, S. Turovets, D. Tucker, Journal of Physics: Conference Series 224, 012007 (2010).
S10. K. Ito, K. Furuya, Y. Okano, L. Hamada, Electronics and Communications in Japan (Part I: Communications) 84, 67 (2001).
S11. D. R. Sparta et al., Construction of implantable optical fibers for long-term optogenetic manipulation of neural circuits. *Nat. Met.*, 7, 12-23 (2012).
S12. M. R. Bruchas et al., Selective p38a MAPK Deletion in Serotonergic Neurons Produces Stress Resilience in Models of Depression and Addiction. *Neuron* 71, 498-511 (2011).
S13. N. R. Zhang et al., Serine 363 is required for NOPR desensitization, internalization, and arrestin signaling. *JBC*, Epub ahead of print, doi: 10.1074/jbc.M112.40569 (2012).
S14. R. D. Airan, K. R. Thompson, L. E. Fenno, H. Bernstein, K. Deisseroth, Temporally precise in vivo control of intracellular signalling. Nature 458, 1025-1029 (2009).
S15. K. M. Tye et al., Amygdala circuitry mediating reversible and bidirectional control of anxiety. Nature 471, 358-362 (2011).
S16. M. E. Carter et al., Tuning arousal with optogenetic modulation of locus coeruleus neurons. Nat. Neuro. 13, 1526-1533 (2011).
S17. K. R. Tan et al., GABA neurons of the VTA drive conditioned place aversion. *Neuron* 73, 1173-1183 (2012).
S18. A. M. Stamatakis , G. D. Stuber. Activation of lateral habenula inputs to the ventral midbrain promotes behavioral avoidance. *Nat. Neuro.* 12, 1105-1107 (2012).
S19. S. Lammel, B. K. Lim, C. Ran, K. W. Huang, M. J. Betley, K. M. Tye, K. Deisseroth, R. C. Malenka. Input specific control of reward and aversion in the ventral tegmental area. *Nature*. 491, 212-217 (2012).

Example 3: Implanted Device for Optical Interfacing with the Sciatic Nerve

FIG. 31.

Implantable or surface mounted biomedical device having printed LEDs that are useful for optogenetic applications. FIGS. 32-33 show the device implanted in a mouse for interfacing with the sciatic nerve. As desired, any other nerve location may be interfaced, such as for optogentic studies or applications. Optionally, the mouse may be transformed to express a protein, channel, or other material that is sensitive to light. A light-responsive protein channel is particularly useful in optogenetic applications, such as channelrhodopsins to excite neurons, halorhodopsin for silencing and fungal opsins and enhanced bacteriorhodopsin for inhibiting neurons, including in freely moving mammals.

In FIG. 32 the devices have been implanted in male wild-type Swiss-Webster infected with a herpes simplex 1 viral construct expressing the optogenetic channel ChR2 under the control of the CMV promoter. The sciatic nerve was exposed by making a small cutaneous incision on the left flank and using blunt dissection to separate a small piece of long head of the biceps femoris from the gluteus maximus and open a window to the underlying nerve. For the preliminary experiments shown in FIG. 30, no techniques to secure the LED device in place over the sciatic were necessary beyond rearranging the fascia to hold the t-shaped ending in place. More recent implantation procedures use resorbable vicryl sutures through the overlying biceps femoris muscle to fix the device in place over the sciatic nerve. The device and method of this Example may be used to decrease inappropriate activity of sensory neurons and thus treat a wide variety of neuropathic pain conditions. The device and method of this Example also may be used to provide short-, intermediate-, and long-term local anesthesia with few side effects. The local nature of the stimulation offers a substantial advantage to current techniques, and the ability of modulate the blockade by adjusting the light intensity of the stimulus is also a significant improvement over pharmacological approaches. The device and method of this Example may also be useful in stimulating motor neurons to aid in physical therapy rehabilitation, for example by optogenetic stimulation that is more effective than electrical stimulation for orderly recruitment of motor units (Llewellyn et. al Nat. Med 2010).

FIGS. 34-35 show the results of an EMG signal from the system of FIG. 33. LED illumination of the sciatic nerve results in a change in the measured EMG voltage that are associated with LED illumination (compare Trials to negative control). To obtain these measurements, the mice are deeply anaesthetized with isofluorane and small incisions are made on the abdomen slightly lateral to the midline. The subcutaneous fat tissue is gently shifted aside, and silver wire electrodes are placed through the superior oblique abdominal muscles to record the EMG waveform generated when the muscles are tensed. After the electrodes have been placed, the anesthesia level is gradually decreased until the mice are very lightly anaesthetized, and become responsive to other nocifensive stimuli such as toe pinches. In this state, nocifensive stimulation of the mouse has been shown to cause contraction of the abdominal muscles, which generates an EMG waveform. Once the mice were appropriately prepared, the LED devices over the sciatic nerve were activated and EMG waveforms were generated in response to the stimulation. The EMG waveforms generated correlate with the intensity of the light generated, as well as the frequency of pulses delivered.

FIG. 36 is a schematic illustration of an implanted biomedical device comprising four LEDs that interface with a nerve of diameter 300 µm. The center-to-center LED separation distance is about 1 mm, and the thicknesses of the various layers as indicated. Optionally, an adhesive layer secures the LEDs to the substrate and the entire device, including BCB encapsulated in a polymer layer to provide additional rigidity and strength, such as be increasing thickness to minimize tearing. FIG. 37. Top view schematic of the biomedical device comprising a plurality of LEDs for optically interfacing with biological tissue. Examples of various materials used as a substrate and/or encapsulating or structural layer(s) include (with attendant refractive index in brackets): SU-8 (Epoxy):1.67~1.8 (ref: website mit.edu/~6.777/matprops/su-8.htm); PET (Polyethylene terephthalate):1.57~1.58 (ref: website en.wikipedia.org/wiki/Polyethylene_terephthalate); BCB (benzocylobutene polymer): 1.55~1.555 (ref: website waset.org/journals/waset/v50/v50-98.pdf). The sciatic nerve (1.368) is assumed to be similar to mouse brain tissue, ref: website opticsinfobase.org/oe/abstract.cfm?uri=oe-19-6-4833.

FIG. 38 shows the light distribution analysis for the implanted biomedical device comprising four LEDs that each interface with a nerve in a living animal at different axial locations along the nerve. The top panel is a contour plot of the relative optical power (log I/log Io) at three different longitudinal cross-sections of the nerve relative to a center location (T=0 mm, 0.25 mm, and 0.5 mm). The bottom panel is a graphical plot of the relative optical power as a function of axial location along the nerve for three different cross section positions.

FIG. 39 illustrates electrical disconnection in the long ACF cable 2 weeks post-implantation (see top panel labeled Current design). In an aspect, the ACF cable is shortened or not used, such as by incorporating a long PET substrate. A wireless connector or wireless adaptor may be used to interface with external controllers, thereby permitting the subject in which the device is implanted to be freely mobile and unconstrained by physical connection to external components. The active electronic components that interface with biological tissue may be positioned at a distal end of the device, such as at a tip end that is blunt (top panel), rounded (bottom panel), shaped to correspond to the geometry of a to-be-interfaced tissue, cells, or cell, or that is sharpened toward a point to facilitate deep-tissue insertion with minimal tissue damage.

Figure 40:
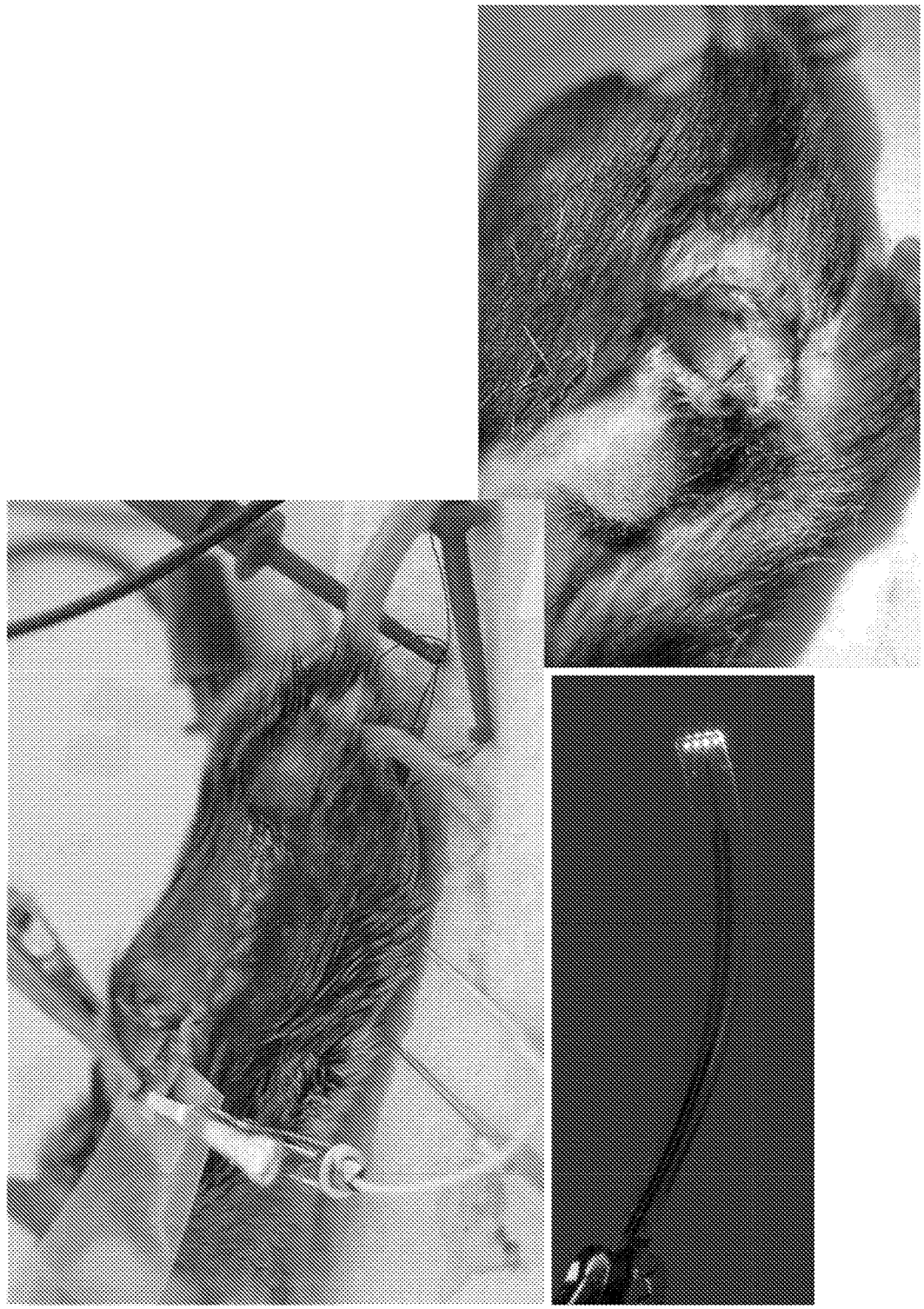

FIG. 40 are photographs of an implanted device that is electrically connected (top left), energized to illuminate the four LEDs (bottom left panel). The bottom right panel is a close-up view of the insertion region.

Figure 41:
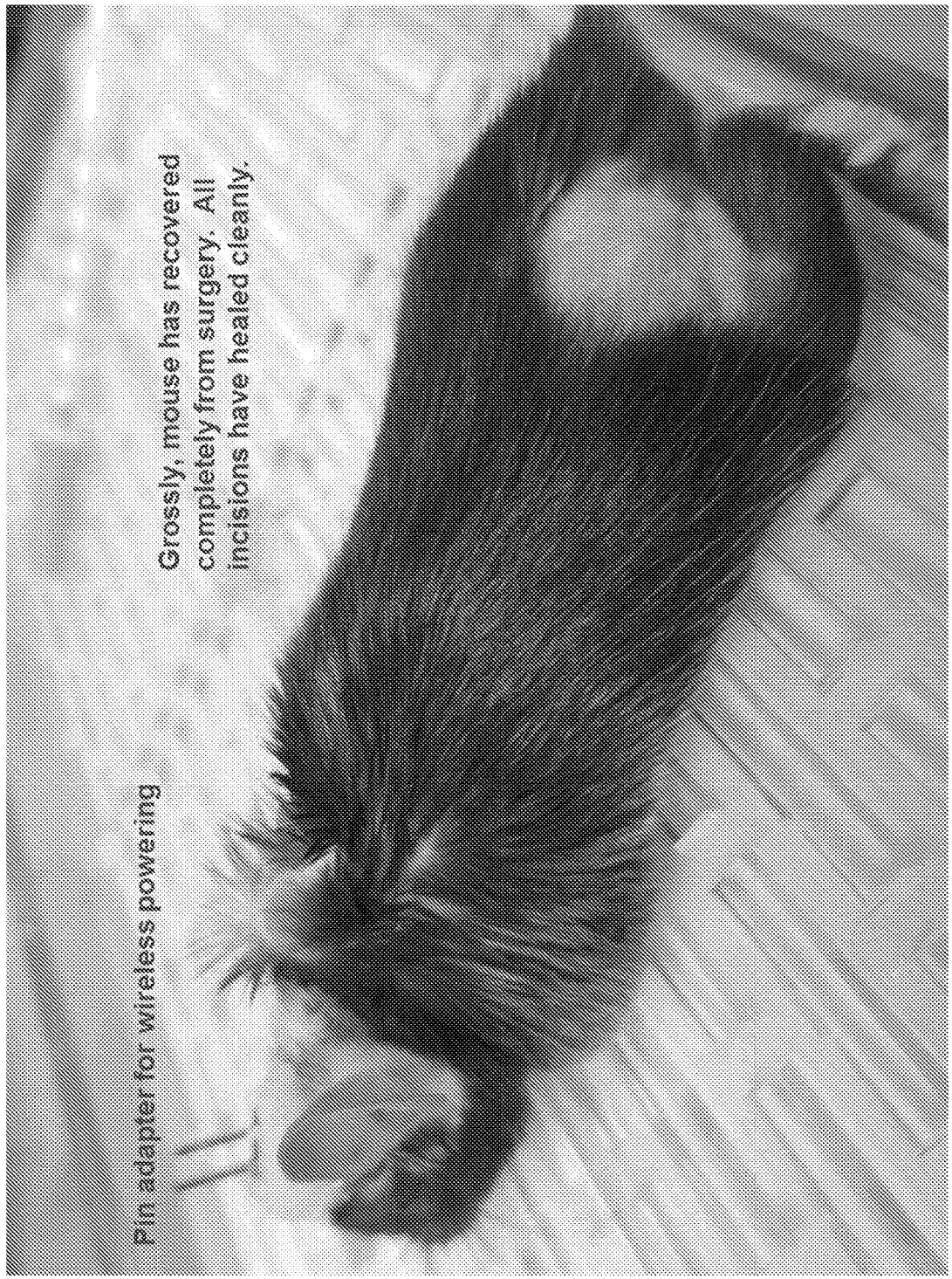

FIG. 41 shows a pin adapter for wireless powering and indicates that grossly, the mouse has recovered completely from surgery and clean healing of the surgical incisions.

Figure 42:
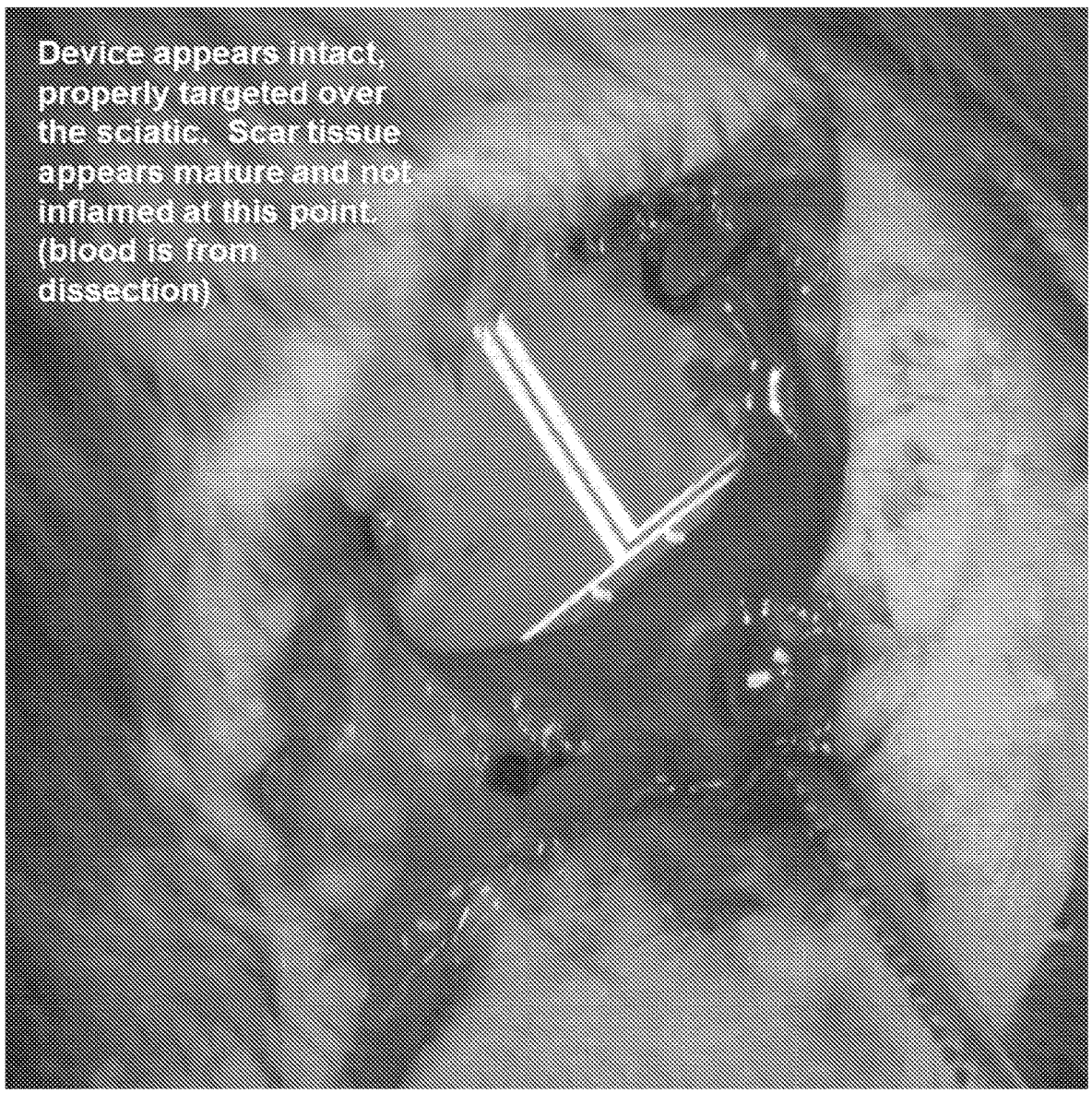

FIG. 42 is a close up view of the implanted device two weeks post implantation. The device appears intact and properly targeted over the sciatic with no observable movement from the initially implanted position. Scar tissue appears mature and not inflamed (note: trauma is from dissection).

Figure 43:
Figure 44:
Figure 45:
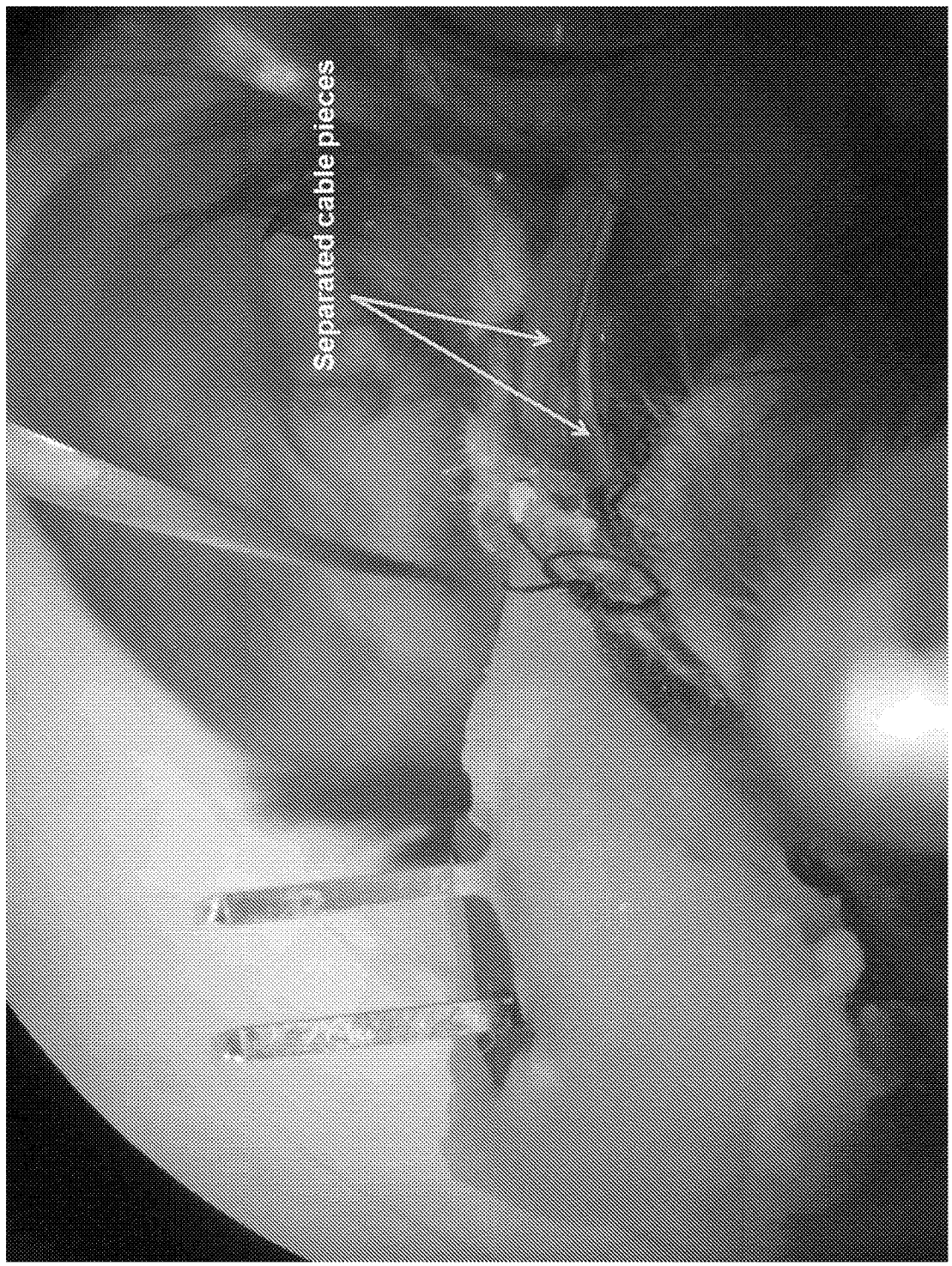

FIG. 43 the tunnel portion of the incision that receives the loop and cable appears intact. Minimal scarring is observed in the tunnel.

FIGS. 44-47 illustrate a potential separation of cable in a proximal location of the device toward the head/circuit board. The device cable appears to have separated at the final joint to the circuit board. FIG. 47 summarizes good electrical connection for the portion of the device that is at and near the distal end of the device that interfaces with the tissue and electrical disconnection at a proximal end far from the interfacing portion and toward the head.

FIG. 48 is a table summary summarizing modifications made to address the disconnection of the device illustrated in FIGS. 44-47. Any one or more of the following may be employed to improve device functionality and prevent unwanted disconnection: (1) substrate composition (thin PET layer (less than 10 µm or about 6 µm) and PDMS) and/or geometry/length; (2) Interconnection to a serpentine configuration to accommodate device stretching, folding, and/or bending; (3) decrease in total device length; (4) decrease in thickness.

These different variations are schematically illustrated in FIG. 49, with the dots indicating optional sutures through the device to secure the device to a specific location in the subject. Accordingly, in an aspect the implantable or surface mounted biomedical device has a width that is sufficient to accommodate passages for receiving a securing means, such as a suture, staple, or biocompatible adhesive. Optionally, the securing means is temporary and is bioresorbed subsequent to implantation when the surgical site has sufficiently healed and the device sufficiently adheres to the site via natural forces (surface pressing into the device and/or extracellular matrix that secures the device to the target tissue or region adjacent thereto). The top panel shows the device, with the middle panels a close up view of a distal portion of the device including the interfacing components (e.g., LEDs) and serpentine interconnects that electrically connect the interfacing components. The left middle panel is a schematic illustration and the right middle panel is a photograph. The bottom panel is a cross-sectional view of the device, showing the LED, Cr/Au, UV curable BCB layer, PET and an adhesive layer to secure the electrical components to the PET, with an encapsulating layer of PDMS. Preferably, the thickness of the entire device including PDMS substrate is about 100 µm, such as less than about 150 µm, or between about 30 µm and 120 µm, and any subranges therein.

FIG. 50 illustrates a design consideration wherein the substrate mechanical properties are insufficient to reliably hold the securing means in place. The left panel shows the device immediately after implantation, and the right panel 5 days post-implantation, wherein the sutures ripped through the substrate. FIG. 51A summarizes strategies to accommodate address this issue for those applications where a suture is desired to secure the implanted device to a specific location. In an aspect the substrate thickness may be increased, such as by adding a more thick polymer film (PDMS) such as up to a thickness where the suture cannot rip the substrate. The thickness may be empirically determined as different applications will have different forces. For example, certain tissues tend to have little stretching or time-varying relative motion (e.g., brain, bone, other body locations) and attendant relatively low forces on the substrate need be accommodated and so the substrate may be relatively thin (e.g., less than 100 µm). In contrast, heart, blood vessels, lung, stomach, esophagus, skin and other locations where there is substantial movement (including leg region of the sciatic nerve), the receiving means suture or staple may exert larger forces on the substrate. Accordingly, the substrate is selected to be thicker (e.g., greater than 100 µm). The specific thickness for a given application may be empirically determined, such as a thickness that is greater than about 10%, greater than 20% or greater than 50% compared to a device positioned in a substantially stationary environment that does not tear. Alternatively, the geometry of the tip may be shaped to further minimize substrate tearing forces, such as from a bell-shaped (left panel) to a more rectangular shape (right panel) or a tip shape (previously illustrated).

Recent modifications to the device design and implantation procedure have significantly improved device targeting and durability. A short piece of PDMS slightly wider than the body of the device has been attached to the device body just before the device ends. This allows the surgeon to anchor the device to the overlying muscle tissue using sutures without compromising the watertight integrity of the LED component (See FIG. 51B). This anchoring prevents the implanted device from moving off target even when the mouse fully flexes or extends its back during its normal range of motion. After these sutures are placed, the muscle layers are closed over the implanted device and the muscle architecture is then reconnected with a suture that runs over the implanted device between the gluteus maximus to the biceps femoris.

Figure 52:
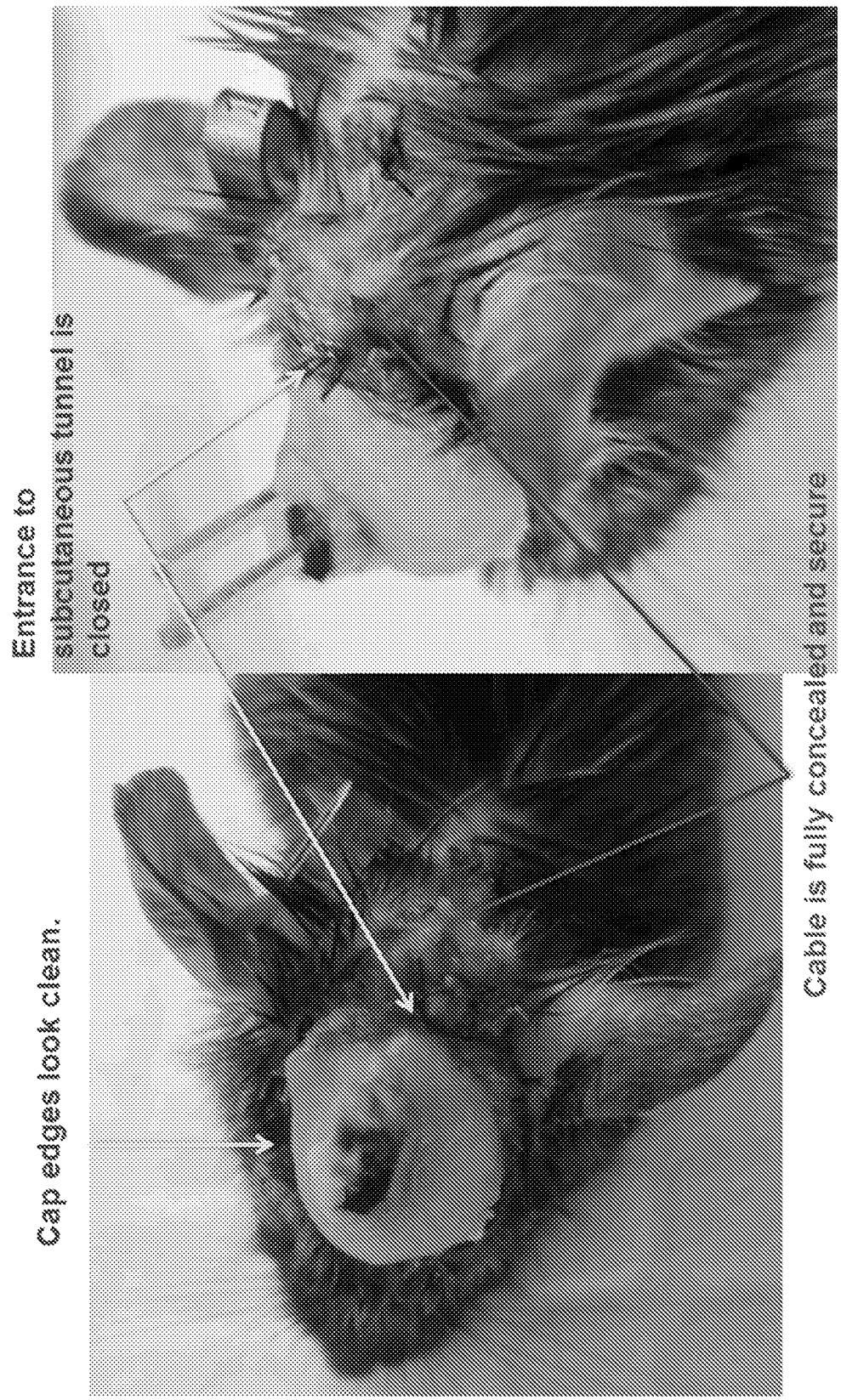
Figure 53:
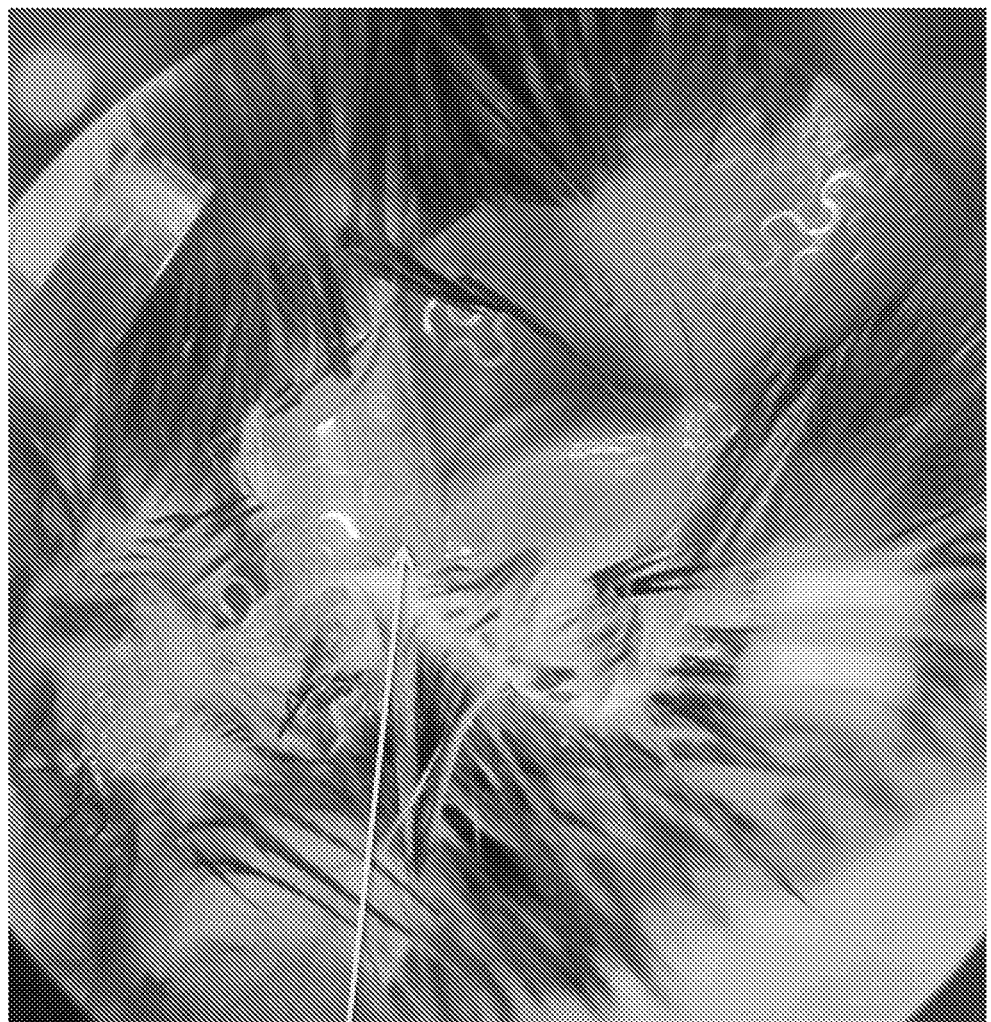
Figure 54:
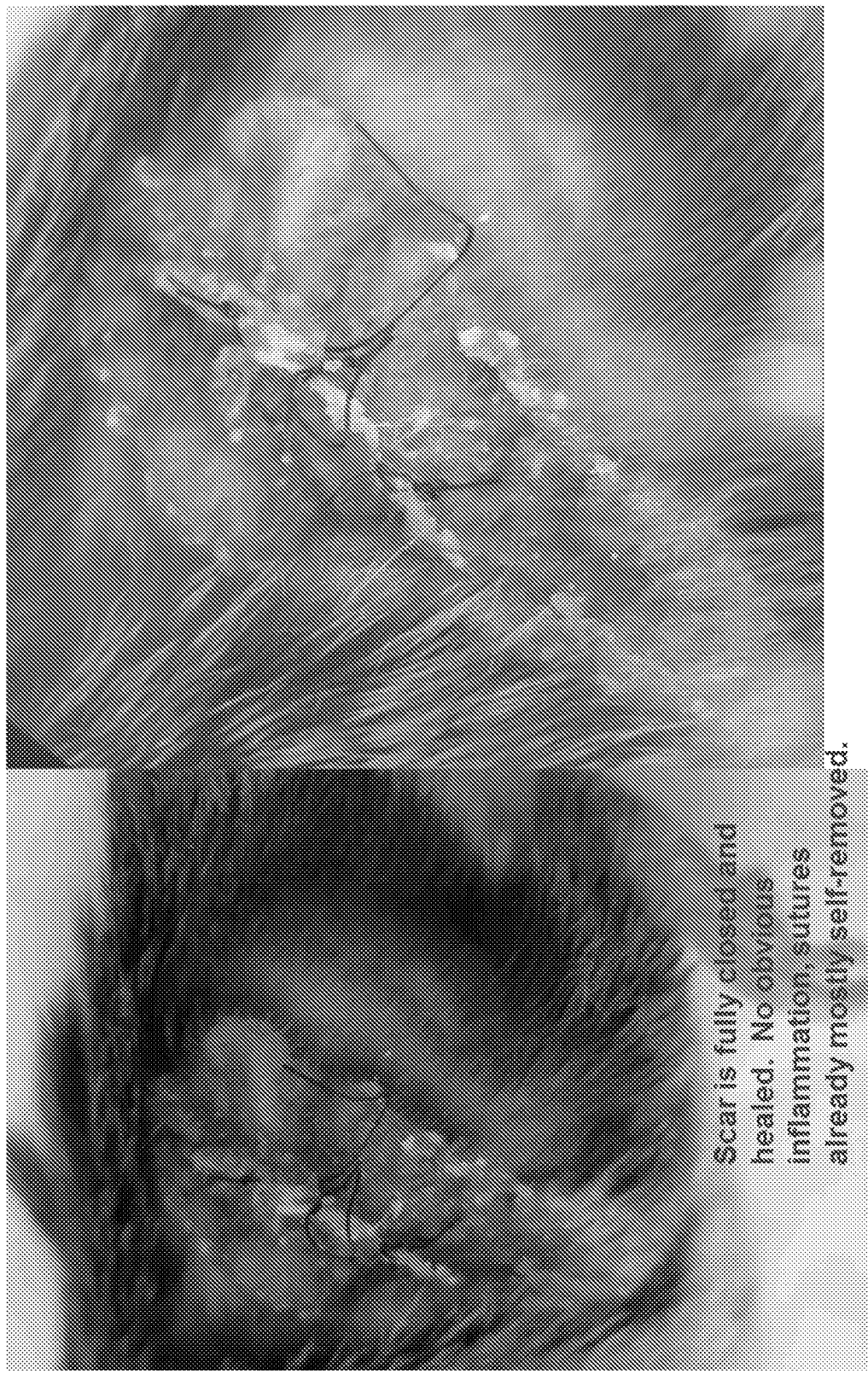
Figure 55:
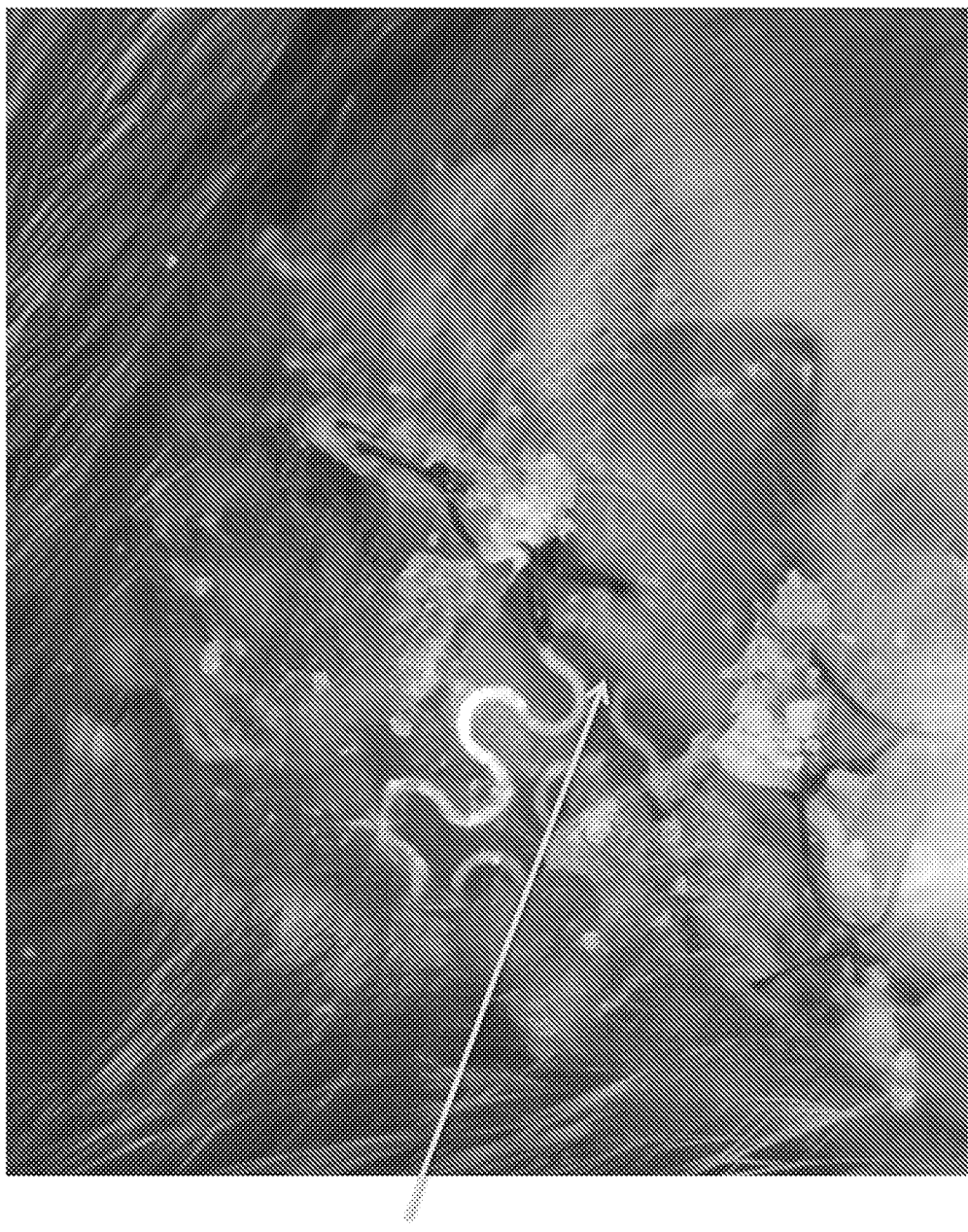
Figure 56:
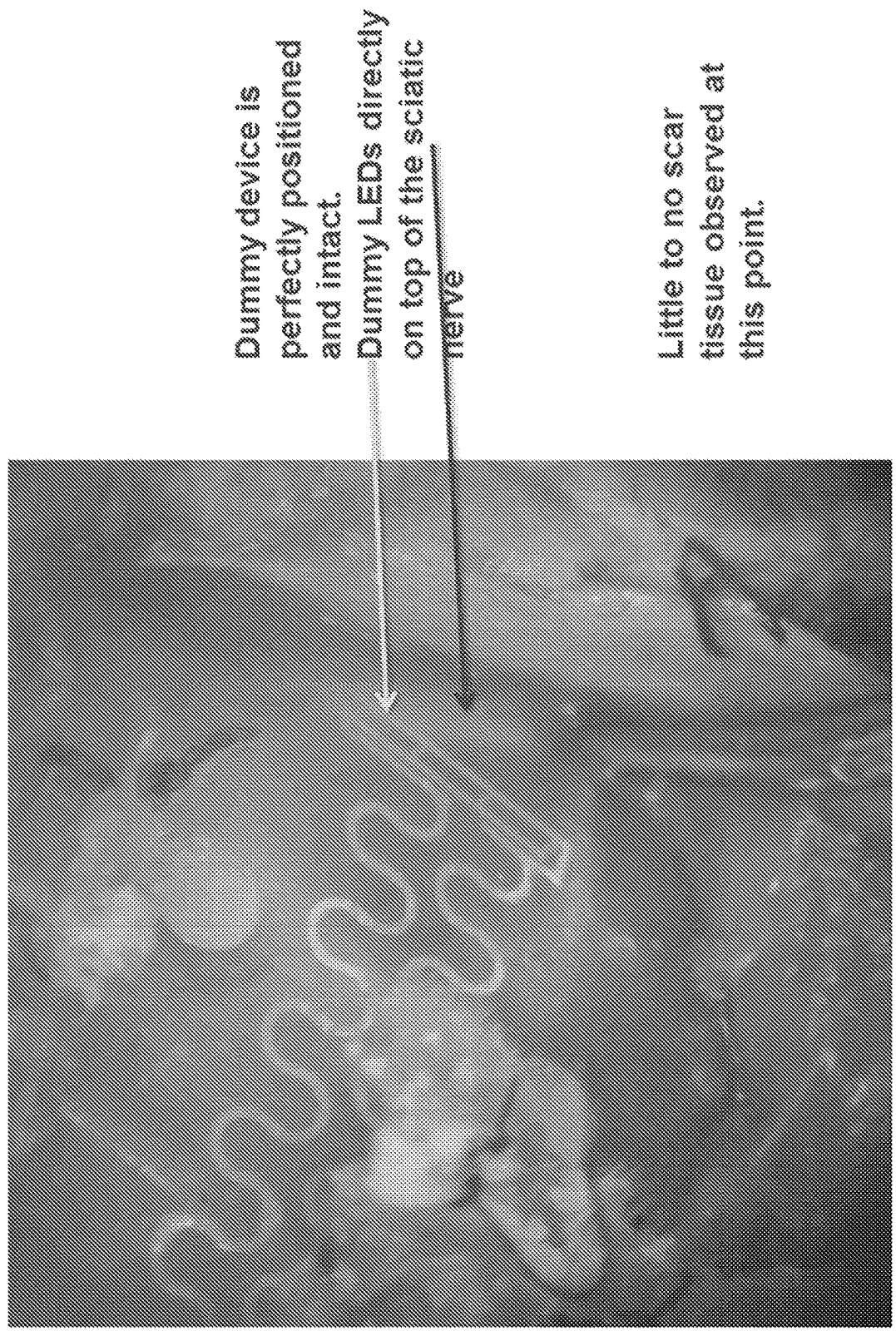
Figure 57:
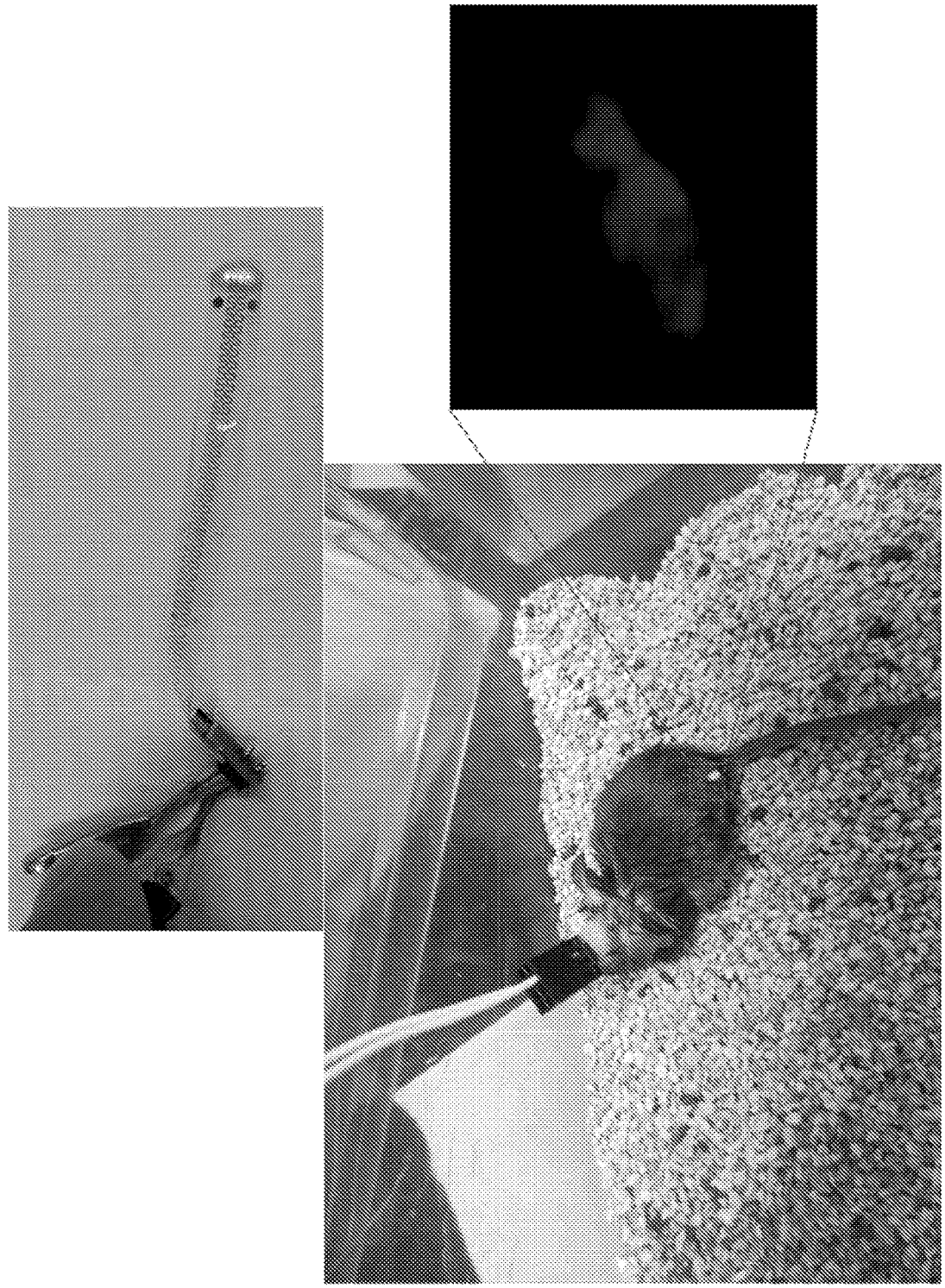

FIGS. 52-57 illustrate that as soon as three days post surgery, various portions of an implanted device having serpentine interconnects and other improvements outlined above result in good device operability and minimal adverse biological effects. FIG. 52 shows scar healing 3d post surgery at the antenna cap (head region). FIG. 53 illustrates subcutaneous tunnel 3d post surgery and no observable scar tissue. The distal end of the implanted device (e.g., region containing the interfacing tissue) presents as fully closed without inflammation (FIG. 54) and the tissue morphology and function unchanged (FIG. 55). The device position is unchanged relative to its initial insertion position over the sciatic nerve (FIG. 56). FIG. 57 shows the energized implantable or surface mounted biomedical device outside the body (top panel), the mouse in which the device is implanted (bottom right panel) and the in vivo illuminated area (bottom right panel).

Example 4: Fabrication of Flexible, Multimodal Light-Emitting Devices for Wireless Optogenetics The present description provides an example of a procedures for making and using certain specific embodiments of the invention. It will be understood by one of skill in the art, the protocol described in this Example is provided to exemplify certain aspects of the invention and is not intended to limit the scope of subject matter described herein.

The rise of optogenetics provides unique opportunities to advance materials and biomedical engineering as well as fundamental understanding in neuroscience. This example describes the fabrication of optoelectronic devices for studying intact neural systems. Unlike optogenetic approaches that rely on rigid fiber optics tethered to external light sources, these novel devices utilize flexible substrates to carry wirelessly powered microscale, inorganic light-emitting diodes (µ-ILEDs) and multimodal sensors inside the brain. We describe the technical procedures for construction of these devices, their corresponding radiofrequency power scavengers, and their implementation in vivo for experimental and therapeutic applications. In total, the timeline of the procedure, including device fabrication, implantation, and preparation to begin in vivo experimentation, can be completed in approximately 3-8 weeks. Implementation of these devices allows for chronic (tested up to six months), wireless optogenetic manipulation of neural circuitry in animals experiencing behaviors such as social interaction, home cage, and other complex natural environments.

INTRODUCTION

Optogenetics is a relatively new field of neuroscience that gives researchers the ability to control cellular signaling and neural activity in a cell-type selective manner. In vivo applications of optogenetics have rapidly aided in the understanding of neural circuit function in behavioral models.[1-10] Despite the success of these studies, tethered fiber optic approaches have restricted opportunities for the study of more complex, ethologically relevant behavioral paradigms such as enclosed homecage behavior, spontaneous pain, wheel-running, and freely-moving social interactions. Here we present a description of the fabrication of flexible devices that carry wirelessly powered microscale, inorganic light-emitting diodes (µ-ILEDs) and multimodal sensors to study neural circuitry in awake, freely moving animals. The devices described in this Example are robust, self-contained, multifunctional, and capable of wireless operation with conventional electronics and power supplies. These fully electronic systems eliminate the need for high-powered light sources, fiber coupling fixtures and optomechanical hardware for in vivo optogenetic experiments.

Development of the Protocol and Comparison with Traditional Light Sources

This Example provides an exemplary protocol that is the result of advances in material science that have led to the development of flexible electronics, biodissolvable adhesives, microscale sensors, and high efficiency µ-ILEDs[12-14,16,17]. While other groups have successfully implemented wireless schemes and LEDs for optogenetics[18-21], the protocol described here provides a completely customizable approach for combining various materials engineering approaches to design and implement devices that can be optimized for an individual laboratory's experimental needs.

The current standard in neuroscience for light delivery into the depth of the brain is to use chronically implanted fiber optics[22], which offer substantial advantages over acute delivery of fibers via metal cannulae[1,11]. These chronic implants, however, have their own limitations. Principally, light from fiber optic implants can only escape from the tip of the implant to illuminate ventral brain structures. While adaptations to this ventral light delivery are possible[10,23,24] (available commercially at www.doriclenses.com), the range of customizability can be limited and often restricts the user to only delivering light without the capability of observing physiology. Furthermore, µ-ILEDs create opportunities to restrict or expand spatial targeting by selecting from a range of sizes (625-10,000 µm$^2$), altering the number and arrangement of µ-ILEDs, and using reflective materials to direct light. This protocol provides a basis from which any combination of µ-ILEDs and sensors can direct light within the brain and measure physiological function without the restriction of enforced light trajectory.

Various strategies have been employed for delivering multiple wavelengths of light into the same animal[23-25]. These approaches require establishing an extensive network of optics and tethered optical equipment external to the behaving animal. Depending on the laboratory behavioral space, such setups can restrict experimental possibilities and requires advanced experience with optics to maintain optimal conditions. This protocol may require access to external facilities for some labs, but the end result is a device that can be operated with basic laboratory equipment already likely to be present in most neuroscience laboratories. Furthermore, the rescue and recycling of these devices for re-use is relatively easy, meaning that these devices can be used for several rounds of behavioral experimentation with different sets of animals (See Box 2 for details). For light-evoked activation of channelrhodopsin-2 [ChR2 (H134)], optically sensitive seven-transmembrane domain receptors (i.e. OPTO-$\alpha_1$, OPTO-$\beta_2$), and other blue light-sensitive optogenetic constructs, GaN µ-ILEDs are appropriate[2,11,26]. A device utilizing these 450 nm-emitting µ-ILEDs will be the focus of this protocol. However, it is important to note that µ-ILEDs emitting at other relevant wavelengths are also possible to fabricate for use in other contexts[11,27]. The combination of µ-ILEDs of different wavelengths provides the user with access to activation spectra of multiple optogenetic constructs with a single implanted, electronic device. Furthermore, the electronic nature of these devices ensures that they can be operated wirelessly. Wireless optogenetic manipulation of neural circuitry has been achieved by other means[19,20], but these approaches can restrict behaviors accessible to study because the animal is required to remain in a fixed environment. By utilizing radiofrequency (RF) power scavenging, the devices and approaches contained in this protocol free the user of constraints on behavioral assays, thereby allowing for experimental testing in any space.

Applications of the Protocol

While the focus of this protocol is on the creation of devices engineered to deliver µ-ILEDs into the brain for optogenetic applications, this same protocol can be used to fabricate devices for the study of electrophysiological, temperature, and other properties of tissue (See Box 1 for details). The flexible nature of these devices provides the potential to extend their application into other intact tissues such as the peripheral nervous system and the circulatory system/cardiac tissue of larger organisms.

Experimental Design

Subjects. This protocol and these devices have been optimized for use in adult (25-35 g) male C57BL/6J mice and mutant mice backcrossed to the C57BL/6J mouse strain. However, as the optogenetic toolbox expands to other mammals[28-33] these devices will likely have broader utility in other animal models. Specifically, larger organisms such as rats and non-human primates will tolerate the ~700 mg wireless antenna with greater ease than mice. Unlike animals with polished fiber optic implants, animals with chronically implanted µ-ILEDs can be housed with other animals, as the metal pin connectors cannot be damaged by cage mates. For this protocol, all procedures were approved by the Animal Care and Use Committee of Washington University and conformed to US National Institutes of Health guidelines.

Controls As noted elsewhere[2,11,22], the proper controls for in vivo optogenetics are mice that express genetically-encoded fluorescent reporters in the absence of an opsin. These control mice will account for any disturbance from viral injection, device implantation, heating confounds from light delivery, and fluorophore fluorescence within the brain. Another important confound to consider when conducting light-evoked single-unit electrophysiological experiments is the potential for generating neural activity downstream of retinal stimulation. These devices prevent the external light escape that is common with fiber optic implants, but activity from the visual system has the potential to activate the retina and retinal ganglion cells from within the brain, depending on the brain region[34]. Recordings performed with an external light stimuli can control for these effects. Additionally, properly counter-balanced within-subject experimental designs are possible with these devices by withholding power to the devices during the behavioral testing period.

Limitations

Subsequent recovery and re-fabrication of the devices is straightforward and accessible to any laboratory. Once the protocol is followed there are few considerations when designing behavioral experiments. First, depending on the panel antenna employed, the signal can be polarized. In current designs, both the panel antenna and the antenna on the scavenger are directional with linear polarization. A maximum efficiency of power transmission and reception is achieved when the polarizations of both antennas are aligned. The power transmitted by the panel antenna can typically be adjusted to accommodate mismatches that can occur in most practical situations. Such issues can be avoided entirely by use of a transmission antenna with circular polarization or multiple panel antennas.. Care should also be taken to ensure that the animal's surroundings do not interfere with the RF signal by powering a free-standing device in the behavioral context[11]. In our experience, commonly used materials for behavioral apparatus (wood, polyvinyl chloride (PVC), Poly(methyl methacrylate) (PMMA; Plexiglass/Perspex) and the metal from cage lids) do not interfere with the RF signal, but can reduce the overall power if they are positioned between the panel antenna and the headstage scavenger.

Second, the current protocol only provides wireless access to power the p-ILEDs and not to receive information from the sensors. This backwards data stream restriction is largely one based on the weight that an animal can endure on the headstage. For a mouse, electrophysiological, temperature, and photo sensors currently require a wired connection. For larger mammals, the devices can be integrated with existing telemetry setups, provided they do not interfere with the RF signal[35,36] (commercially available at www.plexon.com). Finally, independent control of individual μ-ILEDs is also possible with these devices, but the described protocol has not been optimized for these conditions in a wireless control mode. If independent control is a desired feature, it is recommended that smaller connections featuring a number of channels are employed over the pin connectors that we present here (many options commercially available at www.omnetics.com).

Upon completion of the protocol presented here, users can expect to have devices with 4 μ-ILEDs that can be wirelessly powered with suitable light output from two meters away. In our experience, more μ-ILEDs can be added to a single device with relative ease (the maximum we have tested is 25 (5×5) μ-ILEDs from a single power scavenger). Furthermore, the radiofrequency power scavenging approach is appropriately suited for powering multiple μ-ILED devices (presumably in multiple animals) using a different power scavenging headstage antenna for each device. The upper limit on the number of simultaneously powered devices is primarily dependent on the spatial constraints of the experimental space and apparatus to achieve equal powering to all devices.

Notes on the materials and equipment used in this Example Accurate injection of these devices into brain tissue requires an stereotaxic adapter for standard cannula holders. The basic principle of this adapter is that the p-needle can mounted in-line with the existing stereotaxic system. The dimensions of such an adapter will vary by stereotaxic alignment system make and model, but most university machine shops should be able to fashion such an adapter. The adapter presented in this protocol was specifically designed for use with the KOPF Single Cannula Holder (Model 1966). It is also possible that other commercially available electrode holders may be capable of accurately targeting the devices (e.g. KOPF Model 1768). More detailed information on the machining and dimensions of the adapter for the KOPF Model 1966 can be found in FIG. 65.

Post-mortem rescue of the devices for reuse is a delicate, but straightforward process. The dental cement presented here (Lang Dental) allows for such rescue. Other cements and bonding agents can inhibit the process and destroy internal components. It may be necessary to use a stronger bonding agent in some scenarios. In such cases, the re-usability might be compromised.

Materials
Reagents
Preparation of Releasable Polymer Template
  UV curable epoxy (SU-8 2 & 100 photoresist, Microchem) Partially cured or uncured epoxy needle can induce excess chemical contamination in the brain.
  SU-8 developer (Microchem)
  Isopropyl alcohol (IPA) Isopropyl alcohol is flammable.
  Acetone Acetone is flammable.
  Silk adhesive (provided by Tufts university, Details are shown in other papers[13,16,17]
  BCB (Benzocyclobutene, DS-4022 35, Dow corning)
  BCB developer (Advanced Developer, DS2100, Dow corning)
  Water soluble tape (3M)
  Photoresists (AZ 1518, AZ 2070, Capital Scientific)
  AZ 300 MIF developer (Capital Scientific)
  Hydrofluoric acid (HF) HF is extremely corrosive. Wear gloves and use eye protectionwhen using HF.
  Chrome (Cr) etchant, gold (Au) etchant, palladium (Pd) etchant (Transene Inc.)
  Polydimethylsiloxane (PDMS, Sylgard184, Dow corning)
  Polyethylene terephthalate (PET, polyester film, 2.5 and 6 μm thick, Mylar® film, Chemplex® Inc.)
Preparation of Microscale LED
  Gallium nitride (GaN) LED epitaxial materials grown on sapphire substrates (Cermet Cop.)
Injection of Virus and μ-ILEDs into Targeted Brain Structure
  Isoflurane, USP (Isothesia, Butler Schein, cat. no. 029405) Prior to beginning this protocol, the Animal Care and Use Committee of the investigating institution should approve all procedures and conform to US National Institutes of Health guidelines regarding animal research. Ensure proper ventilation and gas scavenging methods are in place to prevent potential inhalation of excess isolflurane.
  Betadine solution (Purdue Products, cat. no. 67618015017)
  Ethanol (Sigma-Aldrich, cat. no. 362808) Ethanol is flammable.
  Hydrogen peroxide, 3% USP (Select Medical Products, cat. no. 117)
  Lidocaine ointment USP, 5% (Fougera)
  Ophthalmic ointment (Altalube Ophthalmic Product)
  Adhesive Luting Cement (C&B-Metabond, Parkell Inc., cat. no. S380)
  Light cured bonding adhesive (VLC One Step Prime & Bond Adhesive, cat. no. 305-006-030)
  Dental cement (Jet Denture Repair, Lang Dental, cat. no. 1223, see REAGENT SETUP) Methyl Methacrylate Monomer, Stabilized is a flammable liquid. It may also cause skin irritation; avoid contact with skin, eyes, and clothing. Use with adequate ventilation.
  0.9% Sodium Chloride Inj., USP ((9 mg/ml NaCl), Hospira, cat. no. RL-0497(9/04))
  Enroflaxin (Baytril, Bayer, cat. no. R30901)
  Antibiotic ointment (Neosporin, Johnson & Johnson, cat. no. 174-73087Q)
  Viruses of interest (Adeno-associated virus and lentiviruses are available from the WUSTL Hope Center Viral Core, website hopecenter.wustl.edu/?page_id=99 and/or the University of North Carolina Viral Vector Core, website genetherapy.unc.edu/services.htm), Herpes Simplex Viruses are available from the MIT Viral Core, website mcgovern.mit.edu/technology/viral-vector) Follow the appropriate safety precautions pertaining to the particular virus in use. It may be necessary to obtain a higher Biosafety Level certification prior to use.
  Artificial cerebral spinal fluid (ACSF; Tocris, cat. no. 3525 or custom, see REAGENT SETUP[1,37]
  Animal(s) to be injected with μ-ILED device. The procedure describes how to use a mouse. Prior to beginning this protocol, the Animal Care and Use Committee of the investigating institution should approve all procedures and conform to US National Institutes of Health guidelines regarding animal research.
Behavioral Procedures Using RF Power Scavenging
  Thermal grease (Wakefield Solutions, cat. no. 120-2)
Equipment
Preparation for μ-ILEDs and Multifunctional Sensors
  Sputter ((AJA international, ATC 200) metal deposition for Au (gold), Ni (nickel), Pt (platinum), etc.)
  Rapid thermal annealing (RTA) High temperature, semi-transparent L-shaped current spreading layer on p-side on GaN LED should be used in thin metal layers (15/15 nm Ni/Au) followed by 500° C. annealing.
  Mask aligner (Karl Suss, MJB)

Inductively coupled plasma (ICP) etcher (PlasmaTherm SLR-700, etching for GaN)

Reactive ion etcher (RIE, PlasmaTherm 790, etching for SiNx)

Plasma enhancement-chemical vapor deposition (PE-CVD, STS mixed frequency nitride deposition system)

Wafer bonder (Electronic Visions, EV501)

Laser lift off (LLO, Krypton Fluoride (KrF)(0.9 J/cm$^2$, 248 nm wavelength, IPG Photonics (website ipgphotonics.com/microprocessing.htm) or Yttrium aluminum garnet (YAG):Nd laser (0.3 J/cm$^2$, 266 nm Single pulse with 5 ns exposure, Sandia National Lab) Avoid eye contact with the laser. Always wear eye protection.

Digital multimeter (Fluke 115 or other commercially available multimeter)

Printed circuit board (PCB) for headstage connection (General Circuits Co.)

Male pins for headstage PCB (2.54 mm spacing male pins (Sunlight Inc, P2540-H254-S180).

Measurement of µ-ILED

Ocean Optics (Ocean Optics HR4000) (for measuring wavelength spectrum, light output power)

Probe station (Agilent 4155) (current-voltage (I-V) characteristics).

Pulse generator (Global specialties, 4001)

Oscilloscope (Agilent, DSOX2004A, 70 MHz)

IR camera (QFI InfraScope II)

Injection of Virus and µ-ILEDs into Targeted Brain Structure

Stereotaxic alignment system (KOPF Model1900) Prior to beginning this protocol, the Animal Care and Use Committee of the investigating institution should approve all procedures and conform to US National Institutes of Health guidelines regarding animal research.

Stereotaxic alignment indicator (KOPF Model 1905)

40× Centering Microscope (KOPF 1915)

Stereotaxic drill (KOPF Model 1911) and #66 drill bit (KOPF cat. no. 8669)

Stereotaxic single cannula holder (KOPF Model 1966)

Stereotaxic adapter for cannula holder (See FIG. 65, WUSTL Machine Shop or other)

Anchoring screws (CMA Microdialysis, cat. no. 7431021)

Needles (Becton-Dickinson, cat. no. 305111)

Micro-injection syringes (Hamilton, cat. no. 88011)

Infusion pump and controller (UltraMicroPump III, World Precision Intstruments, cat. nos. UMP3 and UNC4)

Forceps (Miltex, cat. no. 6-100)

Surgical scissors (Miltex, cat. no. 18-1430)

Hemostats (Miltex, cat. no. MH7-26)

Microspatula (Chemglass, cat. no. CG-1982-12)

Electric clippers (Wahl, cat. no. 8064-900)

Behavioral Procedures Using RF Power Scavenging

RF generator (Agilent, N5181 MXF)

Function generator with standard transistor-transistor logic (TTL) (AMPI Master-9 or other)

RF amplifier (Empower RF systems Inc. 1100/BBM2E4AJP)

RF antenna (ARC wireless solutions, ARC-PA0913B01, ARC 902-928 MHz 12.5 dBi, Flat Panel)

DC power supply (Mastech, cat. no. HY5005E-2)

Relevant behavioral assay apparatus (university machine shops, MED Associates, Harvard Apparatus or other)

Wireless headstage antenna (see PROCEDURE)

Printed circuit board (PCB) for wireless headstage antenna (General Circuits Co.)

Ceramic antenna (W3012, Pulse Electronics)

Schottky diode (Digi-Key, cat. no. MMDL301T1G)

Power meter (Bird Electronic Corp., Thruline 43)

Two SMA Male to N Male Precision cables (Pasternack, cat. no. PE304-120)

Fan-cooled heat sink (Fischer Elektronik, cat. no. LA 17/200 24V)

Behavioral Procedures Using a Wired Connection

Animal(s) with injected µ-ILED device Prior to beginning this protocol, the Animal Care and Use Committee of the investigating institution should approve all procedures and conform to US National Institutes of Health guidelines regarding animal research.

Relevant behavioral assay apparatus (university machine shops, MED Associates, Harvard Apparatus or other)

Function generator for standard transistor-transistor logic (TTL) (AMPI Master-9 or other)

BNC cables (Cables to Go, various lengths and catalog numbers)

Electrical rotary joint (Moog, cat. no. SRA-73683[38])

BNC-to-banana plug adapter (Fluke BP881 or other)

Wire (30 gauge wire, Artistic Wire) and female connector (Single modality devices: TE Connectivity, cat. no. AMP 3-640441-2; Multimodal devices or independent µ-ILED control: TE Connectivity, cat. no. AMP 87631-4)

Reagent Setup

Dental cement The dental cement can be prepared as described elsewhere[22]. In some cases, the viscosity must be adjusted (by increasing or decreasing the amount of methyl methacrylate in the mixture) to properly secure the flexible device in place and/or mount the PCB in the headcap. A starting point is 350 µl of methyl methacrylate monomer added to 225 mg of powder. Adjusting the viscosity alters the working time of the cement.

Virus

Each type of virus has different handling instructions, but all must be stored on ice until immediately prior to the injection. In some cases, dilution of stock titers requires obtaining more of the reagent in which the viral prep was initially concentrated.

ACSF

If not purchased, the solution can be prepared following the recipes described elsewhere[1,37].

Equipment Setup

Preparation of amplifier with proper heat sink. The RF amplifier (1100/BBM2E4AJP, Empower RF Systems Inc.) requires an additional cooling system during operation. Thermal grease applied on top of the heat sink (LA 17/200 24V, Fischer Elektronik Inc.) facilities thermal contact with the amplifier, which is affixed to the sink using screws. The DC power supply operates both the amplifier and the fan attached to the heat sink, by supplying power with voltages of 24 V and 10 V, respectively.

Example Procedure

Preparation of µ-ILEDs●TIMING 7 d

Additional information on production of µ-ILEDs appears in FIG. 64 and a previous manuscript[12].

1. Clean the wafer surface of GaN LED stacks (450 nm emission wavelength; p-type GaN/multi-quantum well (MQW)/spacer/n-type GaN/undoped GaN) grown on sapphire substrate with 5 wt % diluted HCl for 5 min. Proper cleaning enables reduced turn-on voltages and improved efficiencies, both of which minimize production of heat by the operating µ-ILEDs.

2. Deposit metals (Ni/Au, 15/15 nm) immediately after cleaning The deposition should be carried out degree vacuum levels of ~10$^{-6}$ torr or less.

3. Form L-shape patterned metals (Ni/Au) onto the p-type GaN semiconductor layer by photolithography and wet etching with Cr and Ni etchants followed by removal of the photoresist (PR) with acetone (FIG. 64a).

4. Anneal the wafer for 10 min at 500° C. in 20% oxygen and 80% Argon atmosphere to generate p-ohmic contact. The annealed metal layers should be semi-transparent after the procedure 4.

5. Generate 40×40 µm² square hole patterns in a negative tone PR (AZ 2070 PR) and etch (chorine gas based RIE etching) the p-GaN layer, MQW, spacer to open n-side GaN (FIG. 64b).

6. Generate 25×25 µm² square hole patterns in PR for n- and p-type metal contact pads and deposit Cr/Au (10/300 nm) using an electron beam evaporator. Then, remove PR (FIG. 64c).

7. Deposit a low stress layer (200 nm) of SiNx on the substrate, using plasma enhanced-chemical vapor deposition (PE-CVD). Next, pattern a negative tone PR (AZ 2070) to serve as a mask for etching the SiNx and the GaN to define the lateral dimensions of array of µ-ILEDs. Devices with dimensions of 100×100 µm² or less are formed with 20 µm spacings (FIG. 64d).

8. Deposit a layer of SiNx onto the µ-ILEDs to protect the devices and metal pads from further processes. Bond the LED wafer to a silicon substrate using indium (In)-palladium (Pd) metallic alloy. This bonding uses Cr/Pd (15/150 nm) on the LED substrate and Cr/Pd/In (15/150/900 nm) on the silicon. The bonding occurs on contact with a pressure of 400 bar and temperature of 220° C. for 2 hr (FIG. 64e).

9. Use laser illumination through the sapphire to release the µ-ILEDs (FIG. 64f). Details of this laser lift-off (LLO) technique appear elsewhere[12,39].

10. Etch unalloyed metal by immersion in 5 wt % HCl for 30 min (FIG. 64g).

11. Retrieve all µ-ILEDs onto substrate of PDMS with patterns of surface relief, in the geometry of cylindrical pillars with 3 µm diameter and 1.4 µm height and 5 µm spacing. Remove residual metals, including In—Pd alloy and Crare by Pd and Cr etchants (FIG. 64h).

12. Prepare a PDMS stamp with a single relief feature consisting of a post with 100×100 µm² lateral dimensions and 100 µm height. Using a mask aligner for photolithography, retrieve a single µ-ILED with the stamp and transfer it to a needle shaped structure of PET adhered to a thin layer of PDMS on a transparent temporary substrate (FIGS. 58a and 58b).

13. Remove passivation layer, SiNx (deposited in procedure 8) with RIE and spin coat a photosensitive benzocyclobutene (6 µm thick, BCB) onto the µ-ILED.

14. Pass ultraviolet (UV) light through the backside of the substrate and develop the BCB with BCB developer (FIG. 58c) to obtain holes for n- and p-side contacts (FIG. 58c, lower inset) Make sure that BCB covers the µ-ILED surface. Non-uniform coatings of BCB generate interference fringes that are readily visible. (FIG. 58c, upper inset) After further curing BCB, anneal the samples at 250° C. on a hot plate for 3 hr. The annealing should be carried out in Ar atmosphere to avoid high temperature damage to the BCB and polymeric layers.

15. Deposit Cr/Au (15/300 nm) by sputtering, and form metal interconnects using positive tone PR (AZ 15198) followed by metal etching (FIG. 58d and FIG. 64i)
Deterministic Device Assembly by Transfer Printing and Formation of Electrical Interconnects●TIMING 1 d 16. Remove µ-ILEDs fabricated on each temporary substrate as shown in FIG. 58a with water-soluble tape (FIG. 58e). Remove water-soluble tapes in DI water (FIG. 58f) and place the devices on slabs of PDMS (FIG. 58g). Steps 16-20 describe device assembly for µ-ILEDs alone. If you are assembling a multifunctional device, follow the instructions in Box 1 before proceeding.

17. Connect each of the devices with anisotropic conductive film (ACF) cable to a PCB board (FIG. 58h). Apply pressure and high temperature (~150° C.) during ACF cable bonding.

18. Assemble all devices onto injection p-needle formed in SU-8 epoxy. The entire region of injection device should be electrical insulated for in vivo use. Cover the flexible device with SU-8 polymer and the other parts with PDMS for waterproofing (FIG. 58i). Temporarily fix the device to the PDMS slab. Drop PDMS solution (Sylgard 180, Dow corning, weight ratio=10:1 (silicone elastomer precursor: curing agent), see details at website dowcorning.com/applications/search/default.aspx?r=131 en onto the ACF cable and PCB except for the pin connection area. After baking the PDMS in the oven at 70° C. for 2 hrs, the entire area except pin adapter is electrically passivated by PDMS.

19. To check functionality, power the device by connecting to a power supply capable of delivering more than 1 mW (FIG. 58j). Use silk adhesive to bond the devices to the injection p-needle (FIG. 58k, FIG. 58l).
Fabrication of Wireless Power Harvester and Preparation of Wireless Operation●TIMING 1 d 20. The wireless power harvester is constructed from two stacked PCB circuits (FIG. 60b; General Circuits Co., Ltd.). Each PCB includes top and bottom layers that are mostly covered by solid copper ground planes. Electrical components are mounted on the PCB boards through soldering. The first PCB circuit (labeled as 5 in FIG. 60b) contains a ceramic antenna (W3012, Pulse Electronics) operated at 915 MHz with a clearance space of 10.8×8.25 mm to the surrounding ground plane. A capacitor (8.2 pF in capacitance) is connected between the feed line of the antenna and the ground plane to match the impedance of the antenna with the following circuit. A secondary PCB circuit (labeled as 6 in FIG. 60b) contains a voltage multiplier circuit constructed with 6 pairs of capacitors (47 nF in capacitance) and Schottky diodes (MMDL301T1G) in cascaded connection[11]. A connector that is used for the µ-LEDs is mounted to the secondary PCB circuit. The PCB circuits and the connector are joined with flexible copper wires (FIG. 60c), and bonded together with resin epoxy (FIG. 60d). FIG. 60i shows a schematic illustration of the power harvester. The circuit parts, which are labeled with number 5 to 7, corresponding to the same number shown in FIGS. 60b and 60e.

21. The flexible PCB circuit is fabricated on a Kapton film with thickness of 75 µm (FIG. 60f). The film is coated with a layer of copper with 6 µm thickness by electron beam evaporation. The copper is then patterned to form pads for electrical components and interconnection. A polyimide film with 1 µm thickness is spin cast and patterned to expose the electrical contact pads, while passivating the interconnection (FIG. 60f). A ground plane made of copper tape (FIG. 60g) is attached on the bottom of the Kapton film and connected with copper pattern on the top of the Kapton film through channels filled with solder. A schematic illustration of the flexible PCB circuit appears in FIG. 60j 22. The experimental setup for wireless power transmission consists of an RF signal generator (N5181A, Agilent Technologies, Inc.), an RF amplifier (1100/BBM2E4AJP, Empower RF Systems Inc.), a DC power supply (U8031A, Agilent Technologies, Inc.), an antenna (ARC-PA0913B01, ARC Wireless), and a power meter (Thruline 43, bird electronic corp.) (FIG. 60a). The RF signal generator provides a 915 MHz RF signal with a power of −15 to −20 dBm.

The signal is amplitude-modulated through the internal function of the generator to create a pulsed signal with frequency of 10 Hz, and a carrier frequency of 915 MHz. Alternatively, an external TTL function generator can be connected to the RF signal generator to modulate the pulse width and frequency. This signal is directed to the RF amplifier, which amplifies the signal to 30 to 33 dBm. The power supply provides DC voltages of 24 V and 10 V to the RF amplifier and an exhaust fan of a heat sink of the amplifier, respectively. The amplifier is connected to an RF signal generator and an antenna using coaxial cables (SMA Male to N Male Precision Cable Using 160 Series Coax, Pasternack Inc.). The output power of the amplifier is first input into the power meter to measure the intensity. The power meter is then switched to the antenna for transmitting RF power to power the µ-LEDs at a 1~2 meter distance (FIGS. 60e and 60h).

Injection of Virus and µ-ILEDs into Targeted Brain Structure●TIMING 1 d

23. Mount the µ-ILED device in the custom-built cannula holder adapter or other electoral device holder (see EQUIPMENT SETUP) (FIG. 61a and FIG. 65). To do so, grasp the exposed region of the p-needle (FIG. 61b). The device must be placed along the midline of the adapter to achieve proper spatial targeting.

24. Anesthetize the mouse in an isoflurane induction chamber using 4% isoflurane and a flow rate of 1.5 L/min $O_2$. Prior to beginning this protocol, all procedures should be approved by the Animal Care and Use Committee of the investigating institution and conform to US National Institutes of Health guidelines regarding animal research. Ensure that the animal is sufficiently anesthetized prior to transferring to the stereotaxic frame. The animal should have no response to a toe pinch and its breathing rate should reduce to ~1 Hz.

25. Transfer the animal to the stereotaxic frame, ensuring proper airflow of isoflurane to the nosecone (~2.5% isoflurane; 1.5 L/min $O_2$). Isoflurane levels should be monitored throughout the surgery to maintain sufficient anesthesia (no toe pinch response) and breathing (1 Hz). For longer duration surgery, isoflurane levels may be decreased to as low as 1%. Sterile, aseptic conditions should be used at all times to avoid infection. Proper placement in the stereotaxic frame is required for accurate injection of virus and devices.

26. Apply ophthalmic ointment to protect the eyes during surgery.

27. Shave a 2×1 cm area on the animal's scalp (FIG. 61c).

28. Inject 0.1 mL of Enroflaxin into the hindlimb (i.m.) and 0.3 mL saline solution (0.9% (w/v), s.c.) to prevent infection and dehydration, respectively.

29. Using a cotton swab, apply 70% ethanol (vol/vol) and betadine to the shaved area.

30. Carefully grasp the tissue with the forceps and, using the scissors, make an incision the length of the shaved area (FIG. 61d). Ensure that all surgical instruments are sterilized prior to each animal surgery.

31. After the skin separates, use the forceps and scissors to clean and remove any remaining periosteum on the skull surface.

32. Identify the skull sutures, lambda and bregma. Carefully level the skull according to the manufacturer's recommend steps for your stereotaxic frame. For the KOPF Model 1900, use the stereotaxic alignment indicator. It is critical that both lambda and bregma be level, as well as achieving a level plane laterally across the skull.

33. Once the skull is level, move the drill to the coordinates you have selected for anchor screw placement. Carefully drill a hole with a diameter just wide enough for the screws to catch and not so deep as to penetrate the skull (FIG. 61e). Proper anchoring is crucial to ensure that the headcap remains affixed to the skull for the duration of the behavioral experiments. Generally, anchor screws should be placed on either side of the midline within 2 mm of the site of implantation.

34. Use the forceps and microspatula to properly anchor the screws into the skull (FIG. 61f)

35. Move the drill above the injection site. Drill a hole that penetrates the skull, but not the dura. Drilling through the dura can cause widespread damage, bleeding, and inflammation under the skull.

36. Align the infusion pump and lower the injection needle to the dorsal-ventral stereotaxic coordinates of the targeted structure of interest (FIG. 61g). A beveled needle can penetrate the dura safely. If a blunt needle is used the dura should be pierced using a sharp, sterile needle.

37. Using the microcontroller, infuse the virus at a maximum rate of 100 nl/minute. Volume of virus will vary depending on the brain structure and serotype of virus used[1,2,4,40-43]. All viruses should be kept on ice prior, but special care should be taken with lentiviruses and herpes simplex viruses to prolonged exposure to temperatures above 4° C.

38. Once the infusion is complete, allow the injection needle to remain in place for one minute for every 100 nl of virus infused. Slowly remove the needle from the injection site.

39. Position the cannula holder above the drill hole (FIG. 61h). Take care to orient the µ-ILED/other functionalities in the direction suitable for the experiment in order to properly illuminate the opsin expressing brain region of interest. For injection into rodents, rinse with ethanol to sterilize the device prior to injection. For other mammals and primates it might be necessary to use room temperature Ethylene Oxide (EtO) gas sterilization (website anpro.com/sterilizers/anprolene/indexanprolene.html)

40. Slowly lower the device into the brain to the desired dorsal-ventral coordinates.

41. Using a syringe needle, slowly apply ACSF to the skull to dissolve the silk-based adhesive. The brain tissue will dissolve the adhesive inside the skull. Wait at least ten minutes to allow for complete dissolution of the adhesive (FIG. 61i). The adhesive must be completely dissolved prior to p-needle removal. If not, the final placement of the flexible substrates will be affected.

42. Slowly remove the p-needle. Monitor the position of the flexible substrates to ensure that zero movement occurs. If the adhesive is completely dissolved, the p-needle will remove with ease and without movement (FIG. 61j).

43. Prepare the dental cement according the REAGENT SETUP.

44. Using the microspatula, carefully apply a layer of dental cement directly to point of injection to fully secure the placement of the device (FIG. 61k). Allow this layer of cement to completely cure prior to building the structure of remaining headcap.

45. Once the initial layer of cement is fully cured, position the PCB-based connector in the desired orientation. Apply a small amount of dental cement to secure it to the base layer (FIG. 61l). The orientation of the connector will determine the orientation of the RF headstage antenna.

46. Finish the headstage by completely encapsulating the device-related hardware in dental cement. Be sure to leave the pins of the connector exposed to allow for connections to RF or wired functional generator. (FIGS. 61m and 61n).

47. Using a sterile spatula, detach any scalp skin from the cement. If the skin and the cement are connected, the headstage will be less stable over time.

48. Liberally apply (~1 g) the antibiotic ointment and lidocaine ointment to the entire incision area.

49. Remove the animal from the stereotaxic frame and place it in a clean homecage position on top of a heating pad for recovery. The animal should recover rapidly (<15 minutes) and can be returned to its homecage once it displays normal, awake locomotor behaviors. Because the only exposed portion of the devices are the metal connector pins, the animals can be group-housed for the duration of their experimental lifetime. However, if one chooses, the pins can be capped using a dummy connector.

50. The p-needle should be clear of any components of the device. Remove from the cannula holder adapter and sterilize for re-use (FIG. 61o) as described in Box 2 and FIG. 63.

Preparation for Behavioral Testing●TIMING 5 Days

51. House mice until the time at which proteins would be expected to be expressed. The choice of viral expression system will determine expression time, and hence this wait time prior to behavioral experimentation. This duration will vary from one to six weeks. For adeno-associated viral expression typical wait times are 2-3 weeks for expression at cell bodies[1,2,9,11,40].

52. At least five days before experimentation, handle animals to acclimate the animals to manipulation. In particular, connectors should be fitted to the headstage and any areas of the body that will be injected should be gently touched in order to habituate the animal to the manipulations they will experience during behavioral testing (e.g. the nape of the neck for subcutaneous, the abdomen for intraperitoneal, etc.).

53. Also habituate animals to the method of powering the devices. If a wired approach is used, animals should be connected to the wires and allowed to explore a homecage environment for at least 20 minutes once a day for three days. If a wireless approach is used, the RF headstage antenna should be connected in the homecage for the same duration. To eliminate locomotor confounds, the animals must be habituated to carrying the added weight of the antennas.

54. Perform wired (option A) or wireless (option B) behavioural tests. Wireless control of these devices is compatible with a wide-range of behavioral assays. In our hands, the devices have performed well in tests of anxiety-like behavior (open field test, elevated zero maze), reward-related behavior (conditioned place preference, operant behaviors, and self-stimulation), social behaviors (social defeat stress and social aversion), pain behaviors (Hargreaves test), and homecage behaviors[11]. It is reasonable to assume that wireless operation of the devices would be compatible with any behavioral assay in which the behavioral apparatus itself does not interfere with the RF signal[44-46], but care should be taken to ensure proper powering of the devices in every behavioral apparatus used. Once habituated to the RF scavenging headstage antennas, the devices can be controlled using a traditional function generator to drive amplitude modulation of the wireless powering equipment. Amplitude modulation is an internal function available on most RF generators. This function allows an internally or externally supplied modulating signal to control the amplitude of the output RF signal. The internal modulating signal is usually a sinusoidal waveform with a much lower frequency compared to that of the RF output. For the positive region of the sinusoidal signal, the RF generator can output an RF signal whose amplitude is modulated by the low frequency sinusoidal signal, and change from 0 to the maximum set power and then back to 0. For the negative region of the modulating signal, the output RF signal maintains at 0. An external TTL modulating signal is preferable in terms of modulating the amplitude of the output RF signal. Here, the high state of the TTL causes the RF generator to output a constant set power, while in the low state of the TTL, the RF generator outputs 0 power. Thus, the TTL modulating method is more suitable for generating constant light intensity during the high state of the TTL. The pulse width and frequency of photostimulation should be determined and based on physiologically relevant conditions[7,10,44-46]. The timing of the photostimulation will depend on the parameters and goals of the study, but the pulse generation options are well suited for a wide variety of approaches. Any traditional function generator can provide TTL input into the RF signal generator to modulate the pulse width and frequency of the light pulses. If the photostimulation needs to be contingent on the animal's behavior this can be achieved by using live video tracking connected to a TTL output (Noldus Ethovision 9.0 with Trial and Hardware Control and I/O Box or other) or triggering a TTL signal from infrared beam breaks (Med Associates or other).

A) Wired Optogenetic Behavioral Control●TIMING Variable i. Once habituated to the connecting cables, power the devices using a traditional function generator. The pulse width and frequency of photostimulation should be determined and based on physiologically relevant conditions[7,10,44-46]. The timing of the photostimulation will greatly depend on the parameters and goals of the study.

ii. Connect the cable to the function generator using the BNC-to-banana plug adapter.

iii. Route the cabling. For most wired behaviors, the best approach is to route the cabling through an electrical rotary joint as described previously[38].

iv. Carefully scruff the animal and connect the free end of the cable to the headstage of the animal. Place the animal in the behavioral apparatus (FIG. 62a) and perform desired behavioural test.

v. Following the behavioral test, scruff the animal, and remove the cable from the headstage.

B) Wireless Optogenetic Behavioral Control●TIMING Variable i. Connect the function generator to the RF Signal generator, the RF signal generator to the RF power amplifier, and the RF power amplifier to the panel antenna. Be sure that the power supply is connected to the heat sink (see EQUIPMENT SETUP) to avoid damaging the amplifier. Connect the power supply to the RF amplifier. To avoid unnecessary powering of the devices, do not engage the power supply until the beginning of the behavioral session.

ii. Carefully scruff the animal(s) and attach the RF scavenging antenna(s). Place the animal(s) in the behavioral apparatus and perform the behavioral test (FIGS. 62b and 62c).

iii. Following the behavioral test, carefully scruff the animal and remove the scavenging antenna.

iv. After the final behavioral session, if desired kill animals and use tissue for any manner of post-mortem evaluation[11].

Box 1|Combining multifunctional sensors and optoelectronics

One hallmark of these devices is their ability to both deliver light into the brain and record information from the brain. Depending on the experiment, users may wish to outfit the devices with a variety of multiple and optional modalities. The following steps provide information on adding functional layers to the devices. If these optional modalities are desired, Box 1 should be completed prior to Step 16 of the main PROCEDURE.

Fabrication of Temperature Sensors (4$^{th}$ Layer Shown in FIG. 59)

1. Generate PR patterns on a needle-shaped piece of PET (same substrates used in procedure 12) and deposit platinum (Pt, 10 nm) by sputtering.
2. Remove PR by acetone and generate Cr/Au (15/300 nm) metal lines that connect to the Pt resistor.

Temperature Sensor Calibration●TIMING 1 hr

3. Dip the temperature sensor into deionized (DI) water and measure reference resistance using digital multimeter. With precisely controlled temperature of the DI water, measure the changes in resistance. Since the resistance change ($\Delta R$) of the Pt resistor depends linearly on the temperature change ($\Delta T$), the formula for estimated temperature is $\Delta T \sim k \cdot \Delta R$ where k is constant.

Fabrication of μ-IPDs

Additional details of certain aspects are shown in a previous publication[47].

4. Deposit $SiO_2$ by PECVD on a silicon-on-insulator (SOI) wafer, with a top silicon layer thickness of approximately 1 μm.
5. Generate PR patterns to pattern the $SiO_2$ using hydrofluoric acid (HF).
6. Remove PR and clean the wafer surface by RCA cleaning. First perform SC (standard cleaning)-1 with 1:1:5 solution of ammonium hydroxide ($NH_4OH$):Hydrogen peroxide($H_2O_2$):DI water at 80° C. for 15 min. Second remove the $SiO_2$ layer using 1:50 solution of HF:DI water. Finally perform SC-2 with a 1:1:6 solution of hydrochloric acid (HCl):$H_2O_2$:DI water at 80° C. for 15 min (RCA Cleaning: website inside.mines.edu/fs_home/cwolden/chen435/clean.htm).
7. Carry out solid state doping of the silicon to form a p-type region.
8. Repeat above Steps 4 to 6 from for n-type doping.
9. Generate PR hole patterns on the entire wafer surface and etch the silicon layer, to define the lateral dimensions of the photodetectors.
10. Etch the buried oxide (BOx) layer using HF
11. Retrieve a 1 μm thick thin Si membrane photodiode using a PDMS slab and release it onto the needle-shaped PET substrate (described in PROCEDURE, Step 12)
12. Form metal (Cr/Au, 15/300 nm) lines for interconnect.

Fabrication of μ-Electrode for Electrophysiological Sensor (1$^{st}$ Layer Shown in FIG. 59)

13. Generate PR (AZ 2030) lift off patterns
14. Deposit Pt (30 nm) a needle-shaped piece of PET (described in PROCEDURE Step 12) by sputtering. Generate a pattern of SU-8 2 (2 μm thick) with 20×20 μm$^2$ square opening. Additional oxygen descum to remove residual PR layer is recommended. The impedance of the Pt p-electrode should be ~1.0 MΩ at 1 kHz.

Box 2|Recycling the Optoelectronic Devices for Re-Use

1. After sacrificing the animal, use forceps to forcibly remove the headcap from the surface of the skull. Thoroughly remove any visible biological tissue or other build-up from the sides and bottom of the headcap. Take care not to damage the flexible aspect of the device. Once removed and cleaned, the headcap is ready for dissolution (FIG. 63a).
2. Place the headcap into a glass beaker and add methyl methacrylate until the headcap is entirely submerged (FIG. 63b). Cover the beaker with tin foil and place in a properly ventilated fume hood overnight. Methyl Methacrylate Monomer is a flammable liquid. It may also cause skin irritation; avoid contact with skin, eyes, and clothing. Use with adequate ventilation.
3. Following overnight incubation, the dental cement should be completely dissolved. The device and bone screws should be clearly visible in the beaker (FIG. 63c). Wearing gloves and using forceps, remove these items from the beaker. The screws can be cleaned, sterilized, and used for another surgery. The device will normally become inactive after dissolution of the headcap due to concurrent dissolution of the adhesive connecting the ACF cable to both the device and the PCB (FIGS. 63d and 63e). Prior to proceeding to Step 4, use a multimeter to check that all μ-ILEDs still function properly (FIG. 63f). If any of the μ-ILEDs have electrical failure, discard the device and begin the fabrication process anew.
4. Discard the original PCB, and reassemble the device as described in Step 17 (FIGS. 58g and 58h).
5. Apply PDMS to the entire device construction to provide passivation and waterproofing for operation in vivo as in Step 19 (FIG. 58i).
6. Attach the p-needle using the silk adhesive and test the device to ensure proper electrical connection as done previously in Steps 18 and 20 of the PROCEDURE (FIGS. 58j-l, 63g, and 63h). The device is now ready for injection into a fresh animal starting at Step 24 of the PROCEDURE.

Troubleshooting advice can be found in Table 1.

TIMING

Steps 1-22, Preparation of μ-ILEDs, deterministic device assembly, and fabrication of wireless harvester: 9 d Steps 22-50, Viral and device injection: 1 d for procedure, 1-6 weeks for expression Steps 51-63, Behavioral experimentation: 5 d for preparation, variable by experiment Box 1, Combining multifunctional sensors and optoelectronics: 1-4 d depending on modalities Box 2, Rescuing the optoelectronics for re-use: 2 d Results Following successful fabrication and implementation of μ-ILEDs, wireless manipulation of intact mammalian neural circuitry is possible. While this example demonstrates the feasibility of using these devices to investigate reward-related and anxiety-like behaviors[11], nearly any behavioral assay is accessible with these devices. In particular, behaviors that require complete freedom of movement such as social interactions, wheel running, and homecage behaviors are now possible (FIG. 62c). Users can expect injected devices to maintain function for many months, as we have tested devices up to six months following injection and observe that the devices retain their operational functionality[11]. Furthermore, we show here that these devices can be reused in other animals to avoid the lengthy process of remaking new devices for each experiment. Depending on the nature of the experiment, a single panel antenna can power numerous headstage devices. If the stimulation parameters are the same across animals, this approach can greatly increase the experimental throughput for a variety of behavioral assays. Though not presented in detail here, a reasonable extension of this protocol would be to incorporate other existing microscale sensors such as pH, blood oxygen, glucose levels, or neurochemical detection onto μ-ILED devices[48,49].

TABLE 1

| Step | Problem | Possible reason | Possible solution(s) |
|---|---|---|---|
| 14 | Electrical device failure | Un-uniform coating of BCB passivation on μ-ILED | Spincoat BCB again and redo the process. |
| 17, Box 2 | ACF cable bonding failure | Insufficient temperature and/or pressure when bonding | Be certain to apply enough pressure (~1 or 2 MPa) and temperature (150° C.) |
| 24 | Device is damaged prior to or during mounting for surgery | The electrical components are grasped by the cannula holder adapter | Only grasp the upper, exposed portion of the μ-needle. No portion of the electrical components should be grasped by the cannula holder adapter. Be careful to apply appropriate pressure so as to avoid crushing the μ-needle. |
| 25, 32 | Inaccurate tissue targeting | Improperly aligned skull | Follow the instructions provided for your laboratory's stereotaxic equipment for ear bar placement and skull leveling. Species-specific ear bars may be required. If the suture lines for identifying bregma/lambda on the skull are difficult to visualize, a surgical microscope and/or treating the skull with hydrogen peroxide can be a helpful addition. It may be necessary to wait longer after penetration prior to removal of the μ-needle. |
| 33, 36 | Head cap falls off in homecage/ during behavior | Insufficient anchoring or cement application | Dental cement is ideal for reusability, but other adhesives such as VLC One Step Adhesive and C&B Metabond offer stronger bonds to the screws and skull surface. While two screws are normally sufficient, larger the PCB interfaces may require more anchor screws. |
| 37, 63 | Little or no expression of the viral construct | Improper handling and injection of the virus | Thaw virus as close in time to the surgery as possible. Maintain virus on ice until the time of injection. Depending on the promoter that drives expression, some systems will not provide sufficient opsin expression. This should be empirically determined prior to any attempted behavioral experiments. |
| 40 | Dissolution of silk adhesive during sterilization | Too much exposure to ethanol | Most aqueous solutions will dissolve the silk adhesive. Do not soak the devices in ethanol as this will promote dissolution of the adhesive. In our experience, rinsing the device with ethanol for ~15 seconds is sufficient to prevent widespread inflammation in mouse brain tissue[11]. Care should be taken to use appropriate sterilization techniques in higher mammals to avoid immune responses, such as EtO gas sterilization. |
| 60 | Insufficient RF power is reaching the headstage scavenger | The behavioral apparatus is between the panel antenna and scavenger (in an enclosure) | Connect a freestanding device to the scavenging headstage and place it in the behavioral enclosure. Using the gain on the RF signal generator adjust the RF power until sufficient power is available to power the μ-ILEDs to the desired light output. If problems powering the device persist, consider reducing the distance between the panel antenna and the scavenger. |
| Box 2 | Headcap does not fully-dissolve | Insoluble dental cement was used, not enough solvent, or extend duration of exposure to solvent | Some dental cements will not dissolve in methyl methacrylate. Consider using the exact recommended cements where possible. If using Jet Denture Repair, add more solvent or wait a longer durations for cap to dissolve. |

REFERENCES

1. Zhang, F. et al. Optogenetic interrogation of neural circuits: technology for probing mammalian brain structures. Nat. Protoc. 5, 439-456 (2010).
2. Yizhar, O., Fenno, L. E., Davidson, T. J., Mogri, M. & Deisseroth, K. Optogenetics in Neural Systems. Neuron 71, 9-34 (2011).
3. Adamantidis, A. R., Zhang, F., Aravanis, A. M., Deisseroth, K. & de Lecea, L. Neural substrates of awakening probed with optogenetic control of hypocretin neurons. Nature 450, 420-424 (2007).
4. Fenno, L., Yizhar, O. & Deisseroth, K. The Development and Application of Optogenetics. Annu. Rev. Neurosci. 34, 389-412 (2011).
5. Carter, M. E. et al. Tuning arousal with optogenetic modulation of locus coeruleus neurons. Nat. Neurosci. 13, 1526-1533 (2010).
6. Stuber, G. D. et al. Excitatory transmission from the amygdala to nucleus accumbens facilitates reward seeking. Nature 475, 377-380 (2011).
7. Jennings, J. H. et al. Distinct extended amygdala circuits for divergent motivational states. Nature 496, 224-228 (2013).
8. Kim, S.-Y. et al. Diverging neural pathways assemble a behavioural state from separable features in anxiety. Nature 496, 219-223 (2013).
9. Lammel, S. et al. Input-specific control of reward and aversion in the ventral tegmental area. Nature 491, 212-217 (2012).
10. Tye, K. M. et al. Amygdala circuitry mediating reversible and bidirectional control of anxiety. Nature 471, 358-362 (2011).
11. Kim, T. et al. Injectable, Cellular-Scale Optoelectronics with Applications for Wireless Optogenetics. Science 340, 211-216 (2013).
12. Kim, T. et al. High-Efficiency, Microscale GaN Light-Emitting Diodes and Their Thermal Properties on Unusual Substrates. Small 8, 1643-1649 (2012).
13. Kim, D.-H. et al. Dissolvable films of silk fibroin for ultrathin conformal bio-integrated electronics. Nat. Mater. 9, 511-517 (2010).
14. Kim, T., Kim, R.-H. & Rogers, J. A. Microscale Inorganic Light-Emitting Diodes on Flexible and Stretchable Substrates. Ieee Photonics J. 4, 607-612 (2012).
15. Al-Hasani, R., McCall, J. G., Foshage, A. M. & Bruchas, M. R. Locus Coeruleus Kappa Opioid Receptors modulate Reinstatement of Cocaine Place Preference through a 16. Hwang, S.-W. et al. A Physically Transient Form of Silicon Electronics. Science 337, 1640-1644 (2012).
17. Tao, H. et al. Silk-Based Conformal, Adhesive, Edible Food Sensors. Adv. Mater. 24, 1067-1072 (2012).
18. Cao, H., Gu, L., Mohanty, S. K. & Chiao, J.-C. An integrated μLED optrode for optogenetic stimulation and electrical recording. IEEE Trans. Biomed. Eng. 60, 225-229 (2013).
19. Wentz, C. T. et al. A wirelessly powered and controlled device for optical neural control of freely-behaving animals. J. Neural Eng. 8, 046021 (2011).
20. Iwai, Y., Honda, S., Ozeki, H., Hashimoto, M. & Hirase, H. A simple head-mountable LED device for chronic stimulation of optogenetic molecules in freely moving mice. Neurosci. Res. 70, 124-127 (2011).
21. Zhao, Y., Larimer, P., Pressler, R. T., Strowbridge, B. W. & Burda, C. Wireless Activation of Neurons in Brain Slices Using Nanostructured Semiconductor Photoelectrodes. Angew. Chem. Int. Ed. 48, 2407-2410 (2009).
22. Sparta, D. R. et al. Construction of implantable optical fibers for long-term optogenetic manipulation of neural circuits. Nat. Protoc. 7, 12-23 (2011).
23. Zorzos, A. N., Boyden, E. S. & Fonstad, C. G. Multiwaveguide implantable probe for light delivery to sets of distributed brain targets. Opt. Lett. 35, 4133-4135 (2010).
24. Zorzos, A. N., Scholvin, J., Boyden, E. S. & Fonstad, C. G. Three-dimensional multiwaveguide probe array for light delivery to distributed brain circuits. Opt. Lett. 37, 4841-4843 (2012).
25. Stark, E., Koos, T. & Buzsaki, G. Diode probes for spatiotemporal optical control of multiple neurons in freely moving animals. J. Neurophysiol. 108, 349-363 (2012).
26. Airan, R. D., Thompson, K. R., Fenno, L. E., Bernstein, H. & Deisseroth, K. Temporally precise in vivo control of intracellular signalling. Nature 458, 1025-1029 (2009).
27. Park, S.-I. et al. Printed Assemblies of Inorganic Light-Emitting Diodes for Deformable and Semitransparent Displays. Science 325, 977-981 (2009).
28. Diester, I. et al. An optogenetic toolbox designed for primates. Nat. Neurosci. 14, 387-397 (2011).
29. Gerits, A. & Vanduffel, W. Optogenetics in primates: a shining future? Trends Genet. Tig (2013). doi:10.1016/j.tig.2013.03.004
30. Cavanaugh, J. et al. Optogenetic inactivation modifies monkey visuomotor behavior. Neuron 76, 901-907 (2012).
31. Ruiz, O. et al. Optogenetics through windows on the brain in the nonhuman primate. J. Neurophysiol. (2013). doi:10.1152/jn.00153.2013
32. Witten, I. B. et al. Recombinase-driver rat lines: tools, techniques, and optogenetic application to dopamine-mediated reinforcement. Neuron 72, 721-733 (2011).
33. Han, X. et al. Millisecond-Timescale Optical Control of Neural Dynamics in the Nonhuman Primate Brain. Neuron 62, 191-198 (2009).
34. Kravitz, A. V., Owen, S. F. & Kreitzer, A. C. Optogenetic identification of striatal projection neuron subtypes during in vivo recordings. Brain Res. 1511, 21-32 (2013).
35. Szuts, T. A. et al. A wireless multi-channel neural amplifier for freely moving animals. Nat. Neurosci. 14, 263-269 (2011).
36. Harrison, R. R. et al. A wireless neural/EMG telemetry system for freely moving insects. in Circuits Syst. Iscas Proc. 2010 Ieee Int. Symp. 2940-2943 (2010). at website eeexplore.ieee.org/xpls/abs_all.jsp?arnumber=5538034
37. Artificial cerebrospinal fluid (ACSF). Cold Spring Harb. Protoc. 2011, pdb.rec065730 (2011).
38. Du Hoffmann, J., Kim, J. J. & Nicola, S. M. An inexpensive drivable cannulated microelectrode array for simultaneous unit recording and drug infusion in the same brain nucleus of behaving rats. J. Neurophysiol. 106, 1054-1064 (2011).
39. Wong, W. S. et al. InxGa1-xN light emitting diodes on Si substrates fabricated by Pd—In metal bonding and laser lift-off. Appl. Phys. Lett. 77, 2822-2824 (2000).
40. Cardin, J. A. et al. Targeted optogenetic stimulation and recording of neurons in vivo using cell-type-specific expression of Channelrhodopsin-2. Nat. Protoc. 5, 247-254 (2010).
41. Gradinaru, V. et al. Molecular and Cellular Approaches for Diversifying and Extending Optogenetics. Cell 141, 154-165 (2010).
42. Osakada, F. et al. New Rabies Virus Variants for Monitoring and Manipulating Activity and Gene Expression in Defined Neural Circuits. Neuron 71, 617-631 (2011).
43. Osakada, F. & Callaway, E. M. Design and generation of recombinant rabies virus vectors. Nat. Protoc. 8, 1583-1601 (2013).
44. Adamantidis, A. R. et al. Optogenetic interrogation of dopaminergic modulation of the multiple phases of reward-seeking behavior. J. Neurosci. Off. J. Soc. Neurosci. 31, 10829-10835 (2011).
45. Sparta, D. R., Jennings, J. H., Ung, R. L. & Stuber, G. D. Optogenetic strategies to investigate neural circuitry engaged by stress. Behav. Brain Res. doi:10.1016/j.bbr.2013.05.007
46. Tye, K. M. & Deisseroth, K. Optogenetic investigation of neural circuits underlying brain disease in animal models. Nat. Rev. Neurosci. 13, 251-266 (2012).
47. Kim, D.-H. et al. Stretchable and Foldable Silicon Integrated Circuits. Science 320, 507-511 (2008).
48. Clark, J. J. et al. Chronic microsensors for longitudinal, subsecond dopamine detection in behaving animals. Nat. Methods 7, 126-129 (2009).
49. Kim, R.-H. et al. Waterproof AlInGaP optoelectronics on stretchable substrates with applications in biomedicine and robotics. Nat. Mater. 9, 929-937 (2010).

Example 4: Therapeutic and Diagnostic Applications

The devices and methods of the invention are useful for therapeutic and/or diagnostic applications, including the treatment of a range of diseases and other pathological conditions. Therapeutic methods of some aspects of the invention include any of the following: (i) selective transformation of specific cells and/or cell types of a target biological tissue, for example, via administration to a subject an appropriate vector including a nucleic acid providing for selective modulation (e.g., activation or inhibition) of the transformed cells, such as by encoding one or more light responsive proteins such as light responsive receptors; (ii) interfacing any of the present biomedical devices in optical, electrical, thermal and/or fluid communication with the target biological tissue, for example, via injection, surgical implantation or providing the device in physical contact, optionally in conformal contact, with an external surface of the biological tissue; and (iii) actuation of the target biological tissue, for example, by providing an optical, electrical, thermal, acoustic and/or chemical stimulus that interacts selectively with transformed cells of the target biological tissue including optical activation of the transformed cells by exposure to one or more pulses of electromagnetic radiation. Therapeutic methods of some aspects of the invention optionally include the step of in situ and in vivo sensing one or more properties of the target biological tissue prior to, during or after transformation and/or actuation, for example, by determination of one or more optical, electrophysiological, thermal or chemical properties such as temperature, extracellular potential, intensity of scattered light, pH, blood oxygen, glucose levels, and neurochemical detection.

Therapeutic applications of the present devices and methods are further set forth and described below in the context of the treatment, management and/or diagnosis of specific diseases and pathological conditions. As will be readily apparent to one having skill in the art, however, the devices and methods of the invention may be broadly applied for a range of other therapeutic and diagnostic applications.

i. Applications to Deep Brain Stimulation (DBS) for Parkinson's Disease, traumatic Brain Injury (TBI), and Neurodegenerative Diseases.

The devices and methods of the present invention are useful for the treatment and management of a range of motor disorders including Parkinson's disease, Huntington's disease, traumatic brain injury (TBI), and depression. For example, the present micro LED-containing devices can be implemented in several ways to deliver light specifically to various brain regions that are affected (e.g., degenerated or disrupted) by these diseases.

First, some therapeutic and/or diagnostic applications include implantation of microLED-containing devices in the subthalamic nucleus (STN) and globus pallidus with RF transmission of both thin electrical probes/stimulators, and microLEDs. The microscaler size, and optionally biodissolvable nature, of some of the present devices offer decreased neuronal death and inflammation of a region of interest that is being manipulated relative to conventional therapies.

Second, some therapeutic and/or diagnostic applications include implantation of devices for sensing and monitoring, for example, to detect neuronal activity, measure pressure, pH, hemodynamics, and/or tissue parameters that are indicators of the onse, stage and/or progression of a disease, tissue damage, and/or inflammation.

Third, some therapeutic and/or diagnostic applications involve implantation of devices having sensing capability for measuring and/or characterizing neurotransmitter release (e.g., fast scan cyclic voltammetry, microdialyis, peptide/antibody detection, and photodetection).

Fourth, some therapeutic and/or diagnostic applications involve implantation of an array of microLEDs to multiple brain regions, for dual/bi-directional control and inhibition or excitation of desired neuronal activity.

Fifth, some therapeutic and/or diagnostic applications involve inclusion of a microscale, microfluidic implantable or surface mounted device for drug delivery to injury sites, neurodegenerated brain regions, and/or inflamed affected areas.

Devices of the invention provide various configurations of electrodes, sensors, wireless microfluidic elements, microLEDs and/or other sensors or actuators, that enable electric and/or light-dependent modulation of neurons deep within the brain of diseased patients using RF power, and IR power/battery configurations. Modulation of cellular function by these devices can be achieved by multiple light-sensitive and pharmacological mechanisms, including but not limited to:

(i) Light-dependent activation of either optogenetic channels expressed in the cell classes described herein;

(ii) Light-dependent modifications of chemicals or drugs such as light-sensitive (activated or uncaged) drugs, including but not limited to light-activated ion channel modulators such as sodium channel blockers or potassium channel openers, and light-activated (uncaging) analgesic drugs such as opiates/opioid-like ligand.

(iii) Electrode stimulation with wireless fluidics delivery of pharmacological agents;

(iv) Activation of modulation of light-sensitive G-protein coupled receptors (Opioid, Dopamine, CRF, etc) or CRY containing (crytochrome) domain proteins for control of intracellular signaling;

(v) uncaging "light-sensitive" peptide ligands, and small molecules for high resolution temporal control of drug action in vivo.

In this way, the invention may achieve highly localized regulation of neuronal function, sensing, and monitoring in a minimally invasive manner with better clinical outcomes than in conventional therapeutic approaches.

Conditions of the brain to which the present device and methods may be applied include, but are not limited to, brain diseases that involved dissociation and disruption of normal function:

Parkinson's disease, whereby selective loss of dopamine neurons is pronounced

Traumatic Brain Injury for both detection, treatment or monitoring at an injury site.

Chronic and Acute Depression and associated mood disorders, DBS (deep brain stimulation) for treatment of chemical imbalance and/or associated mood disorders. Associated brain regions include, but are not limited to: subgenual cingulate gyrus, nucleus accumbens, ventral capsule/ventral striatum, inferior thalamic peduncle, and the lateral habenula, and the medial forebrain bundle.

Epilepsy, for dampening and modulated neuronal activity in hippocampus, cortical regions, using a "closed looped" methodology.

Coma, or related chronic brain related trauma's, for measurement of brain parameters and sensing as described above such as monitoring pressure, inflammatory mediators, dialysis, drug infusions, and/or temperature.

Tourette's Syndrome, for modulating neuronal activity.

In some therapeutic applications of the invention, modifications are made to allow regulation of sensation and function of the brain in transient devices for acute brain monitoring, fluidics, and/or situations where the function is needed for short term treatments. Examples of electronic systems and devices for these applications are set forth and exemplified throughout the present description and in "Dissolvable Electronics" website sciencemag.org/content/337/6102/1640, and which is hereby incorporated by reference.

ii. Applications to Bladder Pathology.

The devices and methods of the present invention are useful for the management of bladder pain and dysfunction. For example, using micro LED-containing devices to deliver light specifically to the bladder which can be implemented in several ways.

First, some therapeutic and/or diagnostic applications include implantation of microLED-containing devices in the lumen of the bladder to illuminate the bladder wall from the interior. For example, some therapeutic applications utilize devices powered externally and internalized to the bladder lumen, and/or devices that are provided wholly within the bladder lumen, incorporating the micro LED array in conjunction with RF scavenging antennae to power the devices.

Second, some therapeutic and/or diagnostic applications include implantation of an array of micro-LEDs to the bladder surface, within the peritoneum.

Third, some therapeutic and/or diagnostic applications include implantation of an array of microLEDs to the exterior of the peritoneum or subcutaneously on the abdomen over the bladder, enabling transmission of light through tissues to reach the bladder.

Fourth, some therapeutic and/or diagnostic applications include application of skin surface-mounted micro-LED arrays (with reflective backing to direct all light inward).

Devices of the invention provide various configurations of electrodes, sensors, wireless microfluidic elements, micro-LEDs and/or other sensors or actuators, that enable light-dependent modulation of neurons innervating the bladder, of the urothelial cells lining the bladder, or bladder muscles controlling micturition. Modulation of cellular function by these devices can be achieved by multiple light-sensitive mechanisms, including but not limited to:

(i) light-dependent activation of optogenetic channels expressed, such as in the cell classes described above.

(ii) light-dependent modifications of chemicals or drugs such as light-sensitive (activated or uncaged) drugs, including but not limited to light-activated ion channel modulators such as sodium channel blockers or potassium channel openers and/or light-activated analgesic drugs such as opiates.

In this way, the invention may achieve highly localized regulation of bladder sensation and/or function, with a high degree of temporal precision.

Conditions of the bladder for which the present device and methods may be applied include, but are not limited to:

Bladder pain conditions including interstitial cystitis, bladder pain syndrome (BPS), chronic pelvic pain syndrome, and related conditions not involving the bladder including chronic prostatitis.

Overactive bladder.

Urinary Incontinence.

In some therapeutic applications of the invention, modifications are made to allow regulation of sensation and function of the lower digestive tract to relieve pain associated with IBS, colonic inflammation and related conditions, to regulate fecal incontinence, etc.

iii. Applications to Deep Brain Stimulation for Pain Control.

Modulation of firing of amygdala neurons via optogenetic channels may be effective to modulate bladder pain (Kolber et al, 2012 J Neurosci. 2012 Oct. 10; 32(41):14217-26). The methods and device of the present invention may be implemented in combination with optogenetic channels or light-activated chemicals (e.g., drugs or drug precursors) to modulate amygdala function for the control of bladder pain, and also may be more widely applicable to chronic pain in general. This need not be restricted to stimulation or inhibition of amygdala function as described above, but can be generally applied to other therapeutic applications, biological tissues and conditions. Accordingly, therapeutic applications of the invention provide pathways to stimulation or inhibition of other brain regions for pain control. These include, but are not limited to, regulation of firing of periaqueductal gray, rostroventromedial medullar (RVM) or nucleus raphe magnus, thalamic nuclei, or anterior cingulate cortex.

Example 5: Injectable Microfluidic Drug Delivery Device

Aspects of this Example describe the ability to deliver a fluid to a tissue or sample a biological fluid using an injectable device of the invention. For example, injectable microfluidic devices are useful for controllably delivering drugs to isolated parts of the brain over time. Optionally, fluid can also be withdrawn from a tissue using devices of the invention, for example, to allow characterization via optical or chemical sensing techniques. This Example describes one-way and two-way microfluidic systems for interfacing with a tissue.

Devices of an embodiment, for example, provide the ability to influse, deliver and/or withdraw a fluid volume of 0.25 μL or more to or from a tissue. Optionally, the fluid can be infused or withdrawn at a rate of 10 to 100 nL/min. In exemplary embodiments, the devices of this aspect weigh less than 2 g.

In exemplary embodiments, devices of this aspect are used to provide photoactivatable compositions to a tissue, for example, for use in a phototherapeutic procedure or a photodiagnostic procedure. For example, the fluid delivered to the tissue optionally comprises a photoactivatable compositions and an optical source device component, such as an LED, laser or array thereof, of the device is used to photoactivate the composition by exposing the composition to electrogmagnetic radiation. Photoactivation of a phototherapeutic agent, for example, is useful for generating reactive species (e.g., radicals, excited species, ions, etc.) localized to a specific site of the tissue. Photoactivation of a photodiagnostic agent, for example, is useful for generating optically functional probes or agents, such as chromophores or florophores that undergo fluorescence.

The design of an example microfluidic device embodiment is illustrated in FIG. 66. The microfluidic device comprises a micro-LED, a microfluidic channel, thin copper membranes, four reservoirs, an expandable material composite layer, four micro-heaters, and a substrate. The microfluidic channel is only 50 μm-thick and made of PDMS, which is flexible and biocompatible. For long-term storage of liquid, the four reservoirs are patterned in cyclic olefin copolymer (COP), which has very low water vapor permeability (0.023 g·mm/m2·d), and optionally covered with 0.3 μm-thick copper membranes. The copper membranes advantageously prevent undesired diffusion of drug into the tissue when the device is in off-state. Additionally, the copper membranes keep the drug from being evaporated through the vertical channels in the COP. The expandable material composite is made by mixing PDMS with expandable microspheres (Expancel 031 DU 40, AkzoNobel, Sweden) and starts to increase its volume above the threshold temperature of 80 95° C. The heater, made of a 175 nm-thick gold, is fabricated on top of FR-4, which has a low thermal conductivity, in order to achieve maximum heater temperature with minimum power requirement.

FIG. 67 provides an overview of the actuation principle. The principle and technological implementation of this exemplary microfluidic drug delivery device relies on expansion of the expandable composite layer, actuated by a micro-heater. The COP is patterned to have a volume of 0.5 μl in its hemispherical reservoirs. By increasing a temperature of the micro-heater with applied voltage, the expandable composite layer increases its volume, leading to pressure increase in the reservoir. This results in rupturing of the thin copper membrane, thus the drug can be ejected from the reservoir. Since the expansion of the material is irreversible, no backflow occurs. Therefore, each actuation pumps precisely the liquid volumes predefined by the reservoirs through the PDMS microfluidic channel probe without the need for additional sensor control.

FIG. 68 provides images of a fabricated microfluidic device, providing additional details of the design of the device. The four reservoirs are connected to four individual channels (10 µm×10 µm in size), separated by 40 µm. This design increases versatility in application by enabling storage of four different drugs in one device. The microfluidic channel probe is only about 80 µm in thickness (PDMS microfluidic channel is 50 µm in thickness; adhesion layer is 25 µm in thickness; micro-LED is about 6 µm in thickness), therefore making this injectable device minimally invasive. The device has two ribbon cable connectors, one for the micro-LED, and the other for micro-heaters. Using a wireless control circuit, the micro-LED and four micro-heaters can be individually controlled.

Thermal characteristics for the device are depicted in FIG. 69. The property of drug can be influenced if it is exposed to too high temperature. The micro-heaters of this example are operated at a temperature over 110° C. by applying 7.4 V. This high temperature, however, is not problematic since most of heat energy is absorbed by the expandable composite and not transferred to the reservoirs. According to measurements using an infrared camera, the temperature of water in the reservoir increases only up to 30.5° C. when the heater is heated to 117.1° C. This result ensures that thermal actuation does not affect the original property of drug being delivered.

A schematic illustration of a wireless control system for the device is depicted in FIG. 70. The wireless control system is based on serial communication using an infrared (IR) LED in the transmitter and an IR detector in the receiver. The transmitter consists of nine buttons to control four individual micro-heaters, to operate micro-LED in four different mode (5, 10, 20, 40 Hz frequency with 10 ms pulse width), and to activate the power save mode. When the user presses a button, the micro-controller in the transmitter send out a corresponding command signal (ASCII code) and the modulated information is transmitted with a 38 kHz carrier frequency signal using IR light. At the receiver side, this signal is detected by an IR detector and the micro-controller demodulates it, and performs a pre-programmed action.

A schematic diagram of a wireless receiver circuit is depicted in FIG. 71. The wireless receiver circuit for this example comprises four transistors for switching on the heaters, two LEDs for indicating the mode of operation, and one photo-transistor for waking up the microcontroller from the power save mode. This circuit is built on flexible PCB and connected to a microfluidic device upon packaging.

FIG. 72 provides pictures of the wireless receiver circuit on the flexible PCB and batteries. The size of the PCB is 13 mm×14 mm, and the dimensions of a battery (GM300910H, PowerStream Technology, USA) is 3 mm×9 mm×10 mm. The total weight of the device system is 1.855 g (packaging case=0.705 g; battery (×2)=0.66 g; PCB=0.15 g; Microfluidic device=0.34 g), which are well below the required weight of 2 g that can guarantee the mouse's free movement when installed on its head.

FIG. 73 provides images of a case designed for housing the device. The packaging case comprises a water-clear plastic body and lid. Its dimension is 15 mm×7 mm×20 mm when assembled. A wireless receiver PCB and two batteries are packaged into the case, and a microfluidic device is slid into the device holder of the case body. The ribbon cables from the PCB connected to the microfluidic device can be bit and damaged by mice. Therefore, the lid is designed to cover the entire ribbon cables.

The device was implanted into a mouse. To facilitate injection of the flexible PDMS microfluidic channel probes, a SU-8 micro-needle is attached on top of the probe using water-soluble material (silk). Then, the device is mounted on a holder and the probe part is injected into the brain of the mouse. Anchor screws are optionally used to hold the device in place. Upon installation, the silk is melted and the SU-8 micro-needle is subsequently released and removed from the probe. Finally the device is fixed by applying dental cement around the installed device.

FIG. 74 provides data detailing the thermal expansion of the expandable layer and depicts a primary expansion range useful for embodiments of the invention. FIG. 75 provides data showing the temporal variation of temperature when the heater is on for a bare heater with no polymer coating on it. For accumulation of this data, the heater was turned on for about 20 seconds using 7.4 V to actuate the heater. FIG. 76 provides data showing calibration of the heater temperature as a function of the actuation voltage after 20 seconds.

As described above, two-way microfluidics are also provided by aspects of the invention, such as to both deliver a fluid and remove a fluid from a tissue. FIG. 77 provides an overview of a device embodiment providing two-way microfluidics. Here, two way microfluidics are achieved using a polypyrrole (PPy) Actuator. As a current or a voltage is applied, a Reduction/Oxidation reaction occurs in the polypyrrole, providing three states: oxidized (or doped), reductized (or de-doped) and neutral. When it is positively charged, the polypyrrole attracts an anion (oxidation) to balance the removal of the electron from the polymer. Following the same principle, the reduction involves the addition of electron in the polymer and the removal of the anion when it is negatively charged. These anions come from the porous PVDF, which contains an electrolyte. The doping level could be controlled by the voltage applied. The movement of ions, on one hand, and the solvent molecules, on the other, induces a volume expansion or contraction. The volume of the doped PPy layer increases and the volume of the other PPy layer decreases. Furthermore, the polymer backbone interacts electrostatically with the displaced ions. In the doped layer the polymer backbone and the anions are both negatively charged and on in the undoped layer the cation are positively charged. The resultant electrostatic forces cause the PPy layer to expand or contract. This creates the bending motion. As shown in the bottom right panel, opposite voltage application shows a reversal in the displacement direction. Based on this principle, by operating a PPy membrane in the reservoir as shown in FIG. 77, the microfluidic device can either sample or eject liquid.

Example 6: Fully Implantable Optogenetics Devices

This example describes fully implantable device embodiments useful for optogenetics. The devices of this example are improved over earlier embodiments that were bulky and heavy. In embodiments, the devices comprise injectable LED devices having implantable radio frequency receivers. Optionally, the devices are smaller than 7 mm×9 mm (mouse skull size range), and lighter than 2 g including all LED parts, connectors, passivation layers, screws, etc. FIG. 78 provides images of earlier embodiments incorporating a printed circuit board (top left images), where the weight of the device was about 2.54 g. The later generation, flexible devices are shown in the top right images of FIG. 78, with an improved weight of about 0.8 g. A device embodiment of this example is shown at bottom left, next to a penny for scale, and weighs about 0.07 g, not including any passivation materials. The bottom right panel of FIG. 78 provides a size comparison between prior flexible devices and the current generation flexible devices. FIG. 79 provides images of the device showing a comparison between the printed circuit board device and the implantable device of this example (left panel) and the device held with a pair of tweezers with the four GaN µILEDs on an injectable microneedle illuminated (right). Microcalipers were used to measure the dimensions of the device. The length of the device was 8.42 mm, the width of the device was 4.11 mm and the thickness of the device was 1.98 mm.

The wireless function of the devices at 2.4 GHz was tested by placing the devices in saline solution and the devices functioned well. For further testing, the device was implanted into the head of a mouse. Initially, an incision was made in the scalp to expose the top of the skull, next the device was implanted with the antenna encapsulated in soft PDMS. Next the soft tissue was pulled over the antenna and then finally the scalp was sutured together.

To accommodate the reduction of size of the devices of this example, smaller device components were fabricated, with images shown in FIG. 80. A smaller plug for wired data transmission was fabricated, with an almost four fold reduction in weight (reduced from 0.11 g to 0.03 g) and a doubling of the data connections (from 2-pins to 4 pins) as compared with the previous plug connector shown in the top panel of FIG. 80. Additionally, a smaller micro-needle was fabricated, having a thickness of about 50 µm, as measured using a digital microcalipers, compared with a thickness of previous SU-8 needle of about 250 µm, as shown in the bottom panel of FIG. 80.

An injectable UV LED device was fabricated for optofluidics applications. FIG. 81 provides data showing the EL measurement of the LED devices with a peak at 379 nm when driven at 3.5 V (top panel). The UV LEDs were fabricated at a size of about 100 µm, as shown in the bottom right panel of FIG. 81. The UV LEDs were incorporated into an injectable microneedlesystem (middle and lower right panels of FIG. 81). These UV LEDs are useful for photoactivation of fluids delivered to a tissue by exposing the fluid or a component thereof to ultraviolet electromagnetic radiation. For example, the LEDs are useful for UV uncaging of Naloxone.

As an example of the utility of the present invention, stretchable devices were implanted into an animal model for optogenetic control of the sciatic nervous system in a freely moving animal. During implantation, two incision were made near the hind legs, the first allowing for device insertion and sciatic access and the second allowing for positioning of the implanted device. 1 week after implantation, the incisions were healing well with the device fully implanted under the skin of the animal.

As another example, a 7-8 cm long stretchable device was implanted into an animal model providing a head stage connection to the sciatic nerve near the hind legs of the animal. FIG. 82 provides an image of the animal with the implanted device, and a schematic diagram of the implanted device. The device exhibited at least 30% stretching without undergoing damage. This device allowed activation of the GaN LEDs to stimulate the tissue at the sciatic nerve using electromagnetic radiation.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Whenever a range is given in the specification, for example, a temperature range, a time range, or a size range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The following references relate generally to fabrication methods, structures and systems for making electronic devices, including electronic devices for interfacing with biological tissue, and are hereby incorporated by reference to the extent not inconsistent with the disclosure in this application.

TABLE R1

| Atty Ref. | App. No. | Filing Date | Pub. No. | Pub. Date | Pat. No. | Issue Date |
|---|---|---|---|---|---|---|
| 18-04 | 11/115,954 | Apr. 27, 2005 | 2005/0238967 | Oct. 27, 2005 | 7,195,733 | Mar. 27, 2007 |
| 38-04A | 11/145,574 | Jun. 2, 2005 | 2009/0294803 | Dec. 3, 2009 | 7,622,367 | Nov. 24, 2009 |
| 38-04B | 11/145,542 | Jun. 2, 2005 | 2006/0038182 | Feb. 23, 2006 | 7,557,367 | Jul. 7, 2009 |
| 43-06 | 11/421,654 | Jun. 1, 2006 | 2007/0032089 | Feb. 8, 2007 | 7,799,699 | Sep. 21, 2010 |
| 41-06 | 11/423,192 | Jun. 9, 2006 | 2009/0199960 | Aug. 13, 2009 | 7,943,491 | May. 17, 2011 |
| 38-04C | 11/423,287 | Jun. 9, 2006 | 2006/0286785 | Dec. 21, 2006 | 7,521,292 | Apr. 21, 2009 |
| 25-06A | 13/596,343 | Aug. 28, 2012 | 2012/0321785 | Dec. 20, 2012 | 8,367,035 | Feb. 5, 2013 |
| 134-06 | 11/851,182 | Sep. 6, 2007 | 2008/0157235 | Jul. 3, 2008 | 8,217,381 | Jul. 10, 2012 |
| 151-06 | 11/585,788 | Sep. 20, 2007 | 2008/0108171 | May. 8, 2008 | 7,932,123 | Apr. 26, 2011 |
| 216-06 | 11/981,380 | Oct. 31, 2007 | 2010/0283069 | Nov. 11, 2010 | 7,972,875 | Jul. 5, 2011 |
| 213-07 | 12/398,811 | Mar. 5, 2009 | 2010/0002402 | Jan. 7, 2010 | — | — |
| 38-04D | 12/405,475 | Mar. 17, 2009 | 2010/0059863 | Mar. 11, 2010 | 8,198,621 | Jun. 12, 2012 |
| 170-07 | 12/418,071 | Apr. 3, 2009 | 2010/0052112 | Mar. 4, 2010 | — | — |
| 60-09 | 12/778,588 | May. 12, 2010 | 2010/0317132 | Dec. 16, 2010 | — | — |
| 19-10 | 12/916,934 | Nov. 1, 2010 | 2012/0105528 | May. 3, 2012 | — | — |
| 126-09 | 12/968,637 | Dec. 15, 2010 | 2012/0157804 | Jun. 21, 2012 | — | — |
| 137-05 | 11/675,659 | Feb. 16, 2007 | 2008/0055581 | Mar. 6, 2008 | — | — |
| 15-10 | 12/892,001 | Sep. 28, 2010 | 2011/0230747 | Sep. 22, 2011 | — | — |
| 71-07 | 12/669,287 | Jan. 15, 2010 | 2011/0187798 | Aug. 4, 2011 | — | — |
| 145-03 | 11/001,689 | Dec. 1, 2004 | 2006/0286488 | Dec. 21, 2006 | 7,704,684 | Apr. 27, 2010 |
| 38-04A1 | 12/564,566 | Sep. 22, 2009 | 2010/0072577 | Mar. 25, 2010 | 7,982,296 | Jul. 19, 2011 |
| 43-06A | 12/844,492 | Jul. 27, 2010 | 2010/0289124 | Nov. 18, 2010 | 8,039,847 | Oct. 18, 2011 |
| 90-06 | 11/782,799 | Jul. 25, 2007 | 2008/0212102 | Sep. 4, 2008 | 7,705,280 | Apr. 27, 2010 |
| 118-08 | 12/996,924 | Dec. 8, 2010 | 2011/0147715 | Jun. 23, 2011 | — | — |
| 3-10 | 12/947,120 | Nov. 16, 2010 | 2011/0170225 | Jul. 14, 2011 | — | — |
| 150-11 | 61/565,907 | Dec. 1, 2011 | — | — | — | — |
| 29-11 | 13/492,636 | Jun. 8, 2012 | 2013/0041235 | Feb. 14, 2013 | — | — |
| 3-11 | 13/349,336 | Jan. 12, 2012 | 2012/0261551 | Oct. 18, 2012 | — | — |
| 7-11 | 13/486,726 | Jun. 1, 2012 | — | — | — | — |

We claim:

1. An implantable biomedical device for interfacing with a target tissue, said device comprising:
   a substrate; and
   a device component comprising: one or more inorganic semiconductor components comprising one or more light emitting diodes and a wireless power system utilizing radiofrequency power scavenging; wherein said device component is supported by said substrate;
   wherein said one or more light emitting diodes comprise microscale inorganic light emitting diodes (µ-ILEDs);
   wherein steady state operation of said one or more light emitting diodes provides a change in a temperature of said target tissue equal to or less than 1° C.;
   wherein the target tissue is a brain tissue;
   wherein said substrate and said device component in combination have a lateral dimension and a thickness selected to allow for implantation and illumination of a brain with a minimal adverse biological effect to said brain tissue, and wherein said substrate and said device component in combination have a thickness of not greater than 100 μm.

2. The device of claim 1, wherein said device component further comprises one or more electronic devices, optical devices, optoelectronic devices, microfluidic devices or arrays thereof.

3. The device of claim 1, wherein said device component further comprises one or more optical, mechanical, electrophysiological, acoustic, chemical, magnetic or thermal actuators; or one or more optical, mechanical, electrophysiological, acoustic, chemical, magnetic or thermal sensors; or any combinations of these.

4. The device of claim 1, wherein said device component further comprises one or more photodiode, laser, electrode, piezoelectric element, antenna, nanoelectromechanical (NEMS) device, microelectromechanical (MEMS) device, acoustic source, micro- or nano-heater, integrated electronic circuit, energy source, chemical source, biological source, wireless receiver, wireless transmitter or any combinations of these.

5. The device of claim 1, wherein said device component has a thickness selected from a range of 500 nm to 50 μm.

6. The device of claim 1, wherein said device component comprises a flexible or stretchable electronic device, optical device or optoelectronic device.

7. The device of claim 1, wherein said device component or portion thereof is individually addressed to a cell or group of cells of said target tissue.

8. The device of claim 1, wherein said device component has an active area exposed to said target tissue less than or equal to $1 \times 10^6$ μm$^2$.

9. The device of claim 1, wherein said one or more light emitting diodes each independently has an emitting area less than or equal to $1 \times 10^5$ μm$^2$.

10. The device of claim 1, wherein said one or more light emitting diodes each independently has an emitting area selected from a range of $1 \times 10^3$ μm$^2$ to $1 \times 10^5$ μm$^2$ and wherein said one or more light emitting diodes provides a radiant output characterized by a surface power density of 0.1 mW mm$^{-2}$ to 10 mW mm$^{-2}$.

11. The device of claim 10, wherein said one or more light emitting diodes provides the radiant output characterized by a plurality of different wavelength maxima.

12. The device of claim 1, wherein said device component further comprises one or more photodetectors each independently having an active light receiving area less than or equal to $1 \times 10^6$ μm$^2$.

13. The device of claim 1, wherein said device component further comprises one or more electrodes each independently having an active electrode area less than or equal to $1 \times 10^6$ μm$^2$.

14. The device of claim 1, wherein said device component and said substrate form a functional layer comprising a functional electronic device that interfaces with said target tissue.

15. The device of claim 14, comprising at least one additional functional layer, the functional layer and the at least one additional functional layer together comprising a plurality of functional layers arranged in a stacked configuration.

16. The device of claim 15, wherein said plurality of functional layers number from a range that is greater than or equal to 2 and less than or equal to 10, wherein said plurality of functional layers together have a total thickness that is selected from a range that is greater than or equal to 500 nm and less than or equal to 100 μm.

17. The device of claim 15, wherein said stacked configuration has a shape that corresponds to a micro-needle.

18. The device of claim 15, wherein said plurality of functional layers comprises at least two different functional layers to provide a multifunctional implantable or surface mounted biomedical device.

19. The device of claim 18, wherein said multifunctional device electrically, optically and thermally interfaces with said target tissue.

20. The device of claim 19, wherein said plurality of functional layers in said stacked configuration comprises: said one or more light emitting diodes and said wireless power system.

21. The device of claim 19, wherein said multifunctional device electrical, optical and thermal interfacing is simultaneous.

22. The device of claim 15, wherein said plurality of functional layers interface with an interfacing region within a biological tissue, said interfacing region having an interfacing surface area selected from a range that is greater than or equal to 10 μm$^2$ and less than or equal to 100 mm$^2$.

23. The device of claim 22, wherein at least one functional electronic device selectively interfaces with an individual biological cell or biological component thereof within the interfacing region.

24. The device of claim 14, wherein said functional electronic device corresponds to a size of a biological component within the target tissue.

25. The device of claim 24, wherein said size of said biological component is an average diameter selected from a range that is greater than or equal to 1 μm and less than or equal to 100 μm.

26. The device of claim 14, wherein said functional layer comprises an array of independently addressable functional electronic devices for independently interfacing with individual biological cells within said target tissue.

27. The device of claim 1, wherein said one or more inorganic semiconductor components comprise one or more thin film structures.

28. The device of claim 1, wherein said one or more inorganic semiconductor components have a thickness less than or equal to 100 nm.

29. The device of claim 1, wherein each of said one or more inorganic semiconductor components independently comprise a nanomembrane structure.

30. The device of claim 1, wherein at least one of said one or more inorganic semiconductor components is a flexible or a stretchable structure.

31. The device of claim 30, wherein said flexible or stretchable structure is an interconnect that connects island structures.

32. The device of claim 1, wherein at least one of said one or more inorganic semiconductor components is a nanoribbon, a nanomembrane, a nanowire, a transistor channel, a diode, a p-n junction, a photodiode, a light emitting diode, a laser or a combination of these.

33. The device of claim 1, wherein at least one of said one or more inorganic semiconductor components has a Young's modulus selected from a range of 0.5 MPa to 10 GPa.

34. The device of claim 1, wherein at least one of said one or more inorganic semiconductor components has a net bending stiffness less than or equal to $1 \times 10^8$ GPa μm$^4$.

35. The device of claim 1, wherein said substrate comprises a material selected from the group consisting of MgO, silk, collagen, gelatin, PLGA, polyvinylalcohol (PVA), PLA, $SiO_2$, polyanhydrides (polyesters), polyhdroxyalkanates (PHAs), polydimethylsiloxane (PDMS) and polyphosphates.

36. The device of claim 1, wherein said substrate and said device component in combination have a longitudinal length selected from a range that is greater than or equal to 1 mm and less than or equal to 10 cm.

37. The device of claim 1, further comprising an encapsulating material at least partially encapsulating one or more of said inorganic semiconductor components.

38. The device of claim 1, further comprising a barrier layer that covers one or more of said inorganic semiconductor components.

39. The device of claim 1, wherein said substrate has a first end that is tapered for insertion into said target tissue.

40. The device of claim 39, further comprising a delivery substrate that supports said substrate.

41. The device of claim 40, further comprising an adhesive layer between said delivery substrate and said substrate.

42. The device of claim 41, wherein said adhesive layer dissolves or is bioresorbed and said delivery substrate is removed after implantation.

43. The device of claim 41, wherein said adhesive layer comprises a silk material.

44. The device of claim 40, wherein said delivery substrate has a mechanical property that is substantially higher than a corresponding mechanical property of said device component and said substrate, said mechanical property selected to support and protect said device component and said substrate during handling and implantation.

45. The device of claim 44, wherein said mechanical property is effective Young's modulus or net bending stiffness.

46. The device of claim 40, wherein said delivery substrate has a first end that tapers to a tip.

47. The device of claim 46, wherein said device is shaped into a micro-needle geometry and said device is injectable into said target tissue.

48. The device of claim 1, having any cross-sectional surface area of the device less than or equal to 1 $mm^2$.

49. The device of claim 1, wherein said device component is partially or completely embedded within said substrate.

50. The device of claim 1, wherein said target tissue is soft tissue of a living animal.

51. The device of claim 1, wherein said interfacing is at a penetration depth selected from a range that is greater than or equal to 1 mm and less than or equal to 10 cm from a brain surface.

52. The device of claim 1, further comprising a wireless transmitter and a wireless receiver operably connected to said device for wirelessly receiving data and transmitting instructions to said device implanted in said target tissue.

53. The device of claim 1, wherein said substrate has a substrate first end, said device further comprising a probe connected to said substrate first end.

54. The device of claim 53, wherein said probe is a positioning probe to indicate device position within said target tissue.

55. The device of claim 54, wherein said probe is confined to a probe confinement area on said substrate first end that is less than or equal to 1000 $\mu m^2$.

56. The device of claim 1, wherein said device component comprises a microfluidic device.

57. The device of claim 56, wherein said microfluidic device provides one-way or two-way fluid communication with said target tissue.

58. The device of claim 56, wherein said microfluidic device comprises a fluid reservoir positioned proximate to a heat expandable material.

59. The device of claim 58, wherein said heat expandable material is positioned in thermal communication with a heater.

60. The device of claim 1, wherein said substrate has a distal end comprising a minimum lateral dimension selected from a range that is less than 1 $\mu$m.

61. The device of claim 1, wherein said substrate has a distal end that is a taper geometry.

62. The device of claim 1 wherein said microscale inorganic light emitting diodes comprise a plurality of microscale inorganic light emitting diodes.

63. The device of claim 62 wherein said plurality of microscale inorganic light emitting diodes include microscale inorganic light emitting diodes having different wavelength maxima.

64. The device of claim 1 wherein said wireless power system is configured to power said one or more light emitting diodes.

65. The device of claim 1 wherein said wireless power system is configured to control said one or more light emitting diodes.

66. The device of claim 1, wherein said wireless power system is configured for receiving a wireless power transmission.

67. The device of claim 1, wherein said wireless power system is a wireless power harvester.

68. The device of claim 67 wherein a radio frequency power that reaches a biological tissue is less than or equal to 3 $mW/cm^2$.

69. The device of claim 1, wherein said wireless power system comprises one or more antenna.

70. The device of claim 69, wherein said one or more antenna are radio frequency antenna.

71. The device of claim 69, wherein said one or more antenna are flexible antenna.

72. The device of claim 1 wherein said wireless power system further comprises one or more impedance matching inductor, rectifier, voltage multiplexer, amplifier, Schottky diode or any combination of these.

73. The device of claim 1, wherein said lateral dimensions are selected from a range that is greater than or equal to 1 $\mu$m and less than or equal to 10 mm; and/or wherein said thickness selected from a range that is greater than or equal to 100 nm and less than or equal to 1 mm.

74. An injectable and implantable biomedical device for interfacing with a target tissue, said device comprising:
   a substrate;
   a device component comprising: one or more inorganic semiconductor components comprising one or more light emitting diodes and a wireless power system utilizing radiofrequency power scavenging; wherein said device component is supported by said substrate; and
   a delivery substrate having a first end that is tapered for insertion into the target tissue, wherein said delivery substrate supports said substrate and said device component;
   wherein steady state operation of said one or more light emitting diodes provides a change in a temperature of said target tissue equal to or less than 1° C.
   wherein said one or more light emitting diodes comprise microscale inorganic light emitting diodes ($\mu$-ILEDs);
   wherein the target tissue is a brain tissue; and wherein said device has a lateral dimension and a thickness selected to allow for implantation and illumination of a brain with a minimal adverse biological effect to said brain tissue wherein said device has a thickness of not greater than 100 µm.

75. The device of claim 74, wherein said delivery substrate has a thickness selected from a range that is greater than or equal to 1 µm and less than or equal to 100 µm, and said substrate and said device component in combination have a thickness that is less than 10 µm.

76. The device of claim 74, wherein said device component and said substrate form a functional layer comprising a functional electronic device that interfaces with said target tissue.

77. The device of claim 76, comprising at least one additional functional layer, the functional layer and the at least one additional functional layer together comprising a plurality of functional layers arranged in a stacked configuration with said delivery substrate.

78. The device of claim 74, further comprising an adhesive layer that adheres said delivery substrate and said substrate, wherein in response to a stimulus said adhesive layer dissolves or is bioresorbed and said delivery substrate is removed from the substrate.

79. The device of claim 78, wherein said adhesive layer comprises a silk material and said stimulus is a solvent that dissolves said silk material.

80. The device of claim 74, wherein said delivery substrate has a bendability, elasticity, or flexibility that is substantially lower than the substrate that supports the device component.

81. The device of claim 74, wherein an insertion cross-sectional area of said device is less than or equal to 4 mm$^2$.

82. The device of claim 81, wherein after implantation removal of the delivery substrate, an implanted cross sectional area is less than or equal to 1 mm$^2$.

83. The device of claim 74, having a ratio of cross-sectional insertion area to cross-sectional implantation area that is selected from a range that is less than or equal to 10 and greater than or equal to 2.

84. The device of claim 74, wherein said lateral dimension selected from a range that is greater than or equal to 1 µm and less than or equal to 10 mm; and/or wherein said thickness selected from a range that is greater than or equal to 1 µm and less than or equal to 1 mm.

* * * * *